United States Patent
Cheng et al.

(10) Patent No.: US 7,732,604 B2
(45) Date of Patent: Jun. 8, 2010

(54) TRIAZOLOPYRAZINE DERIVATIVES

(75) Inventors: Hengmiao Cheng, San Diego, CA (US); Jingrong Jean Cui, San Diego, CA (US); Jacqui Elizabeth Hoffman, San Diego, CA (US); Lei Jia, San Diego, CA (US); Mary Catherine Johnson, San Diego, CA (US); Robert Steven Kania, San Diego, CA (US); Phuong Thi Quy Le, San Diego, CA (US); Mitchell David Nambu, San Diego, CA (US); Mason Alan Pairish, San Diego, CA (US); Hong Shen, San Diego, CA (US); Michelle Bich Tran-Dubé, San Diego, CA (US)

(73) Assignee: Pfizer Inc., New York, NY (US)

( * ) Notice: Subject to any disclaimer, the term of this patent is extended or adjusted under 35 U.S.C. 154(b) by 163 days.

(21) Appl. No.: 11/745,921

(22) Filed: May 8, 2007

(65) Prior Publication Data

US 2007/0265272 A1     Nov. 15, 2007

Related U.S. Application Data

(60) Provisional application No. 60/799,966, filed on May 11, 2006, provisional application No. 60/893,231, filed on Mar. 6, 2007.

(51) Int. Cl.
| | |
|---|---|
| C07D 471/00 | (2006.01) |
| C07D 487/00 | (2006.01) |
| C07D 491/00 | (2006.01) |
| C07D 495/00 | (2006.01) |
| C07D 497/00 | (2006.01) |

(52) U.S. Cl. ................................ 544/350
(58) Field of Classification Search ............... None
See application file for complete search history.

(56) References Cited

U.S. PATENT DOCUMENTS 6,660,744 B1 * 12/2003 Hirst et al. ............... 514/262.1

FOREIGN PATENT DOCUMENTS

| WO | WO2005/004607 | * | 1/2005 |
|---|---|---|---|
| WO | WO 2005 004607 A1 | | 1/2005 |
| WO | WO 2005 028480 | | 3/2005 |

OTHER PUBLICATIONS

Dorwald F. A. Side Reactions in Organic Synthesis, 2005, Wiley: VCH, Weinheim p. IX of Preface.*
Ma, P., et al., "*c-MET* Mutational Analysis in Small Cell Lung Cancer: Novel Juxtamembrane Domain Mutations Regulating Cytoskeletal Functions," *Cancer Research*, 2003, 6272-6281, vol. 63.
Ma, P., et al., "c-MET: Structure, Functions and Potential for Therapeutic Inhibition," *Cancer and Metastasis Reviews*, 2003, 309-325, vol. 22.
Maulik, G., et al., "Role of the Hepatocyte Growth Factor Receptor, c-MET, in Oncogenesis and Potential for Therapeutic Inhibition," *Cytokine & Growth Factor Reviews*, 2002, 41-59, vol. 13.

* cited by examiner

*Primary Examiner*—James O Wilson
*Assistant Examiner*—Jeffrey H Murray
(74) *Attorney, Agent, or Firm*—Bryan C. Zielinski; Vincent P. Liptak

(57) ABSTRACT

The invention relates to compounds of the formula I

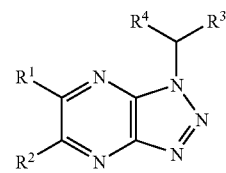

or a pharmaceutically acceptable salt thereof, wherein $R^1$, $R^2$, $R^3$ and $R^4$ are as defined herein. The invention also relates to pharmaceutical compositions containing the compounds of formula I and to methods of treating hyperproliferative disorders in a mammal by administering the compounds of formula I.

11 Claims, No Drawings

TRIAZOLOPYRAZINE DERIVATIVES

This application claims the benefit of U.S. Provisional Application No. 60/799,966 filed May 11, 2006, and U.S. Provisional Application No. 60/893,231 filed Mar. 6, 2007, the contents of which are hereby incorporated by reference in their entireties.

This invention relates to novel triazolopyrazine derivatives that are useful in the treatment of hyperproliferative diseases, such as cancers, in mammals. This invention also relates to a method of using such compounds in the treatment of hyperproliferative diseases in mammals, especially humans, and to pharmaceutical compositions containing such compounds.

BACKGROUND OF THE INVENTION

The hepatocyte growth factor (HGF) receptor (c-Met or HGFR) receptor tyrosine kinase (RTK) has been shown in many human cancers to be involved in oncogenesis, tumor progression with enhanced cell motility and invasion, as well as metastasis (see, e.g., Ma, P. C., Maulik, G., Christensen, J. & Salgia, R. (2003b). *Cancer Metastasis Rev,* 22, 309-25; Maulik, G., Shrikhande, A., Kijima, T., Ma, P. C., Morrison, P. T. & Salgia, R. (2002b). *Cytokine Growth Factor Rev,* 13, 41-59). c-Met (HGFR) can be activated through overexpression or mutations in various human cancers including small cell lung cancer (SCLC) (Ma, P. C., Kijima, T., Maulik, G., Fox, E. A., Sattler, M., Griffin, J. D., Johnson, B. E. & Salgia, R. (2003a). *Cancer Res,* 63, 6272-6281).

c-Met is a receptor tyrosine kinase that is encoded by the Met proto-oncogene and transduces the biological effects of hepatocyte growth factor (HGF), which is also referred to as scatter factor (SF). Jiang et al., *Crit. Rev. Oncol. Hematol.* 29: 209-248 (1999). c-Met and HGF are expressed in numerous tissues, although their expression is normally confined predominantly to cells of epithelial and mesenchymal origin, respectively. c-Met and HGF are required for normal mammalian development and have been shown to be important in cell migration, cell proliferation and survival, morphogenic differentiation, and organization of 3-dimensional tubular structures (e.g., renal tubular cells, gland formation, etc.). In addition to its effects on epithelial cells, HGF/SF has been reported to be an angiogenic factor, and c-Met signaling in endothelial cells can induce many of the cellular responses necessary for angiogenesis (proliferation, motility, invasion).

The c-Met receptor has been shown to be expressed in a number of human cancers. c-Met and its ligand, HGF, have also been shown to be co-expressed at elevated levels in a variety of human cancers (particularly sarcomas). However, because the receptor and ligand are usually expressed by different cell types, c-Met signaling is most commonly regulated by tumor-stroma (tumor-host) interactions. Furthermore, c-Met gene amplification, mutation, and rearrangement have been observed in a subset of human cancers. Families with germline mutations that activate c-Met kinase are prone to multiple kidney tumors as well as tumors in other tissues. Numerous studies have correlated the expression of c-Met and/or HGF/SF with the state of disease progression of different types of cancer (including lung, colon, breast, prostate, liver, pancreas, brain, kidney, ovaries, stomach, skin, and bone cancers). Furthermore, the overexpression of c-Met or HGF have been shown to correlate with poor prognosis and disease outcome in a number of major human cancers including lung, liver, gastric, and breast. c-Met has also been directly implicated in cancers without a successful treatment regimen such as pancreatic cancer, glioma, and hepatocellular carcinoma.

A family of novel compounds have been discovered which exhibit c-Met modulating ability and have an ameliorating effect against disorders related to abnormal c-Met activity. c-Met is an attractive target from a clinical perspective because: 1) c-Met has been implicated in the growth and metastases of most types of cancer; 2) growth at the secondary site appears to be the rate-limiting step in metastasis; and 3) by the time of diagnosis, R is likely that the disease has already spread.

These observations suggest that c-Met kinase inhibitors would be an effective treatment for primary tumors that are driven by c-Met, but more importantly, would prevent disseminated micrometastases from growing into life-threatening metastases. Therefore, the utility of a c-Met inhibitor extends to preventative and adjuvant therapy settings. In addition, certain cancers (e.g., papillary renal cell carcinoma, some gastric and lung cancers) can be treated which are believed to be driven by c-Met mutation/genetic alteration and dependent on c-Met for growth and survival. These cancers are expected to be sensitive to treatment. Furthermore, various human cancers are the primary target indication for c-Met antagonists. These cancers include major cancers such as breast, lung, colorectal, prostate; as well as pancreatic cancer, glioma, liver cancer, gastric cancer, head and neck cancers, melanoma, renal cancer, leukemias, myeloma, and sarcomas. c-Met has been directly implicated in cancers such as pancreatic cancer, glioma, and hepatocellular carcinoma.

Accordingly, c-Met (HGFR) inhibitors and methods of using such inhibitors for the treatment of abnormal cell growth, such as cancer represent a substantial unmet medical need in the treatment of these and possibly other cancers.

SUMMARY OF THE INVENTION

In one embodiment, the present invention relates to a compound of the formula I:

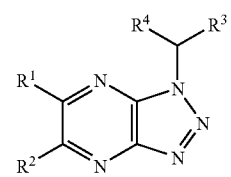

wherein:

$R^1$ and $R^2$ are independently selected from hydrogen, Br, Cl, F, —O(CH$_2$)$_n$CH$_3$, —NR$^{10}$C(O)OR$^{12}$, —(CR$^{12}$R$^{13}$)$_n$NR$^{10}$R$^{11}$, —O(CH$_2$)$_n$OR$^{10}$, —(CH$_2$)$_n$OR$^{10}$, —C(O)R$^{10}$, —C(O)OR$^{10}$, —C(O)NR$^{10}$R$^{11}$, —NR$^{10}$R$^{11}$, —S(O)$_2$R$^{10}$, —S(O)R$^{10}$, —S(O)$_2$NR$^{10}$R$^{11}$, —CF$_3$, —CF$_2$H, —NR$^{10}$C(O)NR$^{10}$R$^{11}$, —NR$^{10}$C(O)R$^{11}$, —NR$^{10}$S(O)$_2$R$^{11}$, —N(CH$_2$)$_n$(C$_3$-C$_8$ cycloalkyl), —CN, —NO$_2$, C$_1$-C$_6$ alkyl, C$_3$-C$_8$ cycloalkyl, 3-8 membered heteroalicyclic, 3-8 membered heteroalicyclic-(3-8 membered heteroalicyclic), 8-10 membered heterobicyclic, 5-7 membered heteroaryl, C$_6$-C$_{10}$ aryl, C$_2$-C$_6$ alkenyl, and C$_2$-C$_6$ alkynyl wherein C$_1$-C$_6$ alkyl, C$_3$-C$_8$ cycloalkyl, 3-8 membered heteroalicyclic, 8-10 membered heterobicyclic, 5-7 membered heteroaryl, C$_6$-C$_{10}$ aryl, C$_2$-C$_6$ alkenyl, and C$_2$-C$_6$ alkynyl are optionally substituted by one or more moieties selected from the group consisting of Br, Cl, F, —(CH$_2$)$_n$CH(OR$^{10}$)CH$_3$, —(CH$_2$)$_n$OR$^{10}$, —(CH$_2$)$_n$C(CH$_3$)$_2$OR$^{10}$, —C(O)R$^{10}$, —C(O)OR$^{10}$, —(CR$^{10}$R$^{11}$)$_n$C(O)OR$^{10}$—C(O)NR$^{10}$R$^{11}$, —(CR$^{10}$R$^{11}$)$_n$C(O)NR$^{10}$R$^{11}$, —(CH$_2$)$_n$NR$^{10}$R$^{11}$, —S(O)$_2$R$^{10}$—S(O)R$^{10}$, —S(O)$_2$NR$^{10}$R$^{11}$, —CF$_3$, —CF$_2$H, —(CH$_2$)$_n$NR$^{10}$C(O)NR$^{10}$R$^{11}$, —(CH$_2$)$_n$NR$^{10}$C(O)OR$^{11}$, —NR$^{10}$C(O)R$^{11}$, —NR$^{10}$C(O)OR$^{11}$, —NR$^{10}$S(O)$_2$R$^{11}$, —CN, —NO$_2$, oxo, C$_1$-C$_6$ alkyl, C$_3$-C$_8$ cycloalkyl, —(CH$_2$)$_n$(3-8 membered heteroalicyclic), —(CH$_2$)$_n$(5-7 membered heteroaryl), —(CH$_2$)$_n$(C$_6$-C$_{10}$ aryl), C$_2$-C$_6$ alkenyl, and C$_2$-C$_6$ alkynyl;

R$^3$ is a moiety of the formula:

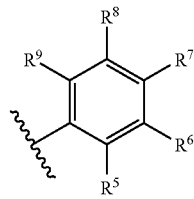

wherein R$^5$, R$^6$, R$^7$, R$^8$ and R$^9$ are independently selected from hydrogen, Br, Cl, F, —(CH$_2$)$_n$OR$^{10}$, —C(O)R$^{10}$, —C(O)OR$^{10}$, —C(O)NR$^{10}$R$^{11}$, —NR$^{10}$R$^{11}$, —S(O)$_2$R$^{10}$—S(O)R$^{10}$—S(O)$_2$NR$^{10}$R$^{11}$, —CF$_3$, —CF$_2$H, —NR$^{10}$C(O)NR$^{10}$R$^{11}$, —NR$^{10}$C(O)R$^{11}$, —NR$^{10}$SO$_2$R$^{11}$, —CN, —NO$_2$, C$_1$-C$_6$ alkyl, C$_3$-C$_8$ cycloalkyl, 3-8 membered heteroalicyclic, 8-10 membered heterobicyclic, 5-7 membered heteroaryl, C$_6$-C$_{10}$ aryl, C$_2$-C$_6$ alkenyl, and C$_2$-C$_6$ alkynyl wherein C$_1$-C$_6$ alkyl, C$_3$-C$_8$ cycloalkyl, 3-8 membered heteroalicyclic, 8-10 membered heterobicyclic, 5-7 membered heteroaryl, C$_6$-C$_{10}$ aryl, C$_2$-C$_6$ alkenyl, and C$_2$-C$_6$ alkynyl are optionally substituted by one or more moieties selected from the group consisting of Br, Cl, F, —(CH$_2$)$_n$OR$^{10}$, —C(O)R$^1$, —C(O)OR$^{10}$, —C(O)NR$^{10}$R$^{11}$, —NR$^{10}$R$^{11}$, —S(O)$_2$R$^{11}$, —S(O)R$^{10}$, —S(O)$_2$NR$^{10}$R$^{11}$, —CF$_3$, —CF$_2$H, —NR$^{10}$C(O)NR$^{10}$R$^{11}$, —NR$^{10}$C(O)R$^{11}$, —NR$^{10}$S(O)$_2$R$^{11}$—CN, —NO$_2$, oxo, C$_1$-C$_6$ alkyl, C$_3$-C$_8$ cycloalkyl, C$_3$-C$_8$ heteroalicyclic, 5-7 membered heteroaryl, C$_6$-C$_{10}$ aryl, C$_2$-C$_6$ alkenyl, and C$_2$-C$_6$ alkynyl;

with the proviso that one of R$^7$ and R$^8$, or R$^8$ and R$^9$ combine to form a ring selected from saturated C$_4$-C$_8$ cycloalkyl, unsaturated C$_5$-C$_8$ cycloalkyl, 3-8 membered heteroalicyclic, 5-7 membered heteroaryl and C$_6$-C$_{10}$ aryl, wherein said ring is optionally substituted by one or more moieties selected from the group consisting of Br, Cl, F, —(CH$_2$)$_n$OR$^{10}$, —C(O)R$^{10}$, —C(O)OR$^{10}$, —C(O)NR$^{10}$R$^{11}$, —NR$^{10}$R$^{11}$, —S(O)$_2$R$^1$, —S(O)R$^1$, —S(O)$_2$NR$^{10}$R$^{11}$, —CF$_3$, —CF$_2$H, —NR$^{10}$C(O)NR$^{10}$R$^{11}$, —NR$^{10}$C(O)R$^{11}$—NR$^{10}$S(O)$_2$R$^{11}$, —CN, —NO$_2$, oxo, C$_1$-C$_6$ alkyl, C$_3$-C$_8$ cycloalkyl, C$_3$-C$_8$ heteroalicyclic, 5-7 membered heteroaryl, C$_6$-C$_{10}$ aryl, C$_2$-C$_6$ alkenyl, and C$_2$-C$_6$ alkynyl;

R$^{10}$ and R$^{11}$ are independently selected from H, —(CH$_2$)$_n$OR$^{12}$, —(CH$_2$)$_n$C(CH$_3$)$_2$OR$^{12}$, —CHR$^{12}$(CH$_2$)$_n$OR$^{13}$, —C(O)OR$^{12}$, —(CH$_2$)$_n$CHR$^{12}$OR$^{13}$, —C(CH$_3$)$_2$(CH$_2$)$_n$OR$^{12}$, —CH$_2$CF$_2$H, —(CH$_2$)$_n$C(CH$_3$)$_2$NR$^{12}$R$^{13}$, —(CH$_2$)$_n$NR$^{12}$R$^{13}$, —(CH$_2$)CHOR$^{12}$(CH$_2$)OR$^{13}$, —(CH$_2$)$_n$(NR$^{12}$R$^{13}$)C(O)NR$^{12}$R$^{13}$, —(CH$_2$)$_n$S(O)$_2$R$^{12}$, —(CH$_2$)$_n$C(O)NR$^{12}$R$^{13}$, —NR$^{12}$(CH$_2$)$_n$(5-7 membered heteroaryl), —NR$^{12}$(CH$_2$)$_n$(3-8 membered heterocycle), —(CH$_2$)$_n$(8-10 membered heterobicyclic), —(CH$_2$)$_n$(3-8 membered heteroalicyclic), C$_1$-C$_6$ alkyl, C$_3$-C$_8$ cycloalkyl, C$_6$-C$_{10}$ aryl, C$_2$-C$_6$ alkenyl and C$_2$-C$_6$ alkynyl, wherein said 5-7 membered heteroaryl, 3-8 membered heterocycle and 8-10 membered heterobicyclic are optionally substituted by one or more moieties selected from the group consisting of —(CH$_2$)$_n$OR$^{12}$, C$_1$-C$_6$ alkyl, C$_3$-C$_8$ cycloalkyl, C$_6$-C$_{10}$ aryl, C$_2$-C$_6$ alkenyl, 3-8 membered heteroalicyclic and C$_2$-C$_6$ alkynyl; or when R$^{10}$ and R$^{11}$ are attached to the same atom, R$^{10}$ and R$^{11}$ optionally combine to form a 3-8 membered heteroalicyclic ring;

R$^{12}$ and R$^{13}$ are independently selected from H, C$_1$-C$_6$ alkyl, —C(O)CH$_3$, C$_3$-C$_8$ cycloalkyl, C$_6$-C$_{10}$ aryl, C$_2$-C$_6$ alkenyl, 5-7 membered heteroaryl and C$_2$-C$_6$ alkynyl, wherein said 5-7 membered heteroaryl is optionally substituted by one or more moieties selected from the group consisting of C$_1$-C$_6$ alkyl, C$_3$-C$_8$ cycloalkyl, C$_6$-C$_{10}$ aryl, C$_2$-C$_6$ alkenyl, and C$_2$-C$_6$ alkynyl; or when R$^{12}$ and R$^{13}$ are attached to the same atom, R$^{12}$ and R$^{13}$ optionally combine to form a 3-8 membered heteroalicyclic ring;

R$^4$ is selected from the group consisting of hydrogen, F, C$_1$-C$_6$ alkyl and aryl; and each n is independently 0, 1, 2, 3 or 4;

or a pharmaceutically acceptable salt thereof.

The present invention contemplates each of the following embodiments separately or in connection with any other embodiment described herein except where an inconsistency in describing the present invention might occur. Based on the present disclosure the person having ordinary skill in the art will readily appreciate what such inconsistencies might be.

In another embodiment, R$^1$ and R$^2$ are independently selected from hydrogen, Br, —OR$^{10}$, —O(CH$_2$)$_n$CH$_3$, —OCH$_2$(CH$_2$)$_n$OR$^{10}$, —C(O)NR$^{10}$R$^{11}$, —NR$^{10}$R$^{11}$, C$_1$-C$_6$ alkyl, 3-8 membered heteroalicyclic, 3-8 membered heteroalicyclic-(3-8 membered heteroalicyclic), 8-10 membered heterobicyclic, 5-7 membered heteroaryl, C$_6$-C$_{10}$ aryl and C$_2$-C$_6$ alkenyl, wherein C$_1$-C$_6$ alkyl, 3-8 membered heteroalicyclic, 3-8 membered heteroalicyclic-(3-8 membered heteroalicyclic), 8-10 membered heterobicyclic, 5-7 membered heteroaryl, C$_6$-C$_{10}$ aryl and C$_2$-C$_6$ alkenyl are optionally substituted by one or more moieties selected from the group consisting of Br, Cl, F, —(CH$_2$)$_n$CH(OR$^{10}$)CH$_3$, —(CH$_2$)$_n$OR$^{10}$—(CH$_2$)$_n$C(CH$_3$)$_2$OR$^{10}$—(CH$_2$)$_n$(3-8 membered heteroalicyclic), —C(O)R$^{10}$, —C(O)OR$^{10}$, —(CR$^{10}$R$^{11}$)$_n$C(O)OR$^{10}$—C(O)NR$^{10}$R$^{11}$, —(CR$^{10}$R$^{11}$)$_n$C(O)NR$^{10}$R$^{11}$, —(CH$_2$)$_n$NR$^{10}$R$^{11}$, —S(O)$_2$R$^{10}$, —S(O)R$^{10}$, —S(O)$_2$NR$^{10}$R$^{11}$, —CF$_3$, —CF$_2$H, —(CH$_2$)$_n$NR$^{10}$C(O)NR$^{10}$R$^{11}$, —(CH$_2$)$_n$NR$^{10}$C(O)OR$^{11}$, —NR$^{10}$C(O)R$^{11}$, —NR$^{10}$C(O)OR$^{11}$, —NR$^{10}$S(O)$_2$R$^{11}$, —CN, —NO$_2$, oxo, C$_1$-C$_6$ alkyl, C$_3$-C$_8$ cycloalkyl, —(CH$_2$)$_n$(3-8 membered heteroalicyclic), —(CH$_2$)$_n$(5-7 membered heteroaryl), —(CH$_2$)$_n$(C$_6$-C$_{10}$ aryl), C$_2$-C$_6$ alkenyl, and C$_2$-C$_6$ alkynyl.

In another embodiment, R$^1$ and R$^2$ are independently selected from —OR$^{10}$, —O(CH$_2$)$_n$CH$_3$, —NR$^{10}$C(O)OR$^{12}$—(CR$^{12}$R$^{13}$)NR$^{10}$R$^{11}$, —OCH$_2$(CH$_2$)$_n$OR$^{10}$, —C(O)NR$^{10}$R$^{11}$, —NR$^{10}$R$^{11}$, C$_1$-C$_6$ alkyl, 3-8 membered heteroalicyclic, 3-8 membered heteroalicyclic-(3-8 membered heteroalicyclic), 8-10 membered heterobicyclic, 5-7 membered heteroaryl, C$_6$-C$_{10}$ aryl and C$_2$-C$_6$ alkenyl, wherein C$_1$-C$_6$ alkyl, 3-8 membered heteroalicyclic, 3-8 membered heteroalicyclic-(3-8 membered heteroalicyclic), 8-10 membered heterobicyclic, 5-7 membered heteroaryl, C$_6$-C$_{10}$ aryl and C$_2$-C$_6$ alkenyl are optionally substituted by one or more moieties selected from the group consisting of Br, Cl, F, —(CH$_2$)$_n$CH(OR$^{10}$)CH$_3$, —(CH$_2$)$_n$OR$^{10}$, —(CH$_2$)$_n$C(CH$_3$)$_2$OR$^{10}$, —(CH$_2$)$_n$(3-8 membered heteroalicyclic), —C(O)R$^{10}$, —C(O)OR$^{10}$, —(CR$^{10}$R$^{11}$)$_n$C(O)OR$^{10}$, —C(O)NR$^{10}$R$^{11}$, —(CR$^{10}$R$^{11}$)$_n$C(O)NR$^{10}$R$^{11}$, —(CH$_2$)$_n$NR$^{10}$R$^{11}$, —S(O)$_2$R$^{10}$, —S(O)R$^{10}$, —S(O)$_2$NR$^{10}$R$^{11}$, —CF$_3$, CF$_2$H, —(CH$_2$)$_n$NR$^{10}$C(O)NR$^{10}$R$^{11}$, —(CH$_2$)$_n$NR$^{10}$C(O)OR$^{11}$, —NR$^{10}$C(O)R$^{11}$, —NR$^{10}$C(O)OR$^{11}$, —NR$^{10}$S(O)$_2$R$^{11}$, —CN, —NO$_2$, oxo, C$_1$-C$_6$ alkyl, C$_3$-C$_8$ cycloalkyl, —(CH$_2$)$_n$(3-8 membered heteroalicyclic), —(CH$_2$)$_n$(5-7 membered heteroaryl), —(CH$_2$)$_n$(C$_6$-C$_{10}$ aryl), C$_2$-C$_6$ alkenyl, and C$_2$-C$_6$ alkynyl.

In another embodiment, $R^1$ is selected from Br, —$OR^{10}$, —$O(CH_2)_nCH_3$, —$NR^{10}C(O)OR^{12}$, —$(CR^{12}R^{13})_nNR^{10}R^{11}$, —$OCH_2(CH_2)_nOR^{10}$, —$C(O)NR^{10}R^{11}$, —$NR^{10}R^{11}$, $C_1$-$C_6$ alkyl, 3-8 membered heteroalicyclic, 3-8 membered heteroalicyclic-(3-8 membered heteroalicyclic), 8-10 membered heterobicyclic, 5-7 membered heteroaryl, $C_6$-$C_{10}$ aryl and $C_2$-$C_6$ alkenyl, wherein $C_1$-$C_6$ alkyl, 3-8 membered heteroalicyclic, 3-8 membered heteroalicyclic-(3-8 membered heteroalicyclic), 8-10 membered heterobicyclic, 5-7 membered heteroaryl, $C_6$-$C_{10}$ aryl and $C_2$-$C_6$ alkenyl are optionally substituted by one or more moieties selected from the group consisting of Br, Cl, F, —$(CH_2)_nCH(OR^{10})CH_3$, —$(CH_2)_nOR^{10}$, —$(CH_2)_nC(CH_3)_2OR^{10}$, —$(CH_2)_n$(3-8 membered heteroalicyclic), —$C(O)R^{10}$, —$C(O)OR^{10}$, —$(CR^{10}R^{11})_nC(O)OR^{10}$, —$C(O)NR^{10}R^{11}$, —$(CR^{10}R^{11})_nC(O)NR^{10}R^{11}$, —$(CH_2)_nNR^{10}R^{11}$, —$S(O)_2R^{10}$—$S(O)R^{10}$—$S(O)_2NR^{10}R^{11}$, —$CF_3$, —$CF_2H$, —$(CH_2)_nNR^{10}C(O)NR^{10}R^{11}$, —$(CH_2)_nNR^{10}C(O)OR^{11}$, —$NR^{10}C(O)R^{11}$, —$NR^{10}C(O)OR^{11}$, —$NR^{10}S(O)_2R^{11}$, —CN, —$NO_2$, oxo, $C_1$-$C_6$ alkyl, $C_3$-$C_8$ cycloalkyl, —$(CH_2)_n$(3-8 membered heteroalicyclic), —$(CH_2)_n$(5-7 membered heteroaryl), —$(CH_2)_n$($C_6$-$C_{10}$ aryl), $C_2$-$C_6$ alkenyl, and $C_2$-$C_6$ alkynyl.

In another embodiment, $R^1$ is a 5-7 membered heteroaryl optionally substituted by one or more moieties selected from the group consisting of Br, Cl, F, —$(CH_2)_nCH(OR^{10})CH_3$, —$(CH_2)_nOR^{10}$, —$(CH_2)_nC(CH_3)_2OR^{10}$, —$(CH_2)_n$(3-8 membered heteroalicyclic), —$C(O)R^{10}$, —$C(O)OR^{10}$, —$(CR^{10}R^{11})_nC(O)OR^{10}$, —$C(O)NR^{10}R^{11}$, —$(CR^{10}R^{11})_nC(O)NR^{10}R^{11}$, —$(CH_2)_nNR^{10}R^{11}$, —$S(O)_2R^{10}$—$S(O)R^{10}$—$S(O)_2NR^{10}R^{11}$, —$CF_3$, $CF_2H$, —$(CH_2)_nNR^{10}C(O)NR^{10}R^{11}$, —$(CH_2)_nNR^{10}C(O)OR^{11}$, —$NR^{10}C(O)R^{11}$, —$NR^{10}C(O)OR^{11}$, —$NR^{10}S(O)_2R^{11}$, —CN, —$NO_2$, oxo, $C_1$-$C_6$ alkyl, $C_3$-$C_8$ cycloalkyl, —$(CH_2)_n$(3-8 membered heteroalicyclic), —$(CH_2)_n$(5-7 membered heteroaryl), —$(CH_2)_n$($C_6$-$C_{10}$ aryl), $C_2$-$C_6$ alkenyl, and $C_2$-$C_6$ alkynyl.

In another embodiment, $R^7$ and $R^8$ combine to form a ring selected from saturated $C_4$-$C_8$ cycloalkyl, unsaturated $C_5$-$C_8$ cycloalkyl, 3-8 membered heteroalicyclic, 5-7 membered heteroaryl and $C_6$-$C_{10}$ aryl, wherein said ring is optionally substituted by one or more moieties selected from the group consisting of Br, Cl, F, —$(CH_2)_nOR^{10}$—$C(O)R^{10}$, —$C(O)OR^{10}$, —$C(O)NR^{10}R^{11}$, —$NR^{10}R^{11}$, —$S(O)_2R^{10}$—$S(O)R^{10}$, —$S(O)_2NR^{10}R^{11}$, —$CF_3$, —$CF_2H$, —$NR^{10}C(O)NR^{10}R^{11}$, —$NR^{10}C(O)R^{11}$, —$NR^{10}S(O)_2R^{11}$, —CN, —$NO_2$, oxo, $C_1$-$C_6$ alkyl, $C_3$-$C_8$ cycloalkyl, $C_3$-$C_8$ heteroalicyclic, 5-7 membered heteroaryl, $C_6$-$C_{10}$ aryl, $C_2$-$C_6$ alkenyl, and $C_2$-$C_6$ alkynyl.

In a further embodiment, $R^9$ is H. In a further embodiment, at least one of $R^1$ and $R^2$ is not hydrogen. In another embodiment, $R^2$ is H. In another embodiment, $R^4$ is H. In another embodiment, $R^4$ is $C_1$-$C_6$ alkyl. In another embodiment, $R^4$ is methyl. In another embodiment, $R^5$ and $R^6$ are H.

In another embodiment, $R^3$ is selected from

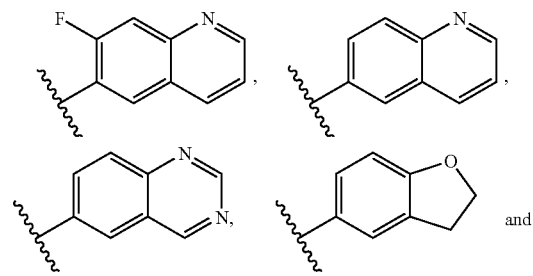

-continued

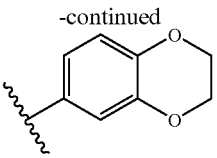

In another embodiment. $R^3$ is selected from

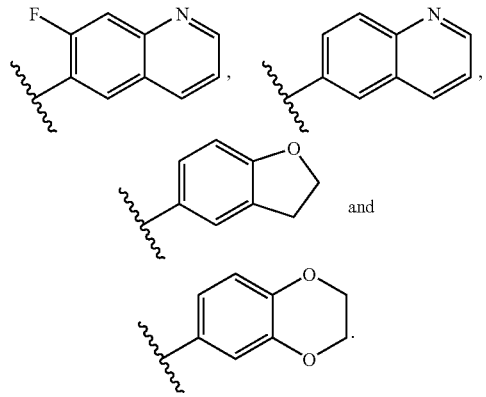

In another embodiment, $R^3$ is

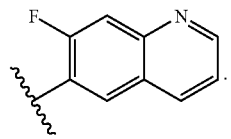

In another embodiment, $R^3$ is

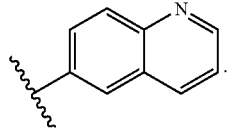

In another embodiment, $R^3$ is

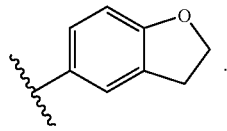

In another embodiment, the present invention relates to a compound selected from 6-((6-(1-methyl-1H-pyrazol-4-yl)-1H-[1,2,3]triazolo[4,5-b]pyrazin-1-yl)methyl)quinoline, N-(piperidin-4-yl)-4-(3-(quinolin-6-ylmethyl)-3H-[1,2,3]triazolo[4,5-b]pyrazin-5-yl)benzamide, N-(2-aminoethyl)-4-(3-(quinolin-6-ylmethyl)-3H-[1,2,3]triazolo[4,5-b]pyrazin-5-yl)benzamide, N-(2-(dimethylamino)ethyl)-4-(3-(quinolin-6-ylmethyl)-3H-[1,2,3]triazolo[4,5-b]pyrazin-5-yl)benzamide, 6-((6-(4-methyl-1H-imidazol-1-yl)-1H-[1,2,3]triazolo[4,5-b]pyrazin-1-yl)methyl)quinoline, N-methyl- 4-(3-(quinolin-6-ylmethyl)-3H-[1,2,3]triazolo[4,5-b]pyrazin-5-yl)benzamide, 6-((6-(3-methoxyphenyl)-1H-[1,2,3]triazolo[4,5-b]pyrazin-1-yl)methyl)quinoline, 6-((6-(4-methoxyphenyl)-1H-[1,2,3]triazolo[4,5-b]pyrazin-1-yl)methyl)quinoline, 6-((6-(1H-pyrazol-4-yl)-1H-[1,2,3]triazolo[4,5-b]pyrazin-1-yl)methyl)quinoline, (R)-1-(3-(quinolin-6-ylmethyl)-3H-[1,2,3]triazolo[4,5-b]pyrazin-5-yl)pyrrolidin-3-amine, (4-(3-(quinolin-6-ylmethyl)-3H-[1,2,3]triazolo[4,5-b]pyrazin-5-yl)phenyl)methanol, (4-(3-(quinolin-6-ylmethyl)-3H-[1,2,3]triazolo[4,5-b]pyrazin-5-yl)phenyl)methanamine, 6-[6-(1-ethoxy-vinyl)-[1,2,3]triazolo[4,5-b]pyrazin-1-ylmethyl]-quinoline, 2-[4-(3-quinolin-6-ylmethyl-3H-[1,2,3]triazolo[4,5-b]pyrazin-5-yl)-pyrazol-1-yl]-ethanol, 6-[6-(2-methyl-5-trifluoromethyl-2H-pyrazol-3-yl)-[1,2,3]triazolo[4,5-b]pyrazin-1-ylmethyl]-quinoline, and 6-[6-(2H-Pyrazol-3-yl)-[1,2,3]triazolo[4,5-b]pyrazin-1-ylmethyl]-quinoline, or a pharmaceutically acceptable salt thereof.

In another embodiment, the present invention relates to a compound selected from [4-(3-Quinolin-6-ylmethyl-3H-[1,2,3]triazolo[4,5-b]pyrazin-5-yl)-pyrazol-1-yl]-acetic acid, 6-[(S)-1-(6-Bromo-[1,2,3]triazolo[4,5-b]pyrazin-1-yl)-ethyl]-quinoline, 6-[(R)-1-(6-Bromo-[1,2,3]triazolo[4,5-b]pyrazin-1-yl)-ethyl]-quinoline, 6-{1-[6-(1-Methyl-1H-pyrazol-4-yl)-[1,2,3]triazolo[4,5-b]pyrazin-1-yl]-ethyl}-quinoline, 6-{(S)-1-[6-(1-Methyl-1H-pyrazol-4-yl)-[1,2,3]triazolo[4,5-b]pyrazin-1-yl]-ethyl}-quinoline, 6-{(R)-1-[6-(1-Methyl-1H-pyrazol-4-yl)-[1,2,3]triazolo[4,5-b]pyrazin-1-yl]-ethyl}-quinoline, 2-{4-[3-(1-Quinolin-6-yl-ethyl)-3H-[1,2,3]triazolo[4,5-b]pyrazin-5-yl)-pyrazol-1-yl}-ethanol, 2-{4-[3-((S)-1-Quinolin-6-yl-ethyl)-3H-[1,2,3]triazolo[4,5-b]pyrazin-5-yl)-pyrazol-1-yl}-ethanol, 2-{4-[3-((R)-1-Quinolin-6-yl-ethyl)-3H-[1,2,3]-triazolo[4,5-b]pyrazin-5-yl]-pyrazol-1-yl}-ethanol, 2-[4-(3-Quinazolin-6-ylmethyl-3H-[1,2,3]triazolo[4,5-b]pyrazin-5-yl)-pyrazol-1-yl]-ethanol, and 6-[6-(1-Methyl-1H-pyrazol-4-yl)-[1,2,3]triazolo[4,5-b]pyrazin-1-ylmethyl]-quinazoline.

In a further embodiment, the present invention relates to a compound selected from any 10 compounds exemplified in Tables 3, 4 and 5.

In a further embodiment, the present invention relates to any one compound exemplified in Tables 3, 4 and 5.

In another embodiment, the present invention provides a crystalline form of the free base of 2-[4-(3-Quinolin-6-ylmethyl-3H-[1,2,3]triazolo[4,5-b]pyrazin-5-yl)-pyrazol-1-yl]-ethanol. In a particular embodiment, the crystalline form of the free base of 2-[4-(3-Quinolin-6-ylmethyl-3H-[1,2,3]triazolo[4,5-b]pyrazin-5-yl)-pyrazol-1-yl]-ethanol is anhydrous. In another embodiment, the crystalline form of the free base of 2-[4-(3-Quinolin-6-ylmethyl-3H-[1,2,3]triazolo[4,5-b]pyrazin-5-yl)-pyrazol-1-yl]-ethanol is a hydrate.

In a further aspect the crystalline form is a polymorph form 1 of the free base of 2-[4-(3-Quinolin-6-ylmethyl-3H-[1,2,3]triazolo[4,5-b]pyrazin-5-yl)-pyrazol-1-yl]-ethanol. In a further aspect, the crystalline form of 2-[4-(3-Quinolin-6-ylmethyl-3H-[1,2,3]triazolo[4,5-b]pyrazin-5-yl)-pyrazol-1-yl]-ethanol has a powder X-ray diffraction pattern comprising a peak at diffraction angle ($2\theta$) of 5.8±0.1. In a further aspect, the crystalline form of 2-[4-(3-Quinolin-6-ylmethyl-3H-[1,2,3]triazolo[4,5-b]pyrazin-5-yl)-pyrazol-1-yl]-ethanol has a powder X-ray diffraction pattern comprising peaks at diffraction angles ($2\theta$) of 5.8±0.1 and 15.5±0.1. In a further aspect, the crystalline form of 2-[4-(3-Quinolin-6-ylmethyl-3H-[1,2,3]triazolo[4,5-b]pyrazin-5-yl)-pyrazol-1-yl]-ethanol has a powder X-ray diffraction pattern comprising peaks at diffraction angles ($2\theta$) of 5.8±0.1, 15.5±0.1, and 16.2±0.1. In a further aspect, the crystalline form of 2-[4-(3-Quinolin-6-ylmethyl-3H-[1,2,3]triazolo[4,5-b]pyrazin-5-yl)-pyrazol-1-yl]-ethanol has a powder X-ray diffraction pattern comprising peaks at diffraction angles ($2\theta$) of 5.8±0.1, 13.6±0.1, 15.5±0.1, and 16.2±0.1. In a further aspect the crystalline form of 2-[4-(3-Quinolin-6-ylmethyl-3H-[1,2,3]triazolo[4,5-b]pyrazin-5-yl)-pyrazol-1-yl]-ethanol has a powder X-ray diffraction pattern comprising peaks at diffraction angles ($2\theta$) of 5.8±0.1, 11.6 0.1, 13.6±0.1, 15.5±0.1, and 16.2±0.1. In a further aspect the crystalline form of 2-[4-(3-Quinolin-6-ylmethyl-3H-[1,2,3]triazolo[4,5-b]pyrazin-5-yl)-pyrazol-1-yl]-ethanol has a powder X-ray diffraction pattern comprising peaks at diffraction angles ($2\theta$) of 5.8±0.1, 11.6±0.1, 13.6±0.1, 15.5±0.1, 16.2±0.1, and 23.4±0.1. In a further aspect the crystalline form of 2-[4-(3-Quinolin-6-ylmethyl-3H-[1,2,3]triazolo[4,5-b]pyrazin-5-yl)-pyrazol-1-yl]-ethanol has a powder X-ray diffraction pattern comprising peaks at diffraction angles ($2\theta$) of 5.8±0.1, 11.6±0.1, 13.6±0.1, 15.5±0.1, 16.2±0.1, 23.4±0.1, and 27.6±0.1.

In another embodiment, the present invention provides a crystalline form of the mesylate salt of 2-[4-(3-Quinolin-6-ylmethyl-3H-[1,2,3]triazolo[4,5-b]pyrazin-5-yl)-pyrazol-1-yl]-ethanol. In a particular embodiment, the crystalline form of the mesylate salt of 2-[4-(3-Quinolin-6-ylmethyl-3H-[1,2,3]triazolo[4,5-b]pyrazin-5-yl)-pyrazol-1-yl]-ethanol is anhydrous. In another embodiment, the crystalline form of the mesylate salt of 2-[4-(3-Quinolin-6-ylmethyl-3H-[1,2,3]triazolo[4,5-b]pyrazin-5-yl)-pyrazol-1-yl]-ethanol is a hydrate.

In a further aspect the crystalline form is a polymorph form 1 of the mesylate salt of 2-[4-(3-Quinolin-6-ylmethyl-3H-[1,2,3]triazolo[4,5-b]pyrazin-5-yl)-pyrazol-1-yl]-ethanol. In a further aspect, the crystalline form of the mesylate salt of 2-[4-(3-Quinolin-6-ylmethyl-3H-[1,2,3]triazolo[4,5-b]pyrazin-5-yl)-pyrazol-1-yl]-ethanol has a powder X-ray diffraction pattern comprising a peak at diffraction angle ($2\theta$) of 18.3±0.1. In a further aspect, the crystalline form of the mesylate salt of 2-[4-(3-Quinolin-6-ylmethyl-3H-[1,2,3]triazolo[4,5-b]pyrazin-5-yl)-pyrazol-1-yl]-ethanol has a powder X-ray diffraction pattern comprising peaks at diffraction angles ($2\theta$) of 18.3±0.1 and 19.3±0.1. In a further aspect, the crystalline form of the mesylate salt of 2-[4-(3-Quinolin-6-ylmethyl-3H-[1,2,3]triazolo[4,5-b]pyrazin-5-yl)-pyrazol-1-yl]-ethanol has a powder X-ray diffraction pattern comprising peaks at diffraction angles ($2\theta$) of 12.3±0.1, 18.3±0.1 and 19.3±0.1. In a further aspect, the crystalline form of the mesylate salt of 2-[4-(3-Quinolin-6-ylmethyl-3H-[1,2,3]triazolo[4,5-b]pyrazin-5-yl)-pyrazol-1-yl]-ethanol has a powder X-ray diffraction pattern comprising peaks at diffraction angles ($2\theta$) of 12.3±0.1, 14.8±0.1, 18.3±0.1 and 19.3±0.1. In a further aspect the crystalline form of the mesylate salt of 2-[4-(3-Quinolin-6-ylmethyl-3H-[1,2,3]triazolo[4,5-b]pyrazin-5-yl)-pyrazol-1-yl]-ethanol has a powder X-ray diffraction pattern comprising peaks at diffraction angles ($2\theta$) of 12.3±0.1, 14.8±0.1, 18.3±0.1, 19.3±0.1 and 23.1±0.1. In a further aspect the crystalline form of the mesylate salt of 2-[4-(3-Quinolin-6-ylmethyl-3H-[1,2,3]triazolo[4,5-b]pyrazin-5-yl)-pyrazol-1-yl]-ethanol has a powder X-ray diffraction pattern comprising peaks at diffraction angles ($2\theta$) of 12.3±0.1, 14.8±0.1, 18.3±0.1, 19.3±0.1, 23.1±0.1, and 24.9±0.1. In a further aspect the crystalline form of the mesylate salt of 2-[4-(3-Quinolin-6-ylmethyl-3H-[1,2,3]triazolo[4,5-b]pyrazin-5-yl)-pyrazol-1-yl]-ethanol has a powder X-ray diffraction pattern comprising peaks at diffraction angles ($2\theta$) of 12.3±0.1, 14.8±0.1, 17.7±0.1, 18.3±0.1, 19.3±0.1, 23.1±0.1, and 24.9±0.1.

In a further aspect, the invention relates to pharmaceutical composition comprising a compound of the formula (I) or a pharmaceutically acceptable salt thereof, and a pharmaceutically acceptable excipient.

In a further aspect, the invention relates to the use of a compound of the formula (I) or a pharmaceutically acceptable salt thereof, for the manufacture of a medicament to treat a c-Met related disorder in a mammal.

In a further aspect, the invention relates to the use of a compound of the formula (I) or a pharmaceutically acceptable salt thereof, for the manufacture of medicament for the treatment of cancer in a mammal.

In a further aspect, the invention relates to the use, wherein the cancer is selected from breast cancer, lung cancer, colorectal cancer, prostate cancer, pancreatic cancer, glioma, liver cancer, gastric cancer, head cancer, neck cancer, melanoma, renal cancer, leukemia, myeloma, and sarcoma.

In a further aspect, the invention relates to a method of treating a mammal having a c-Met related disorder, comprising administering to the mammal a therapeutically effective amount of a compound of the formula (I) or with a pharmaceutically acceptable salt thereof.

In a further aspect, the invention relates to a method of treating a mammal having cancer, comprising administering to the mammal a therapeutically effective amount of a compound of the formula (I) or with a pharmaceutically acceptable salt thereof.

In a further aspect, the invention relates to a method of treating cancer where the cancer is selected from breast cancer, lung cancer, colorectal cancer, prostate cancer, pancreatic cancer, glioma, liver cancer, gastric cancer, head cancer, neck cancer, melanoma, renal cancer, leukemia, myeloma, and sarcoma. In a further embodiment the mammal is a human. In a further embodiment the mammal is a canine.

DEFINITIONS

"Pharmaceutically acceptable salt" refers to those salts, which retain the biological effectiveness and properties of the parent compound. Such salts include:

acid addition salt which is obtained by reaction of the free base of the parent compound with inorganic acids such as hydrochloric acid, hydrobromic acid, hydroiodic acid, nitric acid, phosphoric acid, sulfuric acid, and perchloric acid and the like, or with organic acids such as acetic acid, oxalic acid, (D) or (L) malic acid, maleic acid, methanesulfonic acid, ethanesulfonic acid, p-toluenesulfonic acid, salicylic acid, tartaric acid, benzenesulfonic acid (besylate), benzoic acid, camphorsulfonic acid, citric acid, fumaric acid, gluconic acid, glutamic acid, isethionic acid, lactic acid, maleic acid, malic acid, mandelic acid, mucic acid, pamoic acid, pantothenic acid, succinic acid, tartaric acid, or malonic acid and the like, preferably hydrochloric acid or (L)-malic acid; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

"Pharmaceutically acceptable excipient" or "excipient" refers to an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils, polyethylene glycols, diluents, granulating agents, lubricants, binders, disintegrating agents, and the like.

A "pharmaceutical composition" refers to a mixture of one or more of the compounds described herein, or physiologically acceptable salts thereof, with other chemical components, such as physiologically acceptable carriers and excipients. The purpose of a pharmaceutical composition is to facilitate administration of a compound to an organism.

As used herein, a "physiologically acceptable carrier" refers to a carrier or diluent that does not cause significant irritation to an organism and does not abrogate the biological activity and properties of the administered compound.

The term "method" refers to manners, means, techniques and procedures for accomplishing a given task including, but not limited to, those manners, means, techniques and procedures either known to, or readily developed from known manners, means, techniques and procedures by, practitioners of the chemical, pharmaceutical, biological, biochemical and medical arts.

As used herein, the term "modulation" or "modulating" refers to the alteration of the catalytic activity of c-Met. In particular, modulating refers to the activation of the catalytic activity of c-Met, preferably the activation or inhibition of the catalytic activity of c-Met, depending on the concentration of the compound or salt to which c-Met is exposed or, more preferably, the inhibition of the catalytic activity of c-Met.

The term "contacting" as used herein refers to bringing a compound of this invention and c-Met together in such a manner that the compound can affect the catalytic activity of c-Met, either directly, i.e., by interacting with c-Met itself, or indirectly, i.e., by interacting with another molecule on which the catalytic activity of c-Met is dependent. Such "contacting" can be accomplished in vitro, i.e., in a test tube, a petri dish or the like. In a test tube, contacting may involve only a compound and c-Met or it may involve whole cells. Cells may also be maintained or grown in cell culture dishes and contacted with a compound in that environment. In this context, the ability of a particular compound to affect a c-Met related disorder, i.e., the $IC_{50}$ of the compound, defined below, can be determined before use of the compounds in vivo with more complex living organisms is attempted. For cells outside the organism, multiple methods exist, and are well-known to those skilled in the art, to get c-Met in contact with the compounds including, but not limited to, direct cell microinjection and numerous transmembrane carrier techniques.

"In vitro" refers to procedures performed in an artificial environment such as, e.g., without limitation, in a test tube or culture medium. The skilled artisan will understand that, for example, isolated c-Met may be contacted with a modulator in an in vitro environment. Alternatively, an isolated cell may be contacted with a modulator in an in vitro environment.

As used herein, "in vivo" refers to procedures performed within a living organism such as, without limitation, a mouse, rat, rabbit, ungulate, bovine, equine, porcine, canine, feline, primate, or human.

As used herein, "c-Met related disorder," refers to a condition characterized by inappropriate, i.e., under-activity or, more commonly, over-activity of the c-Met catalytic activity. A "c-Met related disorder" also refers to a condition where there may be a mutation in the gene that produces c-Met, which, in turn, produces a c-Met that has an increased or decreased c-Met catalytic activity.

Inappropriate catalytic activity can arise as the result of either: (1) c-Met expression in cells which normally do not express c-Met, (2) increased c-Met expression leading to unwanted cell proliferation, differentiation and/or growth, or, (3) decreased c-Met expression leading to unwanted reductions in cell proliferation, differentiation and/or growth. Over-activity of a c-Met refers to either amplification of the gene encoding a c-Met or production of a level of c-Met activity which can correlate with a cell proliferation, differentiation and/or growth disorder (that is, as the level of the c-Met increases, the severity of one or more of the symptoms of the cellular disorder increases). Under-activity is, of course, the converse, wherein the severity of one or more symptoms of a cellular disorder increase as the level of the c-Met activity decreases.

As used herein, the terms "treat", "treating" and "treatment" refer to a method of alleviating or abrogating a c-Met mediated cellular disorder and/or its attendant symptoms. With regard particularly to cancer, these terms simply mean that the life expectancy of an individual affected with a cancer will be increased or that one or more of the symptoms of the disease will be reduced.

The term "organism" refers to any living entity comprised of at least one cell. A living organism can be as simple as, for example, a single eukaryotic cell or as complex as a mammal. In a preferred aspect, the organism is a mammal. In a particularly preferred aspect, the mammal is a human being.

The term "therapeutically effective amount" as used herein refers to that amount of the compound being administered which will relieve to some extent one or more of the symptoms of the disorder being treated. In reference to the treatment of cancer, a therapeutically effective amount refers to that amount which has the effect of (1) reducing the size of the tumor, (2) inhibiting (that is, slowing to some extent, preferably stopping) tumor metastasis, (3) inhibiting to some extent (that is, slowing to some extent, preferably stopping) tumor growth, and/or, (4) relieving to some extent (or, preferably, eliminating) one or more symptoms associated with the cancer.

By "monitoring" is meant observing or detecting the effect of contacting a compound with a cell expressing a c-Met. The observed or detected effect can be a change in cell phenotype, in the catalytic activity of c-Met or a change in the interaction of c-Met with a natural binding partner. Techniques for observing or detecting such effects are well-known in the art. For example, the catalytic activity of c-Met may be observed by determining the rate or amount of phosphorylation of a target molecule.

"Cell phenotype" refers to the outward appearance of a cell or tissue or the biological function of the cell or tissue. Examples, without limitation, of a cell phenotype are cell size, cell growth, cell proliferation, cell differentiation, cell survival, apoptosis, and nutrient uptake and use. Such phenotypic characteristics are measurable by techniques well-known in the art.

A "natural binding partner" refers to a polypeptide that binds to a c-Met in a cell. Natural binding partners can play a role in propagating a signal in a c-Met-mediated signal transduction process. A change in the interaction of the natural binding partner with c-Met can manifest itself as an increased or decreased concentration of the c-Met/natural binding partner complex and, as a result, in an observable change in the ability of c-Met to mediate signal transduction.

As used herein, "administer" or "administration" refers to the delivery of a compound or salt of the present invention or of a pharmaceutical composition containing a compound or salt of this invention to an organism for the purpose of prevention or treatment of a c-Met-related disorder.

The terms "abnormal cell growth" and "hyperproliferative disorder" are used interchangeably in this application.

"Abnormal cell growth", as used herein, refers to cell growth that is independent of normal regulatory mechanisms (e.g., loss of contact inhibition), including the abnormal growth of normal cells and the growth of abnormal cells. This includes, but is not limited to, the abnormal growth of: (1) tumor cells (tumors), both benign and malignant, expressing an activated Ras oncogene; (2) tumor cells, both benign and malignant, in which the Ras protein is activated as a result of oncogenic mutation in another gene; (3) benign and malignant cells of other proliferative diseases in which aberrant Ras activation occurs. Examples of such benign proliferative diseases are psoriasis, benign prostatic hypertrophy, human papilloma virus (HPV), and restinosis. "Abnormal cell growth" also refers to and includes the abnormal growth of cells, both benign and malignant, resulting from activity of the enzyme farnesyl protein transferase.

"Alkyl" refers to a saturated aliphatic hydrocarbon including straight chain or branched chain. Preferably, the alkyl group has 1 to 20 carbon atoms (whenever a numerical range; e.g., "1-20", is stated herein, it means that the group, in this case the alkyl group, may contain 1 carbon atom, 2 carbon atoms, 3 carbon atoms, etc. up to and including 20 carbon atoms). More preferably, it is a medium size alkyl having 1 to 10 carbon atoms. Most preferably, it is a lower alkyl having 1 to 6 carbon atoms. The alkyl group may be substituted or unsubstituted. When substituted, each substituent group is preferably one or more individually selected from halogen, -hydroxy, —COR', —COOR', —OCOR', —CONRR', —RNCOR', —NRR', —CN, —NO$_2$, —CF$_3$—SR', —SOR', —SO$_2$R', —SO$_2$OR', —SO$_2$NRR', thiocarbonyl, —RNSO$_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl. R and R' can be independently H, alkyl, or aryl, wherein alkyl or aryl may be further substituted with halogen, (CH$_2$)$_n$N(R")$_2$, (CH$_2$)$_n$CO$_2$R", (CH$_2$)$_n$OR", (CH$_2$)$_n$OC(O)R", alkoxycarbonyl, aryloxycarbonyl, aminocarbonyl, a heteroalicyclic ring, aryl, alkoxy, —OCF$_3$, aryloxy, C(O)NH$_2$ or heteroaryl. R" can be H, alkyl or aryl. n is 0-3.

"Alkenyl" refers to an aliphatic hydrocarbon having at least one carbon-carbon double bond, including straight chain, branched chain or cyclic groups having at least one carbon-carbon double bond. Preferably, the alkenyl group has 2 to 20 carbon atoms (whenever a numerical range; e.g., "2-20", is stated herein, it means that the group, in this case the alkenyl group, may contain 2 carbon atoms, 3 carbon atoms, etc. up to and including 20 carbon atoms). More preferably, it is a medium size alkenyl having 2 to 10 carbon atoms. Most preferably, it is a lower alkenyl having 2 to 6 carbon atoms. Examples, without limitation, of alkenyl groups include 1-propenyl, 1- and 2-butenyl, etc. The alkenyl group may be substituted or unsubstituted. When substituted, each substituent group is preferably one or more individually selected from halogen, -hydroxy, —COR', —COOR', —OCOR', —CONRR', —RNCOR', —NRR', —CN, —NO$_2$, —CF$_3$, —SR', —SOR', —SO$_2$R', —SO$_2$OR', —SO$_2$NRR', thiocarbonyl, —RNSO$_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl. Wherein R and R' are defined herein.

"Alkynyl" refers to an aliphatic hydrocarbon having at least one carbon-carbon triple bond, including straight chain, branched chain or cyclic groups having at least one carbon-carbon triple bond. Preferably, the alkenyl group has 2 to 20 carbon atoms (whenever a numerical range; e.g., "2-20", is stated herein, it means that the group, in this case the alkynyl group, may contain 2 carbon atoms, 3 carbon atoms, etc. up to and including 20 carbon atoms). More preferably, it is a medium size alkynyl having 2 to 10 carbon atoms. Most preferably, it is a lower alkynyl having 2 to 6 carbon atoms. Examples, without limitation, of alkynyl groups include 1-propynyl, 1- and 2-butynyl, etc. The alkynyl group may be substituted or unsubstituted. When substituted, each substituent group is preferably one or more individually selected from halogen, -hydroxy, —COR', —COOR', —OCOR', —CONRR', —RNCOR', —NRR', —CN, —NO$_2$, —CF$_3$, —SR', —SOR', —SO$_2$R', —SO$_2$OR', —SO$_2$NRR', thiocarbonyl, —RNSO$_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl. Wherein R and R' are defined herein.

A "cycloalkyl" or an "alicyclic" group refers to an all-carbon monocyclic or fused ring (i.e., rings which share an adjacent pair of carbon atoms) group wherein one of more of the rings does not have a completely conjugated pi-electron system. Preferably, the cycloalkyl group has from 3-8 carbon atoms in the ring(s). Examples, without limitation, of cycloalkyl groups are cyclopropane, cyclobutane, cyclopentane, cyclopentene, cyclohexane, adamantane, cyclohexadiene, cycloheptane and, cycloheptatriene. A cycloalkyl group may be substituted or unsubstituted. When substituted, each substituent group is preferably one or more individually selected from halogen, -hydroxy, —COR', —COOR', —OCOR', —CONRR', —RNCOR', —NRR', —CN, —NO$_2$, —CF$_3$, —SR', —SOR', —SO$_2$R', —SO$_2$OR', —SO$_2$NRR', thiocarbonyl, —RNSO$_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl. Wherein R and R' are defined herein.

An "aryl" group refers to an all-carbon monocyclic or fused-ring polycyclic (i.e., rings which share adjacent pairs of carbon atoms) groups having a completely conjugated pi-electron system. Preferably, the aryl group has from 6 to 12 carbon atoms in the ring(s). Examples, without limitation, of aryl groups are phenyl, naphthalenyl and anthracenyl. The aryl group may be substituted or unsubstituted. When substituted, each substituted group is preferably one or more selected halogen, hydroxy, alkoxy, aryloxy, —COR', —COOR', —OCOR', —CONRR', —RNCOR', —NRR', —CN, —NO$_2$, —CF$_3$, —SR', —SOR', —SO$_2$R', —SO$_2$OR', —SO$_2$NRR', thiocarbonyl, —RNSO$_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl. Wherein R and R' are defined herein.

As used herein, a "heteroaryl" group refers to a monocyclic group having in the ring one or more atoms selected from the group consisting of nitrogen, oxygen and sulfur with the proviso that heteroaryl groups containing highly unstable heteroatom arrangements, such as O—O, O—O—O and the like, are not contemplated by the present invention. One of ordinary skill in the art will recognize unstable groups that are not contemplated by the invention. In addition, the heteroaryl group has a completely conjugated pi-electron system. Preferably, the heteroaryl group has from 5 to 7 ring atoms. Examples of typical monocyclic heteroaryl groups include, but are not limited to:

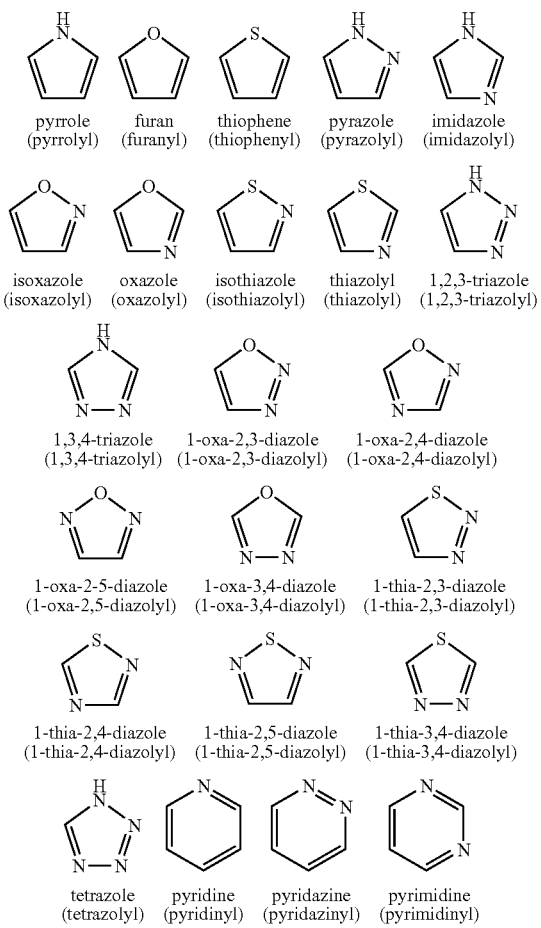

When substituted, each substituted group is preferably one or more selected from halogen, hydroxy, —COR', —COOR', —OCOR', —CONRR', —RNCOR', —NRR', —CN, —NO$_2$, —CF$_3$, —SR', —SOR', —SO$_2$R', —SO$_2$OR', —SO$_2$NRR', thiocarbonyl, —RNSO$_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl. Wherein R and R' are defined herein.

A "heteroalicyclic ring" or "heteroalicycle" or "heterocyclic" or "heterocycle" group refers to a monocyclic group having in the ring one or more atoms selected from the group consisting of nitrogen, oxygen and sulfur. The rings may be saturated and also have one or more double bonds (i.e. partially unsaturated). However, the rings may not have a completely conjugated pi-electron system. Preferably, the heteroalicyclic ring contains from 3 to 8 ring atoms. Examples of suitable saturated heteroalicyclic groups include, but are not limited to:

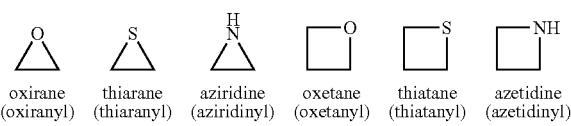

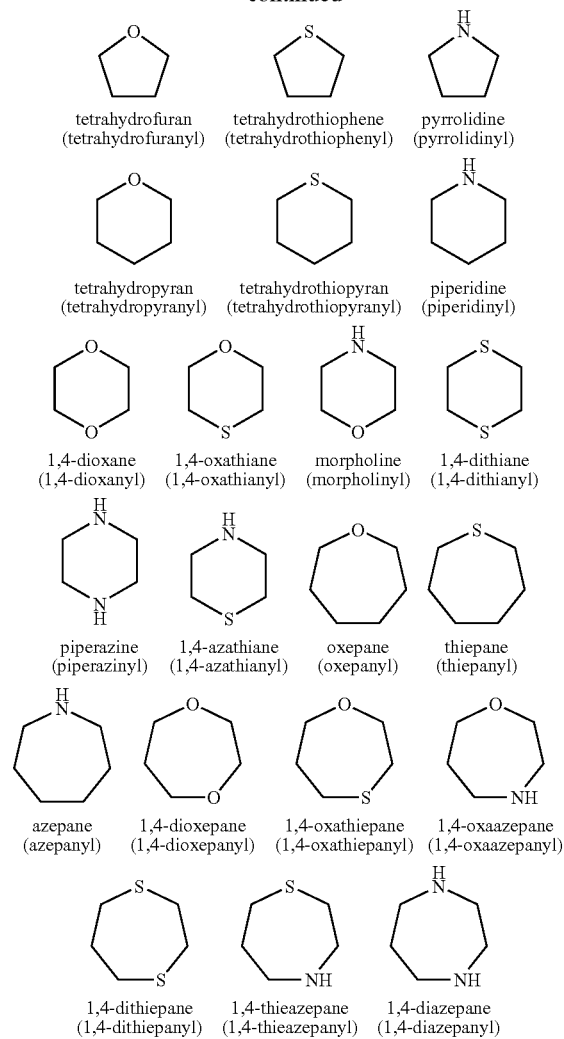

Examples of suitable partially unsaturated heteroalicyclic groups include, but are not limited to:

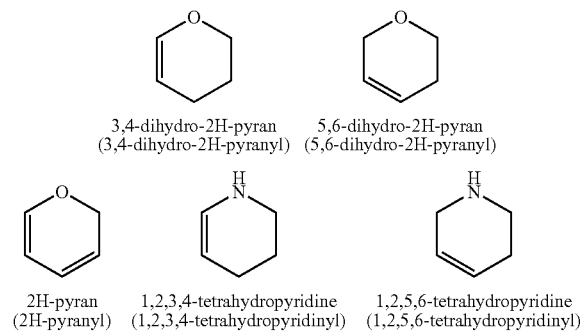

The foregoing groups, as derived from the compounds listed above, may be C-attached or N-attached where such is possible. For instance, a group derived from pyrrole may be pyrrol-1-yl (N-attached) or pyrrol-3-yl (C-attached). The heteroalicyclic ring may be substituted or unsubstituted. The heteroalicyclic ring may contain one or more oxo groups. When substituted, the substituted group(s) is preferably one or more selected halogen, hydroxy, —COR', —COOR', OCOR', —CONRR', —RNCOR', —NRR', —CN, —NO$_2$, —CZ$_3$, —SR', —SOR', —SO$_2$R', —SO$_2$OR', —SO$_2$NRR', thiocarbonyl, —RNSO$_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl. Wherein R and R' are defined herein.

A "3-8 Membered heteroalicyclic-(3-8 membered heteroalicyclic)" group refers to a group having two 3-8 membered heteroalicyclic groups covalently bonded to each other through a single ring atom of each. The 3-8 membered heteroalicyclic rings may be any heteroalicyclic ring as defined above. Furthermore, the heteroalicyclic rings may be substituted or unsubstituted as defined above.

"Heterobicyclic" or "heterobicycle" refers to a fused ring (i.e., rings which share an adjacent pair of atoms) group having in the ring(s) one or more atoms selected from the group consisting of nitrogen, oxygen and sulfur and, in addition, having a completely conjugated pi-electron system (i.e.—aromatic heterobicyclic) or one or more double bonds that does not create a completely conjugated pi-electron system, with the proviso that heterobicyclic groups containing highly unstable heteroatom arrangements, such as O—O, O—O—O and the like, are not contemplated by the present invention. One of ordinary skill in the art will recognize unstable groups that are not contemplated by the invention. Preferably, the heterobicyclic group contains from 8-10 ring atoms. The heterobicyclic ring may be substituted or unsubstituted. The heterobicyclic ring may contain one or more oxo groups. Examples of suitable fused ring aromatic heterobicyclic groups include, but are not limited to:

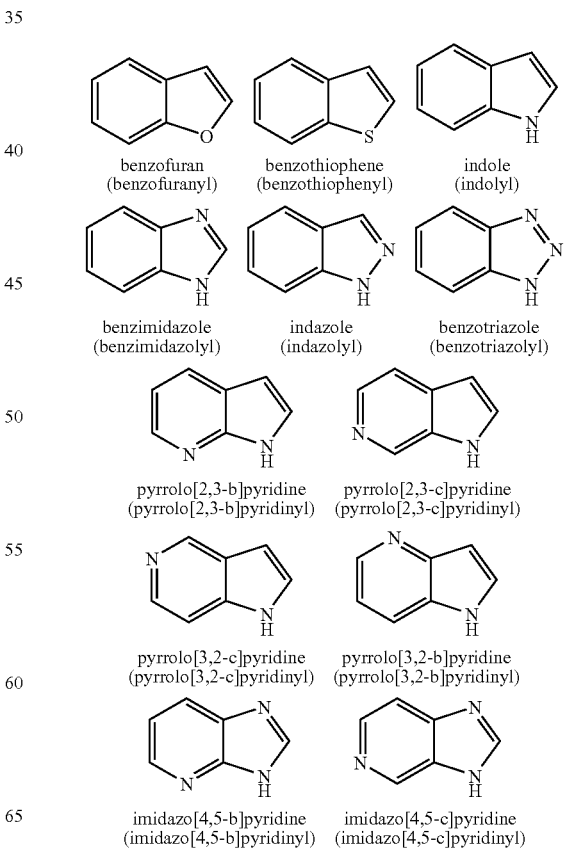

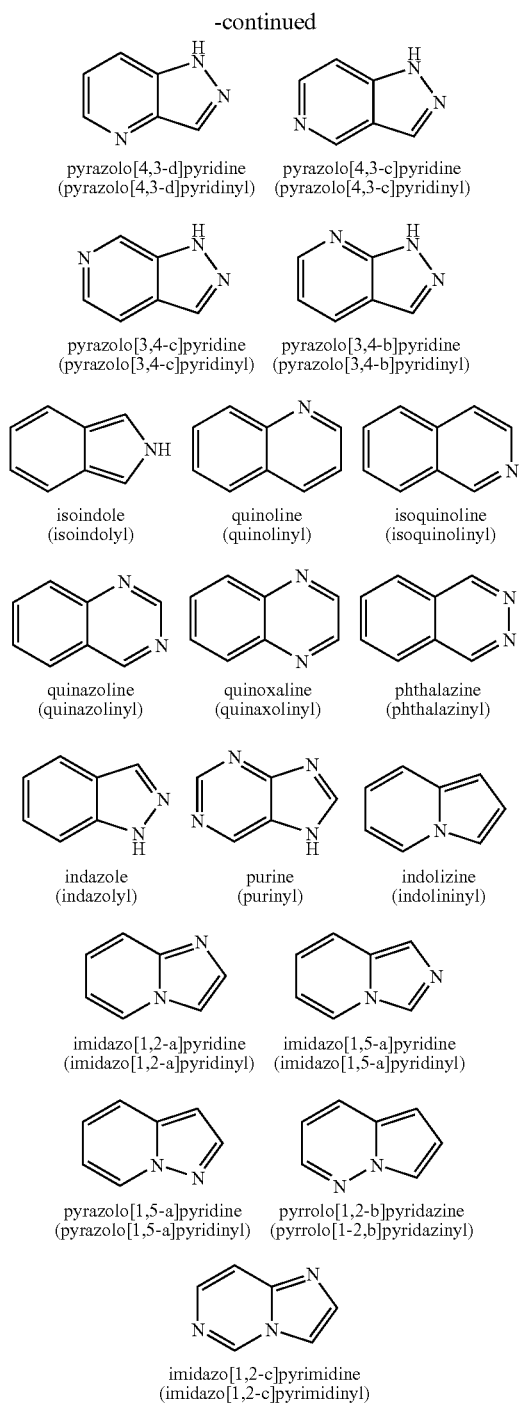

Examples of suitable fused ring heterobicyclic groups include, but are not limited to:

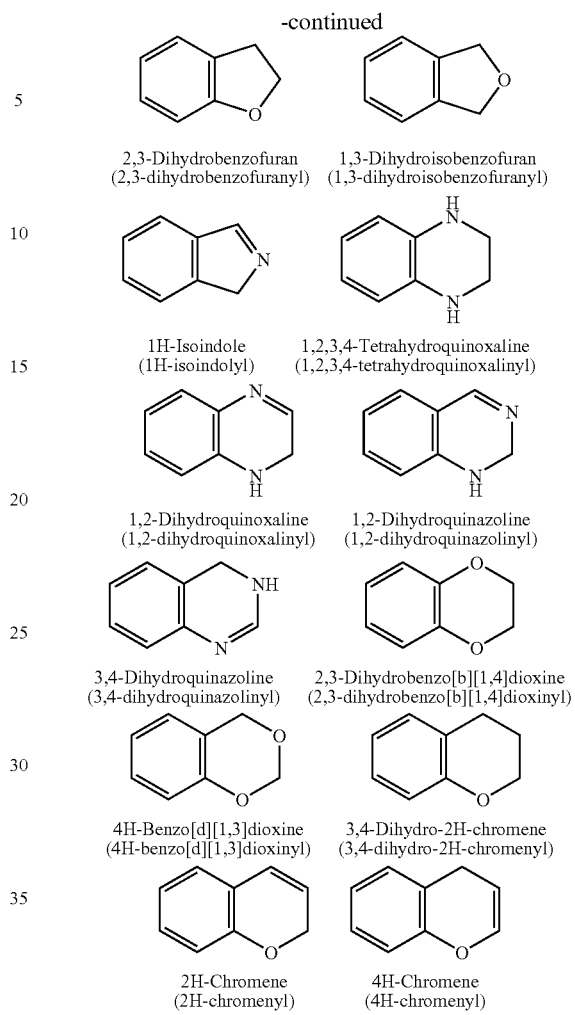

When substituted, the substituted group(s) is preferably one or more selected halogen, hydroxy, —COR', —COOR', OCOR', —CONRR', —RNCOR', —NRR', —CN, —NO$_2$, —CZ$_3$, —SR', —SOR', —SO$_2$R', —SO$_2$OR', —SO$_2$NRR', thiocarbonyl, —RNSO$_2$R', perfluoroalkyl, O-carbamyl, N-carbamyl, O-thiocarbamyl, N-thiocarbamyl, silyl, ammonium, lower alkyl, lower alkenyl, lower alkynyl, cycloalkyl, heteroalicycle, heteroaryl and aryl. Wherein R and R' are defined herein.

When used herein, the R groups on substitutents having two or more R groups on different atoms, such as —(CH$_2$)$_n$(NR$^{12}$R$^{13}$)C(O)NR$^{12}$R$^{13}$ or —NR$^{10}$C(O)NR$^{10}$R$^{11}$, may be the same or different. Specifically, in the exemplary substituent —NR$^{10}$C(O)NR$^{10}$R$^{11}$, the two R$^{10}$ groups may be the same or different with respect to each other, likewise, the two R$^{10}$ groups may be the same or different with respect to the R$^{11}$ group. In, for example, —(CH$_2$)$_n$(NR$^{12}$R$^{13}$)C(O)NR$^{12}$R$^{13}$ the two R$^{12}$ groups may be the same or different with respect to each other, and the two R$^{13}$ groups may be the same or different with respect to each other. Likewise, the two R$^{12}$ groups may be the same or different with respect to the two R$^{13}$ group. In addition, where a single atom is substituted by more than one group, the groups on that atom may be the same or different. So, in —NR$^{10}$C(O)NR$^{10}$R$^{11}$, the R$^{10}$ and R$^{11}$ on the same nitrogen may be the same or different from one another.

An "oxo" group refers to a carbonyl moiety such that alkyl substituted by oxo refers to a ketone group.

A "hydroxy" group refers to an —OH group.

An "alkoxy" group refers to both an —Oalkyl and an —Ocycloalkyl group, as defined herein.

An "alkoxycarbonyl" refers to a —C(O)OR.

An "aminocarbonyl" refers to a —C(O)NRR'.

An "aryloxycarbonyl" refers to —C(O)Oaryl.

An "aryloxy" group refers to both an —Oaryl and an —Oheteroaryl group, as defined herein.

An "arylalkyl" group refers to -alkylaryl, where alkyl and aryl are defined herein.

An "arylsulfonyl" group refers to a —SO$_2$aryl.

An "alkylsulfonyl" group refer to a —SO$_2$alkyl.

A "heteroaryloxyl" group refers to a heteroaryl group with heteroaryl as defined herein.

A "heteroalicycloxy" group refers to a heteroalicyclic-O group with heteroalicyclic as defined herein.

A "carbonyl" group refers to a —C(=O)R.

An "aldehyde" group refers to a carbonyl group where R is hydrogen.

A "thiocarbonyl" group refers to a —C(=S)—R group.

A "trihalomethanecarbonyl" group refers to a Z$_3$CC(O) group, where Z is halogen.

A "C-carboxyl" group refers to a —C(O)OR groups.

An "O-carboxyl" group refers to a RC(O)O group.

A "carboxylic acid" group refers to a C-carboxyl group in which R is hydrogen.

A "halo" or "halogen" group refers to fluorine, chlorine, bromine or iodine.

A "trihalomethyl" group refers to a —CZ$_3$ group.

A "trihalomethanesulfonyl" group refers to a Z$_3$CS(O)$_2$ group.

A "trihalomethanesulfonamido" group refers to a Z$_3$CS(O)$_2$NR-group.

A "sulfinyl" group refers to a —S(O)R group.

A "sulfonyl" group refers to a —S(O)$_2$R group.

An "S-sulfonamido" group refers to a —S(O)$_2$NR-group.

An "N-Sulfonamido" group refers to a —NR—S(O)$_2$R group.

An "O-carbamyl" group refers to a —OC(O)NRR' group.

An "N-carbamyl" group refers to a ROC(O)NR-group.

An "O-thiocarbamyl" group refers to a —OC(S)NRR' group.

An "N-thiocarbamyl" group refers to a ROC(S)NR' group.

An "amino" group refers to an —NH$_2$ or an —NRR'group.

A "C-amido" group refers to a —C(O)NRR' group.

An "N-amido" group refers to a ROC(O)NR group.

A "nitro" group refers to a —NO$_2$ group.

A "cyano" group refers to a —CN group.

A "silyl" group refers to a —Si(R)$_3$ group.

A "phosphonyl" group refers to a —P(=O)(OR)$_2$ group.

An "aminoalkyl" group refers to an -alkylNRR' group.

An "alkylaminoalkyl" group refers to an -alkyl-NR-alkyl group.

A "dialkylamionalkyl" group refers to an -alkylN-(alkyl)$_2$ group.

A "perfluoroalkyl group" refers to an alkyl group where all of the hydrogen atoms have been replaced with fluorine atoms.

Compounds that have the same molecular formula but differ in the nature or sequence of bonding of their atoms or arrangements of their atoms in space are termed "isomers." Isomers that differ in the arrangement of their atoms in space are termed "stereoisomers". Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R- and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". The chemical formulae referred to herein may exhibit the phenomena of tautomerism and structural isomerism. This invention encompasses any tautomeric or structural isomeric form and mixtures thereof which possess the ability to modulate c-Met activity and is not limited to any one tautomeric or structural isomeric form. This invention encompasses any tautomeric or structural isomeric form and mixtures thereof which possess the ability to modulate c-Met activity and is not limited to any one tautomeric or structural isomeric form.

The compounds of this invention may possess one or more asymmetric centers; such compounds can therefore be produced as individual (R)- or (S)-stereoisomers or as mixtures thereof. Unless indicated otherwise, the description or naming of a particular compound in the specification and claims is intended to include both individual enantiomers and mixtures, racemic or otherwise, thereof. The methods for the determination of stereochemistry and the separation of stereoisomers are well-known in the art (see discussion in Chapter 4 of "Advanced Organic Chemistry", 4th edition J. March, John Wiley and Sons, New York, 1992). Thus, this invention also encompasses any stereoisomeric form, their corresponding enantiomers (d- and l- or (+) and (−) isomers) and diastereomers thereof, and mixtures thereof, which possess the ability to modulate c-Met activity and is not limited to any one stereoisomeric form.

The compounds of the Formula (I) may exhibit the phenomena of tautomerism and structural isomerism. For example, the compounds described herein may adopt an E or a Z configuration about a double bond or they may be a mixture of E and Z. This invention encompasses any tautomeric or structural isomeric form and mixtures thereof which possess the ability to modulate c-Met activity and is not limited to any one tautomeric or structural isomeric form.

It is contemplated that compounds of the Formula (I) would be metabolized by enzymes in the body of the organism such as human being to generate a metabolite that can modulate the activity of c-Met. Such metabolites are within the scope of the present invention.

Those compounds of the formula I that are acidic in nature are capable of forming base salts with various pharmacologically acceptable cations. Examples of such salts include the alkali metal or alkaline earth metal salts and particularly, the sodium and potassium salts.

The compounds of the present invention have asymmetric centers and therefore exist in different enantiomeric and diastereomeric forms. This invention relates to the use of all optical isomers and stereoisomers of the compounds of the present invention, and mixtures thereof, and to all pharmaceutical compositions and methods of treatment that may employ or contain them. The compounds of formula I may also exist as tautomers. This invention relates to the use of all such tautomers and mixtures thereof.

This invention also encompasses pharmaceutical compositions containing and methods of treating proliferative disorders or abnormal cell growth through administering prodrugs of compounds of the formula I. Compounds of formula I having free amino, amido, hydroxy or carboxylic groups can be converted into prodrugs. Prodrugs include compounds wherein an amino acid residue, or a polypeptide chain of two or more (e.g., two, three or four) amino acid residues is covalently joined through an amide or ester bond to a free amino, hydroxy or carboxylic acid group of compounds of formula I. The amino acid residues include but are not limited to the 20 naturally occurring amino acids commonly designated by three letter symbols and also includes 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone. Additional types of prodrugs are also encompassed. For instance, free carboxyl groups can be derivatized as amides or alkyl esters. Free hydroxy groups may be derivatized using groups including but not limited to hemisuccinates, phosphate esters, dimethylaminoacetates, and phosphoryloxymethyloxycarbonyls, as outlined in *Advanced Drug Delivery Reviews,* 1996, 19, 115. Carbamate prodrugs of hydroxy and amino groups are also included, as are carbonate prodrugs, sulfonate esters and sulfate esters of hydroxy groups. Derivatization of hydroxy groups as (acyloxy)methyl and (acyloxy)ethyl ethers wherein the acyl group may be an alkyl ester, optionally substituted with groups including but not limited to ether, amine and carboxylic acid functionalities, or where the acyl group is an amino acid ester as described above, are also encompassed. Prodrugs of this type are described in *J. Med. Chem.* 1996, 39, 10. Free amines can also be derivatized as amides, sulfonamides or phosphonamides. All of these prodrug moieties may incorporate groups including but not limited to ether, amine and carboxylic acid functionalities.

DETAILED DESCRIPTION OF THE INVENTION

The compounds presented herein are exemplary and are not to be construed as limiting the scope of the invention.

A general synthetic route to the compounds of the present invention is shown in Scheme 1. One of skill in the art will recognize that this general scheme may be modified and yet still produce the compounds of the present invention. The groups $R^a$, $R^b$, $R^c$, $R^d$ and $R^e$ shown in Scheme 1 include but are not limited to those substituents described herein in connection with the present invention. Further exemplary methods for making the compounds of the invention are outlined in the non-limiting examples below.

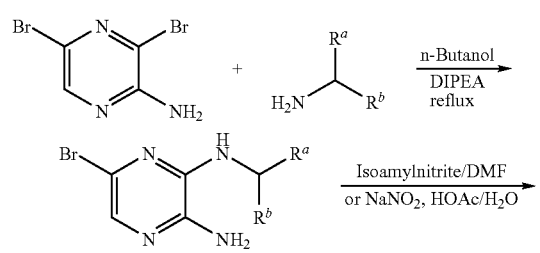

-continued

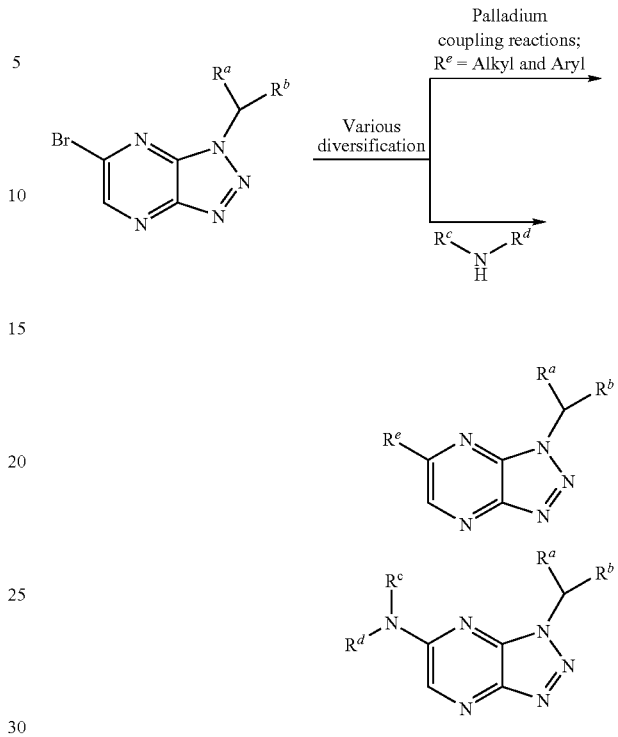

In one aspect, this invention is directed to a pharmaceutical composition comprising one or more compounds of Formula (I) or a pharmaceutically acceptable salt thereof and a pharmaceutically acceptable excipient.

A unique physical form of the free base 2-[4-(3-Quinolin-6-ylmethyl-3H-[1,2,3]triazolo[4,5-b]pyrazin-5-yl)-pyrazol-1-yl]-ethanol has been made. Tabulated data of the powder X-ray diffraction (PXRD) pattern of free base polymorph form 1 is shown in Table 1 below. See Method 42 below.

TABLE 1

PXRD data tabulation for Form 1 of the free base 2-[4-(3-Quinolin-6-ylmethyl-3H-[1,2,3]triazolo[4,5-b]pyrazin-5-yl)-pyrazol-1-yl]-ethanol.

| 2θ (°) | D-Value | Peak Intensity (Counts) | Peak Intensity (%) |
|---|---|---|---|
| 5.8 | 15.1648 | 2244 | 100 |
| 11.6 | 7.6345 | 641 | 28.5 |
| 13.6 | 6.4963 | 1153 | 51.4 |
| 15.5 | 5.7308 | 2058 | 91.7 |
| 16.2 | 5.4736 | 1600 | 71.3 |
| 23.4 | 3.7947 | 527 | 23.5 |
| 27.6 | 3.235 | 519 | 23.1 |

A unique physical form of the mesylate salt of 2-[4-(3-Quinolin-6-ylmethyl-3H-[1,2,3]triazolo[4,5-b]pyrazin-5-yl)-pyrazol-1-yl]-ethanol has been made. Tabulated data of the powder X-ray diffraction (PXRD) pattern of mesylate salt polymorph form 1 is shown in Table 2 below. See Method 42 below.

TABLE 2

PXRD data tabulation for Form 1 of the mesylate salt of 2-[4-(3-Quinolin-6-ylmethyl-3H-[1,2,3]triazolo[4,5-b]pyrazin-5-yl)-pyrazol-1-yl]-ethanol.

| 2θ (°) | D-Value | Peak Intensity (Counts) | Peak Intensity (%) |
|---|---|---|---|
| 12.3 | 7.1688 | 579 | 60.1 |
| 14.8 | 5.9761 | 577 | 59.9 |
| 17.7 | 4.9997 | 498 | 51.6 |
| 18.3 | 4.8401 | 964 | 100 |
| 19.3 | 4.5913 | 715 | 74.1 |
| 23.1 | 3.851 | 570 | 59.1 |
| 24.9 | 3.5698 | 503 | 52.2 |

It is also an aspect of this invention that a compound described herein, or its salt, might be combined with other chemotherapeutic agents for the treatment of the diseases and disorders discussed above. For instance, a compound or salt of this invention might be combined with alkylating agents such as fluorouracil (5-FU) alone or in further combination with leukovorin; or other alkylating agents such as, without limitation, other pyrimidine analogs such as UFT, capecitabine, gemcitabine and cytarabine, the alkyl sulfonates, e.g., busulfan (used in the treatment of chronic granulocytic leukemia), improsulfan and piposulfan; aziridines, e.g., benzodepa, carboquone, meturedepa and uredepa; ethyleneimines and methylmelamines, e.g., altretamine, triethylenemelamine, triethylenephosphoramide, triethylenethiophosphorami-de and trimethylolmelamine; and the nitrogen mustards, e.g., chlorambucil (used in the treatment of chronic lymphocytic leukemia, primary macroglobulinemia and non-Hodgkin's lymphoma), cyclophosphamide (used in the treatment of Hodgkin's disease, multiple myeloma, neuroblastoma, breast cancer, ovarian cancer, lung cancer, Wilm's tumor and rhabdomyosarcoma), estramustine, ifosfamide, novembichin, prednimustine and uracil mustard (used in the treatment of primary thrombocytosis, non-Hodgkin's lymphoma, Hodgkin's disease and ovarian cancer); and triazines, e.g., dacarbazine (used in the treatment of soft tissue sarcoma).

Likewise a compound or salt of this invention might be expected to have a beneficial effect in combination with other antimetabolite chemotherapeutic agents such as, without limitation, folic acid analogs, e.g. methotrexate (used in the treatment of acute lymphocytic leukemia, choriocarcinoma, mycosis fungoides breast cancer, head and neck cancer and osteogenic sarcoma) and pteropterin; and the purine analogs such as mercaptopurine and thioguanine which find use in the treatment of acute granulocytic, acute lymphocytic and chronic granulocytic leukemias.

A compound or salt of this invention might also be expected to prove efficacious in combination with natural product based chemotherapeutic agents such as, without limitation, the vinca alkaloids, e.g., vinblastin (used in the treatment of breast and testicular cancer), vincristine and vindesine; the epipodophyllotoxins, e.g., etoposide and teniposide, both of which are useful in the treatment of testicular cancer and Kaposi's sarcoma; the antibiotic chemotherapeutic agents, e.g., daunorubicin, doxorubicin, epirubicin, mitomycin (used to treat stomach, cervix, colon, breast, bladder and pancreatic cancer), dactinomycin, temozolomide, plicamycin, bleomycin (used in the treatment of skin, esophagus and genitourinary tract cancer); and the enzymatic chemotherapeutic agents such as L-asparaginase.

In addition to the above, a compound or salt of this invention might be expected to have a beneficial effect used in combination with the platinum coordination complexes (cisplatin, etc.); substituted ureas such as hydroxyurea; methylhydrazine derivatives, e.g., procarbazine; adrenocortical suppressants, e.g., mitotane, aminoglutethimide; and hormone and hormone antagonists such as the adrenocorticosteriods (e.g., prednisone), progestins (e.g., hydroxyprogesterone caproate); estrogens (e.g., diethylstilbestrol); antiestrogens such as tamoxifen; androgens, e.g., testosterone propionate; and aromatase inhibitors (such as anastrozole).

Finally, the combination of a compound of this invention might be expected to be particularly effective in combination with mitoxantrone or paclitaxel for the treatment of solid tumor cancers or leukemias such as, without limitation, acute myelogenous (non-lymphocytic) leukemia.

The above method can be carried out in combination with a chemotherapeutic agent selected from the group consisting of mitotic inhibitors, alkylating agents, antimetabolites, cell cycle inhibitors, enzymes, topoisomerase inhibitors, biological response modifiers, anti-hormones, antiangiogenic agents such as MMP-2, MMP-9 and COX-2 inhibitors, and anti-androgens.

Examples of useful COX-II inhibitors include Vioxx™, CELEBREX™ (alecoxib), valdecoxib, paracoxib, rofecoxib, and Cox 189. Examples of useful matrix metalloproteinase inhibitors are described in WO 96/33172 (published Oct. 24, 1996), WO 96/27583 (published Mar. 7, 1996), European Patent Application No. 97304971.1 (filed Jul. 8, 1997), European Patent Application No. 99308617.2 (filed Oct. 29, 1999), WO 98/07697 (published Feb. 26, 1998), WO 98/03516 (published Jan. 29, 1998), WO 98/34918 (published Aug. 13, 1998), WO 98/34915 (published Aug. 13, 1998), WO 98/33768 (published Aug. 6, 1998), WO 98/30566 (published Jul. 16, 1998), European Patent Publication 606,046 (published Jul. 13, 1994), European Patent Publication 931,788 (published Jul. 28, 1999), WO 90/05719 (published May 31, 1990), WO 99/52910 (published Oct. 21, 1999), WO 99/52889 (published Oct. 21, 1999), WO 99/29667 (published Jun. 17, 1999), PCT International Application No. PCT/IB98/01113 (filed Jul. 21, 1998), European Patent Application No. 99302232.1 (filed Mar. 25, 1999), Great Britain patent application number 9912961.1 (filed Jun. 3, 1999), U.S. Provisional Application No. 60/148,464 (filed Aug. 12, 1999), U.S. Pat. No. 5,863,949 (issued Jan. 26, 1999), U.S. Pat. No. 5,861,510 (issued Jan. 19, 1999), and European Patent Publication 780,386 (published Jun. 25, 1997), all of which are incorporated herein in their entireties by reference.

Preferred MMP-2 and MMP-9 inhibitors are those that have little or no activity inhibiting MMP-1. More preferred, are those that selectively inhibit MMP-2 and/or MMP-9 relative to the other matrix-metalloproteinase-s (i.e. MMP-1, MMP-3, MMP-4, MMP-5, MMP-6, MMP-7, MMP-8, MMP-10, MMP-11, MMP-12, and MMP-13). Some specific examples of MMP inhibitors useful in the present invention are AG-3340, RO 32-3555, RS 13-0830, and the compounds recited in the following list:

3-[[4-(4-fluoro-phenoxy)-benzenesulfonyl]-(1-hydroxy-carbamoyl-cyclo-pentyl)-amino]propionic acid; 3-exo-3-[4-(4-fluoro-phenoxy)-benzenesulfon-ylamino]-8-oxa-bicyclo [3.2.1]octane-3-carboxylic acid hydroxyamide; (2R,3R)1-[4-(2-chloro-4-fluoro-benzyloxy)-benzenesulfonyl]-3-hydroxy-3-methyl-piperidine-2-carboxylic acid hydroxyamide; 4-[4-(4-fluoro-phenoxy)-benzenesulfonylamino]tetrahydro-pyran-4-carboxylic acid hydroxyamide; 3-[[4-(4-fluoro-phenoxy)-benzenesulfonyl]-(1-hydroxy-carbamoylcyclobutyl)-amino]-propionic acid; 4-[4-(4-chloro-phenoxy)-benzenesulfonylamino]-tetrahydro-pyran-4-carboxylic acid hydroxyamide; (R)3-[4-(4-chloro-phenoxy)-benzenesulfonyl-amino]-tetrahydro-pyran-3-carboxylic acid hydroxyamide; (2R,3R)1-[4-(4-fluoro-2-methylbenzyloxy)-benzenesulfonyl]-3-hydroxy-3-methyl-piperidine-2-carboxylic acid hydroxyamide; 3-[[(4-(4-fluoro-phenoxy)-benzenesulfonyl]-(1-hydroxycarbamoyl-1-methylethyl)-amino] propionic acid; 3-[[4-(4-fluoro-phenoxy)-benzenesulfonyl]-(4-hydroxycarbamoyl-tetrahydropyran-4-yl)-amino]-propionic acid; 3-exo-3-[4-(4-chloro-phenoxy)-benzenesulfonylamino]-8-oxa-bicyclo[3.2.1]octane-3-carboxylic acid hydroxy-amide; 3-endo-3-[4-(4-fluoro-phenoxy)-benzenesulfonylamino]-8-oxa-bicyclo[3.2.1]octane-3-carboxylic acid hydroxyamide; and (R)3-[4-(4-fluoro-phenoxy)-benzenesulfonylamino]-tetrahydro-furan-3-carboxylic acid hydroxyamide; and pharmaceutically acceptable salts and solvates of said compounds.

Other anti-angiogenesis agents, including other COX-II inhibitors and other MMP inhibitors, can also be used in the present invention.

Compounds of the Formula (I) can also be used with signal transduction inhibitors, such as agents that can inhibit EGFR (epidermal growth factor receptor) responses, such as EGFR antibodies, EGF antibodies, and molecules that are EGFR inhibitors; VEGF (vascular endothelial growth factor) inhibitors; and erbB2 receptor inhibitors, such as organic molecules or antibodies that bind to the erbB2 receptor, for example, HERCEPTIN™. (Genentech, Inc. of South San Francisco, Calif., USA). EGFR inhibitors are described in, for example in WO 95/19970 (published Jul. 27, 1995), WO 98/14451 (published Apr. 9, 1998), WO 98/02434 (published Jan. 22, 1998), and U.S. Pat. No. 5,747,498 (issued May 5, 1998), and such substances can be used in the present invention as described herein.

EGFR-inhibiting agents include, but are not limited to, the monoclonal antibodies C225 and anti-EGFR 22Mab (ImClone Systems Incorporated of New York, N.Y., USA), the compounds ZD-1839 (AstraZeneca), BIBX-1382 (Boehringer Ingelheim), MDX-447 (Medarex Inc. of Annandale, N.J., USA), and OLX-103 (Merck & Co. of Whitehouse Station, N.J., USA), VRCTC-310 (Ventech Research) and EGF fusion toxin (Seragen Inc. of Hopkinton, Mass.).

These and other EGFR-inhibiting agents can be used in the present invention.

VEGF inhibitors can also be combined with a compounds of the Formulae (I). VEGF inhibitors are described in, for example in WO 99/24440 (published May 20, 1999), PCT International Application PCT/IB99/00797 (filed May 3, 1999), in WO 95/21613 (published Aug. 17, 1995), WO 99/61422 (published Dec. 2, 1999), U.S. Pat. No. 5,834,504 (issued Nov. 10, 1998), WO 01/60814, WO 98/50356 (published Nov. 12, 1998), U.S. Pat. No. 5,883,113 (issued Mar. 16, 1999), U.S. Pat. No. 5,886,020 (issued Mar. 23, 1999), U.S. Pat. No. 5,792,783 (issued Aug. 11, 1998), WO 99/10349 (published Mar. 4, 1999), WO 97/32856 (published Sep. 12, 1997), WO 97/22596 (published Jun. 26, 1997), WO 98/54093 (published Dec. 3, 1998), WO 98/02438 (published Jan. 22, 1998), WO 99/16755 (published Apr. 8, 1999), and WO 98/02437 (published Jan. 22, 1998), all of which are incorporated herein in their entireties by reference. Other examples of some specific VEGF inhibitors useful in the present invention are IM862 (Cytran Inc. of Kirkland, Wash., USA); anti-VEGF monoclonal antibody of Genentech, Inc. of South San Francisco, Calif.; and angiozyme, a synthetic ribozyme from Ribozyme (Boulder, Colo.) and Chiron (Emeryville, Calif.). These and other VEGF inhibitors can be used in the present invention as described herein.

ErbB2 receptor inhibitors, such as GW-282974 (Glaxo Wellcome plc), and the monoclonal antibodies AR-209 (Aronex Pharmaceuticals Inc. of The Woodlands, Tex., USA) and 2B-1 (Chiron), can furthermore be combined with a compound of the Formula (I) for example those indicated in WO 98/02434 (published Jan. 22, 1998), WO 99/35146 (published Jul. 15, 1999), WO 99/35132 (published Jul. 15, 1999), WO 98/02437 (published Jan. 22, 1998), WO 97/13760 (published Apr. 17, 1997), WO 95/19970 (published Jul. 27, 1995), U.S. Pat. No. 5,587,458 (issued Dec. 24, 1996), and U.S. Pat. No. 5,877,305 (issued Mar. 2, 1999), which are all hereby incorporated herein in their entireties by reference. ErbB2 receptor inhibitors useful in the present invention are also described in U.S. Provisional Application No. 60/117,341, filed Jan. 27, 1999, and in U.S. Provisional Application No. 60/117,346, filed Jan. 27, 1999, both of which are incorporated in their entireties herein by reference. The erbB2 receptor inhibitor compounds and substance described in the aforementioned PCT applications, U.S. patents, and U.S. provisional applications, as well as other compounds and substances that inhibit the erbB2 receptor, can be used with compounds of the Formula (I), in accordance with the present invention.

Compounds of the Formula (I) can also be used with other agents useful in treating cancer, including, but not limited to, agents capable of enhancing antitumor immune responses, such as CTLA4 (cytotoxic lymphocyte antigen 4) antibodies, and other agents capable of blocking CTLA4; and anti-proliferative agents such as other farnesyl protein transferase inhibitors, for example the farnesyl protein transferase inhibitors described in the references cited in the "Background" section, of U.S. Pat. No. 6,258,824 BI. Specific CTLA4 antibodies that can be used in the present invention include those described in U.S. Provisional Application No. 60/113,647 (filed Dec. 23, 1998) which is incorporated by reference in its entirety, however other CTLA4 antibodies can be used in the present invention.

The above method can be also be carried out in combination with radiation therapy, wherein the amount of a compound of the Formula (I) in combination with the radiation therapy, is effective in treating the above diseases. The level of radiation therapy administered may be reduced to a sub-efficacy dose when administered in combination with the compounds of the preferred embodiments of the present invention.

Techniques for administering radiation therapy are known in the art, and these techniques can be used in the combination therapy described herein. The administration of the compound of the invention in this combination therapy can be determined as described herein.

Another aspect of the invention is directed to the use of compounds of the Formulae (I) in the preparation of a medicament, which is useful in the treatment of a disease mediated by abnormal Met kinase activity.

Indications

A precise understanding of the mechanism by which the compounds of the invention, in particular, the compounds generated in vivo from the compounds of the invention, inhibit c-Met is not required in order to practice the present invention. However, while not hereby being bound to any particular mechanism or theory, it is believed that the compounds interact with the amino acids in the catalytic region of c-Met. The compounds disclosed herein may thus have utility as in vitro assays for c-Met as well as exhibiting in vivo therapeutic effects through interaction with c-Met.

In another aspect, this invention relates to a method for treating or preventing a c-Met related disorder by administering a therapeutically effective amount of a compound of this invention, or a salt thereof, to an organism.

It is also an aspect of this invention that a pharmaceutical composition containing a compound of this invention, or a salt thereof, is administered to an organism for the purpose of preventing or treating a c-Met related disorder.

This invention is therefore directed to compounds that modulate PK signal transduction by affecting the enzymatic activity of c-Met, thereby interfering with the signal transduced by c-Met. More particularly, the present invention is directed to compounds which modulate c-Met mediated signal transduction pathways as a therapeutic approach to treat the many cancers described herein.

A method for identifying a chemical compound that modulates the catalytic activity of c-Met is another aspect of this invention. The method involves contacting cells expressing c-Met with a compound of this invention (or its salt) and monitoring the cells for any effect that the compound has on them. Alternatively, the method can involve contacting the c-Met protein itself (i.e., not in a cell) with a chemical compound of the preferred embodiments of the present invention and monitoring the protein for any effect that the compound has on it. The effect may be observable, either to the naked eye or through the use of instrumentation. The effect may be, for example, a change or absence in a cell phenotype. The change or absence of change in the cell phenotype monitored, for example, may be, without limitation, a change or absence of change in the catalytic activity of c-Met in the cells or a change or absence of change in the interaction of c-Met with a natural binding partner.

Pharmaceutical Compositions and Use

A compound of the present invention or a physiologically acceptable salt thereof, can be administered as such to a human patient or can be administered in pharmaceutical compositions in which the foregoing materials are mixed with suitable carriers or excipient(s). Techniques for formulation and administration of drugs may be found in "Remington's Pharmacological Sciences," Mack Publishing Co., Easton, Pa., latest edition.

Routes of Administration

Suitable routes of administration may include, without limitation, oral, intraoral, rectal, transmucosal or intestinal administration or intramuscular, epicutaneous, parenteral, subcutaneous, transdermal, intramedullary, intrathecal, direct intraventricular, intravenous, intravitreal, intraperitoneal, intranasal, intramuscular, intradural, intrarespiratory, nasal inhalation or intraocular injections. The preferred routes of administration are oral and parenteral.

Alternatively, one may administer the compound in a local rather than systemic manner, for example, via injection of the compound directly into a solid tumor, often in a depot or sustained release formulation.

Furthermore, one may administer the drug in a targeted drug delivery system, for example, in a liposome coated with tumor-specific antibody. The liposomes will be targeted to and taken up selectively by the tumor.

Composition/Formulation

Pharmaceutical compositions of the present invention may be manufactured by processes well known in the art, e.g., by means of conventional mixing, dissolving, granulating, dragee-making, levigating, emulsifying, encapsulating, entrapping, lyophilizing processes or spray drying.

Pharmaceutical compositions for use in the methods of the present invention may be prepared by any methods of pharmacy, but all methods include the step of bringing in association the active ingredient with the carrier which constitutes one or more necessary ingredients. In particular, pharmaceutical compositions for use in accordance with the present invention may be formulated in conventional manner using one or more physiologically acceptable carriers comprising excipients and auxiliaries which facilitate processing of the active compounds into preparations which can be used pharmaceutically. Proper formulation is dependent upon the route of administration chosen.

Dosage forms include tablets, troches, dispersions, suspensions, solutions, capsules, patches, syrups, elixirs, gels, powders, magmas, lozenges, ointments, creams, pastes, plasters, lotions, discs, suppositories, nasal or oral sprays, aerosols and the like.

For injection, the compounds of the invention may be formulated in aqueous solutions, preferably in physiologically compatible buffers such buffers with or without a low concentration of surfactant or cosolvent, or physiological saline buffer. For transmucosal administration, penetrants appropriate to the barrier to be permeated are used in the formulation. Such penetrants are generally known in the art.

For oral administration, the compounds can be formulated by combining the active compounds with pharmaceutically acceptable carriers well known in the art. Such carriers enable the compounds of the invention to be formulated as tablets, pills, lozenges, dragees, capsules, liquids, gels, syrups, slurries, suspensions and the like, for oral ingestion by a patient. Pharmaceutical preparations for oral use can be made using a solid excipient, optionally grinding the resulting mixture, and processing the mixture of granules, after adding other suitable auxiliaries if desired, to obtain tablets or dragee cores. Useful excipients are, in particular, fillers such as sugars, including lactose, sucrose, mannitol, or sorbitol, cellulose preparations such as, for example, maize starch, wheat starch, rice starch and potato starch and other materials such as gelatin, gum tragacanth, methyl cellulose, hydroxypropylmethyl-cellulose, sodium carboxymethylcellulose, and/or polyvinyl-pyrrolidone (PVP). If desired, disintegrating agents may be added, such as cross-linked polyvinyl pyrrolidone, agar, or alginic acid. A salt such as sodium alginate may also be used.

Dragee cores are provided with suitable coatings. For this purpose, concentrated sugar solutions may be used which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical compositions which can be used orally include push-fit capsules made of gelatin, as well as soft, sealed capsules made of gelatin and a plasticizer, such as glycerol or sorbitol. The push-fit capsules can contain the active ingredients in admixture with a filler such as lactose, a binder such as starch, and/or a lubricant such as talc or magnesium stearate and, optionally, stabilizers. In soft capsules, the active compounds may be dissolved or suspended in suitable liquids, such as fatty oils, liquid paraffin, liquid polyethylene glycols, cremophor, capmul, medium or long chain mono-di- or triglycerides. Stabilizers may be added in these formulations, also.

For administration by inhalation, the compounds for use according to the present invention are conveniently delivered in the form of an aerosol spray using a pressurized pack or a nebulizer and a suitable propellant, e.g., without limitation, dichlorodifluoromethane, trichlorofluoromethane, dichlorotetra-fluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

The compounds may also be formulated for parenteral administration, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating materials such as suspending, stabilizing and/or dispersing agents.

Pharmaceutical compositions for parenteral administration include aqueous solutions of a water soluble form, such as, without limitation, a salt, of the active compound. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes. Aqueous injection suspensions may contain substances which increase the viscosity of the suspension, such as sodium carboxymethyl cellulose, sorbitol, or dextran. Optionally, the suspension may also contain suitable stabilizers and/or agents that increase the solubility of the compounds to allow for the preparation of highly concentrated solutions.

Alternatively, the active ingredient may be in powder form for constitution with a suitable vehicle, e.g., sterile, pyrogen-free water, before use.

The compounds may also be formulated in rectal compositions such as suppositories or retention enemas, using, e.g., conventional suppository bases such as cocoa butter or other glycerides.

In addition to the formulations described previously, the compounds may also be formulated as depot preparations. Such long acting formulations may be administered by implantation (for example, subcutaneously or intramuscularly) or by intramuscular injection. A compound of this invention may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

A non-limiting example of a pharmaceutical carrier for the hydrophobic compounds of the invention is a cosolvent system comprising benzyl alcohol, a nonpolar surfactant, a water-miscible organic polymer and an aqueous phase such as the VPD co-solvent system. VPD is a solution of 3% w/v benzyl alcohol, 8% w/v of the nonpolar surfactant Polysorbate 80, and 65% w/v polyethylene glycol 300, made up to volume in absolute ethanol. The VPD co-solvent system (VPD:D5W) consists of VPD diluted 1:1 with a 5% dextrose in water solution. This co-solvent system dissolves hydrophobic compounds well, and itself produces low toxicity upon systemic administration. Naturally, the proportions of such a co-solvent system may be varied considerably without destroying its solubility and toxicity characteristics. Furthermore, the identity of the co-solvent components may be varied: for example, other low-toxicity nonpolar surfactants may be used instead of Polysorbate 80, the fraction size of polyethylene glycol may be varied, other biocompatible polymers may replace polyethylene glycol, e.g., polyvinyl pyrrolidone, and other sugars or polysaccharides may substitute for dextrose.

Alternatively, other delivery systems for hydrophobic pharmaceutical compounds may be employed. Liposomes and emulsions are well known examples of delivery vehicles or carriers for hydrophobic drugs. In addition, certain organic solvents such as dimethylsulfoxide also may be employed, although often at the cost of greater toxicity.

Additionally, the compounds may be delivered using a sustained-release system, such as semipermeable matrices of solid hydrophobic polymers containing the therapeutic agent. Various sustained-release materials have been established and are well known by those skilled in the art. Sustained-release capsules may, depending on their chemical nature, release the compounds for a few weeks up to over 100 days. Depending on the chemical nature and the biological stability of the therapeutic reagent, additional strategies for protein stabilization may be employed.

The pharmaceutical compositions herein also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Many of the PK modulating compounds of the invention may be provided as physiologically acceptable salts wherein the claimed compound may form the negatively or the positively charged species. Examples of salts in which the compound forms the positively charged moiety include, without limitation, quaternary ammonium (defined elsewhere herein), salts such as the hydrochloride, sulfate, carbonate, lactate, tartrate, maleate, sucinate, malate, acetate and methylsulfonate ($CH_3SO_3$), wherein the nitrogen atom of the quaternary ammonium group is a nitrogen of the selected compound of this invention which has reacted with the appropriate acid. Salts in which a compound of this invention forms the negatively charged species include, without limitation, the sodium, potassium, calcium and magnesium salts formed by the reaction of a carboxylic acid group in the compound with an appropriate base (e.g. sodium hydroxide (NaOH), potassium hydroxide (KOH), Calcium hydroxide ($Ca(OH)_2$), etc.).

Dosage

Pharmaceutical compositions suitable for use in the present invention include compositions wherein the active ingredients are contained in an amount sufficient to achieve the intended purpose, i.e., the modulation of PK activity or the treatment or prevention of a PK-related disorder.

More specifically, a therapeutically effective amount means an amount of compound effective to prevent, alleviate or ameliorate symptoms of disease or prolong the survival of the subject being treated.

Determination of a therapeutically effective amount is well within the capability of those skilled in the art, especially in light of the detailed disclosure provided herein.

For any compound used in the methods of the invention, the therapeutically effective amount or dose can be estimated initially from cell culture assays. Then, the dosage can be formulated for use in animal models so as to achieve a circulating concentration range that includes the $IC_{50}$ as determined in cell culture (i.e., the concentration of the test compound which achieves a half-maximal inhibition of c-Met activity). Such information can then be used to more accurately determine useful doses in humans.

Toxicity and therapeutic efficacy of the compounds described herein can be determined by standard pharmaceutical procedures in cell cultures or experimental animals, e.g., by determining the $IC_{50}$ and the $LD_{50}$ (both of which are discussed elsewhere herein) for a subject compound. The data obtained from these cell culture assays and animal studies can be used in formulating a range of dosage for use in humans. The dosage may vary depending upon the dosage form employed and the route of administration utilized. The exact formulation, route of administration and dosage can be chosen by the individual physician in view of the patient's condition. (See e.g., Fingl, et al., 1975, in "The Pharmacological Basis of Therapeutics", Ch. 1 p. 1).

Dosage amount and interval may be adjusted individually to provide plasma levels of the active species which are sufficient to maintain the kinase modulating effects. These plasma levels are referred to as minimal effective concentrations (MECs). The MEC will vary for each compound but can be estimated from in vitro data, e.g., the concentration necessary to achieve 50-90% inhibition of a kinase may be ascertained using the assays described herein. Dosages necessary to achieve the MEC will depend on individual characteristics and route of administration. HPLC assays or bioassays can be used to determine plasma concentrations.

Dosage intervals can also be determined using MEC value. Compounds should be administered using a regimen that maintains plasma levels above the MEC for 10-90% of the time, preferably between 30-90% and most preferably between 50-90%. At present, the therapeutically effective amounts of compounds of the formula I may range from approximately 10 mg/m$^2$ to 1000 mg/m$^2$ per day. Even more preferably 25 mg/m$^2$ to 500 mg/m$^2$.

In cases of local administration or selective uptake, the effective local concentration of the drug may not be related to plasma concentration and other procedures known in the art may be employed to determine the correct dosage amount and interval.

The amount of a composition administered will, of course, be dependent on the subject being treated, the severity of the affliction, the manner of administration, the judgment of the prescribing physician, etc.

Packaging

The compositions may, if desired, be presented in a pack or dispenser device, such as an FDA approved kit, which may contain one or more unit dosage forms containing the active ingredient. The pack may for example comprise metal or plastic foil, such as a blister pack. The pack or dispenser device may be accompanied by instructions for administration. The pack or dispenser may also be accompanied by a notice associated with the container in a form prescribed by a governmental agency regulating the manufacture, use or sale of pharmaceuticals, which notice is reflective of approval by the agency of the form of the compositions or of human or veterinary administration. Such notice, for example, may be of the labeling approved by the U.S. Food and Drug Administration for prescription drugs or of an approved product insert. Compositions comprising a compound of the invention formulated in a compatible pharmaceutical carrier may also be prepared, placed in an appropriate container, and labeled for treatment of an indicated condition. Suitable conditions indicated on the label may include treatment of a tumor, inhibition of angiogenesis, treatment of fibrosis, diabetes, and the like.

EXAMPLES

Compounds of the present invention can be made according to general Methods 1-39 described below. It will be understood by those skilled in the art that the following general methods are not limiting to the invention. It may be possible to alter exact solvents, conditions and reagents and quantities without deleterious effects. Specific embodiments of the present invention are summarized in Tables 1 and 2 below. Examples 174 and 175 as well as examples 176 and 177 are single enantiomers. However, the exact stereochemistry was not determined.

Powder X-ray Diffraction (PXRD): PXRD data shown in Tables 1 and 2 was collected according to the following protocol. A sample (2 mg) was placed on a microscopic glass slide. The sample was then placed in a Discover D8 (Bruker AXS Instruments) equipped with a GADDS detector. The system used a copper X-ray source maintained at 40 kV and 40 mA to provide CUα1 emission at 1.5406 angstroms. Data were collected from 4 to 40°2θ using two-frame acquisition with 60.1 second/frame. Diffraction peaks are typically measured with an error of ±0.1 degrees (2θ).

Abbreviations:
DCM: Dichloromethane (also known as Methylene chloride)
DMF: N,N-dimethylformamide
HPLC: High-performance liquid chromatography (also known as high-pressure liquid chromatography)
AcOH: Acetic acid
HATU: 2-(7-Aza-1H-benzotriazole-1-yl)-1,1,3,3-tetramethyluronium hexafluorophosphate
DME: Dimethyl ether
EtOAc: Ethyl acetate
n-BuOH: n-Butanol
ACN: Acetonitrile
MeOH: Methanol
DMSO: Dimethylsulfoxide
TEA: Triethylamine
NMP: N-Methyl-2-Pyrrolidone
THF: Tetrahydrofuran
DMAC: Dimethyl Acetamide
CDMT: 2-Chloro-4,6-dimethoxy-1,3,5-triazine
TFA: Trifluoroacetic acid
DIPEA: Diisopropylethylamine Method 1:

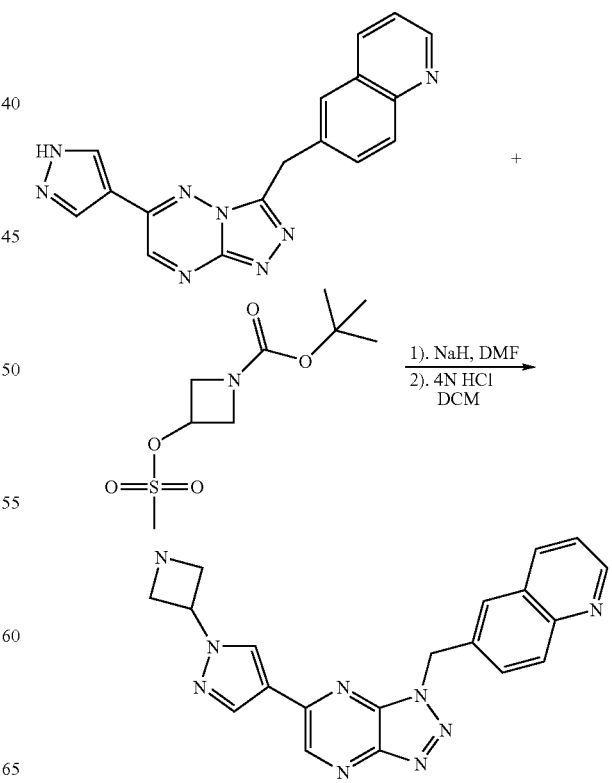

To a stirred solution of 6-((6-(1H-pyrazol-4-yl)-[1,2,4]triazolo[4,3-b][1,2,4]triazin-3-yl)methyl)quinoline (0.05 g, 0.15 mmol) in DMF (2 ml) was added NaH (95%, 0.007 g, 0.26 mmol) under nitrogen, the solution was stirred for 30 min, then tert-butyl 3-(methylsulfonyloxy)azetidine-1-carboxylate (0.047 g, 0.18 mmol) was added, the mixture was stirred for 24 hours, purified by prep-HPLC after lyophilizing gave a solid, this solid was dissolved in DCM (2 ml), 4N HCl (2 ml) was added at rt, stirred for 6 hours, remove solvent, the residue was purified by prep-HPLC to give a solid 6-((6-(1-(azetidin-3-yl)-1H-pyrazol-4-yl)-1H-[1,2,3]triazolo[4,5-b]pyrazin-1-yl)methyl)quinoline (25 mg) yield 34%.

Method 2:

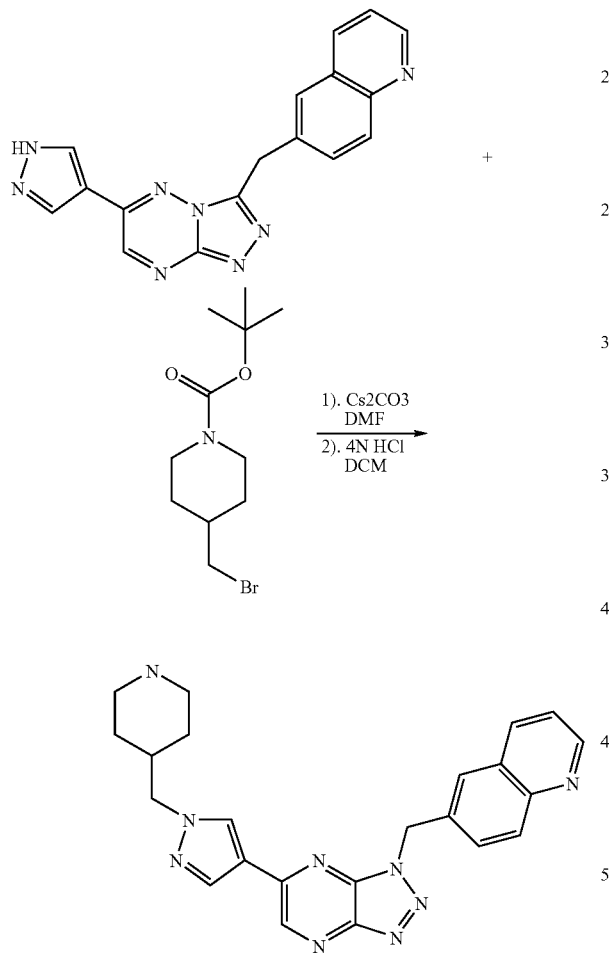

6-((6-(1H-pyrazol-4-yl)-[1,2,4]triazolo[4,3-b][1,2,4]triazin-3-yl)methyl)quinoline (0.05 g, 0.15 mmol) and tert-butyl 4-(bromomethyl)piperidine-1-carboxylate (0.052 g, 0.18 mmol) in DMF (2 ml) were stirred, Cs$_2$CO$_3$ (0.101 g, 0.3 mmol) was added, the mixture was stirred at rt for 24 hours, LCMS checked that reaction was completed, remove solvent, the residue was purified by prep-HPLC, after lyophilizing gave a solid, this solid was dissolved in DCM (2 ml), 4N HCl (1 ml) was added at rt, stirred for 6 hours, remove solvent, the residue was purified by prep-HPLC to give a solid 6-((6-(1-(piperidin-4-ylmethyl)-1H-pyrazol-4-yl)-1H-[1,2,3]triazolo[4,5-b]pyrazin-1-yl)methyl)quinoline (45 mg), yield 56.2%

Method 3:

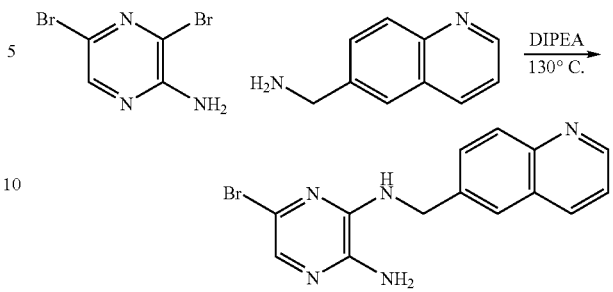

6-bromo-N$^2$-(quinolin-6-ylmethyl)pyrazine-2,3-diamine: A mixture of quinolin-6-ylmethanamine (13 g, 82 mmol), 3,5-dibromopyrazin-2-amine (21 g, 82 mmol) and di-isopropylethylamine (16 mL, 89 mmol) was heated to 130° C. for five hours. The reaction was diluted with dichloromethane:ethanol (9:1) and the resulting suspension was filtered. The precipitate was washed sequentially with water and ether and air dried to afford 6-bromo-N$^2$-(quinolin-6-ylmethyl)pyrazine-2,3-diamine (13 g, 49%).

Method 4:

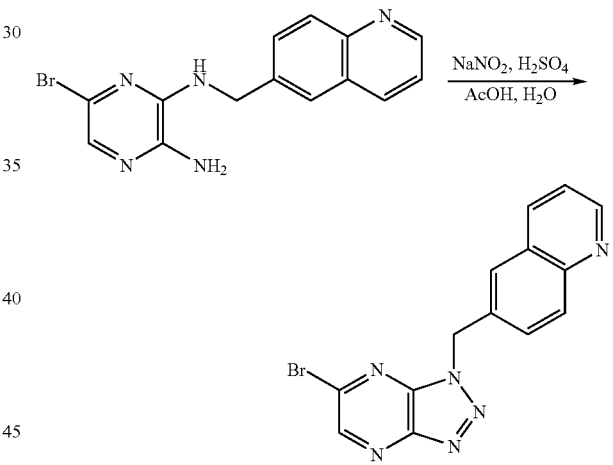

6-((6-bromo-1H-[1,2,3]triazolo[4,5-b]pyrazin-1-yl)methyl)quinoline: To a 6° C. mixture of 6-bromo-N$^2$-(quinolin-6-ylmethyl)pyrazine-2,3-diamine (16 g, 48 mmol), AcOH (97 mL) and H$_2$O (97 mL) was added NaNO$_2$ (4.0 g, 58 mmol) in H$_2$O (12 mL) dropwise over 15 min. After 1.5 hours, a 1:1 mixture of concentrated sulfuric acid and water (6 mL) was added dropwise. After 1.5 hours, NaNO$_2$ (0.5 g, 7 mmol) in H$_2$O (2 mL) and a 1:1 mixture of concentrated sulfuric acid and water (5 mL) were added. The reaction was allowed to warm to room temperature overnight. The reaction was re-cooled in an ice bath and over a period of 1.5 hours, a 1:1 mixture of concentrated sulfuric acid and water (30 mL) and NaNO$_2$ (1.5 g, 22 mmol) in H$_2$O (5 mL) was added. Aqueous 3.75 M NaOH (210 mL) was added dropwise and the resulting suspension was filtered. The precipitate was washed sequentially with water and ether, then suspended in dichloromethane:ethanol (1:1) and filtered. The filtrate was washed sequentially with 1M aqueous Na$_2$CO$_3$ and brine, dried over Na$_2$SO$_4$, filtered and concentrated by rotary evaporation to afford 6-((6-bromo-1H-[1,2,3]triazolo[4,5-b]pyrazin-1-yl)methyl)quinoline (9.6 g, 58%).

Method 5:

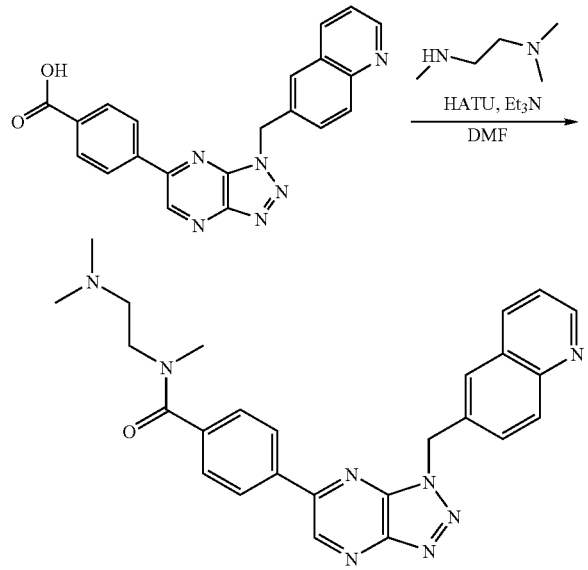

N-(2-(dimethylamino)ethyl)-N-methyl-4-(3-(quinolin-6-ylmethyl)-3H-[1,2,3]triazolo[4,5-b]pyrazin-5-yl)benzamide: HATU (82 mg, 0.22 mmol) was added to a mixture of 4-(3-(quinolin-6-ylmethyl)-3H-[1,2,3]triazolo[4,5-b]pyrazin-5-yl)benzoic acid (75 mg, 0.20 mmol), $N^1,N^1,N^2$-trimethylethane-1,2-diamine (22 mg, 0.22 mmol) and triethylamine (0.060 mL, 0.43 mmol) in DMF (2.0 mL). After stirring for 18 hours, the reaction was partitioned between dichloromethane:ethanol (9:1) and water. The organic layer was separated, dried over $Na_2SO_4$, filtered and concentrated by rotary evaporation to afford 108 mg of crude material. The material was purified by pre-HPLC to give N-(2-(dimethylamino)ethyl)-N-methyl-4-(3-(quinolin-6-ylmethyl)-3H-[1,2,3]triazolo[4,5-b]pyrazin-5-yl)benzamide (54 mg, yield 48%).

Method 6:

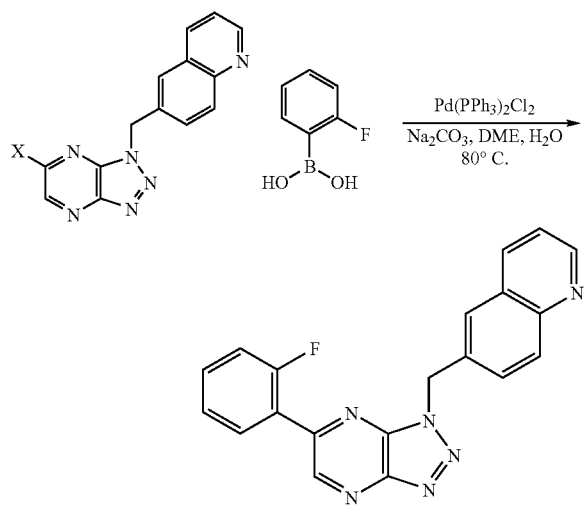

X = Br, Cl 6-((6-(2-fluorophenyl)-1H-[1,2,3]triazolo[4,5-b]pyrazin-1-yl)methyl)quinoline: A mixture of DME (3.0 mL) and 1 M aqueous $Na_2CO_3$ (0.88 mL) was degassed by bubbling in Argon for 10 minutes. The mixture was transferred via syringe to a vial containing 6-((6-bromo-1H-[1,2,3]triazolo[4,5-b]pyrazin-1-yl)methyl)quinoline (100 mg, 0.29 mmol), 2-fluorophenylboronic acid (45 mg, 0.32 mmol) and $Pd(dppf)_2Cl_2 \cdot CH_2Cl_2$ (6.2 mg, 0.01 mmol). The vial was capped and heated to 80° C. for 3.5 hours. The crude reaction mixture was diluted with dichloromethane then washed with water. The dichloromethane was dried over $Na_2SO_4$, filtered and concentrated by rotary evaporation. The residue was purified by column chromatography using gradient elution with ethyl acetate and dichloromethane to afford 6-((6-(2-fluorophenyl)-1H-[1,2,3]triazolo[4,5-b]pyrazin-1-yl)methyl)quinoline (77 mg, 74%).

Method 7:

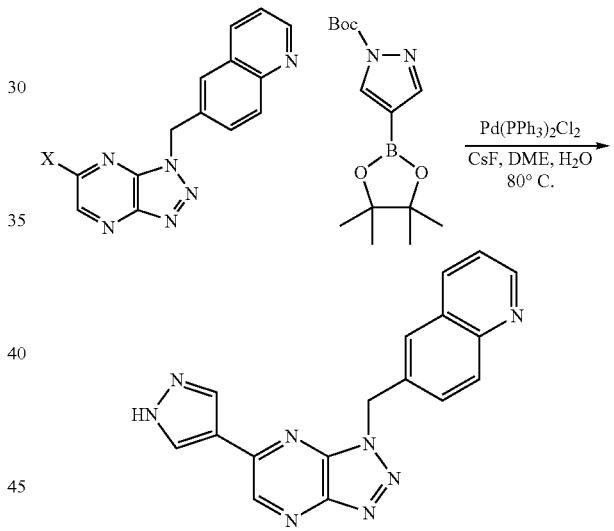

X = Br, Cl 6-((6-(1H-pyrazol-4-yl)-1H-[1,2,3]triazolo[4,5-b]pyrazin-1-yl)methyl)quinoline: A mixture of DME (3.0 mL) and 1 M aqueous CsF (0.88 mL) was degassed by bubbling in Argon for 10 minutes. The mixture was transferred via syringe to a vial containing 6-((6-bromo-1H-[1,2,3]triazolo[4,5-b]pyrazin-1-yl)methyl)quinoline (100 mg, 0.29 mmol), tert-butyl 4-(4,4,5,5-tetramethyl-1,3,2-dioxaborolan-2-yl)-1H-pyrazole-1-carboxylate (95 mg, 0.32 mmol) and $Pd(dppf)_2Cl_2 \cdot CH_2Cl_2$ (6.1 mg, 0.01 mmol). The vial was capped and heated to 80° C. for 16 hours. Water (5 mL) was added to the crude reaction mixture and the resulting suspension was filtered. The precipitate was washed with water and air dried. The precipitate was purified by column chromatography using gradient elution with methanol and dichloromethane to afford 6-((6-(1H-pyrazol-4-yl)-1H-[1,2,3]triazolo[4,5-b]pyrazin-1-yl)methyl)quinoline (60 mg, 62%).

Method 8:

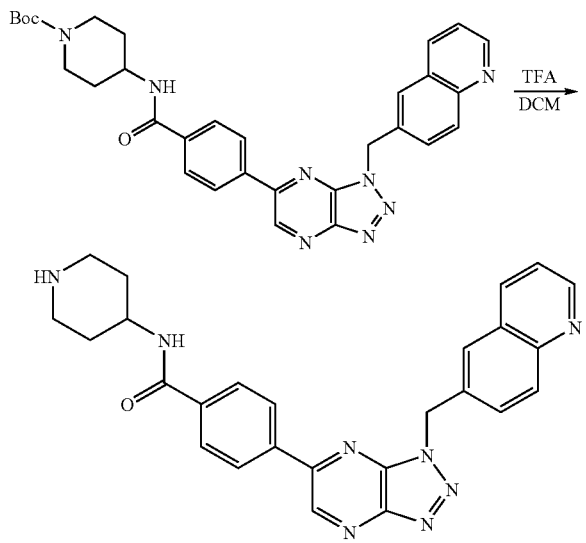

N-(piperidin-4-yl)-4-(3-(quinolin-6-ylmethyl)-3H-[1,2,3]triazolo[4,5-b]pyrazin-5-yl)benzamide: Trifluoroacetic acid (0.33 mL, 4.2 mmol) was added to a solution of tert-butyl 4-(4-(3-(quinolin-6-ylmethyl)-3H-[1,2,3]triazolo[4,5-b]pyrazin-5-yl)benzamido)piperidine-1-carboxylate (72 mg, 0.13 mmol) in DCM (1.0 mL). After 96 hours, the reaction was concentrated by rotory evaporation. The residue was purified by prep-HPLC to give N-(piperidin-4-yl)-4-(3-(quinolin-6-ylmethyl)-3H-[1,2,3]triazolo[4,5-b]pyrazin-5-yl)benzamide (7 mg, yield 25%).

Method 9:

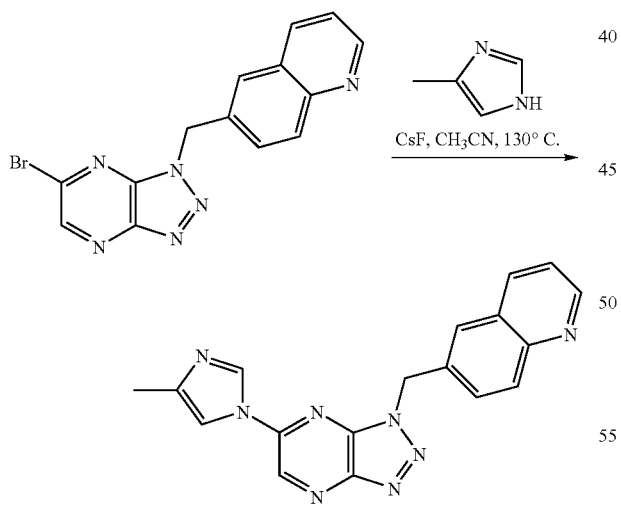

6-((6-(4-methyl-1H-imidazol-1-yl)-1H-[1,2,3]triazolo[4,5-b]pyrazin-1-yl)methyl)quinoline: A mixture of 6-((6-bromo-1H-[1,2,3]triazolo[4,5-b]pyrazin-1-yl)methyl)quinoline (50 mg, 0.15 mmol), 4-methyl-1H-imidazole (36 mg, 0.44 mmol) and CsF (25 mg, 0.16 mmol) in acetonitrile (1.45 mL) was heated in a microwave to 160° C. for 20 minutes. The reaction was diluted with water (5 mL) and the resulting suspension was filtered. The precipitate was washed with water and then purified by column chromatography using gradient elution with methanol and dichloromethane to afford 6-((6-(4-methyl-1H-imidazol-1-yl)-1H-[1,2,3]triazolo[4,5-b]pyrazin-1-yl)methyl)quinoline (28 mg, yield 56%)

Method 10:

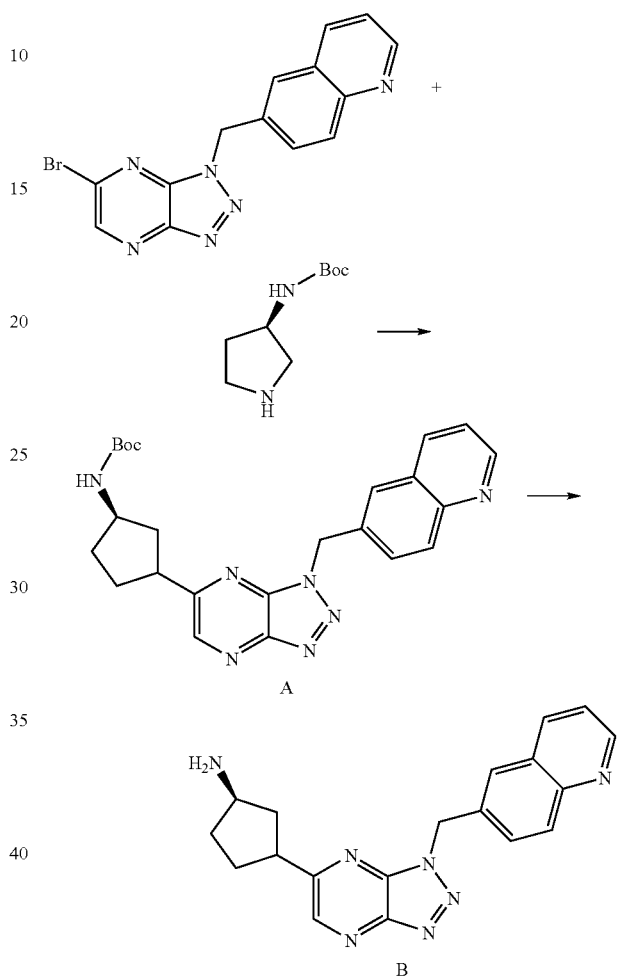

Step 1:

A mixture of 6-((6-bromo-1H-[1,2,3]triazolo[4,5-b]pyrazin-1-yl)methyl)quinoline, (200 mg, 0.5862 mmol), potassium carbonate (243 mg, 1.76 mmol), and (R)-tert-butyl pyrrolidin-3-ylcarbamate, (218 mg, 1.17 mmol) in 2-propanol (6 mL) was heated in the microwave at 80° C. for 20 min. The mixture was allowed to cool and the solids were collected by filtration then purified by flash chromatography eluting with chloroform/ethyl acetate (25-75%) to afford the desired product, A (239 mg, 91%)

Step 2:

To a solution of tert-butyl (1R)-3-(3-(quinolin-6-ylmethyl)-3H-[1,2,3]triazolo[4,5-b]pyrazin-5-yl)cyclopentylcarbamate, A (100 mg, 0.224 mmol) in dichloromethane (2.2 mL) was added hydrochloric acid (4 N in dioxane 560 μL, 2.24 mmol). After stirring at room temperature for 6 hours, the reaction was diluted with dichloromethane and quenched with saturated sodium bicarbonate (~5 mL). The organic layer was separated and concentrated to afford the desired product, B (65 mg, 84%).

Method 11:

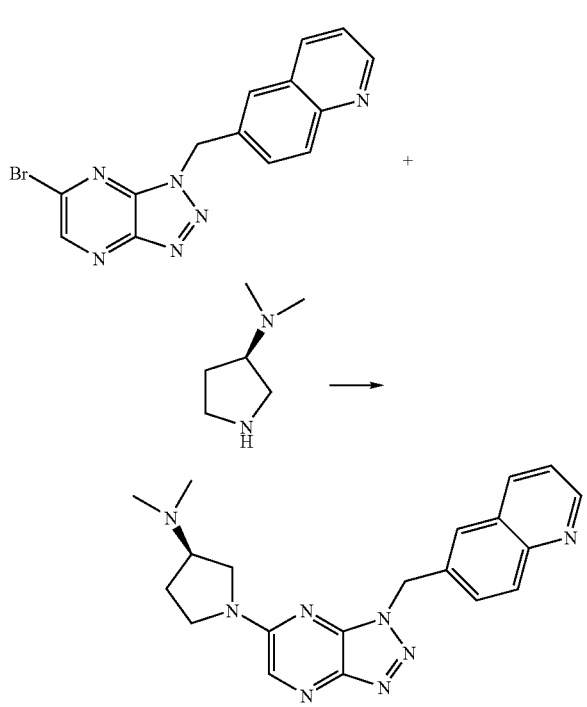

A mixture of 6-((6-bromo-1H-[1,2,3]triazolo[4,5-b]pyrazin-1-yl)methyl)quinoline (50 mg, 0.15 mmol), potassium carbonate (81 mg, 0.59 mmol), and (R)—N,N-dimethylpyrrolidine-3-amine (50 mg, 0.44 mmol) in 2-propanol (1.5 mL) was heated in the microwave at 60° C. for 10 min. The mixture was filtered and the filtrate was concentrated. The residue was purified by flash chromatography eluting with chloroform/7N ammonia in methanol (0.1-3.5%) followed by a second column eluting with chloroform/methanol (1-7%) to afford the desired product (21 mg, 36%).

Method 12:

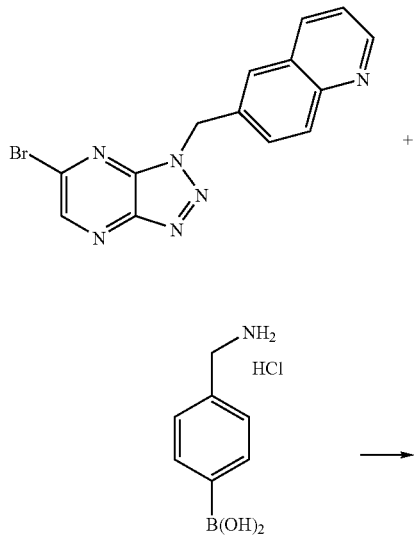

A solution of 6-((6-bromo-1H-[1,2,3]triazolo[4,5-b]pyrazin-1-yl)methyl)quinoline (50 mg, 0.15 mmol), (4-aminomethylphenyl) boronic acid hydrochloride (30 mg, 0.16 mmol), 1M sodium carbonate (601 uL) in dimethoxymethane (1.5 mL) was degassed by alternating between vacuum and nitrogen (3×), then Pd(PPh$_3$)$_2$Cl$_2$ was added and the mixture was heated to 80° C. for 1.5 hr. The reaction was cooled to room temperature and water was added and stirred. The solids were filtered then dissolved in dichloromethane (20 mL) containing ~5 drops TFA. The solution was concentrated and the residue was purified by flash chromatography eluting with chloroform/7N ammonia in methanol (0.5-7%) to afford the desired product (26 mg, 48%).

Method 13:

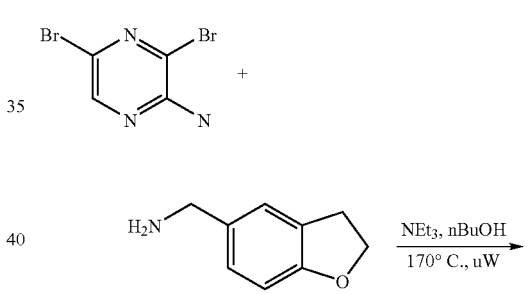

To a microwave vessel was added 3,5-dibromo-pyrazin-2-ylamine (2.0 g, 7.9 mmol), C-(2,3-Dihydro-benzofuran-5-yl)-methylamine, HCl salt (2.36 g, 12.7 mmol), triethylamine (2.22 mL, 15.8 mmol), and n-BuOH (6 mL). The reaction suspension was irradiated at 170° C. for 3 hours. The nBuOH was removed in vacuo. EtOAc (20 mL) was added to the crude mixture and washed with water (20 mL). The aqueous layer was extracted again (3×20 mL). The organics were dried over Na$_2$SO$_4$, concentrated and purified by silica gel chromatography with EtOAc:Hexanes (1:1) to give 6-bromo-N$^2$-(2,3-dihydro-benzofuran-5-ylmethyl)-pyrazine-2,3-diamine (2.11 gram, 84% yield).

Method 14:

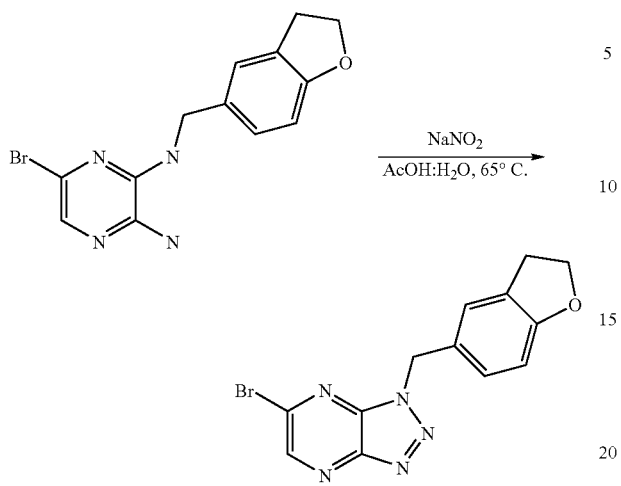

To a solution of 6-bromo-N²-(2,3-dihydro-benzofuran-5-ylmethyl)-pyrazine-2,3-diamine (1.0 g, 3.12 mmol) in AcOH:H2O (8 mL: 8 mL) was added the solution of $NaNO_2$ (2.12 g, 31.2 mmol) in water (5 mL). The mixture was stirred at room temperature for 1 hour, and then heated at 65° C. for 16 hours. The solvents were removed, and then EtOAc (20 mL) and water (20 mL) were added. The aqueous layer was extracted with EtOAc (3×20 mL). The combined extracts were dried over $Na_2SO_4$, concentrated and purified by silica gel chromatography with EtOAc: Hexanes to provide 6-bromo-1-(2,3-dihydro-benzofuran-5-ylmethyl)-1H-[1,2,3]triazolo[4,5-b]pyrazine (543 mg, 52% yield).

Method 15:

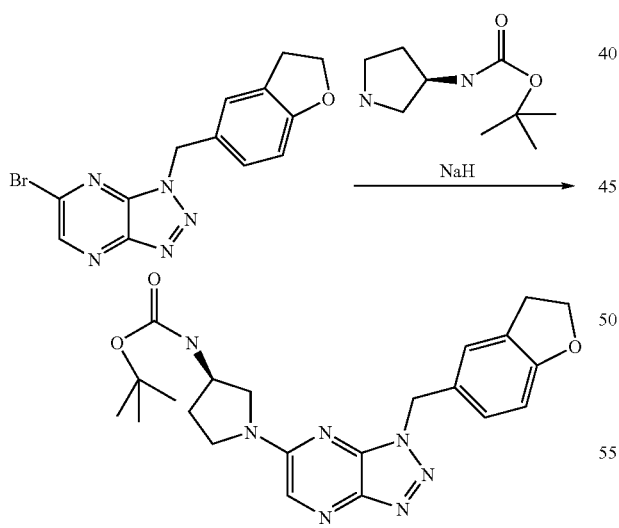

To a solution of (R)-pyrrolidin-3-yl-carbamic acid tert-butyl ester (37 mg, 0.165 mmoL) in anhydrous DMF (2 mL) was added NaH (60% in oil, 7 mg, 0.18 mmol). The solution was stirred at 23° C. for 15 minutes. 6-Bromo-1-(2,3-dihydro-benzofuran-5-ylmethyl)-1H-[1,2,3]triazolo[4,5-b]pyrazine (50 mg, 0.15 mmol) was added and the reaction solution was microwaved at 100° C. for 30 min. Water (10 mL) was added and the aqueous layer was extracted with EtOAc (3×10 mL). The combined extracts were dried with $Na_2SO_4$, and concentrated to provide {(R)-1-[3-(2,3-Dihydro-benzofuran-5-ylmethyl)-3H-[1,2,3]triazolo[4,5-b]pyrazin-5-yl]-pyrrolidin-3-yl}-carbamic acid tert-butyl ester (67 mg, 99% yield).

Method 16:

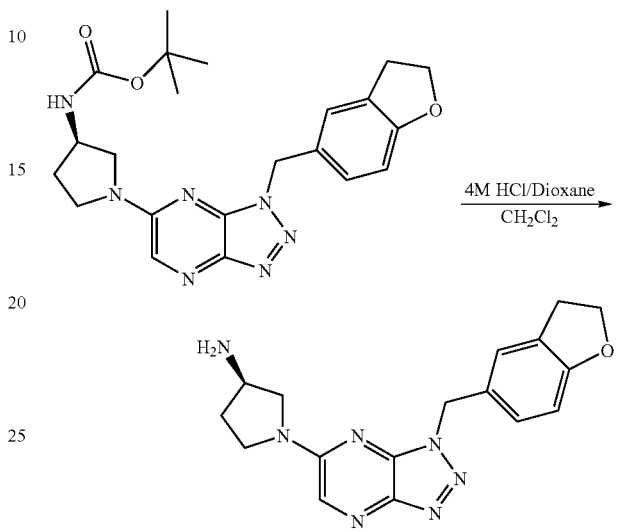

To a solution of {(R)-1-[3-(2,3-Dihydro-benzofuran-5-ylmethyl)-3H-[1,2,3]triazolo[4,5-b]pyrazin-5-yl]-pyrrolidin-3-yl}-carbamic acid tert-butyl ester (67 mg, 0.15 mmol) in $CH_2Cl_2$ (10 mL) was added 4M HCl/Dioxane dropwise (2 mL). The reaction was stirred at room temperature for 2 hours. The organic layer was decanted and the crude solid was purified with a reverse-phased preparative HPLC eluting with acetonitrile-water having 0.1% acetic acid to provide 61 mg of (R)-1-[3-(2,3-Dihydro-benzofuran-5-ylmethyl)-3H-[1,2,3]triazolo[4,5-b]pyrazin-5-yl]-pyrrolidin-3-ylamine as the acetate salt (99% yield).

Method 17:

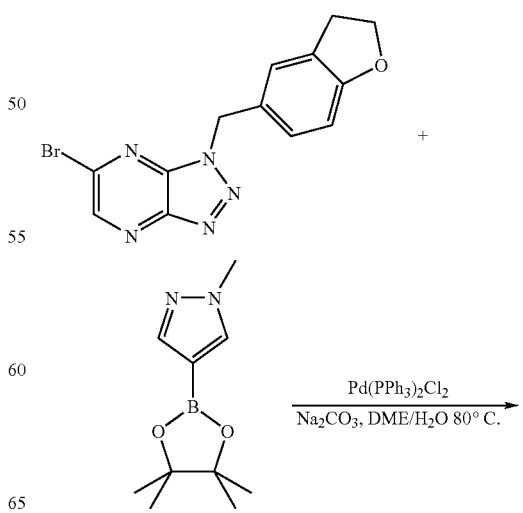

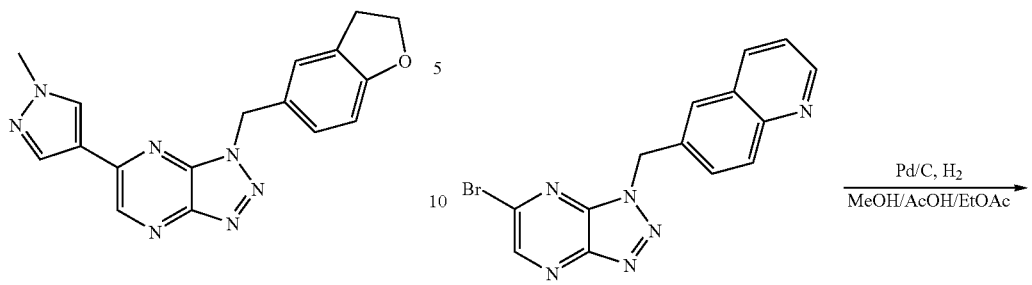

To a solution of 6-bromo-1-(2,3-dihydro-benzofuran-5-yl-methyl)-1H-[1,2,3]triazolo[4,5-b]pyrazine (50 mg, 0.15 mmol), 1-methyl-4-(4,4,5,5-tetramethyl-[1,3,2]dioxaborolan-2-yl)-1H-pyrazole (34 mg, 0.165 mmol), and sodium carbonate (48 mg, 0.45 mmol) in DME/water (4 mL/1 mL) degassed with $N_2$ was added $Pd(PPh_3)_2Cl_2$ (5 mg, 0.008 mmol). The reaction solution was degassed with $N_2$ again and stirred for 16 hours at 80° C. The reaction mixture was filtered through celite, concentrated, and purified with a reverse-phased preparative HPLC eluting with acetonitrile-water having 0.1% acetic acid to give 1-(2,3-dihydro-benzofuran-5-ylmethyl)-6-(1-methyl-1H-pyrazol-4-yl)-1H-[1,2,3]triazolo[4,5-b]pyrazine (12 mg, 24% yield).

Method 18:

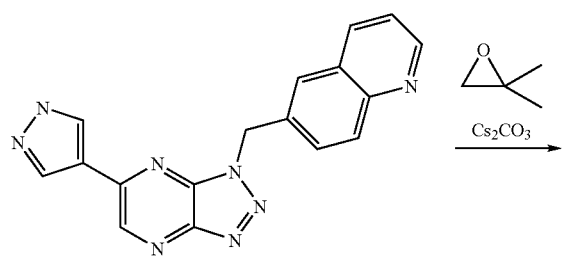

To a suspension of 6-[6-(1H-pyrazol-4-yl)-[1,2,3]triazolo[4,5-b]pyrazin-1-ylmethyl]-quinoline (50 mg, 0.15 mmol) and $Cs_2CO_3$ (50 mg, 0.15 mmol) in DMF (2 mL) was added 2,2-dimethyl-oxirane. The reaction was stirred at 80° C. for 16 hours. The reaction was then purified with a reverse-phased preparative HPLC eluting with acetonitrile-water having 0.1% acetic acid to yield 2-methyl-1-[4-(3-quinolin-6-ylmethyl-3H-[1,2,3]triazolo[4,5-b]pyrazin-5-yl)-pyrazol-1-yl]-propan-2-ol (13 mg, 22% yield).

Method 19:

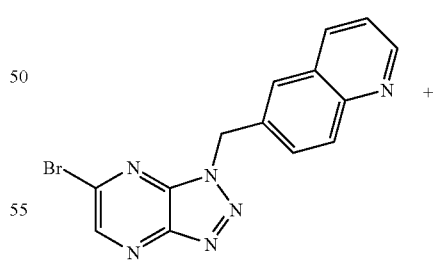

A solution of 6-(6-bromo-[1,2,3]triazolo[4,5-b]pyrazin-1-ylmethyl)-quinoline (200 mg, 0.586 mmol) in MeOH (10 mL):AcOH (1 mL): EtOAc (1 mL) was degassed 3 times with nitrogen. To this solution was added Pd/C (20 mg). A balloon containing hydrogen was added via syringe and the reaction was allowed to stir for 18 hours at room temperature. The reaction did not complete and more Pd/C was added (20 mg) and stirred for 18 hours at room temperature. The reaction was stopped when LCMS showed a ratio of 1:1 (product: starting material). The reaction was filtered over celite and washed with EtOAc (50 mL). The filtered solution was concentrated and purified by Biotage silica gel column chromatography with EtOAc: Hexanes to give 30 mg of the product 6-[1,2,3]triazolo[4,5-b]pyrazin-1-ylmethyl-quinoline (20% yield).

Method 20:

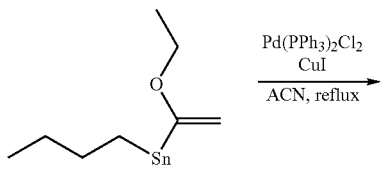

-continued

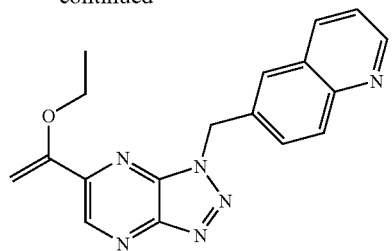

To a solution of 6-(6-bromo-[1,2,3]triazolo[4,5-b]pyrazin-1-ylmethyl)-quinoline (2 g, 5.86 mmol) in ACN (47 mL) (degassed 3 times with nitrogen) was added Pd(PPh$_3$)$_2$Cl$_2$ (205 mg, 0.293 mmol), CuI (167 mg, 0.879 mmol), and butyl-(1-ethoxy-vinyl)-stannane (5.9 mL, 17.59 mmol). The reaction was refluxed for 4 hours until the LC-MS showed complete product. The reaction was filtered over a celite pad and washed with ether (100 mL). The solution was washed with water (1×50 mL), dried over Na$_2$SO$_4$, and concentrated. The crude product was purified by silica gel column chromatography with EtOAc:Hexanes to give 1.05 g of the product 6-[6-(1-ethoxy-vinyl)-[1,2,3]triazolo[4,5-b]pyrazin-1-ylmethyl]-quinoline (55% yield).

Method 21:

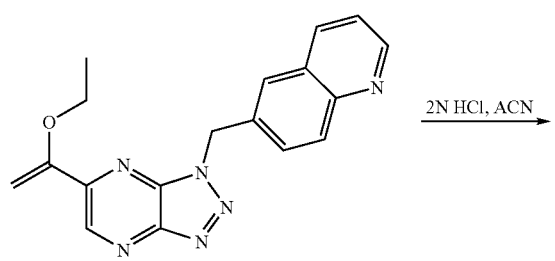

To a solution of the 6-[6-(1-ethoxy-vinyl)-[1,2,3]triazolo[4,5-b]pyrazin-1-ylmethyl]-quinoline (1.0 g, 3.00 mmol) in ACN (50 mL), was added 2 N HCl dropwise. The reaction was refluxed for 1 hour, and then neutralized with NaHCO$_3$. The solution was extracted with EtOAc (3×100 mL) to give the product 1-(3-quinolin-6-ylmethyl-3H-[1,2,3]triazolo[4,5-b]pyrazin-5-yl)-ethanone (950 mg, 99% yield).

Method 22:

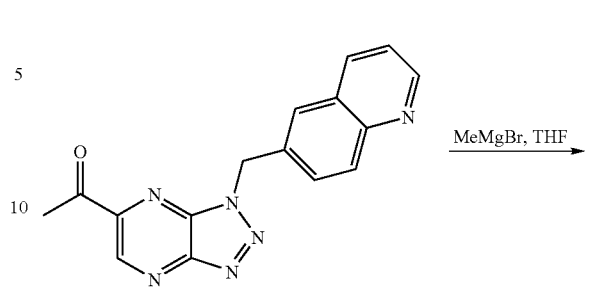

To a solution of 1-(3-quinolin-6-ylmethyl-3H-[1,2,3]triazolo[4,5-b]pyrazin-5-yl)-ethanone (100 mg, 0.33 mmol) in THF was added MeMgBr (0.260 mL, 0.362 mmol, 1.4M in toluene/THF) at 0° C. The reaction was allowed to stir for 16 hours at room temperature. The LC-MS showed a 1:1 ratio (ketone:alcohol), so another equivalent of the MeMgBr was added and the reaction was stirred for an additional 16 hours. The crude reaction was concentrated and purified by a reverse-phase C-18 preparative eluting of ACN—H$_2$O with 0.1% acetic acid HPLC to give 2-(3-quinolin-6-ylmethyl-3H-[1,2,3]triazolo[4,5-b]pyrazin-5-yl)-propan-2-ol (4 mgs, 4% yield).

Method 23:

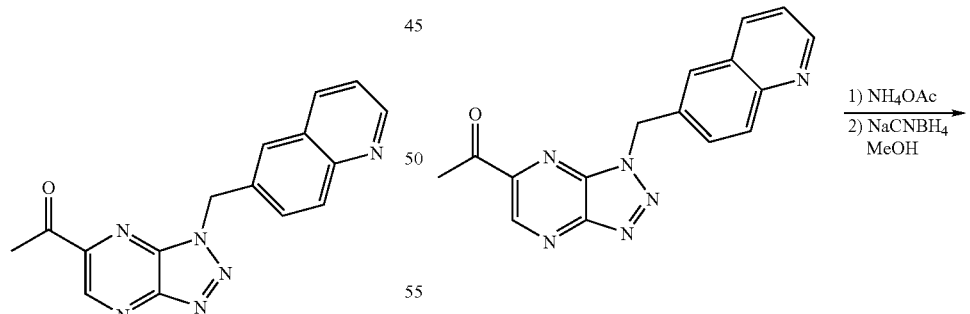

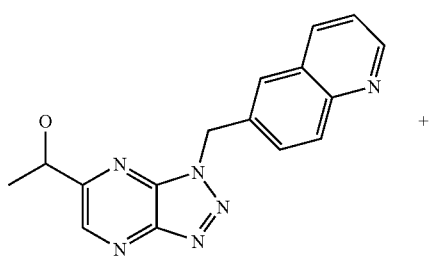

-continued

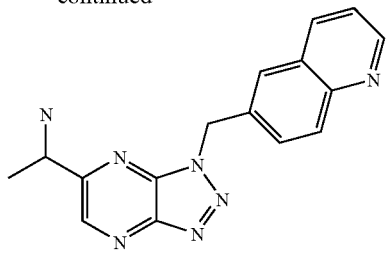

To a solution of 1-(3-quinolin-6-ylmethyl-3H-[1,2,3]triazolo[4,5-b]pyrazin-5-yl)-ethanone (150 mg, 0.493 mmol) in MeOH (5 mL) was added ammonium acetate (76 mg, 0.987 mmol). The reaction was stirred for 2 hours at room temperature. Sodium cyano borohydride (62 mg, 0.987) was added and the reaction was heated to 70° C. for 16 hours. LC-MS showed ~1:1 ratio of alcohol and amine. The reaction was concentrated and purified by a reverse-phase C-18 preparative HPLC eluting with ACN—H$_2$O having 0.1% acetic acid to give 1-(3-quinolin-6-ylmethyl-3H-[1,2,3]triazolo[4,5-b]pyrazin-5-yl)-ethanol (70 mg) and 1-(3-quinolin-6-ylmethyl-3H-[1,2,3]triazolo[4,5-b]pyrazin-5-yl)-ethylamine (20 mg).

Method 24:

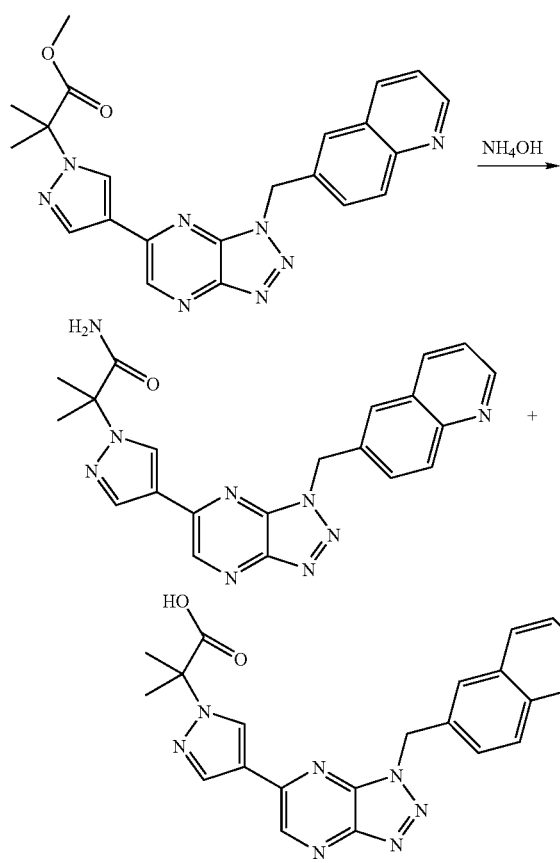

A suspension of 2-Methyl-2-[4-(3-quinolin-6-ylmethyl-3H-[1,2,3]triazolo[4,5-b]pyrazin-5-yl)-pyrazol-1-yl]-propionic acid methyl ester (50 mg, 0.116 mmol) in ammonium hydroxide (2 mL) was irradiated at 100° C. in a microwave for 30 min to give the primary amide and carboxylic acid (1:1 ratio). The reaction was concentrated and purified by Dioxnex HPLC to give 2-[4-(3-quinolin-6-ylmethyl-3H-[1,2,3]triazolo[4,5-b]pyrazin-5-yl)-pyrazol-1-yl]-isobutyramide (20 mg) and 2-methyl-2-[4-(3-quinolin-6-ylmethyl-3H-[1,2,3]triazolo[4,5-b]pyrazin-5-yl)-pyrazol-1-yl]-propionic acid (25 mg).

Method 25:

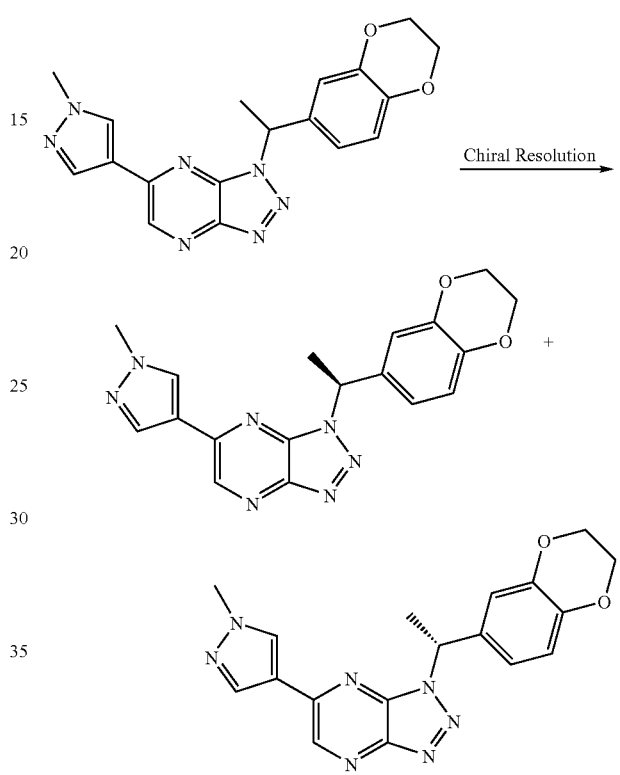

The racemic 1-[1-(2,3-Dihydro-benzo[1,4]dioxin-6-yl)-ethyl]-6-(1-methyl-1H-pyrazol-4-yl)-1H-[1,2,3]triazolo[4,5-b]pyrazine was purified by a chiral column (Chiralpak IA 4.6×250 mm 5 u column) eluting with 50% MeOH and a flow rate of 2.5 uL/min to give 1-[(S)-1-(2,3-Dihydro-benzo[1,4]dioxin-6-yl)-ethyl]-6-(1-methyl-1H-pyrazol-4-yl)-1H-[1,2,3]triazolo[4,5-b]pyrazine with an optical rotation of 0.146° in dichloromethane (5.6 mg/mL) and 1-[(R)-1-(2,3-Dihydro-benzo[1,4]dioxin-6-yl)-ethyl]-6-(1-methyl-1H-pyrazol-4-yl)-1H-[1,2,3]triazolo[4,5-b]pyrazine with an optical rotation of 0.26° in dichloromethane (9.32 mg/mL).

Method 26:

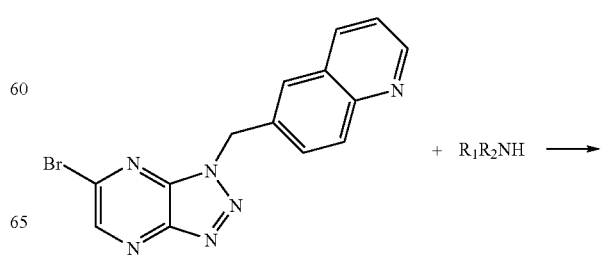

-continued

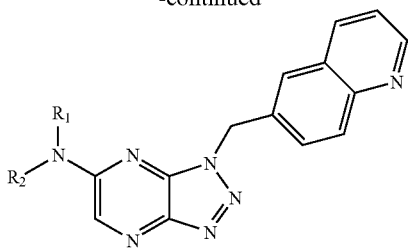

In a glove box, the following was added to a 2.0 mL Personal Chemistry Microwave reaction tube: one triangular stir bar, the appropriate heterohalide solution in NMP (320 µL, 80 µmol, 1.0 eq., 0.25 M), the appropriate amine in NMP (640 µL, 160 µmol, 2.0 eq., 0.25 M), and a solution of TEA in NMP (240 µL, 120 µmol, 1.5 eq., 0.5 M). The microwave tube was sealed with a septum cap, and outside the glove box, the reaction mixtures were heated in a Personal Chemistry Microwave Synthesizer for 15 minutes at 80° C. for secondary amines and 45 minutes at 80° C. for primary amines. The reaction mixtures were transferred into a 10×75 mm test tube. The microwave tubes were washed with DMF (0.5 mL) and the wash DMF was combined with the originally transferred material. The solvents were removed, and the residues were reconstituted in DMSO.

Method 27:

Synthesis of N-2-[1-(quinolin-6-ylmethyl)-1H-[1,2,3]triazolo[4,5-b]pyrazin-6-yl]glycinamide

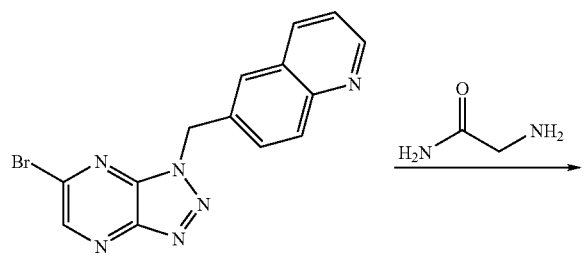

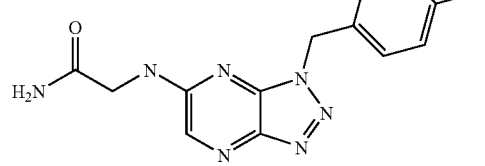

A mixture of 6-((6-bromo-1H-[1,2,3]triazolo[4,5-b]pyrazin-1-yl)methyl)quinoline, (100, 0.293), triethylamine (123 µL, 0.879 mmol), aminoacetamide hydrochloride (49 mg, 0.44 mmol) in 2-propanol (3.0 mL) was heated in the microwave at 100° C. for 10 minutes, then 120° C. for 10 minutes. The reaction mixture was diluted with dichloromethane and filtered. The precipitate was purified by flash chromatography using a Horizon purification system on a 12M column eluting with chloroform/7 N ammonia in methanol (0.1-10%) to afford the title compound (20 mg, 20%).

Synthesis of (3R)—N-methyl-1-[1-(quinolin-6-ylmethyl)-1H-[1,2,3]triazolo[4,5-b]pyrazin-6-yl]pyrrolidin-3-amine

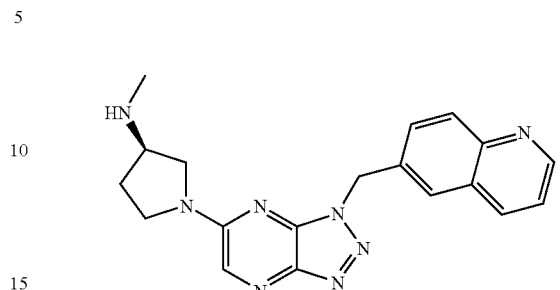

Step 1:

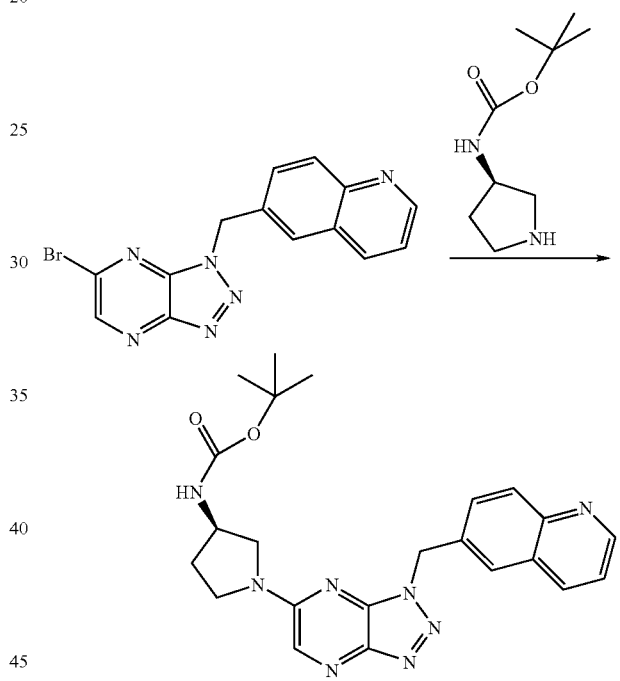

A mixture of 6-((6-bromo-1H-[1,2,3]triazolo[4,5-b]pyrazin-1-yl)methyl)quinoline (200 mg, 0.586 mmol), potassium carbonate (243 mg, 1.76 mmol), and (R)-tert-butyl pyrrolidin-3-ylcarbamate (218 mg, 1.17 mmol) in 2-propanol (6.0 mL) was heated in the microwave at 80° C. for 20 minutes. The mixture was allowed to cool and the solids were collected by filtration then purified by flash chromatography using a Horizon purification system eluting with chloroform/ethyl acetate (25-75%) to afford (R)-tert-butyl 1-(3-(quinolin-6-ylmethyl)-3H-[1,2,3]triazolo[4,5-b]pyrazin-5-yl)pyrrolidin-3-ylcarbamate, (239 mg, 91%).

$^1$H NMR (400 MHz, DMSO-d$_6$) δ ppm 1.38 (s, 9H) 1.88-1.99 (m, 1H) 2.10-2.22 (m, 1H) 3.44 (dd, J=11.49, 4.42 Hz, 1H) 3.61-3.73 (m, 3H) 4.12-4.23 (m, 1H) 5.91 (s, 2H) 7.27 (d, J=5.56 Hz, 1H) 7.53 (dd, J=8.34, 4.29 Hz, 1H) 7.76 (dd, J=8.72, 1.89 Hz, 1H) 7.93 (d, J=1.26 Hz, 1H) 8.00 (d, J=8.84 Hz, 1H) 8.21 (s, 1H) 8.33-8.38 (m, 1H) 8.89 (dd, J=4.29, 1.77 Hz, 1H)

Step 2:

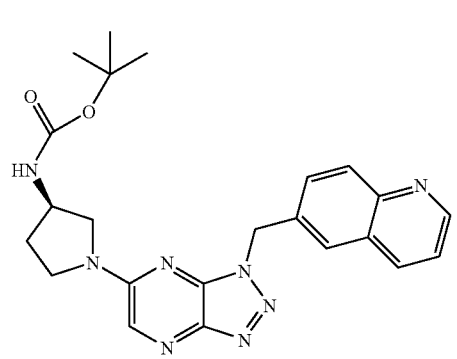

Step 3:

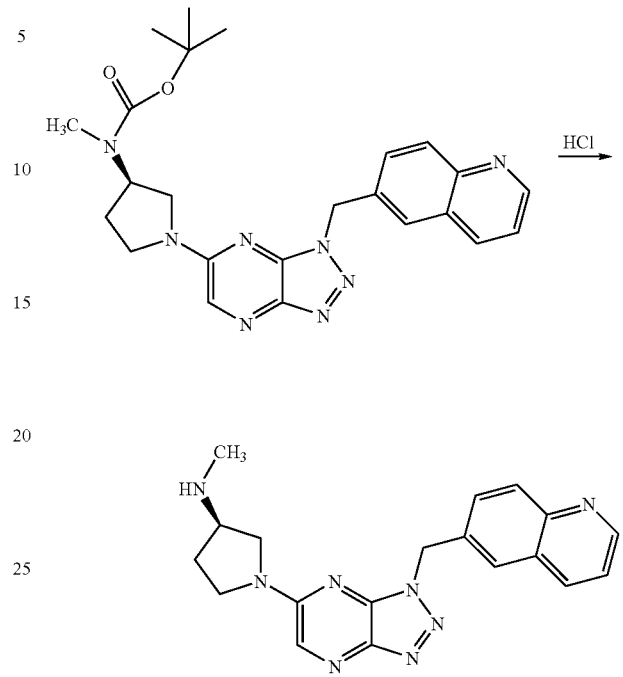

To a cooled (0° C.) solution of (R)-tert-butyl 1-(3-(quinolin-6-ylmethyl)-3H-[1,2,3]triazolo[4,5-b]pyrazin-5-yl)pyrrolidin-3-ylcarbamate (111 mg, 0.249 mmol) in tetrahydrofuran (2.0 mL) was added sodium hydride (60% dispersion in mineral oil, 15 mg, 0.37 mmol). After 30 minutes at 0° C., a solution of methyl iodide (23 uL, 0.37 mmol) in tetrahydrofuran (0.5 mL) was added dropwise over 15 minutes. The reaction mixture was allowed to warm to room temperature as the ice bath melted, stirred overnight, then quenched by adding water (1.0 mL). The tetrahydrofuran was removed in vacuo and the remaining aqueous solution was diluted with ethyl acetate (100 mL). The organic solution was washed with water (20 mL), brine (20 mL), dried (MgSO₄), filtered and concentrated. The crude product was purified by flash chromatography using a Horizon purification system on a 25S column eluting with chloroform/acetone (2-20%) to afford tert-butyl methyl{(3R)-1-[1-(quinolin-6-ylmethyl)-1H-[1,2,3]triazolo[4,5-b]pyrazin-6-yl]pyrrolidin-3-yl}carbamate (104 mg, 91%)

¹H NMR (400 MHz, CHLOROFORM-d) δ ppm 1.50 (s, 9H) 2.14-2.23 (m, 1H) 2.23-2.32 (m, 1H) 2.85 (s, 3H) 3.49 (m, 1H) 3.54-3.64 (m, 1H) 3.80-3.90 (m, 2H) 4.95 (brm, 1H) 5.89 (s, 2H) 7.44 (dd, J=8.08, 4.29 Hz, 1H) 7.82 (d, J=1.77 Hz, 1H) 7.85 (s, 1H) 8.06 (s, 1H) 8.13 (d, J=8.84 Hz, 1H) 8.17 (d, J=8.59 Hz, 1H) 8.92 (dd, J=4.17, 1.39 Hz, 1H).

To a cooled (0° C.) solution of tert-butyl methyl{(3R)-1-[1-(quinolin-6-ylmethyl)-1H-[1,2,3]triazolo[4,5-b]pyrazin-6-yl]pyrrolidin-3-yl}carbamate (101 mg, 0.219 mmol) in dichloromethane (2.2 mL) was added hydrochloric acid (4 N in dioxane, 1.10 mL, 4.39 mmol). The reaction mixture was allowed to warm to room temperature as the ice bath melted, stirred for 3 hrs, then diluted with dichloromethane (20 mL). The organic solution was washed with saturated sodium bicarbonate (5 mL) and separated. The aqueous solution was extracted with dichloromethane (3×20 mL) and the organics were combined and concentrated. The crude product was purified by flash chromatography using a Horizon purification system on a 12M column eluting with chloroform/7 N ammonia in methanol (0.1-3.5%) to afford the title compound as the free base which was converted to the dihydrochloric acid salt (56 mg, 63%)

Method 28:

Synthesis of N,N-dimethyl-2-{[1-(quinolin-6-ylmethyl)-1H-[1,2,3]triazolo[4,5-b]pyrazin-6-yl]oxy}ethanamine

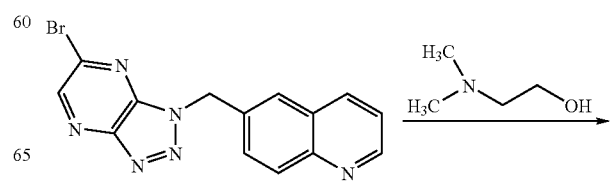

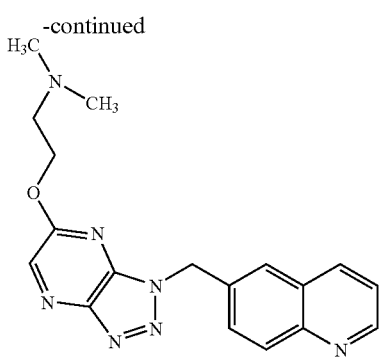

A mixture of 6-((6-bromo-1H-[1,2,3]triazolo[4,5-b]pyrazin-1-yl)methyl)quinoline, (100, 0.293), triethylamine (123 µL, 0.879 mmol), N,N-dimethylethanolamine (959 µL, 0.586 mmol) in n-butanol (3.0 mL) was heated in the microwave at 120° C. for 20 minutes, then concentrated. The crude product was purified by flash chromatography using a Horizon purification system on a 25S column eluting with chloroform/7 N ammonia in methanol (0.1-5%) to afford the title compound (75 mg, 74%).

Method 29:

Synthesis of 1-[1-(quinolin-6-ylmethyl)-1H-[1,2,3]triazolo[4,5-b]pyrazin-6-yl]pyrrolidine-3-carboxamide

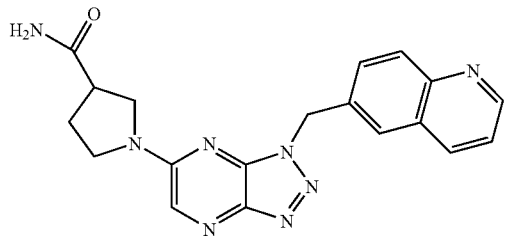

Step 1:

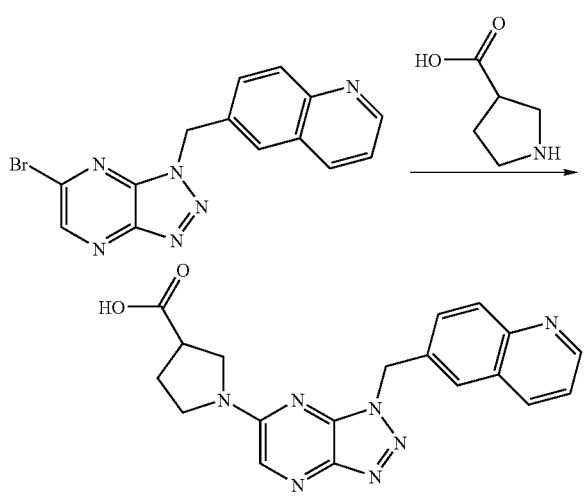

A mixture of 6-((6-bromo-1H-[1,2,3]triazolo[4,5-b]pyrazin-1-yl)methyl)quinoline, (350 mg, 1.03 mmol), potassium carbonate (436 mg, 3.16 mmol), and 3-pyrrolidine carboxylic acid (236 mg, 2.05 mmol) in n-butanol (10.0 mL) was heated in the microwave at 120° C. for 60 minutes. The reaction mixture was cooled to room temperature, filtered, rinsed with ethyl acetate, and the filtrate was concentrated. The crude product was purified by flash chromatography using a Horizon purification system on a 25S column eluting with chloroform containing 0.1% acetic acid/methanol (0.5-7%) to afford 1-[1-(quinolin-6-ylmethyl)-1H-[1,2,3]triazolo[4,5-b]pyrazin-6-yl]pyrrolidine-3-carboxylic acid (152 mg, 39%).

$^1$H NMR (400 MHz, DMSO-d$_6$) δ ppm 2.72-2.81 (m, 1H) 2.81-2.91 (m, 1H) 3.77-3.87 (m, 1H) 4.12-4.31 (m, 2H) 4.32-4.44 (m, 2H) 6.51 (s, 2H) 8.12 (dd, J=8.34, 4.29 Hz, 1H) 8.35 (dd, J=8.84, 2.02 Hz, 1H) 8.53 (d, J=1.52 Hz, 1H) 8.59 (d, J=8.59 Hz, 1H) 8.83 (s, 1H) 8.95 (dd, J=8.34, 1.01 Hz, 1H) 9.48 (dd, J=4.17, 1.64 Hz, 1H) 12.97 (s, 1H)

Step 2:

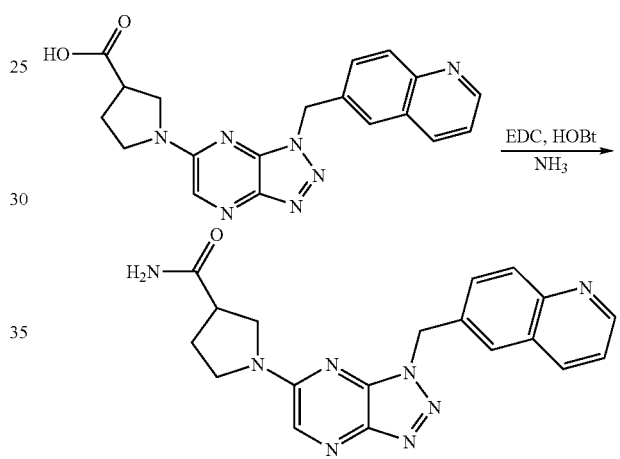

To a solution of 1-[1-(quinolin-6-ylmethyl)-1H-[1,2,3]triazolo[4,5-b]pyrazin-6-yl]pyrrolidine-3-carboxylic acid (143 mg, 0.328 mmol) and 1-hydroxybenzotriazole hydrate (93 mg, 0.69 mmol) in DMF (4.0 mL) was added N-(3-dimethylaminopropyl)-N'-ethylcarbodiimide hydrochloride (132 mg, 0.690 mmol) followed by N-methyl morpholine (159 µL, 1.31 mmol). The resulting solution was stirred for 4 hours at room temperature then ammonia (7 N in methanol, 234 µL, 1.64 mmol) was added and the reaction was stirred overnight. To the reaction was added more 1-hydroxybenzotriazole hydrate, N-(3-Dimethylaminopropyl)-N'-ethylcarbodiimide hydrochloride, and N-methyl morpholine and the solution was stirred for 1 hour at room temperature then ammonia (0.5 N in dioxane) was added. After 6 hours, the solution was diluted with methyl tert-butyl ether (100 mL) and the organic solution was washed with saturated sodium bicarbonate (2×20 mL) and brine (20 mL). The combined aqueous layers were combined and lyophilized. The resulting solids were slurried in 1:1 methanol:chloroform, filtered and the filtrate was concentrated. The crude product was purified by flash chromatography using a Horizon purification system on a 40S column eluting with chloroform/7 N methanolic ammonia (0.1-6%) to afford the title compound as the racemic mixture (86 mg, 70%). The mixture was separated by SCF chromatography to afford pure the enantiomers in 100% ee (peak 1, 37%; peak 2, 42%).

Method 30:

Synthesis of 4,4-dimethyl-1-[1-(quinolin-6-ylmethyl)-1H-[1,2,3]triazolo[4,5-b]pyrazin-6-yl]imidazolidin-2-one

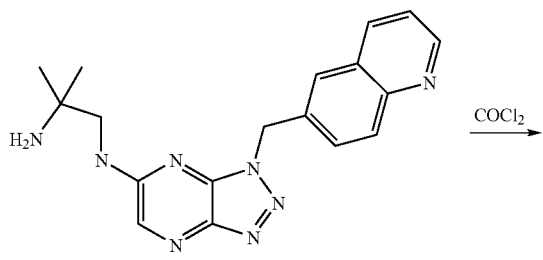

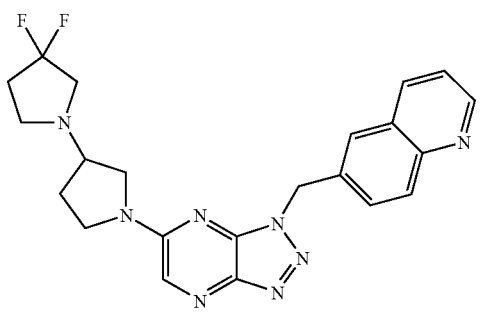

To cooled (0° C.) solution of 2-methyl-N-1-[1-(quinolin-6-ylmethyl)-1H-[1,2,3]triazolo[4,5-b]pyrazin-6-yl]propane-1,2-diamine (80 mg, 0.19 mmol) in THF (2.0 mL) and dimethylacetamide (1.0 mL) was added phosgene (20% in toluene, 110 μL, 0.21 mmol). After 1 hour the reaction mixture was concentrated and the crude product was purified by flash chromatography using a Horizon purification system on a 25S column eluting with chloroform/ethyl acetate (35-95%) to afford the title compound (37 mg, 52%).

Method 31:

Synthesis of 6-{[6-(3,3-difluoro-1,3'-bipyrrolidin-1'-yl)-1H-[1,2,3]triazolo[4,5-b]pyrazin-1-yl]methyl}quinoline

Step 1:

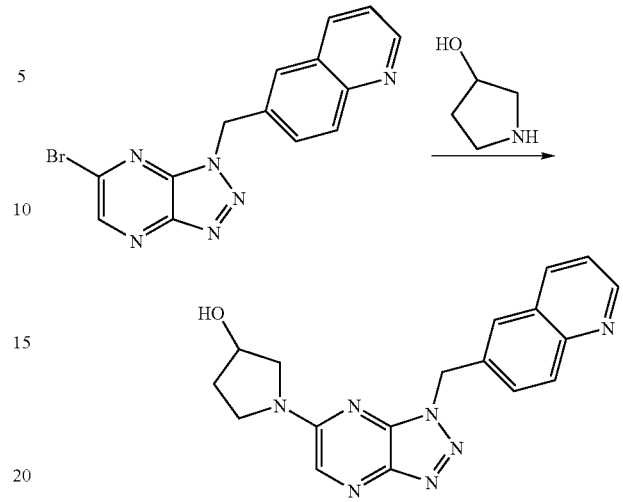

A mixture of 6-((6-bromo-1H-[1,2,3]triazolo[4,5-b]pyrazin-1-yl)methyl)quinoline (5.00 g, 14.7 mmol), pyrrolidin-3-ol (2.55 g, 29.3 mmol), and triethylamine (4.09 mL, 29.3 mmol) in 2-propanol (32 mL) was heated in the microwave for 30 minutes at 70° C. in two vials. The reaction mixtures were combined and concentrated. The crude product was purified by flash chromatography using a Horizon purification system in three batches (2×40M and 1×40S columns) eluting with chloroform/methanol (0.1-8%). The resulting solid was dissolved in chloroform containing 0.1% methanol (810 mL) and washed with water and 1:1 water:brine, dried (MgSO₄), filtered and concentrated to afford 1-[1-(quinolin-6-ylmethyl)-1H-[1,2,3]triazolo[4,5-b]pyrazin-6-yl]pyrrolidin-3-ol (5.08 g, 99%).

$^1$H NMR (400 MHz, DMSO-d6) δ ppm 1.93-1.99 (m, 1H) 2.02-2.07 (m, 1H) 3.49-3.57 (m, 1H) 3.61-3.73 (m, 3H) 4.39-4.50 (m, 1H) 5.04-5.15 (m, 1H) 5.90 (s, 2H) 7.53 (dd, J=8.34, 4.29 Hz, 1H) 7.76 (dd, J=8.72, 1.89 Hz, 1H) 7.93 (s, 1H) 8.00 (d, J=8.59 Hz, 1H) 8.22 (s, 1H) 8.36 (d, J=8.34 Hz, 1H) 8.89 (dd, J=4.17, 1.64 Hz, 1H)

Step 2:

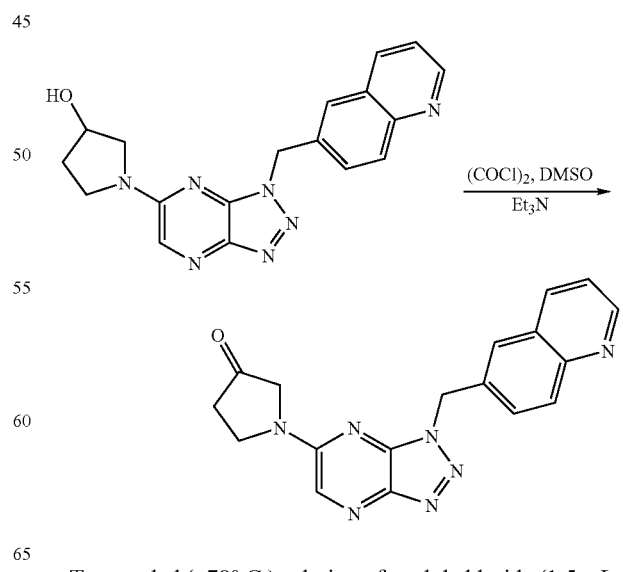

To a cooled (−78° C.) solution of oxalyl chloride (1.5 mL, 17 mmol) in dichloromethane (15 mL) was added dimethyl sulfoxide (2.45 mL, 34.5 mmol) drop wise keeping T<−70° C. After 30 minutes, a suspension of 1-[1-(quinolin-6-ylmethyl)-1H-[1,2,3]triazolo[4,5-b]pyrazin-6-yl]pyrrolidin-3-ol (1.00 g, 2.88 mmol) in dichloromethane (35 mL) was added keeping T<−70° C. After 1 hour 15 minutes, triethylamine (3.61 mL, 25.9 mmol) was added slowly, the dry-ice bath was removed, and the reaction was stirred for 2 hours. The reaction was quenched with water (50 mL), diluted with dichloromethane (150 ml), and separated. The aqueous layer was extracted with dichloromethane (2×50 mL) and the organics were combined and concentrated. The crude product was purified by flash chromatography using a Horizon purification system on a 40M column eluting with chloroform/methanol (0.5-8%) to afford 1-[1-(quinolin-6-ylmethyl)-1H-[1,2,3]triazolo[4,5-b]pyrazin-6-yl]pyrrolidin-3-one (401 mg, 40%).

$^1$H NMR (400 MHz, DMSO-d6) δ ppm 2.75 (t, J=7.71 Hz, 2H) 4.00 (t, J=7.58 Hz, 2H) 4.07 (s, 2H) 5.95 (s, 2H) 7.53 (dd, J=8.21, 4.17 Hz, 1H) 7.78 (dd, J=8.72, 1.89 Hz, 1H) 7.97 (s, 1H) 8.01 (d, J=8.59 Hz, 1H) 8.32 (s, 1H) 8.37 (d, J=8.34 Hz, 1H) 8.89 (dd, J=4.17, 1.64 Hz, 1H)

Step 3:

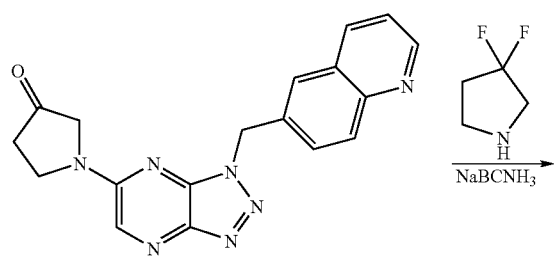

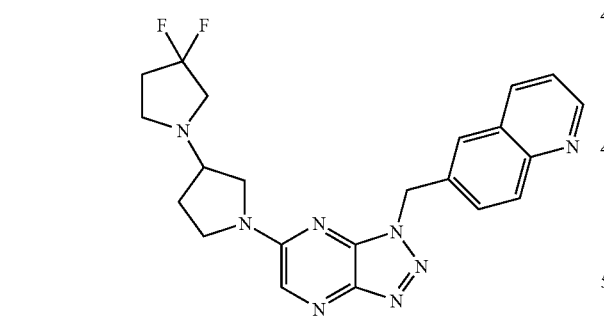

A suspension of 1-[1-(quinolin-6-ylmethyl)-1H-[1,2,3]triazolo[4,5-b]pyrazin-6-yl]pyrrolidin-3-one (50 mg, 0.15 mmol) and 3,3-difluoropyrrolidine (42 mg, 0.29 mmol) in tetrahydrofuran/methanol/dimethylacetamide (1.0 mL each) was heated to 80° C. for 2 hours then NaBCNH$_3$ (18 mg, 0.29 mmol) was added. After 2 hours the solution was cooled to room temperature and concentrated. The crude product was purified by flash chromatography using a Horizon purification system on a 25S column eluting with chloroform/acetone (5-50%) followed by a second column on a 12M cartridge eluting with chloroform/ethyl acetate (25-100%) to afford the title compound (25 mg, 40%).

Method 32:

Synthesis of 7-fluoro-6-{[6-(1-methyl-1H-pyrazol-4-yl)-1H-[1,2,3]triazolo[4,5-b]pyrazin-1-yl]methyl}-quinoline

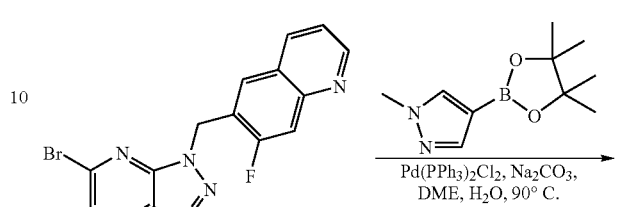

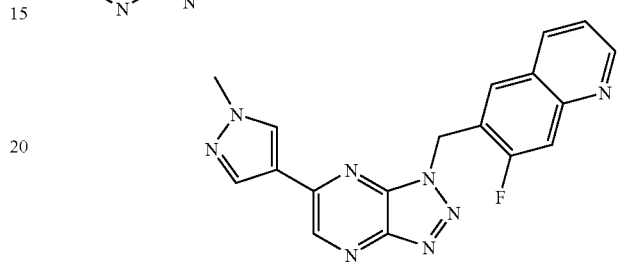

A mixture of 6-[(6-chloro[1,2,4]triazolo[4,3-b]pyridazin-3-yl)methyl]-7-fluoroquinoline (200 mg, 0.557 mmol), 1-methyl-4-(4,4,5,5-tetramethyl-1,3,2-dioxaborolan)-1H-pyrazole (139 mg, 0.668 mmol), and sodium carbonate (177 mg, 1.67 mmol) in dimethoxyethane (4.8 mL) and water (1.2 mL) was degassed by alternating between vacuum and nitrogen (5×). Bis(triphenylphosphine)-palladium(II)chloride (20 mg, 0.028 mmol) was added and the mixture was degassed again (3×). The resulting mixture was refluxed for 3 hours, cooled to room temperature and filtered. The precipitate was slurried in 1:1 methanol/chloroform, filtered and the filtrate was concentrated. The residue was dissolved in methanol/chloroform with trifluoroacetic acid and purified by flash chromatography using a Horizon purification system on a 25M column eluting with chloroform/7 N ammonia in methanol (0.1-10%) The resulting solid was dissolved in methanol/chloroform and filtered through celite to afford the title compound (161 mg, 80%).

Synthesis of 6-[(6-chloro[1,2,4]triazolo[4,3-b]pyridazin-3-yl)methyl]-7-fluoroquinoline

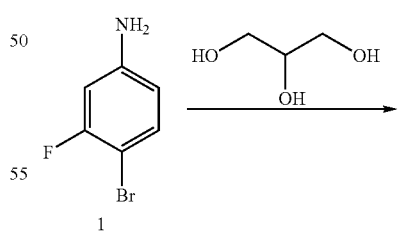

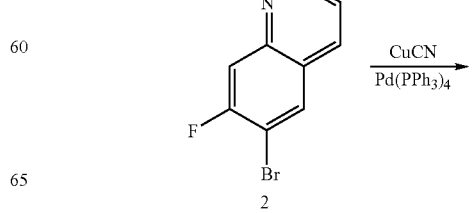

Step 2:

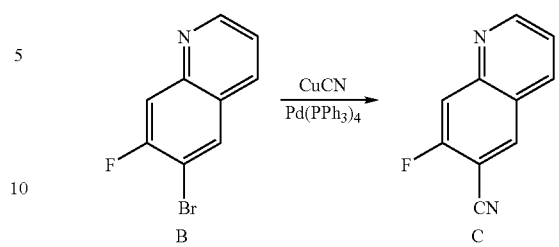

A suspension of compound B (25 g, 0.11 mol) and CuCN (12 g, 0.14 mol) in DMF (400 mL) was degassed by passing through $N_2$, then $Pd(PPh_3)_4$ (6.5 g, 0.0056 mol) was added. The reaction mixture was heated to 120° C. for 12 h. The mixture was allowed to cool to room temperature and DMF was evaporated in vacuum. The residue was poured into water (100 mL) and extracted with $CH_2Cl_2$ (1000 mL×2). The combined organic phases were evaporated and the residue was dried in vacuo to afford crude compound C, which was purified by column chromatography (silica gel, EtOAc/Petroleum ether=1:15) to yield compound C (9 g, 47.6%) as a yellow solid.

$^1$H NMR (400 MHz, MeOH): δ 9.014 (dd, 1H), 8.664 (d, 1H), 8.495 (d, 1H), 7.981 (d, 1H), 7.626 (dd, 1H).

Step 3:

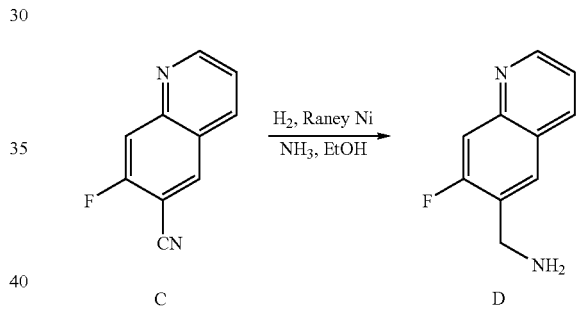

A mixture of compound C (18 g, 0.105 mol) and Raney Ni (40 g) in saturated $NH_3$-EtOH (2 L) was stirred under 1 atm of $H_2$ at room temperature for 16 h. The reaction mixture was filtered and the filtrate was concentrated in vacuum to afford crude compound D (17 g, 92.4%) as a yellow solid, which was used for the next step without purification.

$^1$H NMR (400 MHz, MeOH): δ 8.726 (s, 1H), 8.373 (d, 1H), 7.867 (d, 1H), 7.506 (d, 1H), 7.386 (dd, 1H), 3.966 (s, 2H).

Step 4:

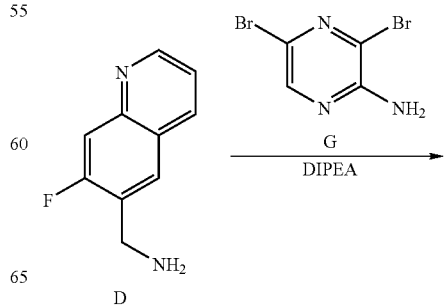

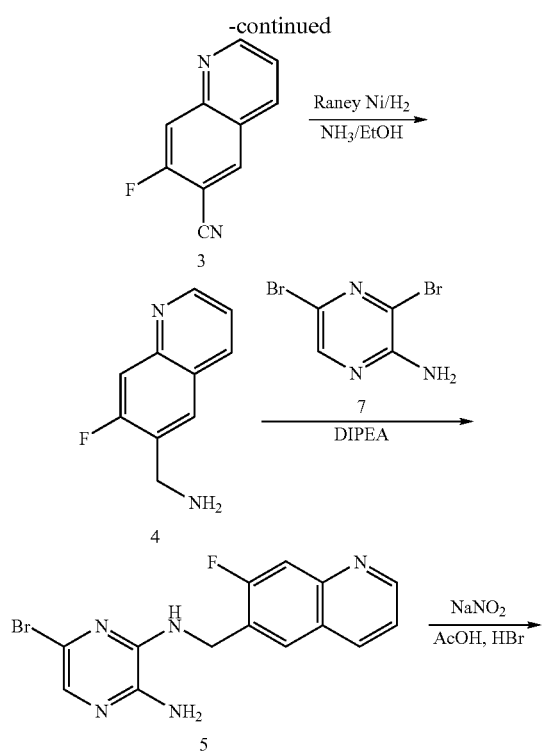

Step 1:

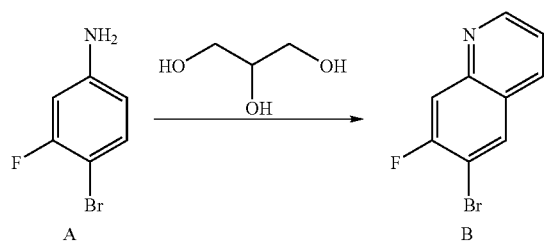

A mixture of compound A (90 g, 0.60 mol), glycerol (1800 g, 1.9 mol), ferrous sulfate (27 g, 0.0954 mol), nitrobenzene (99 mL, 0.95 mol) and concentrated sulfuric acid (261 mL, 4.77 mol) was heated at 130° C. for 14 h. The reaction mixture was allowed to cool to room temperature and basified to pH about 8 by 28% $NH_3$ solution. The resulting mixture was extracted with $CH_2Cl_2$ (1000 mL×3). The combined organic phases was evaporated and the residue was dried in vacuo to afford crude compound B, which was purified by column chromatography (silica gel, EtOAc/Petroleum ether=1:10) to yield compound B (56 g, 51.9%) as a yellow solid.

$^1$H NMR (400 MHz, $CDCl_3$): δ 8.929 (dd, 1H), 8.072 (m, 2H), 7.813 (d, 1H), 7.397 (dd, 1H).

-continued

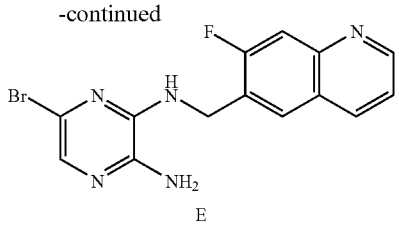

E

Step 6:

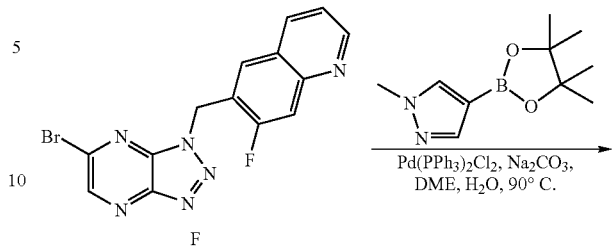

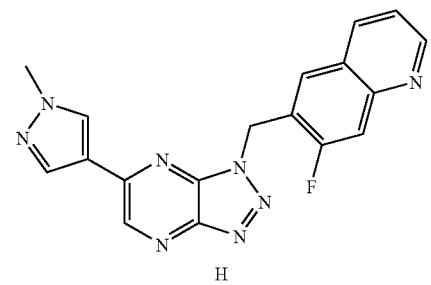

H

A mixture of compound D (17 g, 0.0966 mol), compound G (129 g, 0.116 mol) and DIPEA (18.6 mL, 0.106 mol) in DMF (320 mL) was heated at 130° C. for 14 h. Then the reaction mixture was allowed to cool to room temperature and the DMF was evaporated in vacuum. The residue was poured into ice-water and extracted with EtOAc (200 mL×3). The combined organic phases were washed with brine (200 mL), dried over anhydrous $Na_2SO_4$ and concentrated in vacuo to give crude compound E, which was purified by column chromatography (silica gel, EtOAc/Petroleum ether=1:5) to yield compound E (10 g, 29.8%) as a yellow solid.

$^1$H NMR (400 MHz, MeOH): δ 9.091 (dd, 1H), 8.920 (d, 1H), 8.339 (d, 1H), 7.908 (dd, 1H), 7.221 (s, 1H), 4.916 (d, 2H).

Step 5:

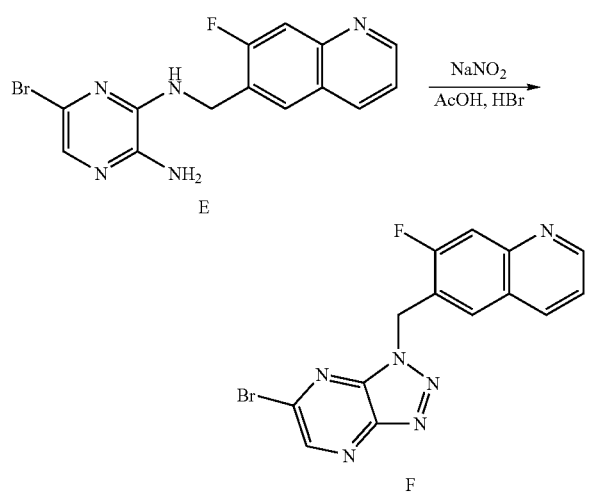

To a suspension of compound E (10 g, 0.0288 mol) in AcOH (200 mL) and water (200 mL) was added dropwise a solution of $NaNO_2$ (3 g, 0.0433 mol) in water (5 mL) at 0° C. After the addition, the resulting mixture was stirred at 0° C. for 4 h. Then the mixture was concentrated in vacuo and HBr (12 mL) was added to the mixture. The resulting mixture was stirred at room temperature for 16 h. The reaction mixture was quenched by addition of water (300 mL) and extracted with $CH_2Cl_2$ (200 mL×3). The combined organic layers were washed with saturated aq. $Na_2CO_3$ (200 mL) and brine (200 mL), dried over anhydrous $Na_2SO_4$ and concentrated in vacuo to afford crude compound F. The crude compound F was pre-purified via column chromatography (silica gel, EtOAc/Petroleum ether=1:5), and the product was washed with MeOH (20 mL) and dried to yield F (3.1 g, 30.0%) as a yellow solid.

$^1$H NMR (400 MHz, $CDCl_3$): δ 8.901 (dd, 1H), 8.761 (s, 1H), 8.101 (d, 1H), 7.776 (s, 1H), 7.752 (d, 1H), 7.393 (dd, 1H), 6.107 (s, 2H).

A mixture of 6-[(6-chloro[1,2,4]triazolo[4,3-b]pyridazin-3-yl)methyl]-7-fluoroquinoline (6) (200 mg, 0.557 mmol), 1-methyl-4-(4,4,5,5-tetramethyl-1,3,2-dioxaborolan)-1H-pyrazole (139 mg, 0.668 mmol), and sodium carbonate (177 mg, 1.67 mmol) in dimethoxyethane (4.8 mL) and water (1.2 mL) was degassed by alternating between vacuum and nitrogen (5×). Bis(triphenylphosphine)palladium(II)chloride (20 mg, 0.028 mmol) was added and the mixture was degassed again (3×). The resulting mixture was refluxed for 3 hours, cooled to room temperature and filtered. The precipitate was slurried in 1:1 methanol/chloroform, filtered and the filtrate was concentrated. The residue was dissolved in methanol/chloroform with trifluoroacetic acid and purified by flash chromatography using a Horizon purification system on a 25M column eluting with chloroform/7 N ammonia in methanol (0.1-10%) The resulting solid was dissolved in methanol/chloroform and filtered through celite to afford the title compound (7) (161 mg, 80%).

Method 33:

Synthesis of 1-(quinolin-6-ylmethyl)-1H-[1,2,3]triazolo[4,5-b]pyrazine-6-carbonitrile

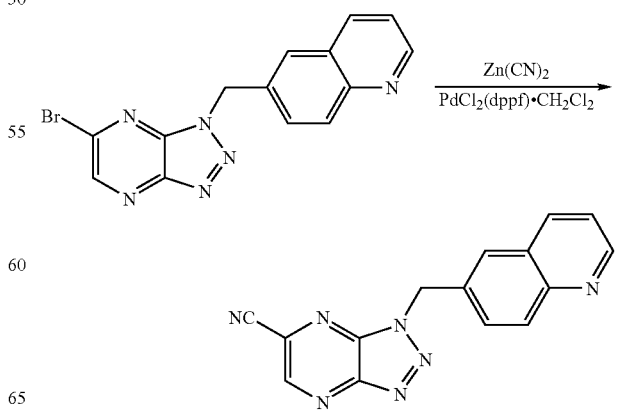

To a suspension of 6-[(6-bromo-1H-[1,2,3]triazolo[4,5-b]pyrazin-1-yl)methyl]quinoline (1.0 g, 2.93 mmol) in DMAC (70 ml) were added zinc cyanide (413 mg, 3.52 mmol). The reaction mixture was degassed then $PdCl_2(dppf) \cdot CH_2Cl_2$ (240 mg, 0.29 mmol) was added followed with triethylamine (0.828 ml) at R.T. The reaction mixture was degassed again. After heating at 85° C., the reaction mixture was filtered through a celite pad and washed with 5.0 ml of $CH_2Cl_2$. The solvents were concentrated under reduced pressure. The resulting residue was purified via flash column chromatography eluted with 1-3% 7N $N_3$ in MeOH:$CH_2Cl_2$ to give the desired product (740 mg, 88%). $^1H$ NMR (400 MHz, DMSO-$d_6$) δ ppm 6.28 (s, 2H) 7.55 (dd, J=8.34, 4.29 Hz, 1H) 7.81 (dd, J=8.72, 2.15 Hz, 1H) 7.99-8.04 (m, 2H) 8.33-8.37 (m, 1H) 8.91 (dd, J=4.04, 1.77 Hz, 1H) 9.41 (s, 1H) APCI (Mz+1) 288.2

Method 34:

Synthesis of methyl 1-(quinolin-6-ylmethyl)-1H-[1,2,3]triazolo[4,5-b]pyrazine-6-carboxylate

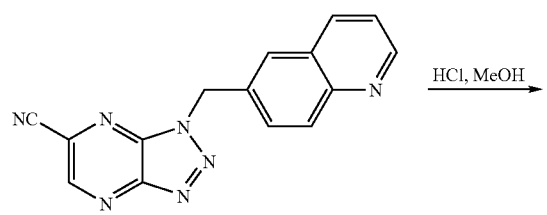

To a suspension of 1-(quinolin-6-ylmethyl)-1H-[1,2,3]triazolo[4,5-b]pyrazine-6-carbonitrile (280 mg, 0.975 mmol) in MeOH (17 ml), $H_2O$ (1.0 ml), DMSO (0.1 ml) was saturated with HCl(g) at R.T. After refluxing for 2.5 h, reaction mixture was stopped and solvents were removed under reduced pressure to give an off white solid which then was diluted in $CH_2Cl_2$ (100 ml) and washed with sat' $NaHCO_3$ (7 ml×3). The aqueous was extracted with $CH_2Cl_2$ (4×30 ml). The organic layers were combined and dried with $K_2CO_3$, filtered and concentrated. The resulting residue was purified via flash column chromatography eluted with 0-3% 7N $N_3$ in MeOH: $CH_2Cl_2$ to give desired product (200 mg, 64%).

Method 35:

Synthesis of 1-(quinolin-6-ylmethyl)-1H-[1,2,3]triazolo[4,5-b]pyrazine-6-carboxylic acid

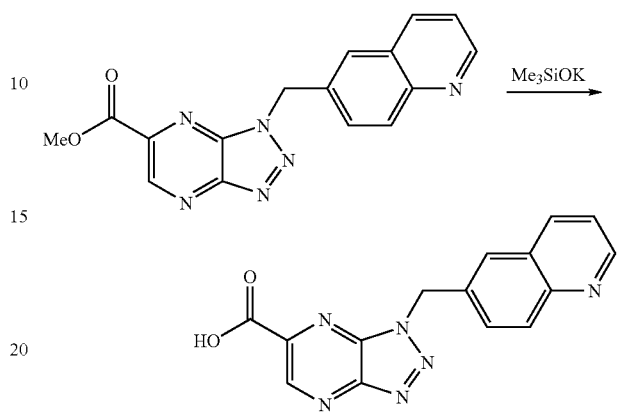

To a suspension of the methyl 1-(quinolin-6-ylmethyl)-1H-[1,2,3]triazolo[4,5-b]pyrazine-6-carboxylate (200 mg, 0.624 mmol) in THF (40 ml) cooled to 5° C. with ice bath was added potassium trimethylsilanoate (80.1 mg, 0.62 mmol). After stirring for 20 mins at 5° C., the reaction mixture was concentrated. The resulting residue was dissolved in 7 ml of DMAC and purified via reversed phase column eluted with 5-75% 0.1% TFA $H_2O$ and 0.1% TFA ACN to afford the desired product (100 mg, 66%).

Method 36:

Synthesis of N-methyl-1-(quinolin-6-ylmethyl)-1H-[1,2,3]triazolo[4,5-b]pyrazine-6-carboxamide

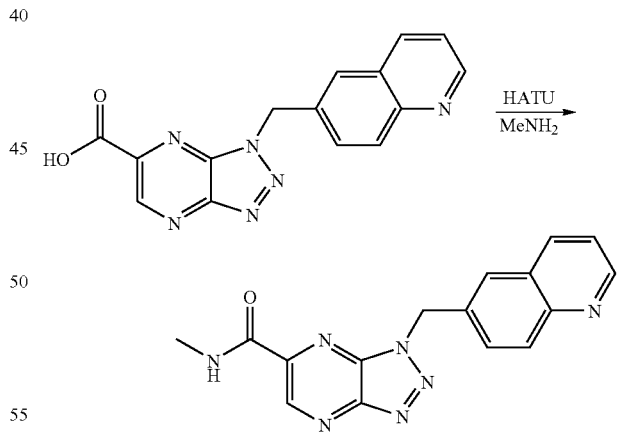

To a solution of 1-(quinolin-6-ylmethyl)-1H-[1,2,3]triazolo[4,5-b]pyrazine-6-carboxylic acid (47 mg, 0.154 mmol) in DMAC (2 ml) and N-methyl morpholine (0.202 ml, 1.84 mmol) was added CDMT (40.4 mg, 0.23 mmol) at R.T. After stirring at R.T. for 45 mins, to the reaction mixture methylamine 2M solution in THF (0.153 ml, 0.31 mmol) was added. After stirring at R.T. for 16, to the reaction mixture HATU (58 mg, 0.15 mmol) was added. After stirring at R.T. for 30 mins to the reaction mixture another 0.2 ml of methylamine 2M solution in THF was added. After stirring for 1.2 h at R.T. the reaction mixture was stopped reaction and purified as was via reversed phase eluted with 5-75% 0.1% TFA in ACN: 0.1% TFA in H₂O to give the desired product (10 mg, 20%).

Method 37:

Synthesis of 3-[(methylamino)methyl]-1-[1-(quinolin-6-ylmethyl)-1H-[1,2,3]triazolo[4,5-b]pyrazin-6-yl]pyrrolidin-3-ol

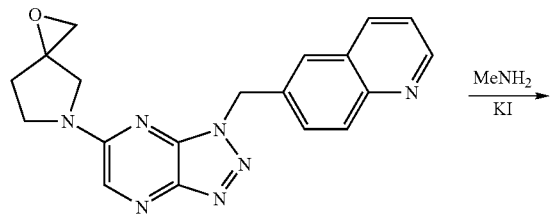

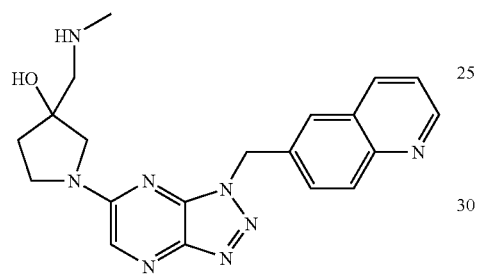

To a solution of 6-{[6-(1-oxa-5-azaspiro[2.4]hept-5-yl)-1H-[1,2,3]triazolo[4,5-b]pyrazin-1-yl]methyl}quinoline (130 mg, 0.36 mmol) in 2:1 MeOH:DMSO (3 ml) were added methylamine (24.7 mg, 0.80 mmol) and potassium iodide (300.4 mg, 1.81 mmol) at R.T. After heating at 80° C. for 3.5 h, the reaction mixture was cooled to R.T. and concentrated under reduced pressure. The resulting residue was purified via flash column chromatography eluted with 0-5% 7N N₃ in MeOH: CH₂Cl₂ to give the desired product (35 mg, 25%).

Preparation of 6-{[6-(1-oxa-5-azaspiro[2.4]hept-5-yl)-1H-[1,2,3]triazolo[4,5-b]pyrazin-1-yl]methyl}quinoline:

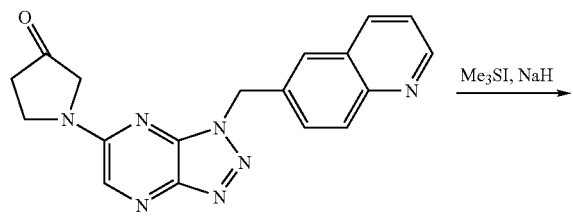

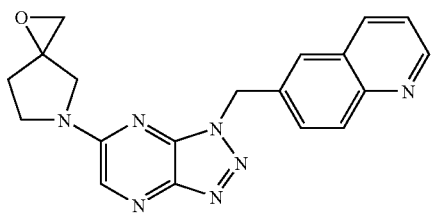

To a flamed dry 3N round bottom flask fitted with a thermometer and condenser was added 95% NaH (69 mg, 2.69 mmol) and anhydrous DMSO (5.0 ml). After stirring for 2 min at R.T. and 70° C. for 45 mins, the reaction mixture was cooled to 3° C. and a solution of trimethylsulfonium iodide (504.1 mg, 2.47 mmol) in DMSO (3.6 ml) was added. After stirring for 30 mins at 3° C., to the reaction mixture, a suspension of 1-[1-(quinolin-6-ylmethyl)-1H-[1,2,3]triazolo[4,5-b]pyrazin-6-yl]pyrrolidin-3-one (200 mg, 0.58 mmol) in 1:1 THF: DMSO (16 ml) was added dropwise. After stirring at 0° C. for 3 h, the reaction mixture was poured into an ice cold water (15 ml) and extracted with CH₂Cl₂ (4×60 ml). The organic layer was washed with brine and dried with MgSO₄ and concentrated under reduced pressure. The resulting residue was purified via flash column chromatography eluted with 10% MeOH:CH₂Cl₂ to give the desired product (130 mg 63%).

Method 38:

Synthesis of 2-({(3R)-1-[1-(quinolin-6-ylmethyl)-1H-[1,2,3]triazolo[4,5-b]pyrazin-6-yl]pyrrolidin-3-yl}amino)ethanol

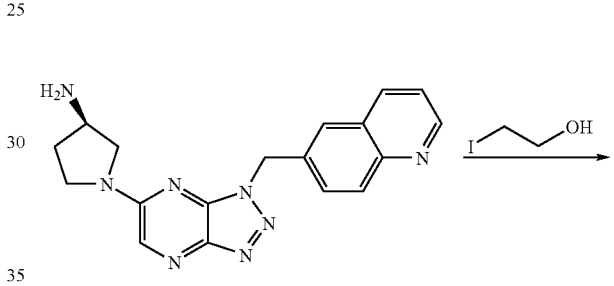

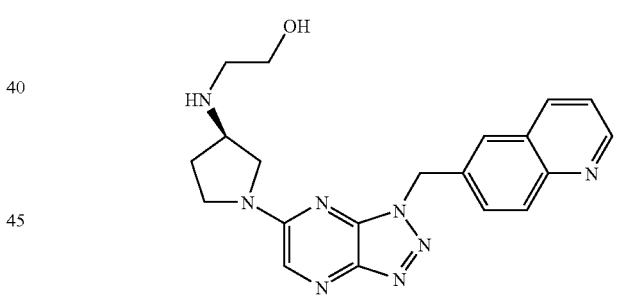

To a solution of tert-butyl {(3R)-1-[1-(quinolin-6-ylmethyl)-1H-[1,2,3]triazolo[4,5-b]pyrazin-6-yl]pyrrolidin-3-yl}carbamate (300 mg, 0.672 mmol) in anhydrous DMF (2.0 ml) was added 95% NaH (25.4 mg, 1.01 mmol). After stirring at R.T. for 10 mins, to the reaction mixture was added iodoethanol (288.9 mg, 1.68 mmol). After stirring at 70° C. for 16 h, to the reaction mixture was added iodoethanol (288.9 mg, 1.68 mmol). After stirring at 90° C. for 7 h, 105° C. for 32 h, the reaction mixture was quenched with water and filtered. The eluent was extracted with 2:1 EtOAc:toluene (2×30 ml). The organic layer was dried with K₂CO₃, filtered and concentrated. The resulting residue was dissolved in CH₂Cl₂ (10 ml) and TFA (0.5 ml) and MeOH (1 pipet drop) were added. After stirring at R.T for 16 h, the reaction mixture was concentrated. The resulting residue was purified via reversed phase column eluted with 0.1% TFA CAN: water to give the desired product (1.6 mg).

Method 39:

Synthesis of 2-(4-{1-[(7-fluoroquinolin-6-yl)methyl]-1H-[1,2,3]triazolo[4,5-b]pyrazin-6-yl}-1H-pyrazol-1-yl)ethanol

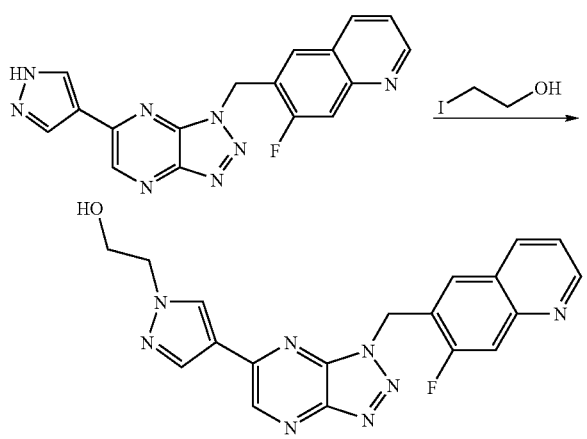

7-fluoro-6-{[6-(1H-pyrazol-4-yl)-1H-[1,2,3]triazolo[4,5-b]pyrazin-1-yl]methyl}quinoline (95 mg, 0.274 mmol), 2-iodoethanol (378 mg, 2.198 mmol), $K_2CO_3$ (75.8 mg, 0.548 mmol), DMAC 95 ml) were combined and heated in microwave at 120° C. for 4 h. The reaction mixture was concentrated and the resulting residue was purified via flash column chromatography eluted with 0-5% MeOH:$CH_2Cl_2$ to give the desired product as a solid (33.9 mg, 31%).

Preparation of 7-fluoro-6-{[6-(1H-pyrazol-4-yl)-1H-[1,2,3]triazolo[4,5-b]pyrazin-1-yl]methyl}-quinoline

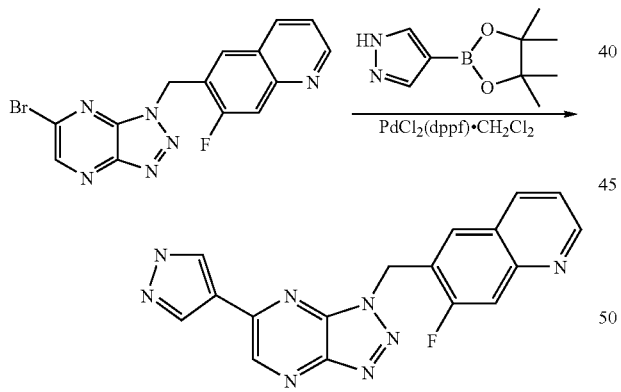

To a suspension of 6-[(6-bromo-1H-[1,2,3]triazolo[4,5-b]pyrazin-1-yl)methyl]-7-fluoroquinoline (250 mg, 0.696 mmol) and 4-(4,4,5,5-tetramethyl-1,3,2-dioxaborolan-2-yl)-pyrazole-1-carboxylic acid tert-butyl ester (225 mg, 0.766 mmol) in dimethoxyethane (8.0 ml) was added CsF (317 mg, 2.09 mmol) and water (1.05 ml) at R.T. After degassed several times, to the suspension, 1,1'-bis(diphenylphosphino)ferrocenedichloro palladium (11) 1:1 complex with $CH_2Cl_2$ (25.5 mg, 0.04 mmol) was added and the reaction mixture was degassed again. After stirring at 85° C. for 16 h, the reaction mixture was cooled down to R.T. diluted with water (10 ml) and filtered. The aqueous layer was extracted with $CH_2Cl_2$ (2×50 ml) EtOAc (1×10 ml). The combined the organic layer was dried with $K_2CO_3$ filtered and combined this with the solid filtered initially, and concentrated under reduced pressure. The resulting residue was purified via flash column chromatography eluted with 0-7% $CH_2Cl_2$:MeOH to give the desired product (220 mg 91%). $^1H$ NMR (400 MHz, DMSO-$d_6$) δ ppm 6.18 (s, 2H) 7.53 (dd, J=8.21, 4.17 Hz, 2H) 7.84 (d, J=11.37 Hz, 1H) 8.17 (d, J=8.59 Hz, 1H) 8.29 (s, 1H) 8.41-8.46 (m, 1H) 8.70 (s, 1H) 8.92 (dd, J=4.29, 1.77 Hz, 1H) 9.25 (s, 1H).

Method 40

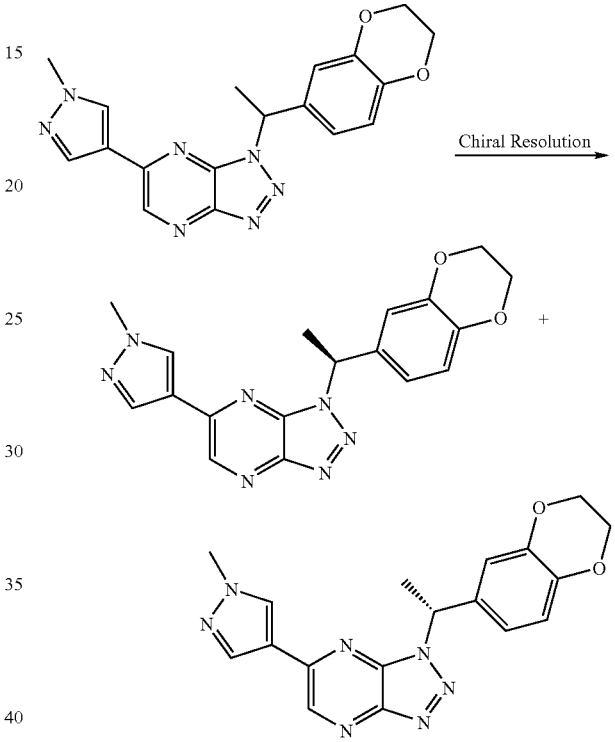

The racemic 1-[1-(2,3-Dihydro-benzo[1,4]dioxin-6-yl)-ethyl]-6-(1-methyl-1H-pyrazol-4-yl)-1H-[1,2,3]triazolo[4,5-b]pyrazine was purified by a chiral column (Chiralpak IA 4.6×250 mm 5 u column) eluting with 50% MeOH and a flow rate of 2.5 uL/min to give 1-[(S)-1-(2,3-Dihydro-benzo[1,4]dioxin-6-yl)-ethyl]-6-(1-methyl-1H-pyrazol-4-yl)-1H-[1,2,3]triazolo[4,5-b]pyrazine with an optical rotation of 0.146° in dichloromethane (5.6 mg/mL) and 1-[(R)-1-(2,3-Dihydro-benzo[1,4]dioxin-6-yl)-ethyl]-6-(1-methyl-1H-pyrazol-4-yl)-1H-[1,2,3]triazolo[4,5-b]pyrazine with an optical rotation of 0.26° in dichloromethane (9.32 mg/mL).

Method 41

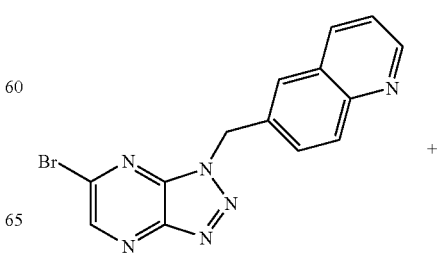

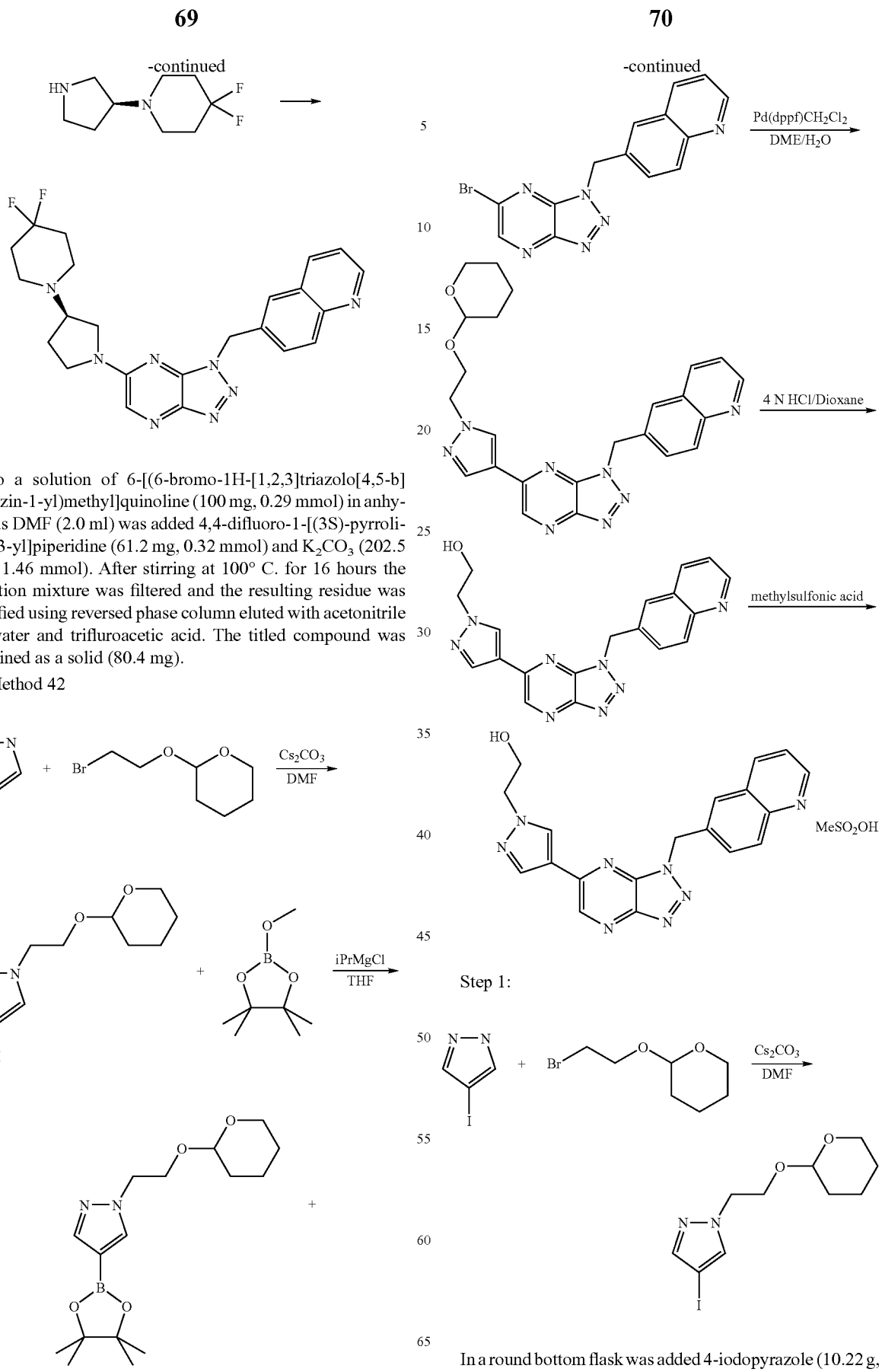

To a solution of 6-[(6-bromo-1H-[1,2,3]triazolo[4,5-b]pyrazin-1-yl)methyl]quinoline (100 mg, 0.29 mmol) in anhydrous DMF (2.0 ml) was added 4,4-difluoro-1-[(3S)-pyrrolidin-3-yl]piperidine (61.2 mg, 0.32 mmol) and K$_2$CO$_3$ (202.5 mg, 1.46 mmol). After stirring at 100° C. for 16 hours the reaction mixture was filtered and the resulting residue was purified using reversed phase column eluted with acetonitrile in water and trifluroacetic acid. The titled compound was obtained as a solid (80.4 mg).

Method 42

Step 1:

In a round bottom flask was added 4-iodopyrazole (10.22 g, 52.70 mmol), Cs$_2$CO$_3$ (20.6 g, 63.2 mmol), and anhydrous DMF (100 mL). The suspension was stirred at 23° C. for 5 min. 2-(2-bromoethoxy)tetrahydro-2H pyran (9.95 mL, 63.2 mmol) was added and the reaction was stirred at 70° C. for 16 hours. After cooling down, EtOAc (100 mL) and water (100 mL) was added to the reaction. The organic layer was collected, and the aqueous layer was extracted with EtOAc (3×100 mL). The combined organic layers were washed with water (3×100 mL), dried over $Na_2SO_4$, and concentrated to afford dark brown oil. The crude product was purified on a silica gel column eluting with ethyl acetate and hexanes to provide 4-iodo-1-[2-(tetrahydro-pyran-2-yloxy)-ethyl]-1H-pyrazole as yellow oil (14.78 g, 87% yield). $^1$H NMR (300 MHz, DMSO-d6) δ 7.89 (s, 1H) 7.52 (s, 1H) 4.47-4.56 (m, 1H) 4.25-4.35 (m, 2H) 3.81-3.96 (m, 1H) 3.66-3.75 (m, 1H) 3.45-3.57 (m, J=2.83 Hz, 1H) 3.32-3.40 (m, 1H) 1.34-1.71 (m, 6H).

Step 2:

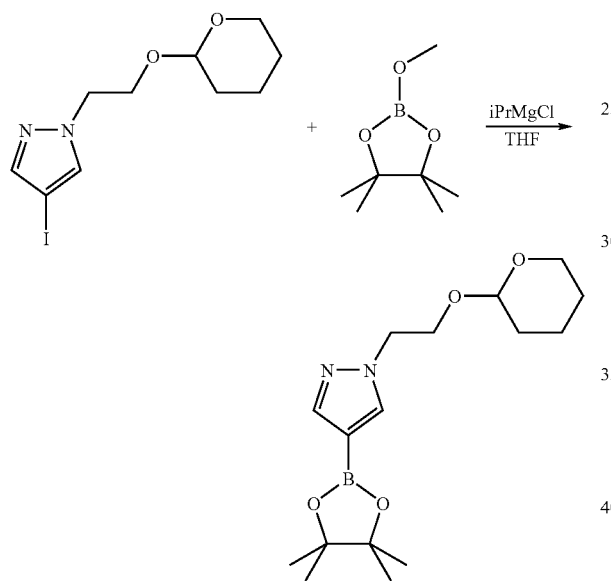

To a solution of 4-iodo-1-[2-(tetrahydro-pyran-2-yloxy)-ethyl]-1H-pyrazole (1.0 g, 3.1 mmol) in anhydrous THF (8 mL) was added iPrMgCl (2M in THF, 3.10 mL, 6.21 mmol) at 0° C. drop by drop under nitrogen. The reaction was stirred for 1 hour at 0° C. under nitrogen. To the solution was added 2-methoxy-4,4,5,5-tetramethyl-1,3,2-dioxaborolane (0.736 g, 4.66 mmoL) at 0° C. and the resulting yellow solution was allowed to stir for 1 hour at ambient temperature under nitrogen. The reaction was quenched with sat. aqueous solution of $NH_4Cl$ (10 mL). EtOAc (50 mL) and sat aqueous $NH_4Cl$ solution (10 mL) were added. The organic layer was separated, and the aqueous layer was extracted with EtOAc (3×50 mL), dried over $Na_2SO_4$, and concentrated to give the crude product as yellow oil. The oil was purified a silica gel column eluting with EtOAc and hexanes to provide 1-[2-(tetrahydro-pyran-2-yloxy)-ethyl]-4-(4,4,5,5-tetramethyl-[1,3,2]dioxaborolan-2-yl)-1H-pyrazole as clear oil (800 mgs, 80% yield). $^1$H NMR (300 MHz, DMSO-d$_6$) δ 7.91 (s, 1H) 4.48-4.54 (m, 1H) 4.26-4.33 (m, 2H) 3.86-3.90 (m, 1H) 3.66-3.76 (m, 1H) 3.45-3.57 (m, 1H) 3.33-3.39 (m, 1H) 1.33-1.70 (m, 6H) 1.24 (s, 12H).

Step 3:

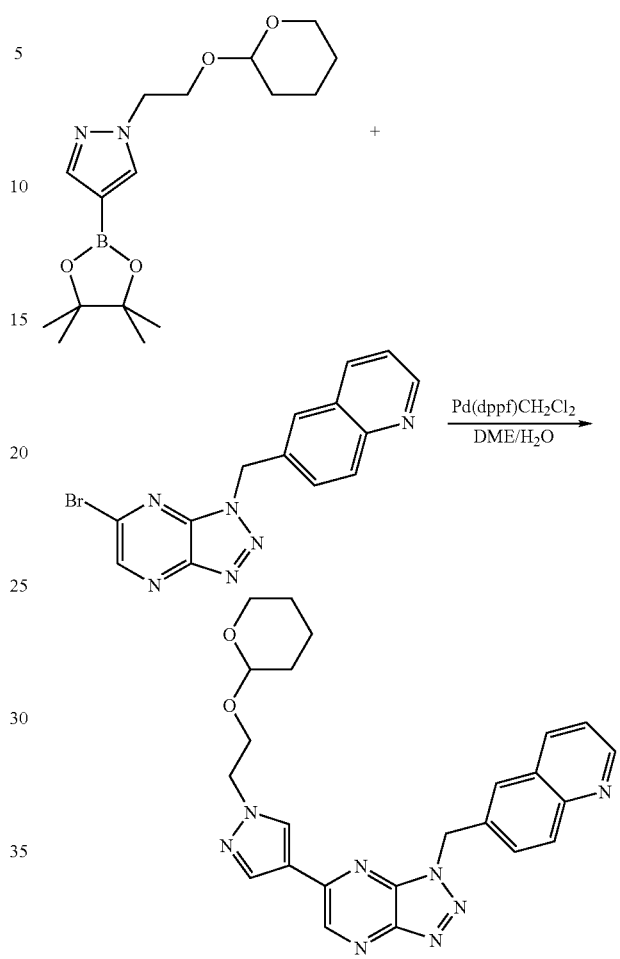

To a solution of 6-(6-bromo-[1,2,3]triazolo[4,5-b]pyrazin-1-ylmethyl)-quinoline (845 mg, 2.48 mmol) in DME (16 mL) was added 1-[2-(tetrahydro-pyran-2-yloxy)-ethyl]-4-(4,4,5,5-tetramethyl-[1,3,2]dioxaborolan-2-yl)-1H-pyrazole (800 mgs, 2.48 mmol) and $Cs_2CO_3$ (2.42 g, 7.43 mmol) in $H_2O$ (4 mL). The reaction mixture was degassed and charged with nitrogen for three times. The palladium catalyst Pd(dppf).$CH_2Cl_2$ (101 mg, 0.124 mmol) was added and the reaction mixture was degassed and charged with nitrogen for three times, and stirred for 16 hours at 80° C. under nitrogen. The reaction mixture was then filtered over a pad of Celite, and washed with EtOAc (50 mL) and water (25 mL). The filtrate was extracted with EtOAc (3×50 mL). The organics were dried over $Na_2SO_4$, filtered, and concentrated in vacuo. The crude product was purified with a Biotage silica gel column chromatography (40+S, 0-50% EtOAc/Hexanes 5CV (column volume), 50-100% EtOAc/Hexanes 10 CV, 100% EtOAc 10 CV) to provide 6-(6-{1-[2-(tetrahydro-pyran-2-yloxy)-ethyl]-1H-pyrazol-4-yl}-[1,2,3]triazolo[4,5-b]pyrazin-1-ylmethyl)-quinoline (910 mgs, 81% yield) as a solid. $^1$H NMR (300 MHz, DMSO-d6) δ 9.23 (s, 1H) 8.82-8.95 (m, 1H) 8.67 (s, 1H) 8.28-8.45 (m, 2H) 7.92-8.08 (m, 2H) 7.77-7.90 (m, 1H) 7.53 (dd, J=8.29, 4.14 Hz, 1H) 6.15 (s, 2H) 4.49-4.62 (m, 2H) 4.30-4.47 (m, 2H) 3.91-4.00 (m, 1H) 3.67-3.87 (m, J=5.46 Hz, 1H) 3.47-3.60 (m, 1H) 3.35-3.42 (m, 1H) 1.48-1.66 (m, 2H) 1.32-1.45 (m, 3H).

Step 4:

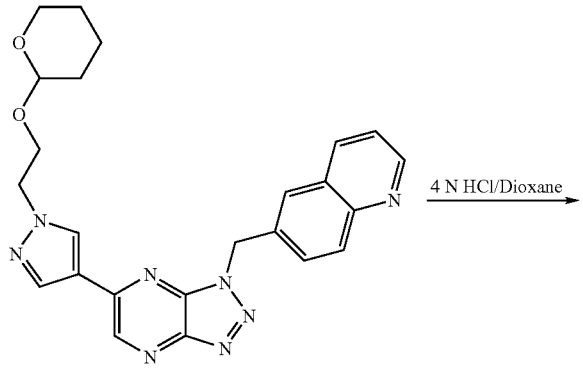

To a solution of 6-(6-{1-[2-(tetrahydro-pyran-2-yloxy)-ethyl]-1H-pyrazol-4-yl}-[1,2,3]triazolo[4,5-b]pyrazin-1-yl-methyl)-quinoline (780 mg, 1.71 mmol) in CH₂Cl₂ (20 mL) was added the anhydrous HCl dioxane solution dropwise (4N, 1.07 mL, 4.27 mmol). A white solid was precipitated out. The reaction mixture was stirred for 1 hour and the LCMS showed the completion of the reaction. The reaction mixture was concentrated, and the residue was dissolved in distilled water (15 mL). The solution was adjusted to pH 7 with Na₂CO₃. An off-white solid was crashed out, which was filtered, washed with water, and dried on a high vacuum for 1 hour. The solid was re-crystallized from EtOH (50 mL) to provide 2-[4-(3-Quinolin-6-ylmethyl-3H-[1,2,3]triazolo[4,5-b]pyrazin-5-yl)-pyrazol-1-yl]-ethanol (400, 63% yield) as a white crystalline solid with a melting point of 222° C. ¹H NMR (400 MHz, DMSO-d6) δ 9.22 (s, 1H) 8.89 (dd, J=4.14, 1.70 Hz, 1H) 8.63 (s, 1H) 8.37 (dd, J=8.38, 1.04 Hz, 1H) 8.32 (s, 1H) 7.98-8.04 (m, 2H) 7.82 (dd, J=8.67, 2.07 Hz, 1H) 7.53 (dd, J=8.29, 4.14 Hz, 1H) 6.15 (s, 2H) 4.96 (t, J=5.27 Hz, 1H) 4.24 (t, J=5.46 Hz, 2H) 3.78 (q, J=5.46 Hz, 2H).

Step 5:

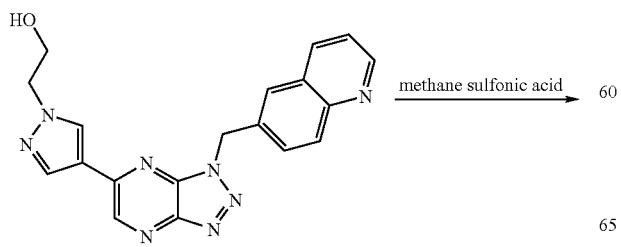

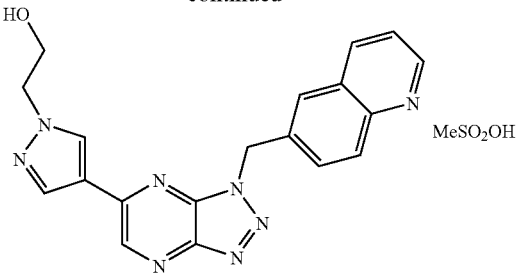

In an Erlenmeyer flask (500 mL) containing 2-[4-(3-quinolin-6-ylmethyl-3H-[1,2,3]triazolo[4,5-b]pyrazin-5-yl)-pyrazol-1-yl]-ethanol (3.76 mmol, 1.469 g) was added EtOH (180 mL). The solution was heated until it started boiling (not all of solid was dissolved), and a freshly prepared ethanol solution of methane sulfonic acid (1.28 M, 3.09 mL, 3.95 mmol) was added. A clear solution was obtained after addition of acid. The solution was then heated to boil, and cooled to ambient temperature naturally with stirring for overnight. The small crystals began to form after cooling about 5 minutes. After stirring for overnight at ambient temperature, the crystalline solid was filtered, washed with small amount of ethanol, and dried under high vacuum for 3 hours. A white crystalline solid was obtained (1.623 g, 92% yield); melting point: 202-203° C. Elemental Analysis: Calc: C-51.28%, H 4.30%, N 23.92%; Found: C-51.27%, H-4.32%, N 24.04%; ¹H NMR (400 MHz, DMSO-d6) δ 9.24 (s, 1H) 9.12 (d, J=4.71 Hz, 1H) 8.79 (d, J=8.48 Hz, 1H) 8.64 (s, 1H) 8.33 (s, 1H) 8.10-8.22 (m, 2H) 7.98-8.09 (m, 1H) 7.83 (dd, J=8.48, 4.71 Hz, 1H) 6.22 (s, 2H) 4.24 (t, J=5.27 Hz, 2H) 3.79 (t, J=5.37 Hz, 2H), 2.32 (s, 3H).

Method 43

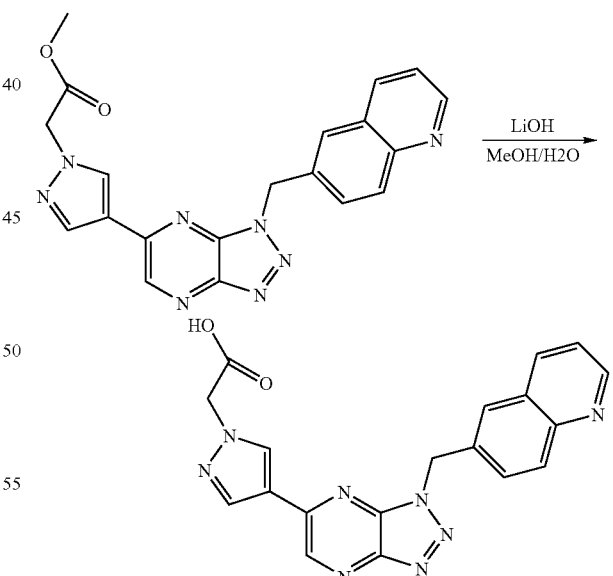

To a solution of [4-(3-quinolin-6-ylmethyl-3H-[1,2,3]triazolo[4,5-b]pyrazin-5-yl)-pyrazol-1-yl]-acetic acid methyl ester (242 mgs, 0.60 mmol) in MeOH (4 mL) was added a freshly prepared solution of LiOH (72 mgs, 3.02 mmol) in water (1 mL). The reaction was stirred for 16 hours at ambient temperature. The white suspension was then neutralized to pH 7 with 1 N HCl, and a white solid precipitated out. The solid was filtered, washed with water, and dried under a high vacuum for 16 hours to afford [4-(3-quinolin-6-ylmethyl-3H-[1,2,3]triazolo[4,5-b]pyrazin-5-yl)-pyrazol-1-yl]-acetic acid (131 mgs, 56% yield).

Method 44

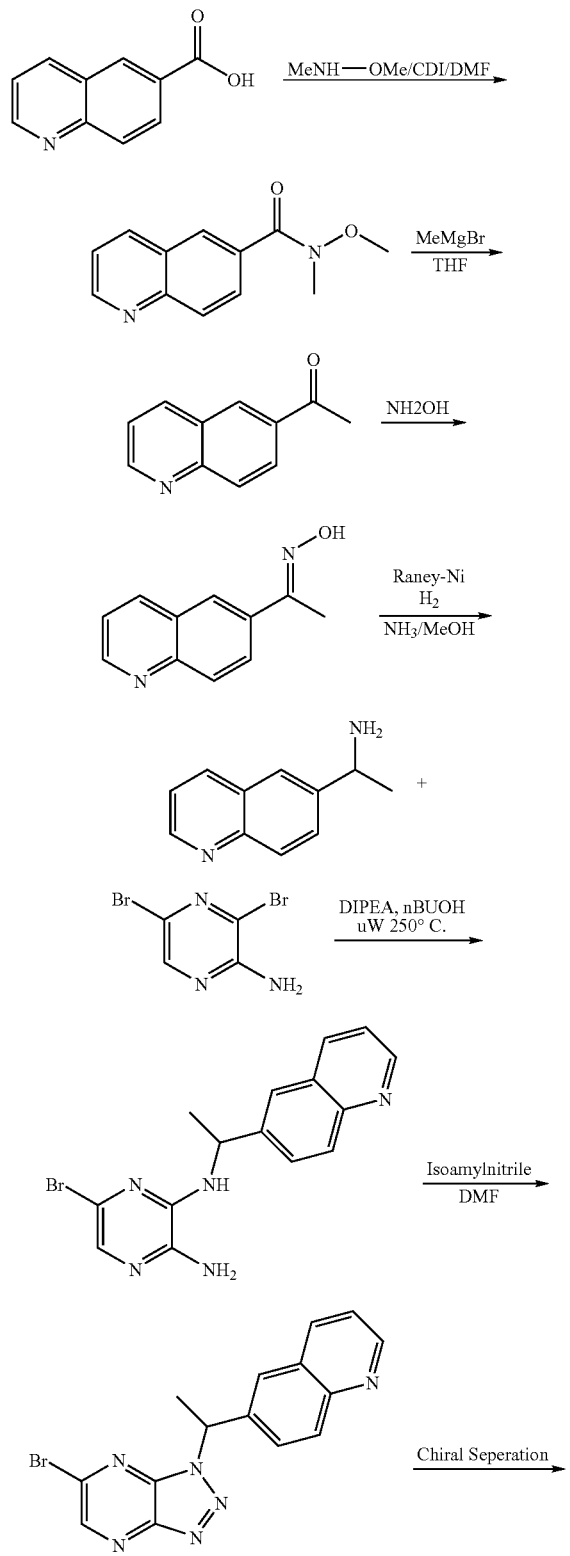

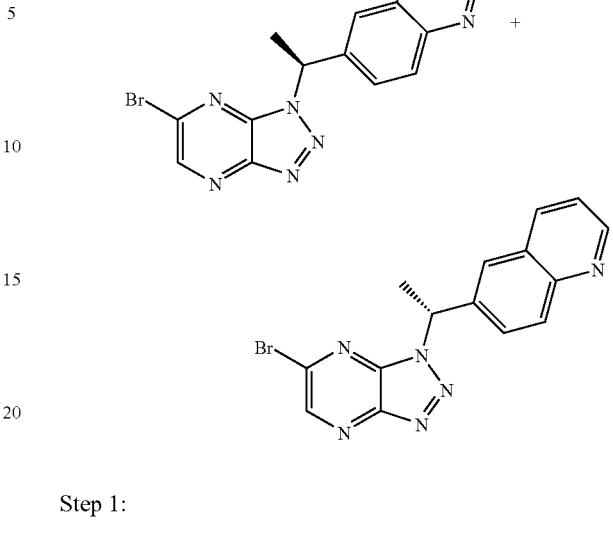

Step 1:

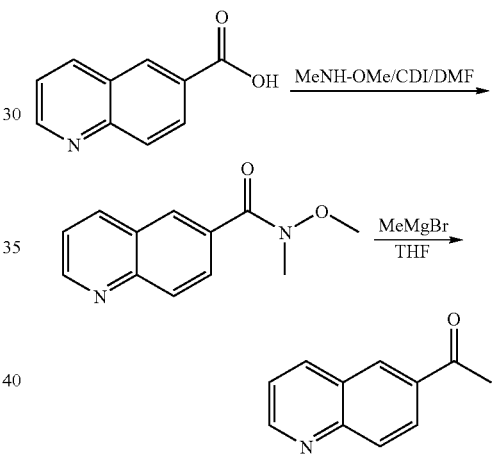

To a solution of quinoline-6-carboxylic acid (10 g, 57.75 mmol) in DMF (200 mL) was added carbonyl diimidazole (10.3 g, 62.5 mmol) under nitrogen. The reaction was stirred for 1 hour. To the solution was added N,O-dimethyl hydroxylamine (5.6 g, 57.75 mmol), and the reaction was stirred at ambient temperature for 16 hours. The reaction was diluted with EtOAc (150 mL) and water (150 mL). The organic layer was separated, and the aqueous layer was extracted with EtOAc (5×100 mL). The organics were combined and washed with water (3×100 mL), brine (2×100 mL), dried over $Na_2SO_4$, filtered and concentrated to give quinoline-6-carboxylic acid methoxy-methyl-amide (11.97 g, 97% yield).

To a solution of quinoline-6-carboxylic acid methoxy-methyl-amide (11.97 g, 55.35 mmol) in anhydrous THF (200 mL) was added MeMgBr (1.5 M in THF, 55 mL, 83 mmol) at 0° C. under nitrogen. The reaction was allowed to warm to ambient temperature over 16 hours. Sat. $NH_4Cl$ (20 mL) was added to quench the reaction. The reaction solution was then extracted with EtOAc (3×50 mL). The combined organics were dried over $Na_2SO_4$, filtered, and concentrated to give 1-quinolin-6-yl-ethanone (9.2 g, 97% yield).

Step 2:

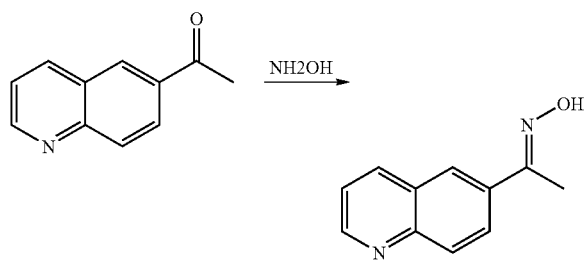

To a suspension of hydroxylamine hydrochloride in EtOH (150 mL) was added a suspension of NaOH (2.4 g, 59.7 mmol) in EtOH (25 mL). The reaction mixture was stirred at ambient temperature for 15 minutes. The precipitated sodium hydrochloride was filtered off. A solution of 1-quinolin-6-yl-ethanone (9.3 g, 54.25 mmol) in EtOH (150 mL) was added. The reaction solution was stirred for 16 hours at ambient temperature. EtOH was removed in vacuum to give 1-quinolin-6-yl-ethanone oxime (10.1 g, >99% yield).

Step 3:

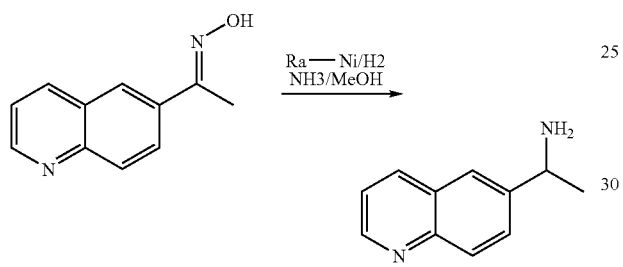

To a solution of 1-quinolin-6-yl-ethanone oxime (4.54 g, 24.4 mmol) in EtOH (50 mL) was added methanol solution of $NH_3$ (7N, 12 mL, 80 mmol). A slurry of Raney Nickel (washed 3× with EtOH) about 2 g was added followed by a hydrogen-filled balloon. The reaction was stirred at ambient temperature for 16 hours under hydrogen-filled balloon. The reaction mixture was filtered over a pad of celite and the mother liquor was concentrated to give quantitative 1-quinolin-6-yl-ethylamine (4.1 g).

Step 4:

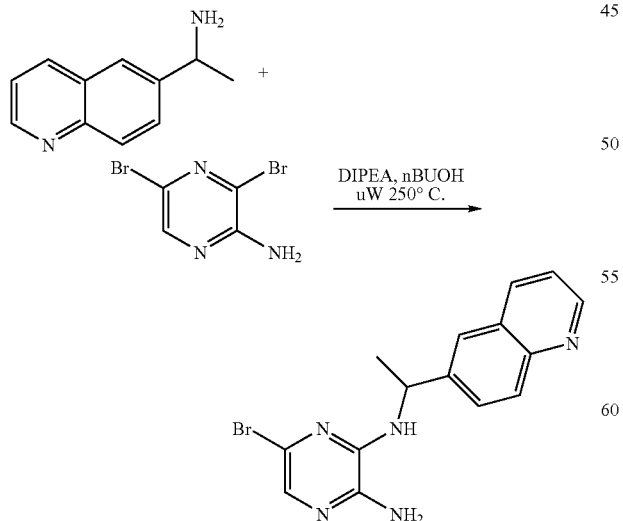

To a solution of 2-amino-dibromopyrazine (5.1 g, 20 mmol) and 1-quinolin-6-yl-ethylamine (3.43 g, 20 mmol) in n-BuOH (5 mL) was added DIPEA (10.5 mL, 60 mmol). The reaction was irradiated in a microwave at 225° C. for 1 hour. The reaction mixture was concentrated and purified by column chromatography Biotage 40+M 0-50% EtOAc:Hexanes (7 column volume), 50-100% (10 column volume), and EtOAc with 10% MeOH to give 5-bromo-N*3*-(1-quinolin-6-yl-ethyl)-pyrazine-2,3-diamine (2.1 g, 66%).

Step 5:

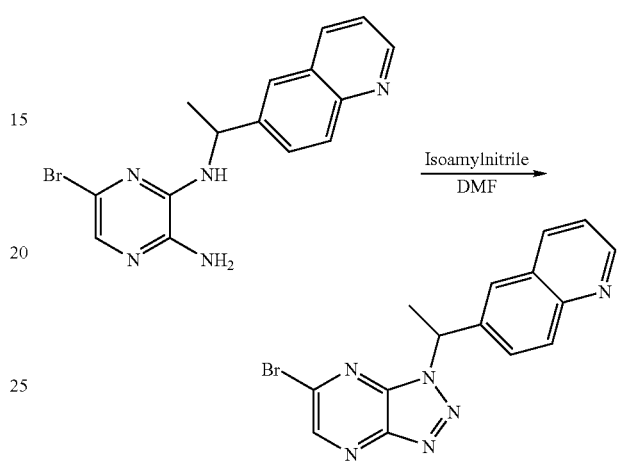

To a solution of the 5-bromo-N*3*-(1-quinolin-6-yl-ethyl)-pyrazine-2,3-diamine in anhydrous DMF (25 mL) was added isoamyl nitrile (0.98 mL, 1.2 mmol) at 0° C. The reaction was stirred at 0° C. for 5 min, then the ice bath was removed and allowed to stir at ambient temperature for 5 min. The reaction was then heated at 70° C. for 1 hour, cooled and quenched with sat. aqueous solution of $Na_2SO_3$ (10 mL). Water (50 mL) and EtOAc (50 mL) were added. The organic layer was separated and the aqueous layer was extracted with EtOAc (4×100 mL). The combined organics were washed with $NaHCO_3$ (50 mL) and water (3×50 mL), dried over $Na_2SO_4$, filtered and concentrated to give 6-[1-(6-bromo-[1,2,3]triazolo[4,5-b]pyrazin-1-yl)-ethyl]-quinoline (1.56 g, 72% yield).

Step 6:

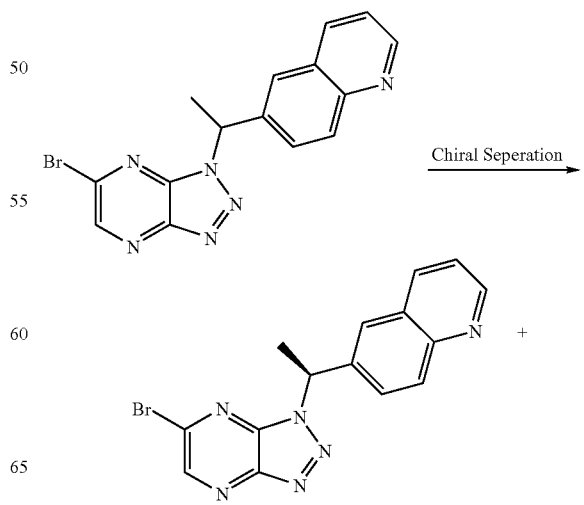

-continued

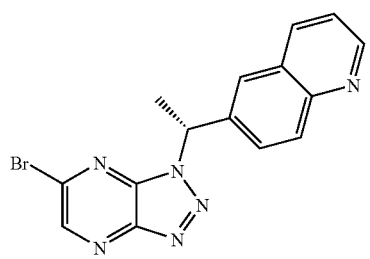

Racemic 6-[1-(6-bromo-[1,2,3]triazolo[4,5-b]pyrazin-1-yl)-ethyl]-quinoline was purified on a chiral SFC column using MeOH and liquid CO2 as elution system to provide 6-[(R)-1-(6-bromo-[1,2,3]triazolo[4,5-b]pyrazin-1-yl)-ethyl]-quinoline with an $[\alpha]_D$ of +204.94°, and 6-[(S)-1-(6-bromo-[1,2,3]triazolo[4,5-b]pyrazin-1-yl)-ethyl]-quinoline with an $[\alpha]_D$ of −212.73°.

Method 45

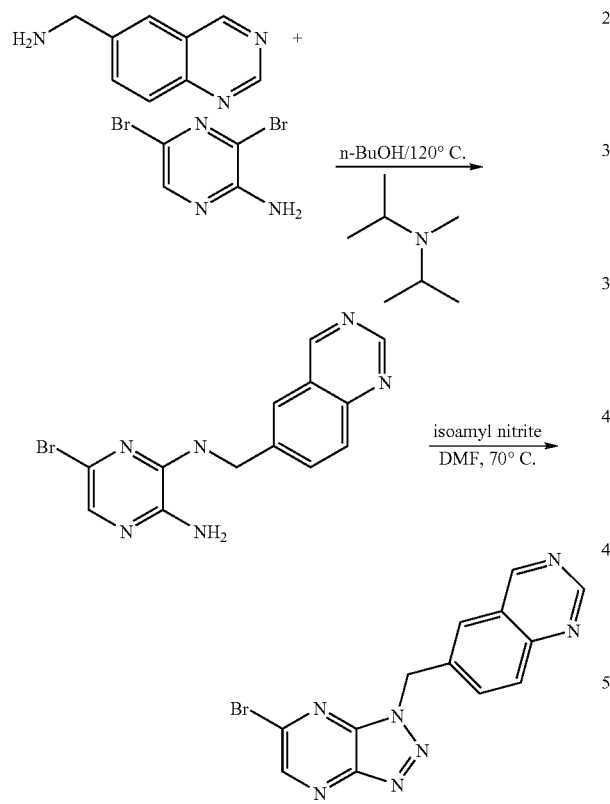

Step 1:

To the solution of C-quinazolin-6-yl-methylamine (1.2 g, 7.916 mmol) and 2.06 gram of 3,5-dibromo-pyrazin-2-ylamine (2.06 g, 7.916 mmol) in n-BuOH (18 mL) was added diisopropylethylamine (7.0 mL, 40 mmol) at room temperature. The reaction mixture was heated up to 120° C. for two days under nitrogen. The reaction was cooled down, n-BuOH is evaporated directly via rotavapor, followed by purification via a silica gel column to get 5-Bromo-N*3*-quinazolin-6-ylmethyl-pyrazine-2,3-diamine (1.02 g, yield 42%).

Step 2:

To the solution of 5-bromo-N*3*-quinazolin-6-ylmethyl-pyrazine-2,3-diamine (1.02 g) in anhydrous DMF (12 mL) was added isoamyl nitrite (0.5 mL, 1.2 eq) at 0° C. dropwise. The ice bath was removed and the mixture was stirred for 5 minutes at room temperature, then at 70° C. for three hours. The reaction was cooled down to ambient temperature and quenched by 3 ml Sat'd $Na_2SO_3$. A precipitate was formed, and filtered. The mother liquor was extracted with ethyl acetate (2×200 ml) twice, and the combined extracts were washed twice by Sat'd $NaHCO_3$ (2×100 ml), dried over $Na_2SO_4$, and concentrated to get the crude product which was dissolved in MeOH (10 ml), and a precipitate was formed. The solid was filtered to get 6-(6-Bromo-[1,2,3]triazolo[4,5-b]pyrazin-1-ylmethyl)-quinazoline (0.112 g, yield 13%).

Method 46

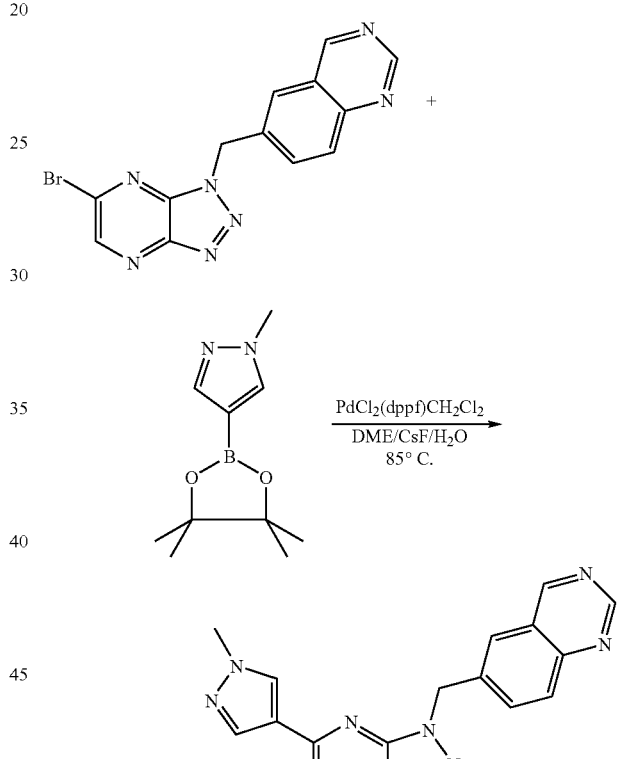

To the solution of 6-(6-bromo-[1,2,3]triazolo[4,5-b]pyrazin-1-ylmethyl)-quinazoline (100 mg, 0.32 mmol) and 1-methyl-4-(4,4,5,5-tetramethyl-[1,3,2]dioxaborolan-2-yl)-1H-pyrazole (130 mg, 0.6 mmol) in 5 ml DME was added a freshly prepared solution of $Cs_2CO_3$ (306.9 mg, 0.96 mmol)) in water (0.45 mL) and the catalyst $PdCl_2(dppf)CH_2Cl_2$ (13 mg, 0.15 mmol)). The mixture was degassed and charged with nitrogen for three times, then was heated at 85° C. for overnight. The solvent was evaporated directly, and the crude product was suspended in $CH_2Cl_2$ (5 mL) and filtered. The mother liquor was concentrated, and MeOH (2 mL) was added. The suspension was filtered, and the solid was then washed by ether (2×10 ml) to get the product (37 mg, yield 37%).

TABLE 3

| Example | Structure | Name | NMR/LC-MS | Method |
|---|---|---|---|---|
| 1 | 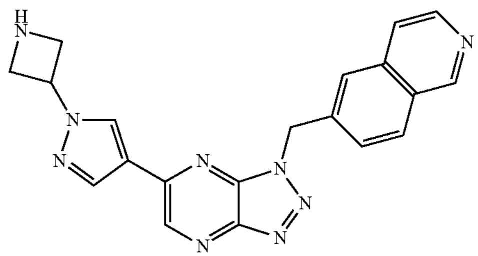 | 6-((6-(1-(azetidin-3-yl)-1H-pyrazol-4-yl)-1H-[1,2,3]triazolo[4,5-b]pyrazin-1-yl)methyl)-quinoline | 1H NMR(400 MHz, DMSO-d6) δ ppm 9.27(s, 1H), 9.12(s, 1H), 8.93(dd, J=4.29, 1.77Hz, 1H), 8.89(s, 1H), 8.79(s, 1H), 8.55(s, 1H), 8.42(d, J=7.83Hz, 1H), 8.05(d, J=8.84Hz, 1H), 8.00(s, 1H), 7.85(dd, J=8.72, 1.89Hz, 1H), 7.58(dd, J=8.34, 4.29Hz, 1H), 6.17(s, 2H), 5.47-5.57(m, 1H), 4.35-4.47(m, 4H). LC-MS 383. | 1 |
| 2 | 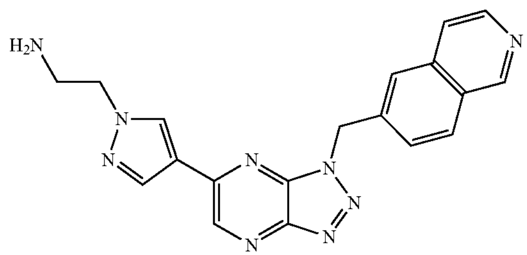 | 2-(4-(3-(quinolin-6-ylmethyl)-3H-[1,2,3]triazolo[4,5-b]pyrazin-5-yl)-1H-pyrazol-1-yl)ethanamine | 1H NMR(400 MHz, DMSO-d6) δ ppm 9.26(s, 1H), 8.92(dd, J=4.29, 1.77Hz, 1H), 8.71(s, 1H), 8.43(s, 1H), 8.40(d, J=8.34Hz, 1H), 8.04(d, J=8.59Hz, 1H), 7.99(s, 1H), 7.91(s, 2H), 7.84(dd, J=8.59, 2.02Hz, 1H), 7.56(dd, J=8.34, 4.29Hz, 1H), 6.17(s, 2H), 4.45(t, J=6.06Hz, 2H), 3.29-3.38(m, 3H). LC-MS 371. | 1 |
| 3 | 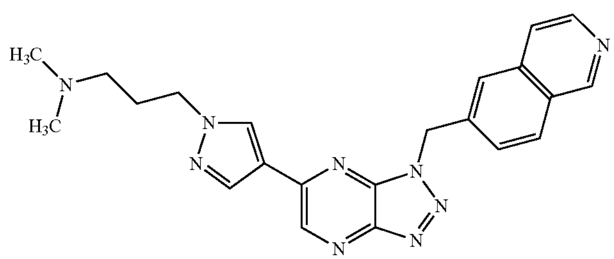 | N,N-dimethyl-3-(4-(3-(quinolin-6-ylmethyl)-3H-[1,2,3]triazolo[4,5-b]pyrazin-5-yl)-1H-pyrazol-1-yl)propan-1-amine | 1H NMR(400 MHz, DMSO-d6) δ ppm 9.47(s, 1H), 9.24(s, 1H), 8.94(dd, J=4.29, 1.77Hz, 1H), 8.70(s, 1H), 8.44(d, J=7.83Hz, 1H), 8.38(s, 1H), 8.06(d, J=8.59Hz, 1H), 8.00(s, 1H), 7.85(dd, J=8.72, 1.89Hz, 1H), 7.59(dd, J=8.34, 4.29Hz, 1H), 6.17(s, 2H), 4.30(t, J=6.69Hz, 2H), 3.07(s, 2H), 2.77(d, J=4.55Hz, 6H), 2.16-2.25(m, 2H). LC-MS 413. | 1 |

TABLE 3-continued

| Example | Structure | Name | NMR/LC-MS | Method |
|---|---|---|---|---|
| 4 | 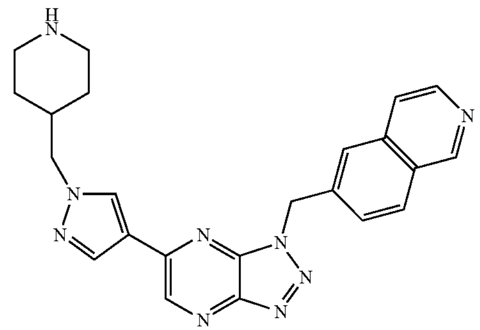 | 6-((6-(1-piperidin-4-ylmethyl)-1H-pyrazol-4-yl)-1H-[1,2,3]triazolo[4,5-b]pyrazin-1-yl)methyl)-quinoline | 1H NMR(400 MHz, DMSO-d6) δ ppm 9.23(s, 1H), 8.99(dd, J=4.29, 1.52Hz, 1H), 8.70(s, 1H), 8.58(s, 1H), 8.53(d, J=8.59Hz, 1H), 8.36(s, 1H), 8.24(d, J=9.09Hz, 1H), 8.08(d, J=8.59Hz, 1H), 8.05(s, 1H), 7.90(dd, J=8.72, 1.89Hz, 1H), 7.65(dd, J=8.34, 4.55Hz, 1H), 6.18(s, 2H), 4.17(d, J=6.82Hz, 2H), 3.26(d, J=12.38Hz, 2H), 2.80-2.91(m, 2H), 2.17(s, 1H), 1.68(d, J=13.39Hz, 2H), 1.32-1.43(m, 2H). LC-MS 426. | 2 |
| 5 | 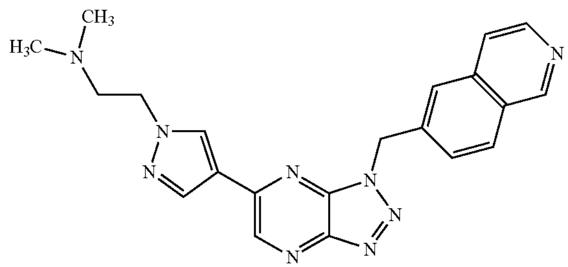 | N,N-dimethyl-2-(4-(3-(quinolin-6-ylmethyl)-3H-[1,2,3]triazolo[4,5-b]pyrazin-5-yl)-1H-pyrazol-1-yl)-ethanamine | 1H NMR(400 MHz, DMSO-d6) δ ppm 9.51(s, 1H), 9.27(s, 1H), 8.93(dd, J=4.17, 1.64Hz, 1H), 8.76(s, 1H), 8.46(s, 1H), 8.43(d, J=8.34Hz, 1H), 8.05(d, J=8.59Hz, 1H), 8.00(d, J=1.25Hz, 1H), 7.85(dd, J=8.72, 1.89Hz, 1H), 7.58(dd, J=8.21, 4.17Hz, 1H), 6.17(s, 2H), 4.64(t, J=6.19Hz, 2H), 3.63(s, 2H), 2.83(s, 6H). LC-MS 399. | 2 |
| 6 | 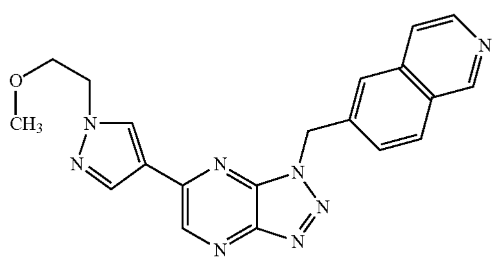 | 6-((6-(1-(2-methoxyethyl)-1H-pyrazol-4-yl)-1H-[1,2,3]triazolo[4,5-b]pyrazin-1-yl)methyl)-quinoline | 1H NMR(400 MHz, DMSO-d6) δ ppm 9.23(s, 1H), 8.92-8.97(m, 1H), 8.64(s, 1H), 8.46(s, 1H), 8.33(s, 1H), 8.02-8.07(m, 2H), 7.88(dd, J=8.59, 1.77Hz, 1H), 7.60(dd, J=8.34, 4.29Hz, 1H), 6.17(s, 2H), 4.36(t, J=5.18Hz, 2H), 3.73(t, J=5.18Hz, 2H), 3.23(s, 3H). LC-MS 386. | 2 |

TABLE 3-continued

| Example | Structure | Name | NMR/LC-MS | Method |
|---|---|---|---|---|
| 7 | 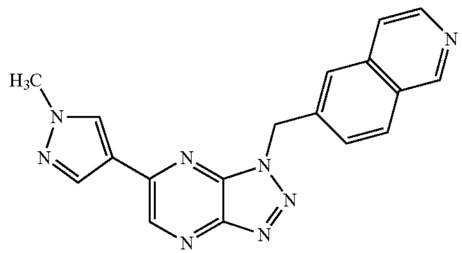 | 6-((6-(1-methyl-1H-pyrazol-4-yl)-1H-[1,2,3]triazolo[4,5-b]pyrazin-1-yl)methyl)-quinoline | 1H NMR(400 MHz, DMSO-d6) δ ppm 9.21(s, 1H), 8.98(dd, J=4.29, 1.52Hz, 1H), 8.64(s, 1H), 8.52(d, J=7.83Hz, 1H), 8.30(s, 1H), 8.04-8.10(m, 2H), 7.91(dd, J=8.72, 1.89Hz, 1H), 7.64(dd, J=8.34, 4.29Hz, 1H), 6.17(s, 2H), 3.94(s, 3H). LC-MS 342. | 2 |
| 8 | 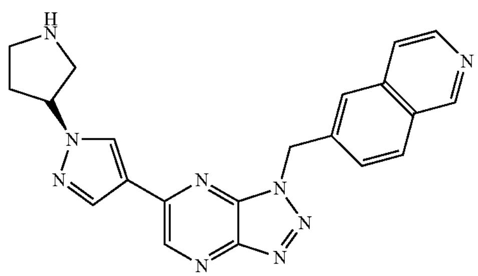 | 6-((6-(1-((R)-pyrrolidin-3-yl)-1H-pyrazol-4-yl)-1H-[1,2,3]triazolo[4,5-b]pyrazin-1-yl)methyl)-quinoline | 1H NMR(400 MHz, DMSO-d6) δ ppm 9.26(s, 1H), 9.17(s, 2H), 8.93-8.97(m, 1H), 8.82(s, 1H), 8.44(s, 2H), 8.06(d, J=8.84Hz, 1H), 8.01(s, 1H), 7.86(d, J=8.84Hz, 1H), 7.59(ddd, J=6.19, 4.17, 2.02Hz, 1H), 6.17(s, 2H), 5.27-5.35(m, 1H), 3.69(dt, J=12.69, 6.41Hz, 1H), 3.58-3.64(m, 1H), 3.38-3.49(m, 2H), 2.43-2.48(m, 1H), 2.32-2.39(m, 1H), 2.30(s, 1H). LC-MS 397. | 2 |
| 9 | 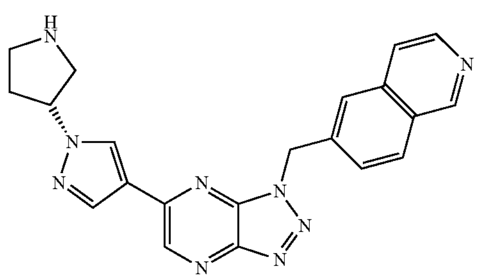 | 6-((6-(1-((S)-pyrrolidin-3-yl)-1H-pyrazol-4-yl)-1H-[1,2,3]triazolo[4,5-b]pyrazin-1-yl)methyl)-quinoline | 1H NMR(400 MHz, DMSO-d6) δ ppm 9.26(s, 1H), 9.16(s, 2H), 8.94(dd, J=4.29, 1.52Hz, 1H), 8.82(s, 1H), 8.42-8.47(m, 2H), 8.06(d, J=8.84Hz, 1H), 8.01(d, J=1.52Hz, 1H), 7.86(dd, J=8.84, 2.02Hz, 1H), 7.59(dd, J=8.34, 4.29Hz, 1H), 6.18(s, 2H), 5.27-5.34(m, J=7.17, 7.17, 3.92, 3.73Hz, 1H), 3.64-3.73(m, J=12.73, 6.69, 6.46, 6.46Hz, 1H), 3.57-3.64(m, 1H), 3.38-3.49(m, 2H), 2.46(d, J=7.33Hz, 1H), 2.43(s, 1H), 2.29-2.38(m, 1H). LC-MS 397. | 2 |

TABLE 3-continued

| Example | Structure | Name | NMR/LC-MS | Method |
|---|---|---|---|---|
| 10 | 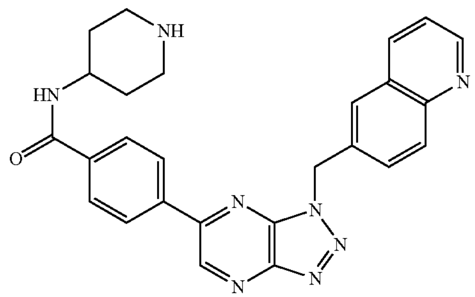 | N-(piperidin-4-yl)-4-(3-(quinolin-6-ylmethyl)-3H-[1,2,3]triazolo[4,5-b]pyrazin-5-yl)benzamide | 1H NMR(400 MHz, MeOD) δ ppm 1.81–1.93(m, 2H) 2.23(d, J=11.37Hz, 2H) 3.14(td, J=12.82, 2.91Hz, 2H) 3.42–3.52(m, 2H) 4.16–4.25(m, J=11.05, 11.05, 3.92, 3.79Hz, 1H) 6.31(s, 2H) 7.58(dd, J=8.46, 4.42Hz, 1H) 7.97(dd, J=8.84, 2.02Hz, 1H) 8.02–8.09(m, 3H) 8.12(d, J=1.52Hz, 1H) 8.35–8.43(m, 3H) 8.88(dd, J=4.42, 1.64Hz, 1H) 9.44(s, 1H). LC-MS 465. | 5 & 8 |
| 11 | 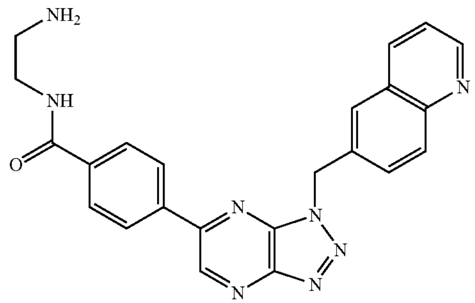 | N-(2-aminoethyl)-4-(3-(quinolin-6-ylmethyl)-3H-[1,2,3]triazolo[4,5-b]pyrazin-5-yl)benzamide | 1H NMR(400 MHz, MeOD) δ ppm 3.17(t, J=5.94Hz, 2H) 3.69(t, J=6.06Hz, 2H) 6.30(s, 2H) 7.57(dd, J=8.34, 4.29Hz, 1H) 7.96(dd, J=8.72, 1.89Hz, 1H) 8.04–8.13(m, 4H) 8.39(ddd, J=6.69, 2.27, 2.15Hz, 3H) 8.87(dd, J=4.42, 1.64Hz, 1H) 9.43(s, 1H). LC-MS 425. | 5 & 8 |
| 12 | 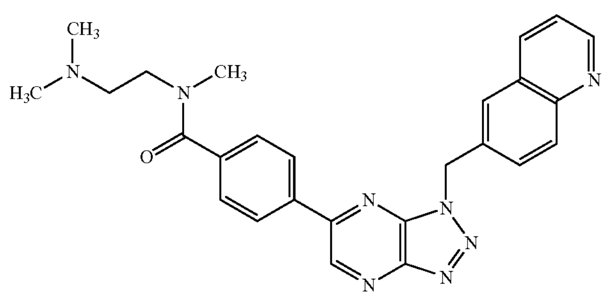 | N-(2-(dimethylamino)ethyl)-N-methyl-4-(3-(quinolin-6-ylmethyl)-3H-[1,2,3]triazolo[4,5-b]pyrazin-5-yl)benzamide | 1H NMR(400 MHz, MeOD) δ ppm 3.08(s, 6H) 3.13(s, 3H) 3.52(t, J=6.19Hz, 2H) 3.98(t, J=5.94Hz, 2H) 6.34(s, 2H) 7.70–7.78(m, 3H) 8.06–8.11(m, 1H) 8.11–8.16(m, 1H) 8.22(s, 1H) 8.40(d, J=8.59Hz, 2H) 8.66(d, J=8.08Hz, 1H) 8.99(dd, J=4.80, 1.52Hz, 1H) 9.44(s, 1H). LC-MS 467. | 5 |

TABLE 3-continued

| Example | Structure | Name | NMR/LC-MS | Method |
|---|---|---|---|---|
| 13 | 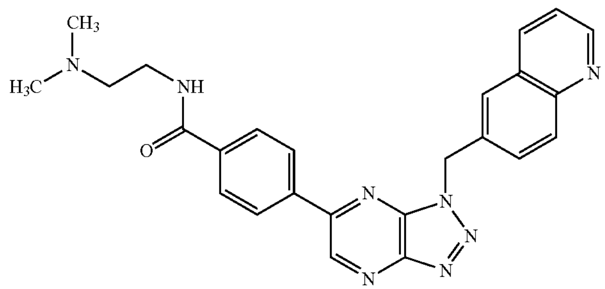 | N-(2-(dimethylamino)ethyl)-4-(3-(quinolin-6-ylmethyl)-3H-[1,2,3]triazolo[4,5-b]pyrazin-5-yl)benzamide | 1H NMR(400 MHz, MeOD) δ ppm 3.03(s, 6H) 3.44(t, J=5.94Hz, 2H) 3.82(t, J=5.81Hz, 2H) 6.34(s, 2H) 7.76(dd, J=8.34, 4.55Hz, 1H) 8.06-8.11(m, 3H) 8.12-8.17(m, 1H) 8.23(d, J=1.52Hz, 1H) 8.40(d, J=8.59Hz, 2H) 8.68(d, J=7.58Hz, 1H) 9.00(dd, J=4.67, 1.64Hz, 1H) 9.45(s, 1H). LC-MS 453. | 5 |
| 14 | 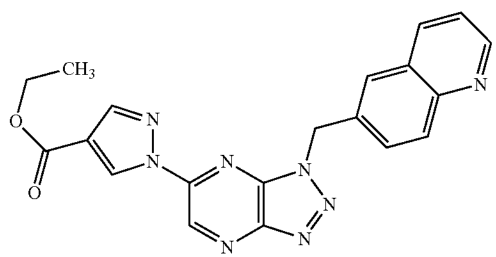 | ethyl 1-(3-(quinolin-6-ylmethyl)-3H-[1,2,3]triazolo[4,5-b]pyrazin-5-yl)-1H-pyrazole-4-carboxylate | 1H NMR(400 MHz, DMSO-d6) δ ppm 1.33(t, J=7.07Hz, 3H) 4.33(q, J=7.07Hz, 2H) 6.25(s, 2H) 7.55(dd, J=8.34, 4.29Hz, 1H) 7.88(dd, J=8.72, 1.89Hz, 1H) 8.03(d, J=8.84Hz, 1H) 8.07(d, J=1.52Hz, 1H) 8.35-8.39(m, 1H) 8.41(s, 1H) 8.91(dd, J=4.17, 1.64Hz, 1H) 9.27(s, 1H) 9.48(s, 1H). LC-MS 401. | 9 |
| 15 | 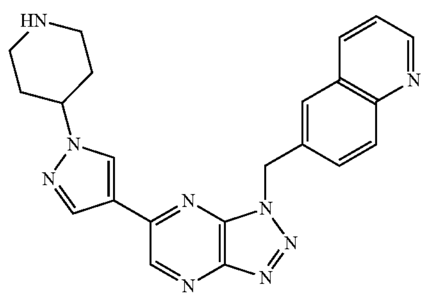 | 6-((6-(1-(piperidin-4-yl)-1H-pyrazol-4-yl)-1H-[1,2,3]triazolo[4,5-b]pyrazin-1-yl)methyl)-quinoline | 1H NMR(400 MHz, DMSO-d6) δ ppm 1.83(qd, J=12.00, 3.92Hz, 2H) 2.01(d, J=10.11Hz, 2H) 2.57-2.68(m, 2H) 3.07(d, J=12.63Hz, 2H) 4.26-4.36(m, 1H) 11.56, 4.04, 3.92Hz, 1H) 6.16(s, 2H) 7.54(dd, J=8.34, 4.04Hz, 1H) 7.84(dd, J=8.59, 2.02Hz, 1H) 7.99-8.06(m, 2H) 8.31(s, 1H) 8.38(d, J=8.59Hz, 1H), 8.73(s, 1H) 8.90(dd, J=4.17, 1.64Hz, 1H) 9.24(s, 1H). LC-MS 412. | 6 & 8 |

TABLE 3-continued

| Example | Structure | Name | NMR/LC-MS | Method |
|---|---|---|---|---|
| 16 | 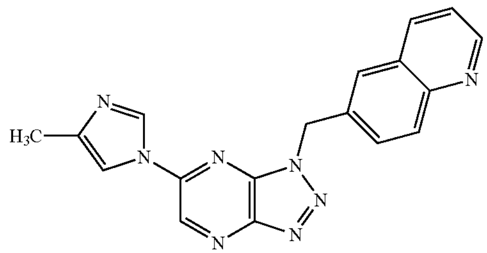 | 6-((6-(4-methyl-1H-imidazol-1-yl)-1H-[1,2,3]triazolo[4,5-b]pyrazin-1-yl)methyl)quinoline | 1H NMR(400 MHz, DMSO-d6) δ ppm 2.22(s, 3H) 6.17(s, 2H) 7.55(dd, J=8.34, 4.04Hz, 1H) 7.81-7.90(m, 2H) 8.00-8.08(m, 2H) 8.38(d, J=7.58Hz, 1H) 8.74(s, 1H) 8.90(dd, J=4.17, 1.64Hz, 1H) 9.35(s, 1H). LC-MS 343. | 9 |
| 17 | 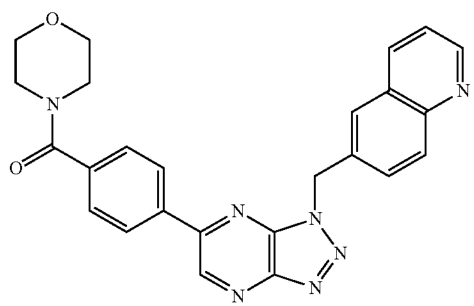 | morpholino(4-(3-(quinolin-6-ylmethyl)-3H-[1,2,3]triazolo[4,5-b]pyrazin-5-yl)phenyl)methanone | 1H NMR(400 MHz, CHLOROFORM-d) δ ppm 3.52(s, 2H) 3.69(s, 2H) 3.82(s, 4H) 6.17(s, 2H) 7.43(dd, J=8.34, 4.04Hz, 1H) 7.60-7.70(m, 2H) 7.84-7.92(m, 1H) 7.95(d, J=1.52Hz, 1H) 8.13(dd, J=16.29, 8.46Hz, 2H) 8.19(d, J=8.34Hz, 2H) 8.92(dd, J=4.17, 1.64Hz, 1H) 9.23(s, 1H). LC-MS 452. | 6 |
| 18 | 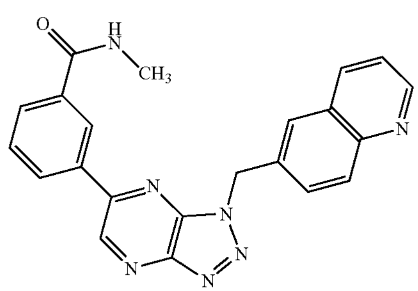 | N-methyl-3-(3-(quinolin-6-ylmethyl)-3H-[1,2,3]triazolo[4,5-b]pyrazin-5-yl)benzamide | 1H NMR(400 MHz, DMSO-d6) δ ppm 2.85(d, J=4.55Hz, 3H) 6.32(s, 2H) 7.68-7.78(m, 2H) 7.98-8.07(m, 2H) 8.16(d, J=12.13Hz, 2H) 8.43(d, J=7.83Hz, 1H) 8.70(d, J=18.69Hz, 3H) 9.06(d, J=4.55Hz, 1H) 9.58(s, 1H). LC-MS 396. | 6 |

| Example | Structure | Name | NMR/LC-MS | Method |
|---|---|---|---|---|
| 19 | 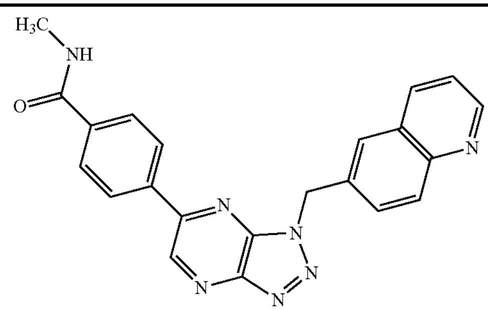 | N-methyl-4-(3-(quinolin-6-ylmethyl)-3H-[1,2,3]triazolo[4,5-b]pyrazin-5-yl)benzamide | 1H NMR(400 MHz, DMSO-d6) δ ppm 2.82(d, J=4.29Hz, 3H) 6.34(s, 2H) 7.85(dd, J=8.21, 4.67Hz, 1H) 8.02-8.13(m, 3H) 8.19-8.30(m, 2H) 8.40(d, J=8.34Hz, 2H) 8.66(d, J=4.29Hz, 1H) 8.81(d, J=8.08Hz, 1H) 9.13(d, J=4.55Hz, 1H) 9.59(s, 1H). LC-MS 396. | 6 |
| 20 | 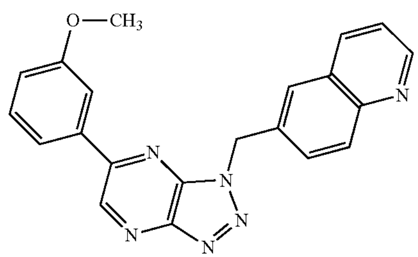 | 6-((6-(3-methoxyphenyl)-1H-[1,2,3]triazolo[4,5-b]pyrazin-1-yl)methyl)-quinoline | 1H NMR(400 MHz, DMSO-d6) δ ppm 3.86(d, J=1.77Hz, 3H) 6.33(s, 2H) 7.17(d, J=8.08Hz, 1H) 7.48-7.55(m, 1H) 7.79-7.90(m, 3H) 8.07(d, J=8.84Hz, 1H) 8.18-8.25(m, 2H) 8.79(d, J=8.34Hz, 1H) 9.12(d, J=4.80Hz, 1H) 9.54(d, J=1.77Hz, 1H). LC-MS 369. | 6 |
| 21 | 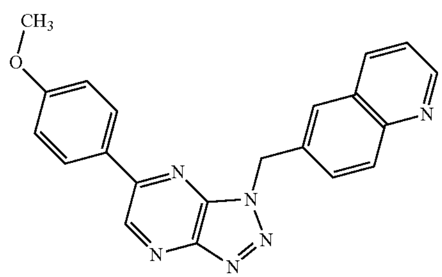 | 6-((6-(4-methoxyphenyl)-1H-[1,2,3]triazolo[4,5-b]pyrazin-1-yl)methyl)-quinoline | 1H NMR(400 MHz, DMSO-d6) δ ppm 3.86(s, 3H) 6.29(s, 2H) 7.13-7.17(m, 2H) 7.82(dd, J=8.34, 4.55Hz, 1H) 8.05(dd, J=8.72, 1.90Hz, 1H) 8.16-8.23(m, 2H) 8.27-8.32(m, 2H) 8.77(d, J=8.34Hz, 1H) 9.11(dd, J=4.67, 1.39Hz, 1H) 9.48(s, 1H). LC-MS 369. | 6 |
| 22 | 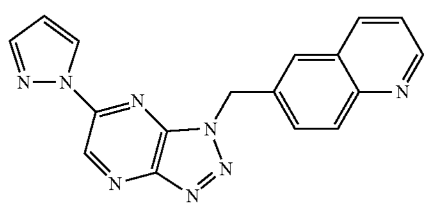 | 6-((6-(1H-pyrazol-1-yl)-1H-[1,2,3]triazolo[4,5-b]pyrazin-1-yl)methyl)-quinoline | 1H NMR(400 MHz, DMSO-d6) δ ppm 6.12(s, 2H) 6.67-6.72(m, 1H) 7.47(dd, J=4.29Hz, 1H) 7.80(dd, J=8.59, 2.02Hz, 1H) 7.94-8.01(m, 3H) 8.30(s, 1H) 8.74(d, J=2.78Hz, 1H) 8.83(dd, J=4.29, 1.77Hz, 1H) 9.38(s, 1H). LC-MS 329. | 9 |

TABLE 3-continued

| Example | Structure | Name | NMR/LC-MS | Method |
|---|---|---|---|---|
| 23 | 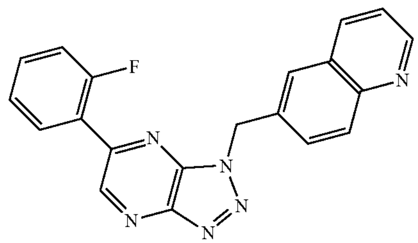 | 6-((6-(2-fluorophenyl)-1H-[1,2,3]triazolo[4,5-b]pyrazin-1-yl)methyl)-quinoline | 1H NMR(400 MHz, DMSO-d6) δ ppm 6.26(s, 2H) 7.44-7.56(m, 3H) 7.59-7.70(m, 1H) 7.85(dd, J=8.84, 2.02Hz, 1H) 7.98-8.06(m, 3H) 8.34-8.40(m, 1H) 8.90(dd, J=4.17, 1.64Hz, 1H) 9.25(d, J=2.27Hz, 1H). LC-MS 357. | 6 |
| 24 | 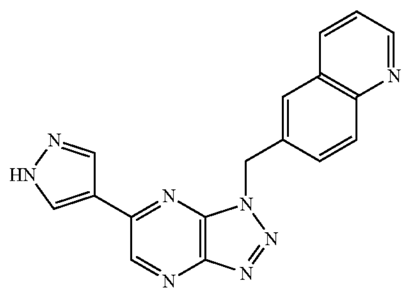 | 6-((6-(1H-pyrazol-4-yl)-1H-[1,2,3]triazolo[4,5-b]pyrazin-1-yl)methyl)-quinoline | 1H NMR(400 MHz, DMSO-d6) δ ppm 6.16(s, 2H) 7.54(dd, J=8.34, 4.29Hz, 1H) 7.84(dd, J=8.97, 1.64Hz, 1H) 8.00-8.07(m, 2H) 8.38(d, J=8.59Hz, 1H) 8.56(s, 1H) 8.90(dd, J=4.17, 1.64Hz, 1H) 9.26(s, 1H) 13.47(s, 1H). LC-MS 329. | 7 |
| 25 | 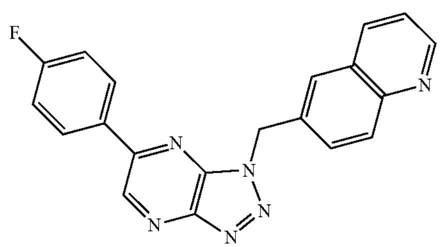 | 6-((6-(4-fluorophenyl)-1H-[1,2,3]triazolo[4,5-b]pyrazin-1-yl)methyl)-quinoline | 1H NMR(400 MHz, CHLOROFORM-d) δ ppm 6.15(s, 2H) 7.24-7.30(m, 3H) 7.43(dd, J=8.34, 4.29Hz, 1H) 7.86(dd, J=8.84, 2.02Hz, 1H) 7.93(d, J=1.77Hz, 1H) 8.10-8.17(m, 3H) 8.92(dd, J=4.17, 1.64Hz, 1H) 9.18(s, 1H). LC-MS 357. | 6 |
| 26 | 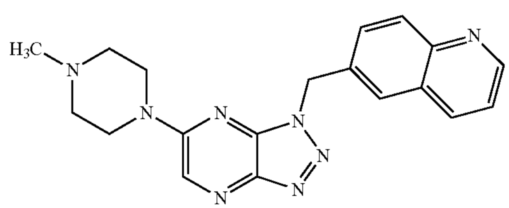 | 6-((6-(4-methylpiperazin-1-yl)-1H-[1,2,3]triazolo[4,5-b]pyrazin-1-yl)methyl)-quinoline | 1H NMR(400 MHz, CHLOROFORM-d) δ ppm 2.39(s, 3H) 2.54-2.65(m, 4H) 3.79-3.89(m, 4H) 5.88(s, 2H) 7.41(dd, J=8.34, 4.29Hz, 1H) 7.77(dd, J=8.72, 1.89Hz, 1H) 7.80-7.85(m, 1H) 8.08(d, J=8.84Hz, 1H) 8.10-8.13(m, 1H) 8.30(s, 1H) 8.88-8.98(m, 1H). LC-MS 361. | 11 |

TABLE 3-continued

| Example | Structure | Name | NMR/LC-MS | Method |
|---|---|---|---|---|
| 27 | 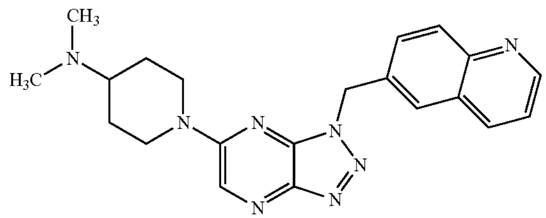 | N,N-dimethyl-1-(3-(quinolin-6-yl-methyl)-3H-[1,2,3]tri-azolo[4,5-b]pyrazin-5-yl)piperidin-4-amine | 1H NMR(400 MHz, CHLOROFORM-d) δ ppm 1.50-1.62(m, 2H) 2.01(d, J=11.87Hz, 2H) 2.34(s, 6H) 2.49-2.60(m, 1H) 3.04-3.14(m, 2H) 4.49-4.60(m, J=13.39Hz, 2H) 5.87(s, 2H) 7.41(dd, J=8.34, 4.29Hz, 1H) 7.78(dd, J=8.72, 1.89Hz, 1H) 7.83(s, 1H) 8.08(d, J=8.84Hz, 1H) 8.12(d, J=8.34Hz, 1H) 8.32(s, 1H) 8.91(dd, J=4.04, 1.52Hz, 1H). LC-MS 389. | 11 |
| 28 | 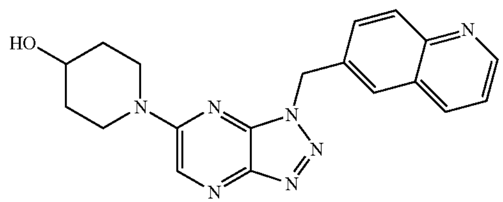 | 1-(3-(quinolin-6-yl-methyl)-3H-[1,2,3]tri-azolo[4,5-b]pyrazin-5-yl)piperidin-4-ol | 1H NMR(400 MHz, CHLOROFORM-d) δ ppm 1.61-1.71(m, 2H) 1.97-2.05(m, 8.56, 8.56, 3.79Hz, 2H) J=9.54, 6.44, 3.54, 3.38, 3.38Hz, 2H) 2.23(s, 1H) 3.49-3.57(m, 2H) 4.03-4.10(m, J=7.86, 7.86, 3.85, 3.66Hz, 1H) 4.16(ddd, J=13.33, 6.63, 4.04Hz, 2H) 5.88(s, 2H) 7.45(dd, J=8.34, 4.29Hz, 1H) 7.81(dd, J=8.72, 1.89Hz, 1H) 7.85(s, 1H) 8.15(dd, J=12.76, 8.46Hz, 2H) 8.32(s, 1H) 8.92(dd, J=4.29, 1.77Hz, 1H). LC-MS 362. | 11 |
| 29 | 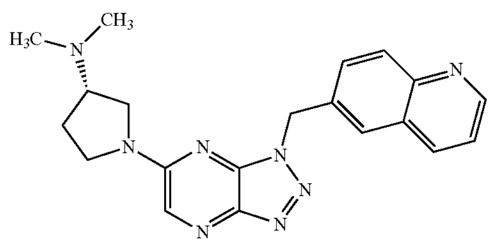 | (S)-N,N-di-methyl-1-(3-(quino-lin-6-yl-methyl)-3H-[1,2,3]tri-azolo[4,5-b]pyr-azin-5-yl)pyr-rolidin-3-amine | 1H NMR(400 MHz, CHLOROFORM-d) δ ppm 1.95-2.07(m, 1H) 2.26-2.32(m, 1H) 2.35(s, 6H) 2.85-2.95(m, 1H) 3.41(dd, J=10.36, 8.59Hz, 1H) 3.58(td, J=10.48, 7.07Hz, 1H) 3.81-3.92(m, 2H) 5.88(s, 2H) 7.41(dd, J=8.34, 4.29Hz, 1H) 7.78-7.84(m, 2H) 8.05-8.13(m, 2H) 8.90(dd, J=4.17, 1.64Hz, 1H). LC-MS 375. | 11 |
| 30 | 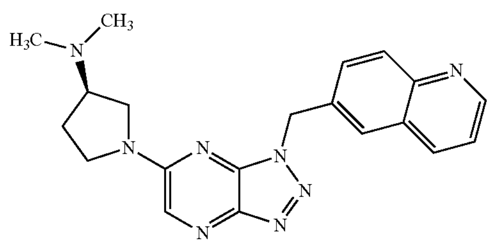 | (R)-N,N-di-methyl-1-(3-(quino-lin-6-yl-methyl)-3H-[1,2,3]tri-azolo[4,5-b]pyr-azin-5-yl)pyr-rolidin-3-amine | 1H NMR(400 MHz, CHLOROFORM-d) δ ppm 1.94-2.06(m, 1H) 2.25-2.33(m, 1H) 2.35(s, 6H) 2.85-2.95(m, 1H) 3.40(dd, J=10.48, 8.46Hz, 1H) 3.58(td, J=10.42, 7.20Hz, 1H) 3.81-3.91(m, 2H) 5.88(s, 2H) 7.40(dd, J=8.34, 4.29Hz, 1H) 7.78-7.84(m, 2H) 8.04(s, 1H) 8.09(dd, J=17.56, 8.46Hz, 2) 8.90(dd, J=4.29, 1.52Hz, 1H). LC-MS 375. | 11 |

TABLE 3-continued

| Example | Structure | Name | NMR/LC-MS | Method |
|---|---|---|---|---|
| 31 | (structure) | (R)-1-(3-(quinolin-6-ylmethyl)-3H-[1,2,3]triazolo[4,5-b]pyrazin-5-yl)piperidin-3-amine dihydrochloride | 1H NMR(400 MHz, MeOD) δ ppm 1.71-1.82(m, 2H) 1.88-1.98(m, 1H) 2.12-2.21(m, 1H) 3.41-3.47(m, 1H) 3.51-3.62(m, 2H) 4.15(td, J=8.97, 4.29Hz, 1H) 4.48(dd, J=13.52, 3.66Hz, 1H) 6.08(s, 2H) 8.09(dd, J=8.34, 5.56Hz, 1H) 8.21-8.27(m, 2H) 8.35(s, 1H) 8.52(s, 1H) 9.17-9.22(m, 2H), LC-MS 361. | 10 |
| 32 | (structure) | (S)-1-(3-(quinolin-6-ylmethyl)-3H-[1,2,3]triazolo[4,5-b]pyrazin-5-yl)piperidin-3-amine dihydrochloride | 1H NMR HCl salt(400 MHz, MeOD) δ ppm 0.15-0.25(m, 2H) 0.33-0.41(m, 1H) 0.57-0.65(m, 1H) 1.84-1.91(m, 1H) 1.94-2.06(m, 2H) 2.54-2.62(m, 1H) 2.92(dd, J=13.39, 3.54Hz, 1H) 4.52(s, 2H) 6.51(dd, J=8.46, 5.43Hz, 1H) 6.64-6.70(m, 2H) 6.78(s, 1H) 6.96(s, 1H) 7.59-7.64(m, 2H), LC-MS 361. | 10 |
| 33 | (structure) | 6-((6-(piperazin-1-yl)-1H-[1,2,3]triazolo[4,5-b]pyrazin-1-yl)methyl)quinoline | (400 MHz, MeOD) δ ppm 2.90-2.95(m, 4H) 3.76-3.81(m, 4H) 5.93(s, 2H) 7.52(dd, J=8.34, 4.29Hz, 1H) 7.80(dd, J=8.84, 2.02Hz, 1H) 7.94(d, J=1.26Hz, 1H) 7.99(d, J=8.84Hz, 1H) 8.33(dd, J=8.34, 0.76Hz, 1H) 8.44(s, 1H) 8.82(dd, J=4.29, 1.77Hz, 1H). LC-MS 347. | 10 |
| 34 | (structure) | tert-butyl 1-(3-(quinolin-6-ylmethyl)-3H-[1,2,3]triazolo[4,5-b]pyrazin-5-yl)piperidin-4-ylcarbamate | (400 MHz, DMSO-d₆) δ ppm 1.30-1.40(m, 2H) 1.39(s, 9H) 1.78-1.87(m, 2H) 3.12-3.22(m, 2H) 3.53-3.63(m 1H) 4.44(d, J=13.64Hz, 2H) 5.91(s, 2H) 6.88(d, J=7.33Hz, 1H) 7.53(dd, J=8.34, 4.29Hz, 1H) 7.76(dd, J=8.84, 2.02Hz, 1H) 7.96(d, J=1.52Hz, 1H) 8.00(d, J=8.59Hz, 1H) 8.36(d, J=7.58Hz, 1H) 8.58(s, 1H) 8.89(dd, J=4.29, 1.77Hz, 1H). LC-MS 461. | 10 |

TABLE 3-continued

| Example | Structure | Name | NMR/LC-MS | Method |
|---|---|---|---|---|
| 35 | 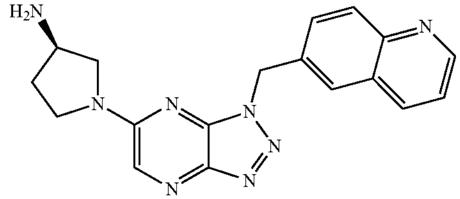 | (R)-1-(3-(quinolin-6-ylmethyl)-3H-[1,2,3]triazolo[4,5-b]pyrazin-5-yl)pyrrolidin-3-amine | (400 MHz, MeOD) δ ppm 1.85-1.96(m, 1H) 2.19-2.30(m, 1H) 3.37-3.44(m, 1H) 3.63-3.72(m, 2H) 3.74-3.83(m, 2H) 5.92(s, 2H) 7.52(dd, J=8.34, 4.29Hz, 1H) 7.81(dd, J=8.72, 1.89Hz, 1H) 7.92(s, 1H) 7.98(d, J=8.84Hz, 1H) 8.12(s, 1H) 8.32(d, J=7.58Hz, 1H) 8.81(dd, J=4.42, 1.64Hz, 1H). LC-MS 347. | 10 |
| 36 | 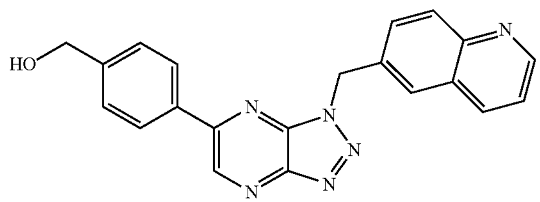 | (4-(3-(quinolin-6-ylmethyl)-3H-[1,2,3]triazolo[4,5-b]pyrazin-5-yl)phenyl)methanol | (400 MHz, DMSO-d$_6$) δ ppm 4.60(d, J=5.56Hz, 2H) 5.37(t, J=5.68Hz, 1H) 6.25(s, 2H) 7.54(d, J=8.34, 2.02Hz, 3H) 7.86(dd, J=8.72, 1.89Hz, 1H) 8.01-8.05(m, 2H) 8.28(d, J=8.34Hz, 2H) 8.38(d, J=7.33Hz, 1H) 8.90(dd, J=4.29, 1.77Hz, 1H) 9.50(s, 1). LC-MS 369. | 12 |
| 37 | 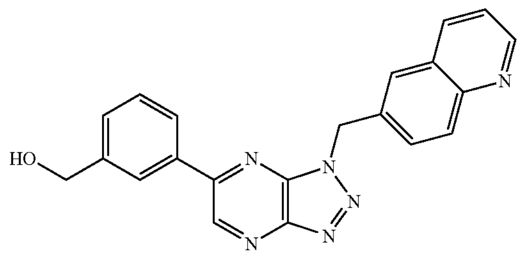 | (3-(3-(quinolin-6-ylmethyl)-3H-[1,2,3]triazolo[4,5-b]pyrazin-5-yl)phenyl)methanol | (400 MHz, DMSO-d$_6$) δ ppm 4.62(d, J=5.56Hz, 2H) 5.38(t, J=5.68Hz, 1H) 6.25(s, 2H) 7.52-7.59(m, 3H) 7.85(dd, J=8.72, 1.89Hz, 1H) 8.01-8.06(m, 2H) 8.17(d, J=6.82Hz, 1H) 8.24(s, 1H) 8.38(d, J=8.34Hz, 1H) 8.90(dd, J=4.17, 1.64Hz, 1H) 9.49(s, 1H). LC-MS 369. | 12 |
| 38 | 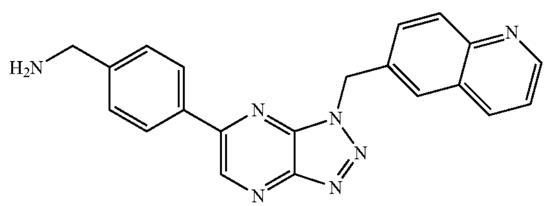 | (4-(3-(quinolin-6-ylmethyl)-3H-[1,2,3]triazolo[4,5-b]pyrazin-5-yl)phenyl)methanamine | (400 MHz, MeOD) δ ppm 3.88(s, 2H) 6.23(s, 2H) 7.51-7.55(m, 3H) 7.91(dd, J=8.84, 2.02Hz, 1H) 8.02(d, J=8.84Hz, 1H) 8.07(d, J=1.77Hz, 1H) 8.19-8.23(m, 2H) 8.34-8.38(m, 1H) 8.83(dd, J=4.29, 1.77Hz, 1H) 9.32(s, 1H). LC-MS 368. | 12 |

TABLE 3-continued

| Example | Structure | Name | NMR/LC-MS | Method |
|---|---|---|---|---|
| 39 | 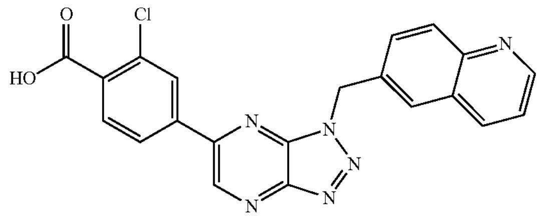 | 2-chloro-4-(3-(quinolin-6-ylmethyl)-3H-[1,2,3]triazolo[4,5-b]pyrazin-5-yl)benzoic acid | (400 MHz, DMSO-d₆) δ ppm 6.26(s, 2H) 7.43(d, J=7.83Hz, 1H) 7.54(dd, J=8.21, 4.17Hz, 1H) 7.85(dd, J=8.84, 2.02Hz, 1H) 8.03(d, J=8.84Hz, 1H) 8.05(d, J=1.52Hz, 1H) 8.13(dd, J=7.96, 1.64Hz, 1H) 8.19(d, J=1.77Hz, 1H) 8.37(dd, J=8.34, 1.01Hz, 1H) 8.89(dd, J=4.17, 1.64Hz, 1H) 9.50(s, 1H). LS-MS 417. | 12 |
| 40 | 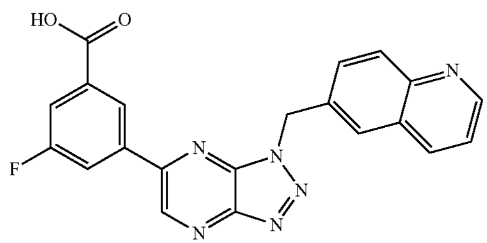 | 3-fluoro-5-(3-(quinolin-6-ylmethyl)-3H-[1,2,3]triazolo[4,5-b]pyrazin-5-yl)benzoic acid | (400 MHz, DMSO-d₆) δ ppm 6.28(s, 2H) 7.54(dd, J=8.34, 4.04Hz, 1H) 7.86(dd, J=8.84, 2.02Hz, 1H) 8.02(s, 1H) 8.04-8.07(m, 2H) 8.24(s, 1H) 8.25-8.28(m, 1H) 8.38(dd, J=8.21, 0.88Hz, 1H) 8.90(dd, J=4.17, 1.64Hz, 1H) 9.60(s, 1H) 13.55(s, 1H). LC-MS 401. | 12 |
| 41 | 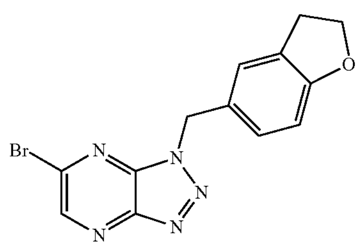 | 6-Bromo-1-(2,3-dihydrobenzofuran-5-ylmethyl)-1H-[1,2,3]triazolo[4,5-b]pyrazine | 1H NMR(400 MHz, DMSO-D6) δ ppm 8.97(s, 1H) 7.25(s, 1H) 7.16(dd, J=8.34, 1.77Hz, 1H) 6.73(d, J=8.34Hz, 1H) 4.48(t, J=8.72Hz, 2H) 3.11(t, J=8.72Hz, 2H). LC-MS 332, 334. | 14 |
| 42 | 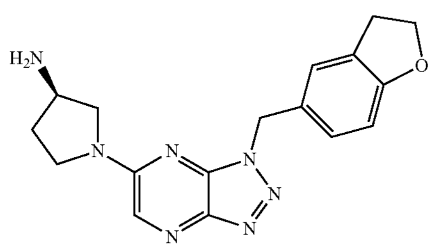 | (R)-1-[3-(2,3-Dihydrobenzofuran-5-ylmethyl)-3H-[1,2,3]triazolo[4,5-b]pyrazin-5-yl]-pyrrolidin-3-ylamine | 1H NMR(400 MHz, DMSO-D6) δ ppm 8.17(s, 1H) 7.24(s, 1H) 7.14(d, J=8.34Hz, 1H) 6.70(d, J=8.08Hz, 1H) 5.56(s, 2H) 4.47(t, J=8.72Hz, 3H) 3.59-3.76(m, 2H) 3.26-3.41(m, 2H) 3.11(t, J=8.72Hz, 2H) 2.04-2.15(m, 1H) 1.84-1.91(m, 1H) 1.77-1.82(m, 1H). LC-MS 338. | 16 |

TABLE 3-continued

| Example | Structure | Name | NMR/LC-MS | Method |
|---|---|---|---|---|
| 43 | 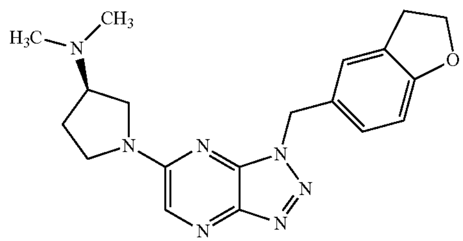 | {(R)-1-[3-(2,3-Dihydrobenzofuran-5-ylmethyl)-3H-[1,2,3]triazolo[4,5-b]pyrazin-5-yl]-pyrrolidin-3-yl]-dimethylamine | 1H NMR(400 MHz, DMSO-D6) δ ppm 8.20(s, 1H) 7.25(s, 1H) 7.14(d, J=8.08Hz, 1H) 6.70(d, J=8.08Hz, 1H) 5.56(s, 2H) 4.47(t, J=8.72Hz, 2H) 3.83-3.96(m, 1H) 3.75-3.84(m, 1H) 3.43-3.58(m, 2H) 3.11(t, J=8.72Hz, 2H) 2.75-2.92(m, 1H) 2.21(s, 6H) 1.79-1.88(m, 1H). LC-MS 366. | 15 |
| 44 | 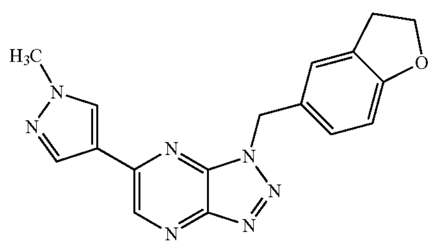 | 1-(2,3-Dihydrobenzofuran-5-ylmethyl)-6-(1-methyl-1H-pyrazol-4-yl)-1H-[1,2,3]triazolo[4,5-b]pyrazine | 1H NMR(400 MHz, DMSO-D6) δ ppm 9.17(s, 1H) 8.64(s, 1H) 8.30(s, 1H) 7.30(s, 1H) 7.18-7.26(m, 1H) 6.72(d, J=8.08Hz, 1H) 5.80(s, 2H) 4.47(t, J=8.72Hz, 2H) 3.94(s, 3H) 3.11(t, J=8.72Hz, 2H). LC-MS 334. | 17 |
| 45 | 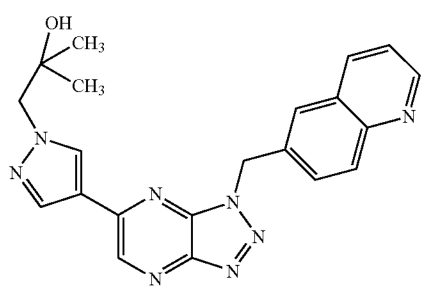 | 2-Methyl-1-{4-(3-quinolin-6-ylmethyl-3H-[1,2,3]triazolo[4,5-b]pyrazin-5-yl)-pyrazol-1-yl]-propan-2-ol | 1H NMR(400 MHz, DMSO-D6) δ ppm 9.24(s, 1H) 8.88(dd, J=4.17, 1.64Hz, 1H) 8.56(s, 1H) 8.35-8.37(m, 1H) 8.31(s, 1H) 8.02(d, J=8.59Hz, 1H) 7.98(d, J=1.52Hz, 1H) 7.82(dd, J=8.59, 2.02Hz, 1H) 7.52(dd, J=8.21, 4.17Hz, 1H) 6.15(s, 2H) 4.80(s, 1H) 4.11(s, 2H) 1.10(s, 6H). LC-MS 401. | 18 |

TABLE 3-continued

| Example | Structure | Name | NMR/LC-MS | Method |
|---|---|---|---|---|
| 46 | 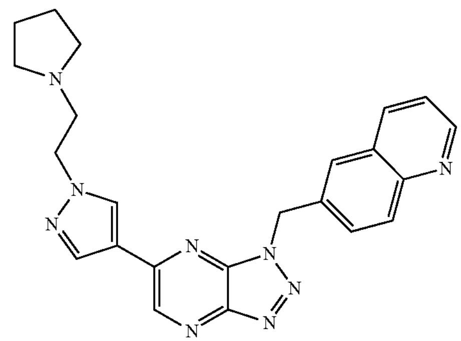 | 6-{6-[1-(2-Pyrrolidin-1-yl-ethyl)-1H-pyrazol-4-yl]-[1,2,3]triazolo[4,5-b]pyrazin-1-yl-methyl}-quinoline | 1H NMR(400 MHz, DMSO-D6) δ ppm 9.20(s, 1H) 8.88(dd, J=4.29, 1.77Hz, 1H) 8.66(s, 1H) 8.34-8.38(m, 1H) 8.30(s, 1H) 7.97-8.04(m, 2H) 7.82(dd, J=8.59, 2.02Hz, 1H) 7.52(dd, J=8.34, 4.04Hz, 1H) 6.14(s, 2H) 4.29(t, J=6.44Hz, 2H) 2.85(t, J=6.44Hz, 2H) 1.59-1.65(m, 4H). LC-MS 426. | 18 |
| 47 | 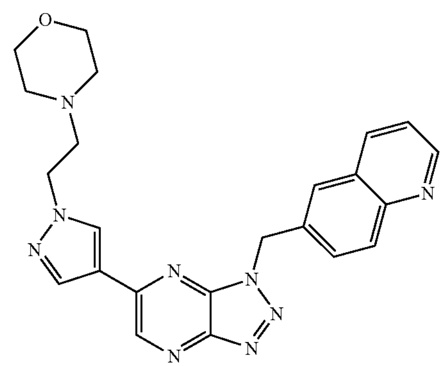 | 5-{6-[1-(2-Morpholin-4-yl-ethyl)-1H-pyrazol-4-yl]-[1,2,3]triazolo[4,5-b]pyrazin-1-ylmethyl}-quinoline | 1H NMR(400 MHz, DMSO-D6) δ ppm 9.15(s, 1H) 8.83(dd, J=4.04, 1.77Hz, 1H) 8.62(s, 1H) 8.28-8.33(m, 1H) 8.25(s, 1H) 7.92-7.98(m, 2H) 7.77(dd, J=8.59, 2.02Hz, 1H) 7.47(dd, J=8.34, 4.29Hz, 1H) 6.09(s, 2H) 4.26(t, J=6.44Hz, 2H) 3.44-3.49(m, 4H) 2.69(t, J=6.32Hz, 2H) 2.33-2.38(m, 4H). LC-MS 442. | 18 |
| 48 | 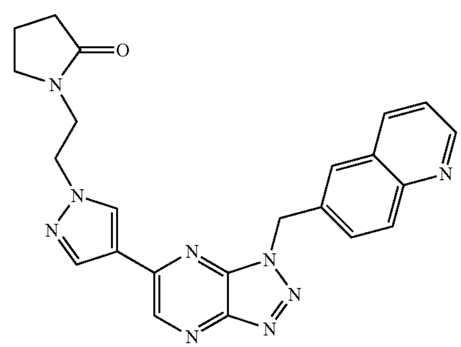 | 1-{2-[4-(3-Quinolin-6-yl-methyl-3H-[1,2,3]triazolo[4,5-b]pyrazin-5-yl)-pyrazol-1-yl]-ethyl}-pyrrolidin-2-one | 1H NMR(400 MHz, DMSO-D6) δ ppm 9.21(s, 1H) 8.88(dd, J=4.04, 1.77Hz, 1H) 8.67(s, 1H) 8.36(d, J=7.33Hz, 1H) 7.97-8.04(m, 2H) 7.82(dd, J=8.84, 2.02Hz, 1H) 7.52(dd, J=8.34, 4.29Hz, 1H) 6.14(s, 2H) 4.32(t, J=5.94Hz, 2H) 3.60(t, J=6.95Hz, 2H) 3.16(t, J=6.95Hz, 2H) 2.10(t, J=7.96Hz, 2H) 1.77-1.85(m, J=7.58Hz, 2H). LC-MS 440. | 18 |

TABLE 3-continued

| Example | Structure | Name | NMR/LC-MS | Method |
|---|---|---|---|---|
| 49 | 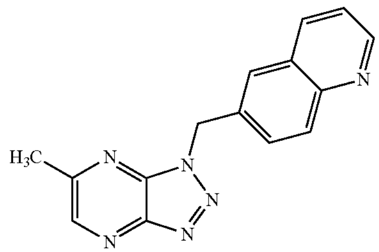 | 6-(6-Methyl-[1,2,3]tri-azolo[4,5-b]py-razin-1-yl-methyl)-quinoline | 1H NMR(400 MHz, DMSO-D6) δ ppm 8.78(s, 1H) 8.35(d, J=7.58Hz, 1H) 8.00(d, J=8.84Hz, 1H) 7.91(d, J=1.52Hz, 1H) 7.74(dd, J=8.59, 2.02Hz, 1H) 7.52(dd, J=8.34, 4.29Hz, 1H) 6.16(s, 2H) 2.73(s, 1H). LC-MS 277. | 17 |
| 50 | 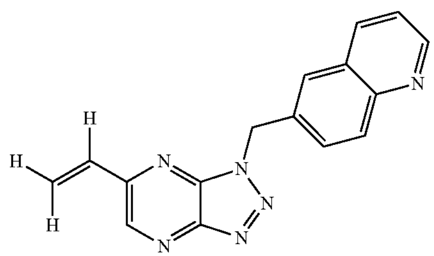 | 6-(6-Vinyl-[1,2,3]tri-azolo[4,5-b]py-razin-1-yl-methyl)-quinoline | 1H NMR(400 MHz, DMSO-D6) δ ppm 9.08(s, 1H) 8.89(dd, J=4.17, 1.64Hz, 1H) 8.31-8.40(m, 1H) 8.01(d, J=8.84Hz, 1H) 7.95(d, J=1.52Hz, 1H) 7.79(dd, J=8.84, 2.02Hz, 1H) 7.52(dd, J=8.34, 4.04Hz, 1H) 7.10(dd, J=17.56, 10.99Hz, 1H) 6.58-6.64(m, 1H) 6.17(s, 2H) 5.86(d, J=11.87Hz, 1H). LC-MS 289. | 17 |
| 51 | 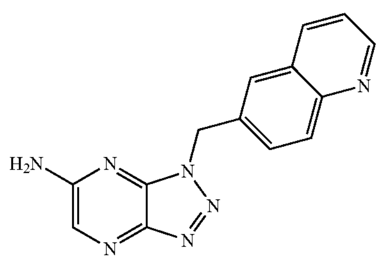 | 3-Quinoli-6-yl-methyl-3H-[1,2,3]tri-azolo[4,5-b]py-razin-5-ylamine | 1H NMR(400 MHz, DMSO-D6) δ ppm 8.88(dd, J=4.17, 1.64Hz, 1H) 8.30-8.38(m, 1H) 8.02(s, 1H) 8.00(d, J=8.59Hz, 1H) 7.78(d, J=1.52Hz, 1H) 7.67(dd, J=8.84, 2.02Hz, 1H) 7.48-7.56(m, 3H) 5.86(s, 2H). LC-MS 278. | 15 |

TABLE 3-continued

| Example | Structure | Name | NMR/LC-MS | Method |
|---|---|---|---|---|
| 52 | 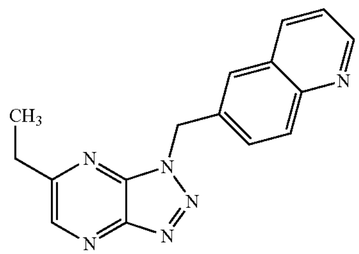 | 6-(6-Ethyl-[1,2,3]tri-azolo[4,5-b]py-razin-1-yl-methyl)-quinoline | 1H NMR(400 MHz, DMSO-D6) δ ppm 8.89(dd, J=4.17, 1.64Hz, 1H) 8.81(s, 1H) 8.34(d, J=8.34Hz, 1H) 8.00(d, J'8.59Hz, 1H) 7.95(s, 1H) 7.77(dd, J=8.59, 2.02Hz, 1H) 7.52(dd, J=8.34, 4.04Hz, 1H) 6.16(s, 2H) 3.05(q, J=7.58Hz, 2H) 1.31(t, J=7.58Hz, 3H). LC-MS 291. | 17 |
| 53 | 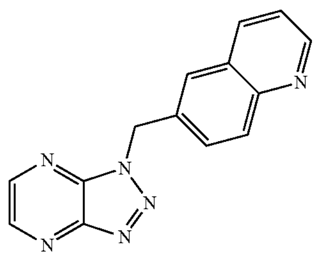 | 6-[1,2,3]Tri-azolo[4,5-b]py-razin-1-yl-methyl)-quinoline | 1H NMR(400 MHz, DMSO-D6) δ ppm 8.82-9.00(m, 3H) 8.34(dd, J=8.56, 1.01Hz, 1H) 8.00(d, J=8.81Hz, 1H) 7.95(d, J=1.51Hz, 1H) 7.76(dd, J=8.69, 2.14Hz, 1H) 7.52(dd, J=8.31, 4.28Hz, 1H) 6.22(s, 2H). LC-MS 263. | 17 |
| 54 | 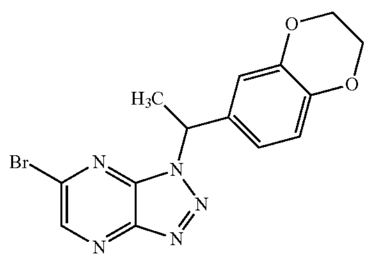 | 6-Bromo-1-[1-(2,3-di-hydro-benzo[1,4]di-oxin-6-yl)-ethyl]-1H-[1,2,3]tri-azolo[4,5-b]pyrazine | 1H NMR(400 MHz, DMSO-d6) δ ppm 8.97(s, 1H) 6.94(d, J=2.02Hz, 1H) 6.85-6.90(m, 1H) 6.79-6.84(m, 1H) 6.21-6.29(m, 1H) 2.00-2.05(m, 3H). LC-MS 362, 364. | 14 |
| 55 | 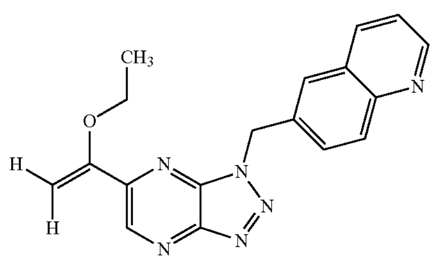 | 6-[6-(1-Ethoxy-vinyl)-[1,2,3]tri-azolo[4,5-b]py-razin-1-yl-methyl]-quinoline | 1H NMR(400 MHz, DMSO-d6) δ ppm 9.12(s, 1H) 8.90(s, 1H) 8.35(d, J=8.34Hz, 1H) 7.92-8.07(m, 2H) 7.81(dd, J=8.59, 2.02Hz, 1H) 7.54(dd, J=8.34, 4.04Hz, 1H) 6.20(s, 2H) 5.54(d, J=2.27Hz, 1H) 4.75(d, J=2.53Hz, 1H) 4.03(q, J=6.99Hz, 2H) 1.41(t, J=6.95Hz, 3H). LC-MS 333. | 20 |

TABLE 3-continued

| Example | Structure | Name | NMR/LC-MS | Method |
|---|---|---|---|---|
| 56 | 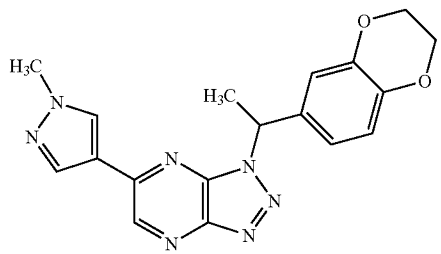 | 1-[1-(2,3-Dihydro-benzo[1,4]dioxin-6-yl)-ethyl]-6-(1-methyl-1H-pyrazol-4-yl)-1H-[1,2,3]triazolo[4,5-b]pyrazine | 1H NMR(400 MHz, DMSO-D6) δ ppm 9.16(s, 1H) 8.63(s, 1H) 8.29(s, 1H) 7.00(d, J=2.27Hz, 1H) 6.93(dd, J=8.46, 2.15Hz, 1H) 6.81(d, J=8.34Hz, 1H) 6.23(d, J=7.33Hz, 1H) 4.18(s, 4H) 3.94(s, 3H) 2.07(d, J=7.33Hz, 3H). LC-MS 364. | 17 |
| 57 | 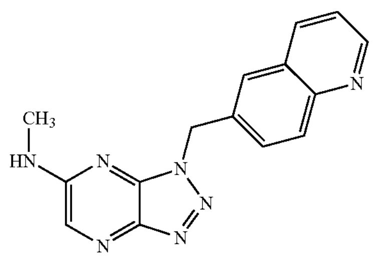 | Methyl-(3-quinolin-6-yl-methyl-3H-[1,2,3]triazolo[4,5-b]pyrazin-5-yl)-amine | 1H NMR(400 MHz, DMSO-D6) δ ppm 8.88(dd, J=4.17, 1.64Hz, 1H) 8.34(s, 1H) 8.19(s, 1H) 8.03(s, 1H) 7.97-8.03(m, 1H) 7.90(m, 1H) 7.74(dd, J=8.59, 1.77Hz, 1H) 7.52(dd, J=8.34, 4.04Hz, 1H) 5.84-5.91(m, 2H) 2.88(dd, J=4.80Hz, 3H). LC-MS 292. | 15 |
| 58 | 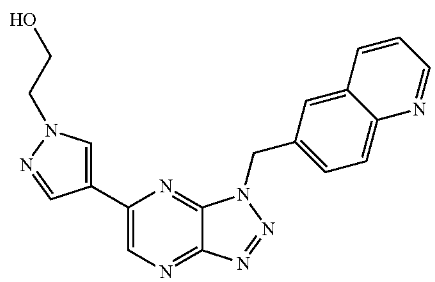 | 2-[4-(3-Quinolin-6-yl-methyl-3H-[1,2,3]triazolo[4,5-b]pyrazin-5-yl)-pyrazol-1-yl]-ethanol | 1H NMR(400 MHz, DMSO-d6) δ ppm 9.06-9.30(m, 1H) 8.89(dd, J=4.17, 1.64Hz, 1H) 8.64(s, 1H) 8.33-8.40(m, 1H) 8.33(s, 1H) 7.94-8.09(m, 2H) 7.82(dd, J=8.59, 2.02Hz, 1H) 7.53(dd, J=8.34, 4.04Hz, 1H) 6.15(s, 2H) 5.01(s, 1H) 4.24(t, J=5.31Hz, 2H) 3.78(t, J=5.31Hz, 2H). LC-MS 373. | 18 |

TABLE 3-continued

| Example | Structure | Name | NMR/LC-MS | Method |
|---|---|---|---|---|
| 59 | 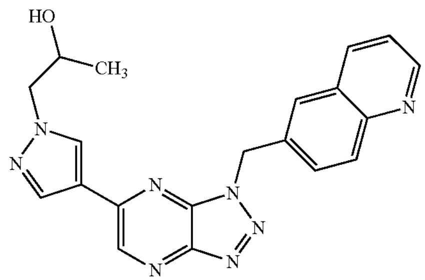 | 1-[4-(3-Quinolin-6-ylmethyl-3H-[1,2,3]triazolo[4,5-b]pyrazin-5-yl]pyrazol-1-yl]-propan-2-ol | H NMR(400 MHz, DMSO-d6) δ ppm 9.24(s, 1H) 8.90(dd, J=4.17, 1.64Hz, 1H) 8.62(s, 1H) 8.38(d, J=7.58Hz, 1H) 8.33(s, 1H) 7.93-8.08(m, 2H) 7.83(dd, J=8.59, 2.02Hz, 1H) 7.54(dd, J=8.34, 4.04Hz, 1H) 6.16(s, 2H) 4.88-5.17(m, 1H) 3.93-4.24(m, 3H) 1.08(d, J=6.06Hz, 3H). LC-MS 387. | 18 |
| 60 | 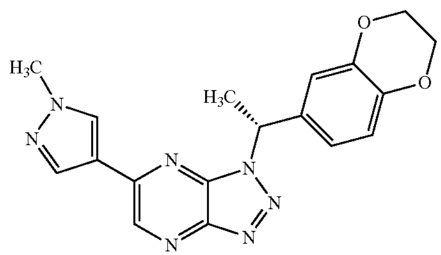 | 1-[(S)-1-(2,3-Dihydrobenzo[1,4]dioxin-6-yl)-ethyl]-6-(1-methyl-1H-pyrazol-4-yl)-1H-[1,2,3]triazolo[4,5-b]pyrazine | 1H NMR(400 MHz, DMSO-D6) δ ppm 9.16(s, 1H) 8.63(s, 1H) 8.29(s, 1H) 7.00(d, J=2.27Hz, 1H) 6.93(dd, J=8.46, 2.15Hz, 1H) 6.81(d, J=8.34Hz, 1H) 6.23(d, J=7.33Hz, 1H) 4.18(s, 4H) 3.94(s, 3H) 2.07(d, J=7.33Hz, 3H). LC-MS 364. | 25 |
| 61 | 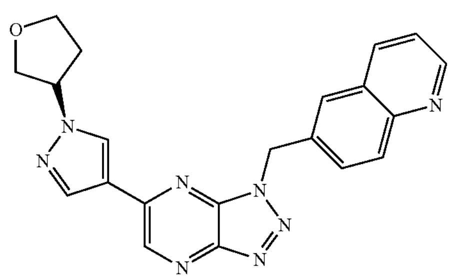 | 6-{6-[(R)-1-(Tetrahydrofuran-3-yl)-1H-pyrazol-4-yl]-[1,2,3]triazolo[4,5-b]pyrazin-1-ylmethyl}-quinoline | 1H NMR(300 MHz, DMSO-d6) δ ppm 9.23(s, 1H) 8.88(dd, J=4.14, 1.70Hz, 1H) 8.72(s, 1H) 8.34(s, 1H) 8.33(s, 1H) 7.97-8.05(m, 2H) 7.81(dd, J=8.85, 2.07Hz, 1H) 7.52(dd, J=8.19, 4.24Hz, 1H) 6.15(s, 1H) 5.08-5.19(m, 1H) 3.91-4.12(m, 3H) 3.79-3.88(m, J=5.46Hz, 1H) 2.29-2.43(m, 1H). LC-MS 399. | 18 |

TABLE 3-continued

| Example | Structure | Name | NMR/LC-MS | Method |
|---|---|---|---|---|
| 62 | 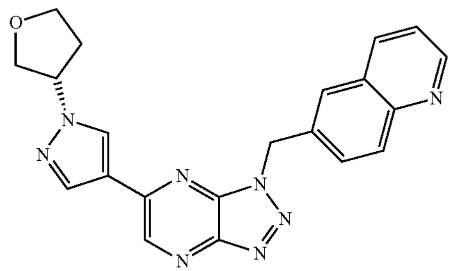 | 6-[6-[(S)-1-(Tetrahydrofuran-3-yl)-1H-pyrazol-4-yl]-[1,2,3]triazolo[4,5-b]pyrazin-1-ylmethyl]-quinoline | 1H NMR(300 MHz, DMSO-d6) δ ppm 9.25(s, 1H) 8.90(dd, J=4.14, 1.70Hz, 1H) 8.73(s, 1H) 8.37(d, J=8.85Hz, 1H) 8.34(s, 1H) 7.98-8.07(m, 2H) 7.83(dd, J=8.67, 2.07Hz, 1H) 7.53(dd, J=8.29, 4.14Hz, 1H) 6.16(s, 2H) 5.09-5.20(m, J=7.91Hz, 1H) 3.94-4.07(m, 3H) 3.80-3.91(m, 1H) 2.26-2.44(m, 2H). LC-MS 399. | 18 |
| 63 | 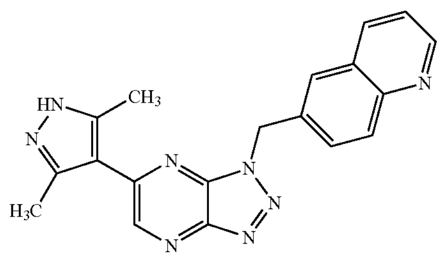 | 6-[6-(3,5-Dimethyl-1H-pyrazol-4-yl)-[1,2,3]triazolo[4,5-b]pyrazin-1-ylmethyl]-quinoline | 1H NMR(400 MHz, DMSO-d6) δ ppm 8.94(dd, J=4.42, 1.64Hz, 1H) 8.91(s, 1H) 8.43-8.49(m, 1H) 8.01-8.09(m, 2H) 7.84(dd, J=8.72, 1.89Hz, 1H) 7.61(dd, J=8.34, 4.29Hz, 1H) 6.18(s, 2H) 2.38(s, 6H). LC-MS 357. | 17 |
| 64 | 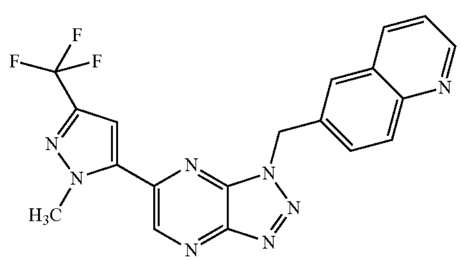 | 6-[6-(2-Methyl-5-trifluoromethyl-2H-pyrazol-3-yl)-[1,2,3]triazolo[4,5-b]pyrazin-1-ylmethyl]-quinoline | 1H NMR(400 MHz, DMSO-d6) δ ppm 9.39(s, 1H) 8.82-8.97(m, 1H) 8.31-8.44(m, 1H) 8.10(d, J=1.77Hz, 1H) 8.03(d, J=8.84Hz, 1H) 7.79-7.89(m, 2H) 7.55(dd, J=8.21, 4.17Hz, 1H) 6.28(s, 2H) 4.22(s, 3H). LC-MS 411. | 20 |

TABLE 3-continued

| Example | Structure | Name | NMR/LC-MS | Method |
|---|---|---|---|---|
| 65 | 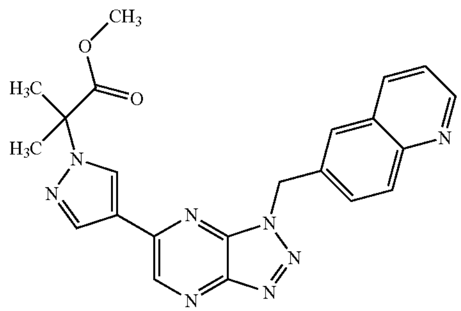 | 2-Methyl-2-[4-(3-quinolin-6-yl-methyl-3H-[1,2,3]triazolo[4,5-b]pyrazin-5-yl)-pyrazol-1-yl]-propionic acid methyl ester | 1H NMR(400 MHz, DMSO-d6) δ ppm 9.29(s, 1H) 8.82-8.98(m, 2H) 8.38(d, J=7.33Hz, 1H) 8.35(s, 1H) 7.99-8.06(m, 2H) 7.83(dd, J=8.72, 1.89Hz, 2H) 7.54(dd, J=8.34, 4.04Hz, 2H) 6.17(s, 2H) 3.64(s, 3H) 1.85(s, 6H). LC-MS 429. | 17 |
| 66 | 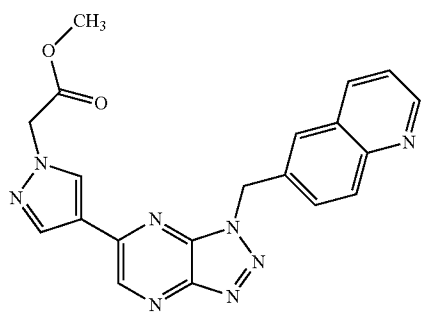 | [4-(3-Quinolin-6-yl-methyl-3H-[1,2,3]triazolo[4,5-b]pyrazin-5-yl)-pyrazol-1-yl]-acetic acid methyl ester | 1H NMR(400 MHz, DMSO-d6) δ ppm 9.24(s, 1H) 8.89(dd, J=4.17, 1.64Hz, 1H) 8.68(s, 1H) 8.33-8.41(m, 2H) 8.02(d, J=8.84Hz, 1H) 7.99(s, 1H) 7.83(dd, J=8.59, 2.02Hz, 1H) 7.53(dd, J=8.34, 4.29Hz, 1H) 6.16(s, 2H) 5.23(dd, J=8.34, 4.29Hz, 1H) 6.16(s, 2H) 5.23(s, 2H) 3.70(s, 3h). LC-MS 401. | 17 |
| 67 | 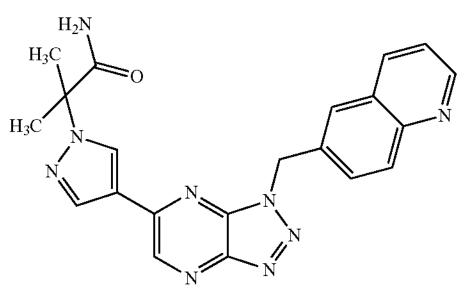 | 2-[4-(3-Quinolin-6-yl-methyl-3H-[1,2,3]triazolo[4,5-b]pyrazin-5-yl)-pyrazol-1-yl]-isobutyramide | 1H NMR(400 MHz, DMSO-d6) δ ppm 9.29(s, 1H) 8.89(dd, J=4.17, 1.64Hz, 1H) 8.80(s, 1H) 8.35-8.42(m, 1H) 8.33(s, 1H) 7.98-8.05(m, 2H) 7.83(dd, J=8.72, 1.89Hz, 1H) 7.53(dd, J=8.34, 4.29Hz, 1H) 7.26(s, 1H) 7.07(s, 1H) 6.17(s, 2H) 1.78(s, 6H). LC-MS 414. | 24 |

TABLE 3-continued

| Example | Structure | Name | NMR/LC-MS | Method |
|---|---|---|---|---|
| 68 | 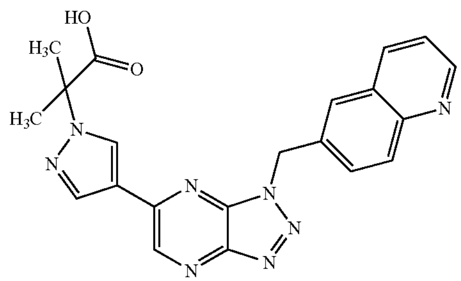 | 2-Methyl-2-[4-(3-quinolin-6-ylmethyl-3H-[1,2,3]triazolo[4,5-b]pyrazin-5-yl)-pyrazol-1-yl]-propionic acid | 1H NMR(400 MHz, DMSO-d6) δ ppm 9.25(s, 1H) 8.88(dd, J=4.04, 1.77Hz, 1H) 8.73(s, 1H) 8.37(dd, J=8.34, 1.52Hz, 1H) 8.24(s, 1H) 7.98-8.05(m, 2H) 7.82(dd, J=8.84, 2.02Hz, 1H) 7.52(dd, J=8.34, 4.04Hz, 1H) 6.15(s, 2H) 1.70(s, 6H). LC-MS 415. | 24 |
| 69 | 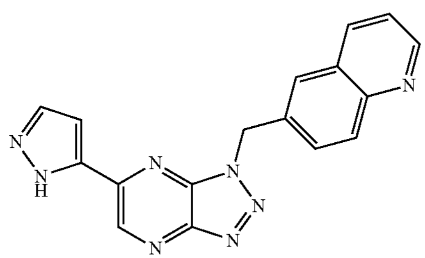 | 6-[6-(2H-Pyrazol-3-yl)-[1,2,3]triazolo[4,5-b]pyrazin-1-ylmethyl]-quinoline | 1H NMR(300 MHz, DMSO-d6) δ ppm 13.53(s, 1H) 9.45(s, 1H) 8.90(dd, J=3.96, 1.70Hz, 1H) 8.36(d, J=1.32Hz, 1H) 7.93-8.11(m, 2H) 7.85(dd, J=8.67, 1.88Hz, 1H) 7.54(dd, J=8.29, 4.14Hz, 1H) 6.98-7.11(m, 1H) 6.21(s, 2H). LC-MS 329. | 17 |

TABLE 4

| Example | Structure | Name | NMR/LC-MS | Method |
|---|---|---|---|---|
| 70 | 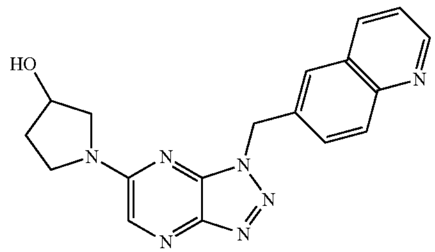 | 1-[1-(quinolin-6-yl-methyl)-1H-[1,2,3]tri-azolo[4,5-b]py-razin-6-yl]pyr-rolidin-3-ol | 1H NMR(500 MHz, DMSO-d6) δ ppm 3.63-3.72(m, 4H) 4.40-4.49(m, 1H) 5.91(s, 2H) 7.54(dd, J=8.52, 4.12Hz, 1H) 7.77(dd, J=8.52, 1.92Hz, 1H) 7.94(s, 1H) 8.02(d, J=8.52Hz, 1H) 8.21(br. s., 1H) 8.36(d, J=7.97Hz, 1H) 8.85-8.93(m, 1H) (two aliphatic protons not resolved, due to water peak). LC-MS 348. | 26 |
| 71 | 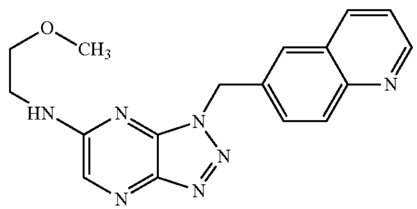 | N-(2-meth-oxyethyl)-1-(quino-lin-6-yl-methyl)-1H-[1,2,3]tri-azolo[4,5-b]py-razin-6-amine | 1H NMR(400 MHz, DMSO-d6) δ ppm 3.21(s, 3H) 3.45-3.54(m, 4H) 5.88(s, 2H) 7.53(dd, J=8.34, 4.29Hz, 1H) 7.74(dd, J=8.84, 2.02Hz, 1H) 7.92(d, J=1.26Hz, 1H) 8.00(d, J=8.59Hz, 1H) 8.10(s, 1H) 8.29(t, J=5.05Hz, 1H) 8.36(d, J=7.33Hz, 1H) 8.89(dd, J=4.17, 1.64Hz, 1H). LC-MS 335. | |
| 72 | 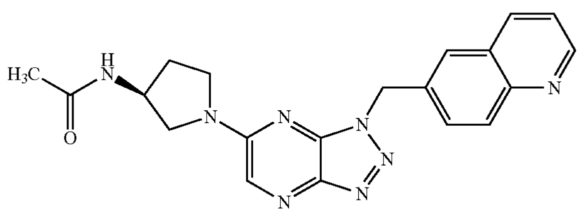 | N-{(3S)-1-[1-(quino-lin-6-yl-methyl)-1H-[1,2,3]tri-azolo[4,5-b]py-razin-6-yl]pyr-rolidin-3-yl}acetamide | 1H NMR(500 MHz, DMSO-d6) δ ppm 1.79-1.84(m, 3H) 3.64-3.74(m, 2H) 3.76-3.84(m, 2H) 4.35-4.44(m, 1H) 5.91(s, 2H) 7.54(dd, J=8.20, 2.20Hz, 1H) 7.95(s, 1H) 8.01(d, J=8.79Hz, 1H) 8.16(br. s., 1H) 8.22(br. s., 1H) 8.36(d, J=8.24Hz, 1H) 8.87-8.93(m, 1H) (two aliphatic proton not resolved, due to solvent peak). LC-MS-389. | 26 |
| 73 | 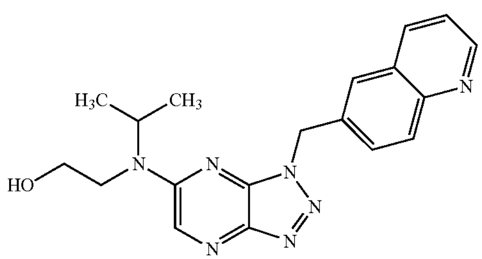 | 2-[isopropyl[1-(quino-lin-6-yl-methyl)-1H-[1,2,3]tri-azolo[4,5-b]py-razyl-6-yl]ami-no}ethanol | 1H NMR(500 MHz, DMSO-d6) δ ppm 1.20(d, J=6.32Hz, 6H) 3.54-3.66(m, 4H) 3.87-3.96(m, 1H) 5.84-5.96(m, 2H) 7.54(dd, J=8.10, 4.26Hz, 1H) 7.78(dd, J=8.50, 1.80Hz, 1H) 7.98-8.03(m, 2H) 8.35(d, J=8.52Hz, 1H) 8.40-8.43(m, 1H) 8.87-8.91(m, 1H). LC-MS 364. | 26 |

TABLE 4-continued

| Example | Structure | Name | NMR/LC-MS | Method |
|---|---|---|---|---|
| 74 | 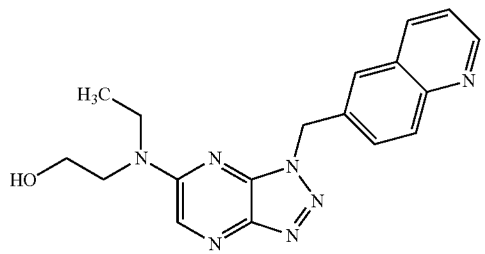 | 2-{ethyl[1-(quinolin-6-ylmethyl)-1H-[1,2,3]triazolo[4,5-b]pyrazin-6-yl]amino}ethanol | 1H NMR(500 MHz, DMSO-d6) δ ppm 1.13(t, J=7.20Hz, 3H) 3.62-3.71(m, 4H) 5.89(s, 2H) 7.54(dd, J=8.10, 4.37Hz, 1H) 7.78(dd, J=8.10, 1.95Hz, 1H) 7.98-8.01(m, 1H) 8.01-8.03(m, 1H) 8.33-8.36(m, 1H) 8.37(d, J=5.50Hz, 1H) 8.89(d, J=3.57Hz, 1H)(two aliphatic protons not resolved, due to water peak). LC-MS 350. | 26 |
| 75 | 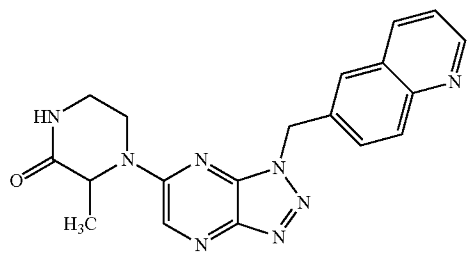 | 3-methyl-4-[1-(quinolin-6-ylmethyl)-1H-[1,2,3]triazolo[4,5-b]pyrazin-6-yl]piperazin-2-one | 1H NMR(500 MHz, DMSO-d6) δ ppm 1.38(d, J=6.59Hz, 3H) 3.52(br. s., 2H) 5.95(s, 2H) 5.22Hz, 2H) 7.54(dd, J=8.10, 4.12Hz, 1H) 7.77(dd, J=8.40, 2.00Hz, 1H) 7.95-8.03(m, 2H) 8.10(s, 1H) 8.35(d, J=8.24Hz, 1H) 8.48-8.54(m, 1H) 8.89(d, J=4.12Hz, 1H)(three aliphatic protons not resolved, due to water peak). LC-MS 375. | 26 |
| 76 | 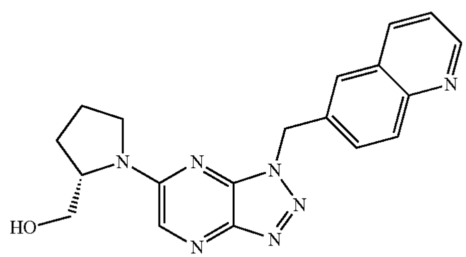 | {(2S)-1-[1-(quinolin-6-ylmethyl)-1H-[1,2,3]triazolo[4,5-b]pyrazin-6-yl]pyrrolidin-2-yl}methanol | 1H NMR(500 MHz, DMSO-d6) δ ppm 1.97(br. s, 2H) 2.03(br. s., 2H) 3.65(s, 2H) 5.89(s, 2H) 7.54(dd, J=8.10, 3.85Hz, 1H) 7.79(d, J=8.10, 2.20Hz, 2H) 7.96-8.03(m, 2H) 8.23-8.31(m, 1H) 8.37(d, J=7.14Hz, 1H) 8.86-8.94(m, 1H) (three aliphatic protons not resolved, due to water peak). LC-MS 362. | 26 |
| 77 | 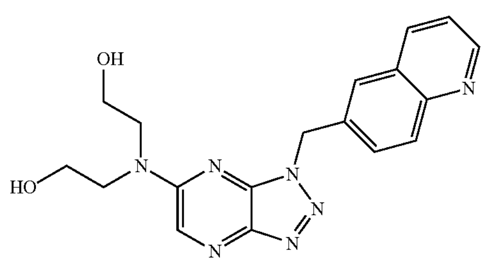 | 2,2'-{[1-(quinolin-6-ylmethyl)-1H-[1,2,3]triazolo[4,5-b]pyrazin-6-yl]imino}diethanol | 1H NMR(500 MHz, DMSO-d6) δ ppm 3.64(t, J=4.67Hz, 4H) 3.75(t, J=5.20Hz, 4H) 5.89(s, 2H) 7.54(dd, J=8.10, 4.12Hz, 1H) 7.79(dd, J=8.24, 1.37Hz, 2H) 7.99-8.04(m, 2H) 8.37(d, J=8.24Hz, 1H) 8.40-8.43(m, 1H) 8.87-8.92(m, 1H). LC-MS 366. | 26 |

TABLE 4-continued

| Example | Structure | Name | NMR/LC-MS | Method |
|---|---|---|---|---|
| 78 | 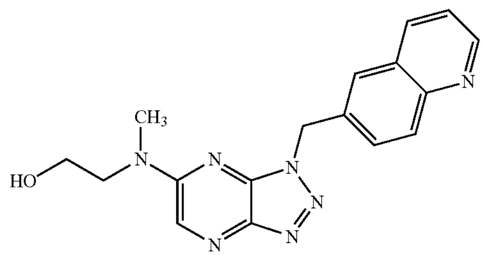 | 2-{[methyl][1-(quinolin-6-ylmethyl)-1H-[1,2,3]triazolo[4,5-b]pyrazin-6-yl]amino}ethanol | 1H NMR(500 MHz, DMSO-d6) δ ppm 3.23(br. s, 3H) 3.64(t, J=5.22Hz, 2H) 3.75(t, J=5.22, 0.01Hz, 2H) 5.90(s, 1H) 7.54(dd, J=8.10, 4.26Hz, 1H) 7.78(d, J=8.52Hz, 1H) 7.98(s, 1H) 8.01(d, J=8.52Hz, 1H) 8.36(d, J=8.52Hz, 1H) 8.41(s, 1H) 8.84-8.95(m, 1H). LC-MS 336. | 26 |
| 79 | 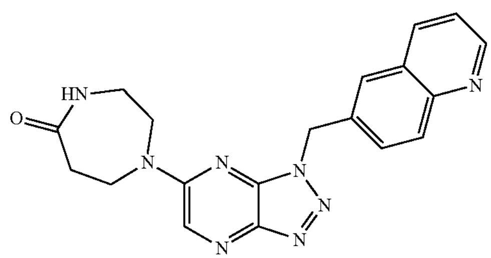 | 1-[1-(quinolin-6-ylmethyl)-1H-[1,2,3]triazolo[4,5-b]pyrazin-6-yl]-1,4-diazepan-5-one | 1H NMR(500 MHz, DMSO-d6) δ ppm 2.65-2.74(m, 2H) 3.83-4.06(m, 2H) 5.93(s, 2H) 7.54(dd, J=8.20, 3.85Hz, 1H) 7.61(br. s, 1H) 7.80(dd, J=8.40, 2.00Hz, 1H) 7.98-8.03(m, 2H) 8.32-8.41(m, 1H) 8.53-8.56(m, 1H) 8.85-8.93(m, 1H)(four aliphatic protons not resolved, due to water peak). LC-MS 375. | 26 |
| 80 | 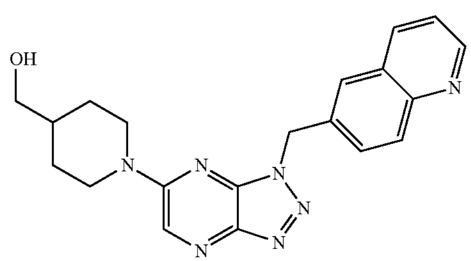 | {1-[1-(quinolin-6-ylmethyl)-1H-[1,2,3]triazolo[4,5-b]pyrazin-6-yl]piperidin-4-yl}methanol | 1H NMR(500 MHz, DMSO-d6) δ ppm 1.12-1.21(m, 2H) 1.71-1.80(m, 3H) 5.91(s, 2H) 7.54(dd, J=8.24, 4.12Hz, 1H) 7.76(dd, J=8.00, 1.92Hz, 1H) 7.96(s, 1H) 8.01(d, J=8.79Hz, 1H) 8.35(d, J=7.97Hz, 1H) 8.52-8.57(m, 1H) 8.90(d, J=4.40Hz, 1H)(six aliphatic protons not resolved, due to water peak). LC-MS 376. | 26 |

TABLE 4-continued

| Example | Structure | Name | NMR/LC-MS | Method |
|---|---|---|---|---|
| 81 | 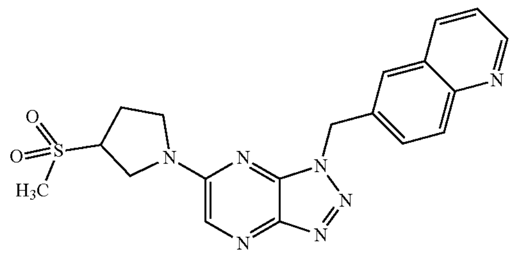 | 6-({6-[3-(methylsulfonyl)pyrrolidin-1-yl]-1H-[1,2,3]triazolo[4,5-b]pyrazin-1-yl}methyl)quinoline | 1H NMR(500 MHz, DMSO-d6) δ ppm 3.10(s, 3H) 3.68-3.76(m, 1H) 3.79-3.87(m, 1H) 3.92-4.09(m, 2H) 4.11-4.22(m, 1H) 5.94(s, 2H) 7.53(dd, J=8.10, 4.26Hz, 1H) 7.78(dd, J=8.38, 1.79Hz, 1H) 7.97(s, 1H) 8.01(d, J=8.52Hz, 1H) 8.24-8.31(m, 1H) 8.36(d, J=7.97Hz, 1H) 8.89(d, J=4.12Hz, 1H)(two sliphatic protons not resolved, due to solvent peak). LC-MS 410. | 26 |
| 82 | 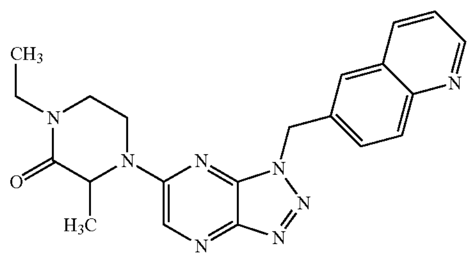 | 1-ethyl-3-methyl-4-[1-(quinolin-6-ylmethyl)-1H-[1,2,3]triazolo[4,5-b]pyrazin-6-yl]piperazin-2-one | 1H NMR(500 MHz, DMSO-d6) δ ppm 1.06(t, J=7.00Hz, 3H) 1.38(d, J=6.59Hz, 3H) 5.94(s, 2H) 7.54(dd, J=8.20, 4.12Hz, 1H) 7.77(d, J=8.52Hz, 1H) 7.96-8.05(m, 2H) 8.35(d, J=7.69Hz, 1H) 8.47-8.54(m, 1H) 8.86-8.92(m, 1H)(seven aliphatic protons not resolved, due to water peak). LC-MS 403. | 26 |
| 83 | 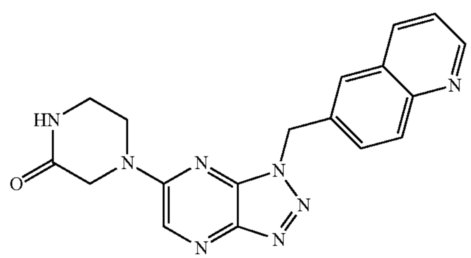 | 4-[1-(quinolin-6-ylmethyl)-1H-[1,2,3]triazolo[4,5-b]pyrazin-6-yl]piperazin-2-one | 1H NMR(500 MHz, DMSO-d6) δ ppm 3.88-3.99(m, J=1.10Hz, 2H) 4.21-4.32(m, 2H) 5.95(s, 2H) 7.54(dd, J=8.24, 4.40Hz, 1H) 7.78(d, J=8.52Hz, 1H) 7.97(s, 1H) 8.02(d, J=9.61Hz, 1H) 8.16-8.23(m, 1H) 8.36(d, J=7.97Hz, 1H) 8.47-8.57(m, 1H) 8.86-8.94(m, 1H) (two aliphatic protons not resolved, due to water peak). LC-MS 361. | 26 |
| 84 | 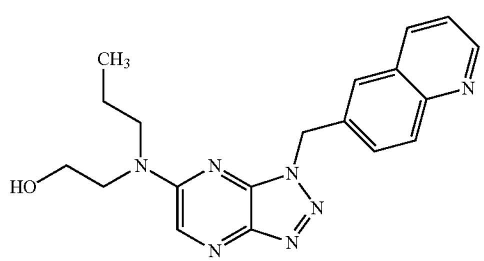 | 2-{propyl[1-(quinolin-6-ylmethyl)-1H-[1,2,3]triazolo[4,5-b]pyrazin-6-yl]amino}ethanol | 1H NMR(500 MHz, DMSO-d6) δ ppm 0.85(t, J=7.00Hz, 3H) 1.52-1.63(m, 2H) 3.57(t, J=9.89Hz, 2H) 3.60-3.65(m, 2H) 3.69(t, J=4.94Hz, 2H) 5.89(s, 2H) 7.54(dd, J=8.38, 3.98Hz, 1H) 7.77(d, J=6.87Hz, 1H) 7.97-8.03(m, 2H) 8.32-8.40(m, 2H) 8.89(d, J=4.12Hz, 1H). LC-MS 364. | 26 |

TABLE 4-continued

| Example | Structure | Name | NMR/LC-MS | Method |
|---|---|---|---|---|
| 85 | 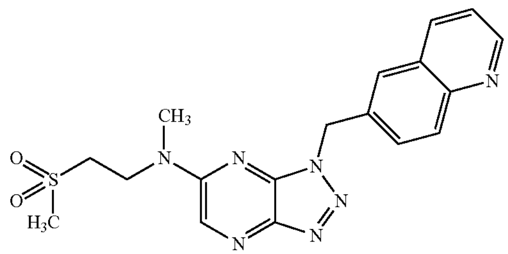 | N-methyl-N-[2-(methylsulfonyl)ethyl]-1-(quinolin-6-yl-methyl)-1H-[1,2,3]triazolo[4,5-b]pyrazin-6-amine | 1H NMR(500 MHz, DMSO-d6) δ ppm 3.01(s, 3H) 3.49-3.51(m, 2H) 4.07(d, J=6.59Hz, 2H) 5.82-6.06(m, 2H) 7.54(dd, J=8.10, 4.12Hz, 1H) 7.80(d, J=8.79Hz, 1H) 7.98-8.04(m, 2H) 8.37(d, J=8.24Hz, 1H) 8.39-8.42(m, 1H) 8.90(d, J=5.77Hz, 1H)(three aliphatic protons not resolved, due to water and solvent peaks). LC-MS 398. | 26 |
| 86 | 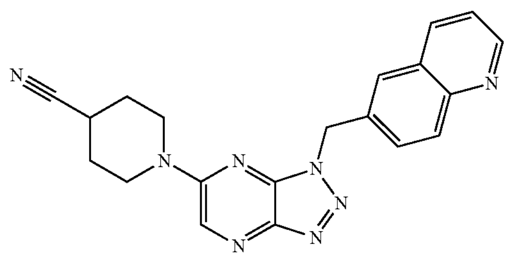 | 1-[1-(quinolin-6-yl-methyl)-1H-[1,2,3]triazolo[4,5-b]pyrazin-6-yl]piperidine-4-carbonitrile | 1H NMR(500 MHz, DMSO-d6) δ ppm 1.75-1.83(m, 2H) 1.95-2.02(m, 2H) 3.58-3.62(m, 4H) 5.92-5.94(m, 2H) 7.54(dd, J=8.20, 4.12Hz, 1H) 7.77(dd, J=8.20, 2.00Hz, 1H) 7.94-7.99(m, 1H) 8.02(d, J=8.52Hz, 1H) 8.36(d, J=8.24Hz, 1H) 8.51-8.61(m, 1H) 8.83-8.95(m, 1H)(one aliphatic proton not resolved, due to solvent peak). LC-MS 371. | 26 |
| 87 | 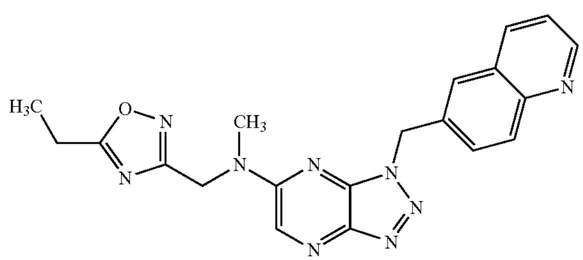 | N-[(5-ethyl-1,2,4-oxadiazol-3-yl)methyl]-N-methyl-1-(quinolin-6-yl-methyl)-1H-[1,2,3]triazolo[4,5-b]pyrazin-6-amine | 1H NMR(500 MHz, DMSO-d6) δ ppm 1.20(t, J=7.42Hz, 3H) 2.85(q, J=7.42Hz, 2H) 5.06(s, 2H) 5.90(s, 2H) 7.54(dd, J=8.20, 4.10Hz, 1H) 7.73(dd, J=8.20, 1.65Hz, 1H) 7.92-7.98(m, 2H) 8.33(d, J=7.69Hz, 1H) 8.49-8.54(m, 1H) 8.90(d, J=4.00Hz, 1H)(three aliphatic protons not resolved, due to water and solvent peaks). LC-MS 402. | 26 |

| Example | Structure | Name | NMR/LC-MS | Method |
|---|---|---|---|---|
| 88 | 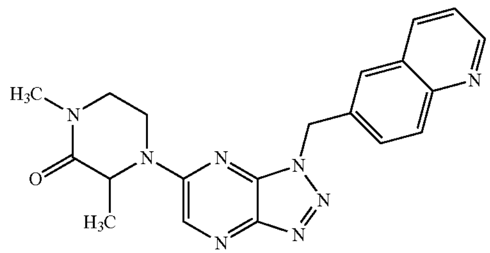 | 13-dimethyl-4-[1-(quinolin-6-ylmethyl)-1H-[1,2,3]triazolo[4,5-b]pyrazin-6-yl]piperazin-2-one | 1H NMR(500 MHz, DMSO-d6) δ ppm 1.38(d, J=6.59Hz, 3H) 2.89-2.91(m, 3H) 5.94(s, 2H) 7.54(dd, J=8.20, 4.12Hz, 1H) 7.78(d, J=8.52Hz, 1H) 7.94-8.05(m, 2H) 8.35(d, J=7.97Hz, 1H) 8.48-8.59(m, 1H) 8.89(br. s., 1H)(five aliphatic protons not resolved, due to water peak). LC-MS 389. | 26 |
| 89 | 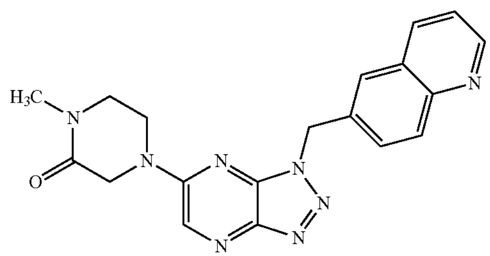 | 1-methyl-4-[1-(quinolin-6-ylmethyl)-1H-[1,2,3]triazolo[4,5-b]pyrazin-6-yl]piperazin-2-one | 1H NMR(500 MHz, DMSO-d6) δ ppm 2.92(s, 3H) 3.46-3.54(m, 2H) 4.03(t, J=5.22Hz, 2H) 4.28-4.37(m, 2H) 5.96(s, 2H) 7.54(dd, J=8.20, 4.40Hz, 1H) 7.78(dd, J=8.20, 1.92Hz, 1H) 7.96-7.99(m, 1H) 8.02(d, J=9.06Hz, 1H) 8.37(d, J=7.97Hz, 1H) 8.53-8.56(m, 1H) 8.85-8.95(m, 1H). LC-MS 375. | 26 |
| 90 | 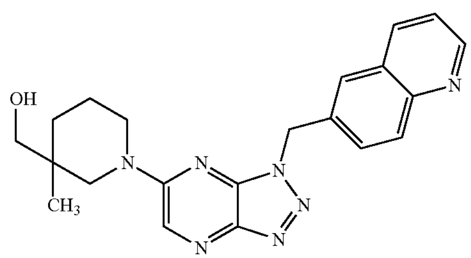 | {3-methyl-1-[1-(quinolin-6-ylmethyl)-1H-[1,2,3]triazolo[4,5-b]pyrazin-6-yl]piperidin-3-yl}methanol | 1H NMR(500 MHz, DMSO-d6) δ ppm 0.73-0.91(m, 1H) 1.22-1.40(m, 1H) 1.55-1.66(m, 3H) 3.12-3.23(m, 2H) 3.59-3.69(m, 2H) 3.78-3.88(m, 2H) 5.89(s, 2H) 7.54(dd, J=8.38, 3.98Hz, 1H) 7.77(dd, J=8.10, 2.33Hz, 1H) 7.97(s, 1H) 8.01(d, J=8.79Hz, 1H) 8.35(d, J=7.97Hz, 1H) 8.47-8.55(m, 1H) 8.84-8.95(m, 1H). LC-MS 390. | 26 |
| 91 | 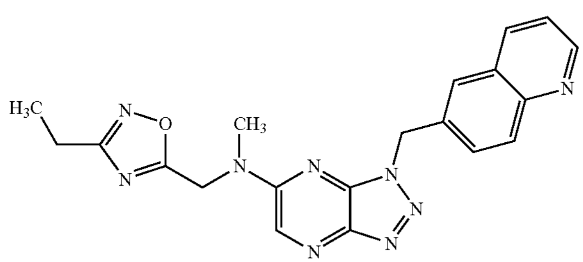 | N-[(3-ethyl-124-oxadiazol-5-yl)methyl]-N-methyl-1-(quinolin-6-ylmethyl)-1H-[1,2,3]triazolo[4,5-b]pyrazin-6-amine | 1H NMR(500 MHz, DMSO-d6) δ ppm 1.10(t, J=7.14Hz, 3H) 5.21(s, 2H) 5.87(s, 2H) 7.54(dd, J=8.52, 4.40Hz, 1H) 7.66(d, J=7.97Hz, 1H) 7.90(s, 1H) 7.94(d, J=7.97Hz, 1H) 8.32(d, J=7.42Hz, 1H) 8.49-8.60(m, 1H) 8.84-8.94(m, 1H) (five aliphatic protons not resolved, due to water peak). LC-MS 402. | 26 |

TABLE 4-continued

| Example | Structure | Name | NMR/LC-MS | Method |
|---|---|---|---|---|
| 92 | 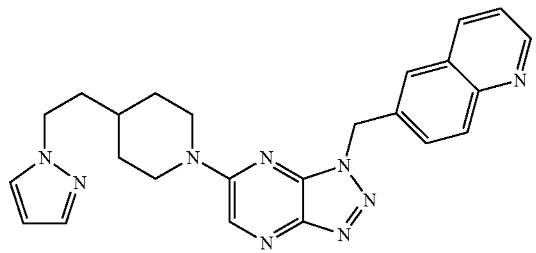 | 6-[(6-{4-[2-(1H-pyrazol-1-yl)ethyl]piperidin-1-yl}-1H-[1,2,3]triazolo[4,5-b]pyrazin-1-yl)methyl]quinoline | 1H NMR(500 MHz, DMSO-d6) δ ppm 1.17(s, 2H) 1.47-1.58(m, 1H) 1.67-1.81(m, 4H) 4.16(t, J=6.87Hz, 2H) 5.91(s, 2H) 6.23(s, 1H) 7.42(s, 1H) 7.54(dd, J=8.24, 4.12Hz, 1H) 7.76(d, J=8.79Hz, 1H) 7.96(s, 1H) 8.01(d, J=8.24Hz, 1H) 8.35(d, J=8.24Hz, 1H) 8.51-8.58(m, 1H) 8.85-8.92(m, 1H)(four aliphatic protons not resolved, due to water or solvent peaks). LC-MS 440. | 26 |
| 93 | 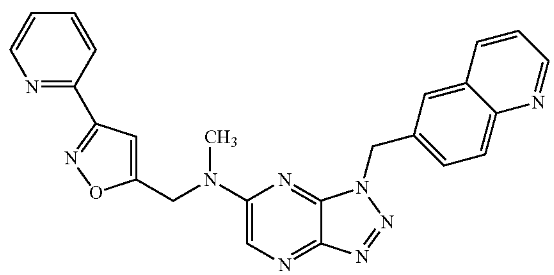 | N-methyl-N-[(3-pyridin-2-ylisoxazol-5-yl)methyl]-1-(quinolin-6-ylmethyl)-1H-[1,2,3]triazolo[4,5-b]pyrazin-6-amine | 1H NMR(500 MHz, DMSO-d6) δ ppm 5.18(s, 2H) 5.92(s, 2H) 6.90-6.96(m, 1H) 7.41(dd, J=8.24, 3.30Hz, 1H) 7.47-7.53(m, 1H) 7.89(d, J=8.40, 1.60Hz, 1H) 7.94(d, J=6.32Hz, 3H) 8.23(d, J=7.69Hz, 1H) 8.54(d, J=8.20Hz, 1H) 8.59-8.65(m, 1H) 8.78-8.85(m, 1H)(three aliphatic protons not resolved, due to water peak). LC-MS 450. | 26 |
| 94 | 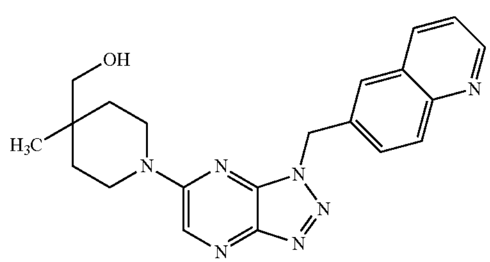 | {4-methyl-1-[1-(quinolin-6-ylmethyl)-1H-[1,2,3]triazolo[4,5-b]pyrazin-6-yl]piperidin-4-yl}methanol | 1H NMR(500 MHz, DMSO-d6) δ ppm 0.73-0.91(m, 3H) 1.22-1.40(m, 1H) 1.55-1.66(m, 3H) 3.12-3.23(m, 2H) 3.59-3.69(m, 2H) 3.78-3.88(m, 2H) 5.89(s, 2H) 7.54(dd, J=8.38, 3.98Hz, 1H) 7.77(dd, J=8.10, 2.33Hz, 1H) 7.97(s, 1H) 8.01(d, J=8.79Hz, 1H) 8.35(d, J=7.97Hz, 1H) 8.47-8.55(m, 1H) 8.84-8.94(m, 1H)(four aliphatic protons not resolved, due to water peak). LC-MS 390. | 26 |

| Example | Structure | Name | NMR/LC-MS | Method |
|---|---|---|---|---|
| 95 | 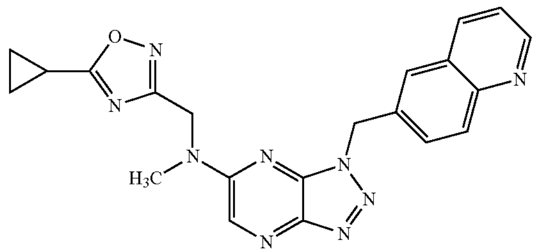 | N-{(5-cyclopropyl-1,2,4-oxadiazol-3-yl)methyl]-N-methyl-1-(quinolin-6-ylmethyl)-1H-[1,2,3]triazolo[4,5-b]pyrazin-6-amine | 1H NMR(500 MHz, DMSO-d6) δ ppm 0.97-1.04(m, 3H) 1.15-1.22(m, J=7.97, 2.75Hz, 2H) 5.02(s, 2H) 5.89(s, 2H) 7.54(dd, J=8.20, 4.40Hz, 1H) 7.72(d, J=7.42Hz, 1H) 7.89-8.00(m, 2H) 8.32(d, J=7.69Hz, 1H) 8.43-8.59(m, 1H) 8.79-8.99(m, 1H)(four aliphatic proton not resolved, due to solvent and water peaks). LC-MS 414. | 26 |
| 96 | 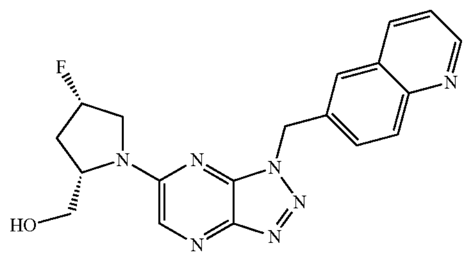 | {(2S,4S)-4-fluoro-1-[1-(quinolin-6-ylmethyl)-1H=8 1,2,3][triazolo[4,5-b]pyrrolidin-2-yl]methanol | 1H NMR(500 MHz, DMSO-d6) δ ppm 2.08-2.42(m, 2H) 3.79-3.86(m, 2H) 3.89-3.96(m, 1H) 4.04-4.14(m, 1H) 4.37-4.48(m, 1H) 5.02-5.10(m, 1H) 5.92(s, 2H) 7.54(dd, J=8.24, 4.40Hz, 1H) 7.83(m, 1H) 7.96-8.07(m, 2H) 8.32-8.43(m, J=8.24Hz, 2H) 8.83-8.95(m, 1H). LC-MS 380. | 26 |
| 97 | 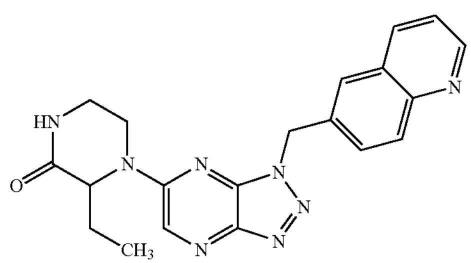 | 3-ethyl-4-[1-(quinolin-6-ylmethyl)-1H-[1,2,3]triazolo[4,5-b]pyrazin-6-yl]piperazin-2-one | 1H NMR(500 MHz, DMSO-d6) δ ppm 0.85(t, J=7.14Hz, 3H) 1.78-2.03(m, 2H) 3.52-3.66(m, 4H) 4.24-4.46(m, 1H) 5.94(s, 2H) 7.54(dd, J=8.24, 4.40Hz, 1H) 7.76(dd, J=8.20, 2.20Hz, 1H) 7.95-8.02(m, 2H) 8.05(s, 1H) 8.34(d, J=8.24Hz, 1H) 8.49-8.56(m, 1H) 8.86-8.92(m, 1H). LC-MS 389. | 26 |
| 98 | 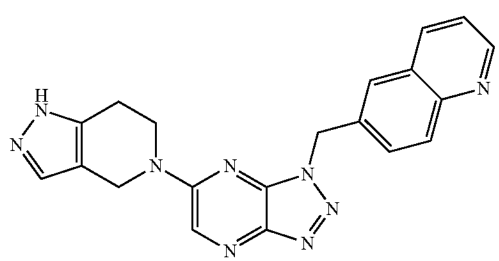 | 6-[[6-(1,4,6,7-tetrahydro-5H-pyrazolo[4,3-c]pyridin-5-yl)-1H-[1,2,3]triazolo[4,5-b]pyrazin-1-yl]methyl]quinoline | 1H NMR(500 MHz, DMSO-d6) δ ppm 2.77-2.83(m, 2H) 4.07-4.13(m, 2H) 4.77-4.82(m, 2H) 5.94(s, 2H) 7.47-7.50(m, 1H) 7.75-7.82(m, 1H) 7.96-8.04(m, 2H) 8.37(d, J=8.36Hz, 1H) 8.59-8.67(m, 1H) 8.85-8.93(m, 1H). LC-MS 384. | 26 |

TABLE 4-continued

TABLE 4-continued

| Example | Structure | Name | NMR/LC-MS | Method |
|---|---|---|---|---|
| 99 | 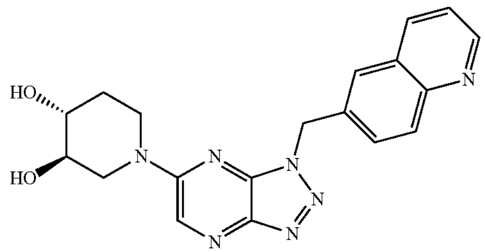 | (3R,4R)-1-[1-(quinolin-6-ylmethyl)-1H-[1,2,3]triazolo[4,5-b]pyrazin-6-yl]piperidine-3,4-diol | 1H NMR(500 MHz, DMSO-d6) δ ppm 1.34-1.47(m, 1H) 1.87-2.00(m, 1H) 3.59-3.66(m, 2H) 3.90-3.99(m, 2H) 4.05-4.14(m, 2H) 5.90(s, 2H) 7.54(dd, J=8.24, 4.40Hz, 1H) 7.78(dd, J=8.20, 1.65Hz, 1H) 7.97(s, 1H) 8.02(d, J=8.79Hz, 1H) 8.36(d, J=8.52Hz, 1H) 8.50-8.57(m, 1H) 8.84-8.95(m, 1H). LC-MS 378. | 26 |
| 100 | 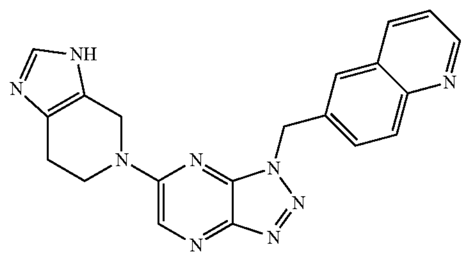 | 6-[[6-(3,4,6,7-tetrahydro-5H-imidazo[4,5-c]pyridin-5-yl)-1H-[1,2,3]triazolo[4,5-b]pyrazin-1-yl]methyl]quinoline | 1H NMR(500 MHz, DMSO-d6) δ ppm 2.74-2.88(m, 2H) 4.06-4.20(m, 2H) 4.73-4.91(m, 2H) 5.95(s, 2H) 7.54(dd, J=8.24, 3.85Hz, 1H) 7.79(dd, J=8.20, 1.92Hz, 1H) 7.97(s, 1H) 7.99-8.09(m, 2H) 8.36(d, J=7.69Hz, 1H) 8.63-8.70(m, 1H) 8.85-8.93(m, 1H). LC-MS 384. | 26 |
| 101 | 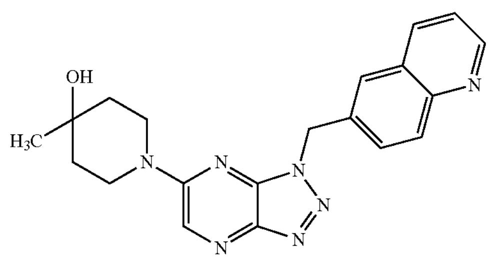 | 4-methyl-1-[1-(quinolin-6-ylmethyl)-1H-[1,2,3]triazolo[4,5-b]pyrazin-6-yl]piperidin-4-ol | 1H NMR(500 MHz, DMSO-d6) δ ppm 1.14(s, 3H) 1.42-1.61(m, 4H) 4.01-4.22(m, 4H) 5.90(s, 2H) 7.54(dd, J=8.38, 4.26Hz, 1H) 7.76(d, J=6.32Hz, 1H) 7.96(s, 1H) 8.01(d, J=8.24Hz, 1H) 8.35(d, J=8.52Hz, 1H) 8.52-8.57(m, 1H) 8.86-9.91(m, 1H). LC-MS 376. | 26 |

TABLE 4-continued

| Example | Structure | Name | NMR/LC-MS | Method |
|---|---|---|---|---|
| 102 | 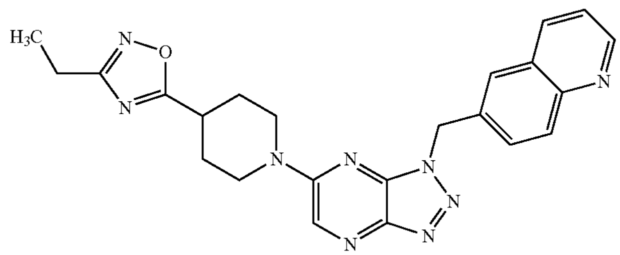 | 6-({6-[4-(3-eth-yl-124-oxa-diazol-5-yl)pipe-ridin-1-yl]-1H-[1,2,3]tri-azolo[4,5-b]pyra-zin-1-yl}meth-yl)quinoline | 1H NMR(500 MHz, DMSO-D6) δ ppm 1.21(t, 3H) 1.69-1.83(m, 2H) 2.09-2.17(m, 2H) 2.40-2.44(m, 1H) 2.65-2.73(m, 4H) 4.43-4.58(m, 2H) 5.93(s, 2H) 7.52(dd, J=8.52, 4.40Hz, 1H) 7.73-7.85(m, 1H) 7.95-8.09(m, 2H) 8.29-8.40(m, 1H) 8.55-8.67(m, 1H) 8.89(d, J=4.40Hz, 1H). LC-MS 442. | 26 |
| 103 | 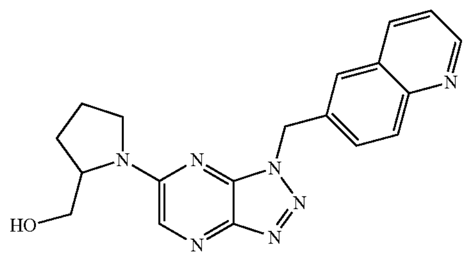 | {1-[1-(quinolin-6-yl-methyl)-1H-[1,2,3]tri-azolo[4,5-b]pyrro-lidin-2-yl}methanol | 1H NMR(500 MHz, DMSO-D6) δ ppm 1.91-2.01(m, 2H) 2.01-2.11(m, 2H) 3.61-3.72(m, 3H) 4.23-4.37(m, 2H) 4.74-5.04(m, 1H) 5.89(s, 2H) 7.46-7.62(m, 1H) 7.79(d, J=6.59Hz, 1H) 7.94-8.09(m, 2H) 8.27(s, 1H) 8.37(d, 1H) 8.89(s, 1H). LC-MS 362. | 26 |
| 104 | 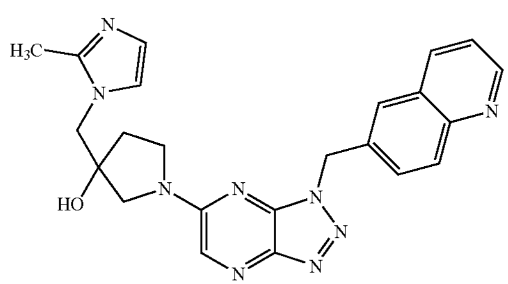 | 3-[(2-methyl-1H-imi-dazol-1-yl)meth-yl]-1-[1-(quino-lin-6-yl-methyl)-1H-[1,2,3]tri-azolo[4,5-b]pyra-zin-6-yl]pyrro-lidin-3-ol | 1H NMR(500 MHz, DMSO-D6) δ ppm 1.91-2.01(m, 1H) 2.12-2.25(m, 1H) 2.66(s, 3H) 3.65-3.93(m, J=82.13Hz, 4H) 4.32-4.47(m, 2H) 5.57-5.68(m, 1H) 5.92(s, 2H) 7.50-7.66(m, 3H) 7.70-7.80(m, 1H) 7.89-7.96(m, 1H) 7.98-8.06(m, 1H) 8.20-8.28(m, 1H) 8.31-8.40(m, 1H) 8.90(s, 1H). LC-MS 442. | 26 |

TABLE 4-continued

| Example | Structure | Name | NMR/LC-MS | Method |
|---|---|---|---|---|
| 105 | 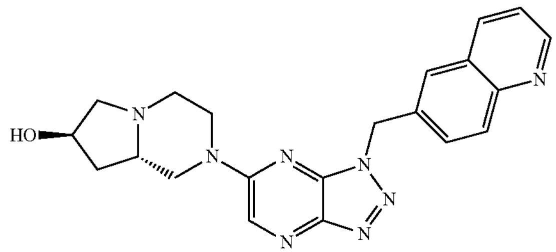 | (7R,8aS)-2-[1-(quinolin-6-ylmethyl)-1H-[1,2,3]triazolo[4,5-b]pyrazin-6-yl]octahydropyrrolo[12-a]pyrazin-7-ol | 1H NMR(500 MHz, DMSO-D6) δ ppm 1.82-2.04(m, 2H) 2.44(s, 2H) 2.66-2.70(m, 2H) 3.14-3.20(m, 2H) 3.61-3.72(m, 2H) 4.38-4.48(m, 2H) 5.92-5.95(m, 1H) 5.95(s, 2H) 7.55(dd, J=8.52, 3.85Hz, 1H) 7.73-7.83(m, 1H) 7.98(s, 1H) 8.02(d, J=8.79Hz, 1H) 8.33-8.41(m, J=1.37Hz, 1H) 8.53(s, 1H) 8.90(d, J=3.85Hz, 1H). LC-MS 403. | 26 |
| 106 | 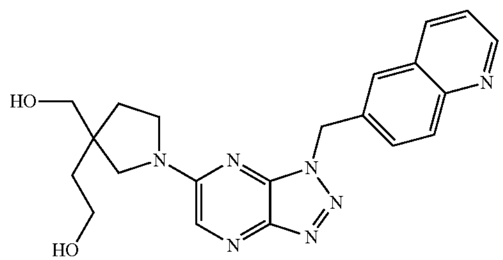 | 2-{3-(hydroxymethyl)-1-[1-(quinolin-6-ylmethyl)-1H-[1,2,3]triazolo[4,5-b]pyrazin-6-yl]pyrrolidin-3-yl}ethanol | 1H NMR(500 MHz, DMSO-D6) δ ppm 1.61-1.73(m, 2H) 1.76-1.87(m, 1H) 1.92-2.08(m, 1H) 2.44(m, 2H) 2.65-2.70(m, 2H) 3.15-3.22(m, 2H) 3.62-3.74(m, 4H) 4.46-4.60(m, 1H) 4.78-4.99(m, 1H) 7.54(dd, J=8.24, 4.12Hz, 1H) 7.71-7.80(m, 1H) 7.94(s, 1H) 7.97-8.06(m, J=8.52Hz, 1H) 8.14-8.21(m, 1H) 8.29-8.40(m, 1H) 8.89(s, 1H). LC-MS 406. | 26 |
| 107 | 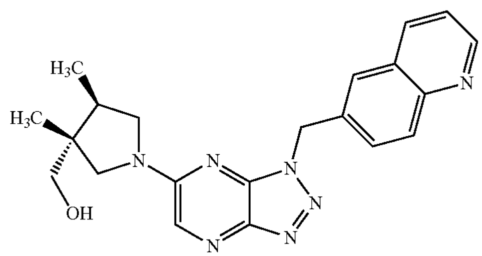 | {(3R,4R)-3,4-dimethyl-1-[1-(quinolin-6-ylmethyl)-1H-[1,2,3]triazolo[4,5-b]pyrazin-6-yl]pyrrolidin-3-yl}methanol | 1H NMR(500 MHz, DMSO-D6) δ ppm 0.88(s, 3H) 0.95(d, J=6.59Hz, 4H) 3.08-3.24(m, 2H) 3.62-3.70(m, 2H) 3.80-3.95(m, 2H) 4.80-4.93(m, 1H) 5.90(s, 2H) 7.48-7.58(m, 1H) 7.72-7.81(m, 1H) 7.88-7.96(m, 1H) 7.97-8.05(m, 1H) 8.16(s, 1H) 8.27-8.40(m, 1H) 8.83-8.97(m, 1H). LC-MS 390. | 26 |
| 108 | 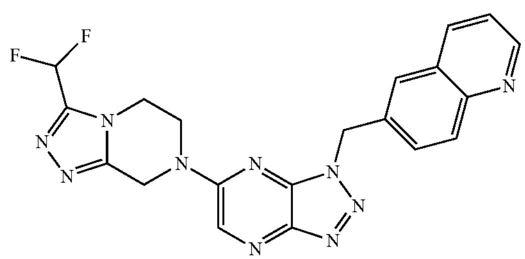 | 6-({6-[3-(difluoromethyl)-5,6-dihydro[1,2,4]triazolo[4,3-a]pyrazin-7(8H)-yl]-1H-[1,2,3]triazolo[4,5-b]pyrazin-1-yl}methyl)quinoline | 1H NMR(500 MHz, DMSO-D6) δ ppm 4.31(s, 2H) 7.51-7.56(m, 1H) 7.78-7.83(m, 1H) 7.99-8.04(m, 2H) 8.35-8.39(m, 1H) 8.70-8.77(m, 1H) 8.89(d, J=4.12Hz, 1H). LC-MS 435. | 26 |

| Example | Structure | Name | NMR/LC-MS | Method |
|---|---|---|---|---|
| 109 | 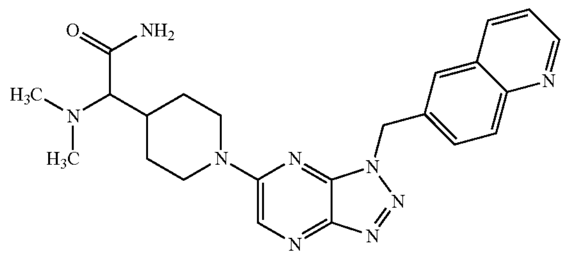 | 2-(dimethyl-amino)-2-{1-[1-(quinolin-6-yl-methyl)-1H-[1,2,3]triazolo[4,5-b]pyrazin-6-yl]piperidin-4-yl}acetamide | 1H NMR(500 MHz, DMSO-D6) δ ppm 1.24-1.37(m, 2H) 1.68-1.77(m, 1H) 1.86-2.00(m, 1H) 2.27-2.36(m, 1H) 2.41(s, 3H) 2.67(s, 3H) 2.71-2.83(m, 1H) 3.01-3.13(m, 2H) 3.18(s, 2H) 4.55-4.68(m, 2H) 5.86-5.96(m, 2H) 7.51-7.57(m, 1H) 7.67(d, J=4.67Hz, 1H) 7.74-7.79(m, 1H) 7.96(s, 1H) 7.99-8.04(m, 1H) 8.33-8.38(m, 1H) 8.58(s, 1H) 8.88-8.92(m, 1H). LC-MS 446. | 26 |
| 110 | 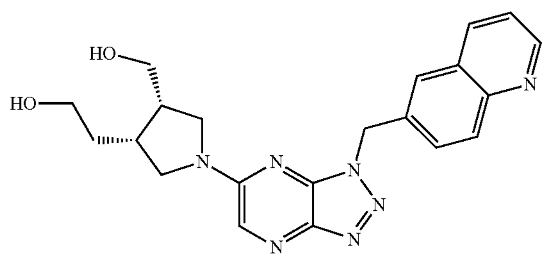 | 2-{(3R,4S)-4-(hydroxymethyl)-1-[1-(quinolin-6-yl-methyl)-1H-[1,2,3]triazolo[4,5-b]pyrazin-6-yl]pyrrolidin-3-yl}ethanol | 1H NMR(500 MHz, DMSO-D6) δ ppm 1.46-1.55(m, 1H) 1.63-1.74(m, 1H) 2.38-2.45(m, 2H) 3.61-3.65(m, 4H) 3.67-3.79(m, 4H) 4.58-4.70(m, 1H) 5.87-5.92(m, 3H) 7.54(dd, J=8.24, 4.39Hz, 1H) 7.75-7.80(m, 1H) 7.94(s, 1H) 8.01(d, J=8.52Hz, 1H) 8.16-8.21(m, 1H) 8.33-8.38(m, 1H) 8.89(d, J=4.12Hz, 1H). LC-MS 406. | 26 |
| 111 | 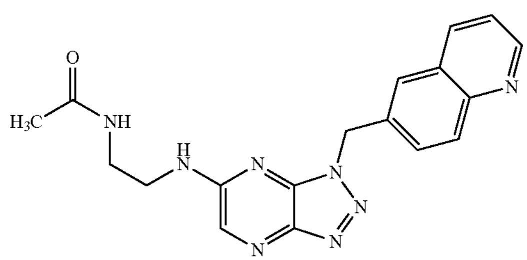 | N-(2-{[1-(quinolin-6-yl-methyl)-1H-[1,2,3]triazolo[4,5-b]pyrazin-6-yl]amino}ethyl)acetamide | 1H NMR(500 MHz, DMSO-D6) δ ppm 1.72-1.87(m, 3H) 2.40-2.45(m, 2H) 3.15-3.24(m, 2H) 5.88(s, 2H) 7.54(dd, J=8.24, 4.12Hz, 1H) 7.79(d, J=6.59Hz, 1H) 7.93(s, 1H) 7.96-8.08(m, 3H) 8.19(s, 1H) 8.36(d, J=7.97Hz, 1H) 8.89(d, J=4.12Hz, 1H). LC-MS 363. | 26 |

| Example | Structure | Name | NMR/LC-MS | Method |
|---|---|---|---|---|
| 112 | 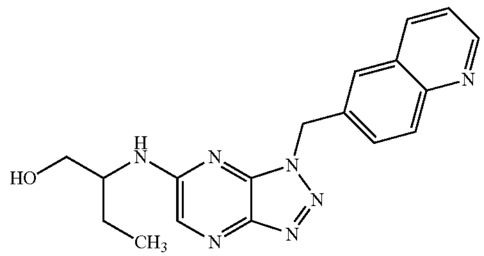 | 2-{[1-(quinolin-6-yl-methyl)-1H-[1,2,3]tri-azolo[4,5-b]pyra-zin-6-yl]ami-no}butan-1-ol | 1H NMR(500 MHz, DMSO-D6) δ ppm 0.85(t, J=7.28Hz, 3H) 1.44-1.54(m, 1H) 1.61-1.73(m, 1H) 3.17-3.24(m, 1H) 3.63-3.64(m, 2H) 3.89-3.97(m, 1H) 5.79-5.91(m, 2H) 7.54(dd, J=8.52, 4.12Hz, 1H) 7.75-7.80(m, 1H) 7.88-7.94(m, 1H) 7.97(s, 1H) 8.00(d, J=8.52Hz, 1H) 8.08-8.12(m, 1H) 8.33-8.37(m, 1H) 8.87-8.92(m, 1H). LC-MS 350. | 26 |
| 113 | 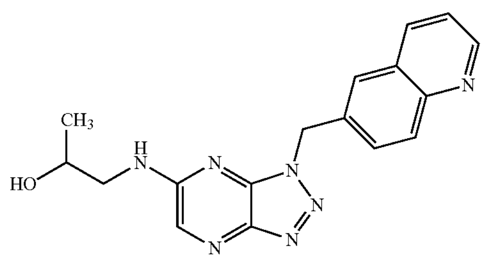 | 1-{[1-(quinolin-6-yl-methyl)-1H-[1,2,3]tri-azolo[4,5-b]pyra-zin-6-yl]ami-no}propan-2-ol | 1H NMR(500 MHz, DMSO-D6) δ ppm 1.08(d, J=5.77Hz, 3H) 2.41-2.44(m, 2H) 3.17-3.24(m, 1H) 3.79-3.90(m, 1H) 5.87(s, 2H) 7.54(dd, J=8.24, 4.40Hz, 1H) 7.76(d, J=6.59Hz, 1H) 7.95(s, 1H) 8.01(d, J=8.79Hz, 1H) 8.10-8.17(m, 2H) 8.35(d, J=8.24Hz, 1H) 8.90(d, J=3.85Hz, 1H). LC-MS 336. | 26 |
| 114 | 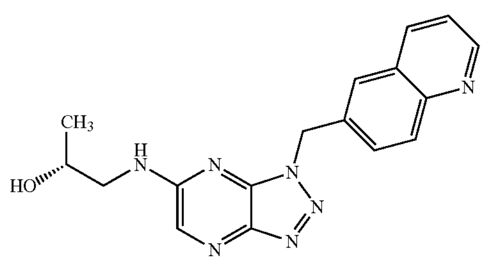 | (2R)-1-{[1-(quino-lin-6-yl-methyl)-1H-[1,2,3]tri-azolo[4,5-b]pyra-zin-6-yl]ami-no}propan-2-ol | 1H NMR(500 MHz, DMSO-D6) δ ppm 1.08(d, J=6.04Hz, 3H) 3.17-3.23(m, 2H) 3.79-3.91(m, 1H) 4.60-5.03(m, 1H) 5.80-5.92(m, 2H) 7.54(dd, J=8.24, 4.12Hz, 1H) 7.76(d, J=6.04Hz, 1H) 7.95(s, 1H) 8.01(d, J=8.52Hz, 1H) 8.10-8.17(m, 2H) 8.32-8.39(m, 1H) 8.90(d, J=4.12Hz, 1H). LC-MS 336. | 26 |
| 115 | 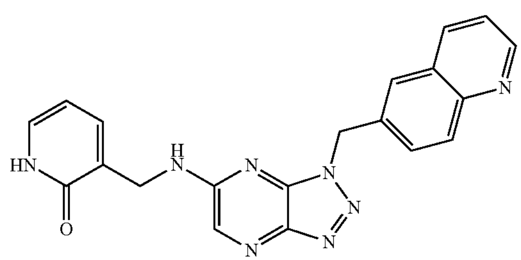 | 3-({[1-(quinolin-6-yl-methyl)-1H-[1,2,3]tri-azolo[4,5-b]pyra-zin-6-yl]ami-no}meth-yl)pyridin-2(1H)-one | 1H NMR(500 MHz, DMSO-D6) δ ppm 4.31-4.42(m, J=5.49Hz, 2H) 5.85-5.89(m, 2H) 7.21-7.29(m, 1H) 7.31-7.38(m, 1H) 7.43-7.63(m, J=8.52, 4.40Hz, 2H) 7.71(d, J=6.87Hz, 1H) 7.90-7.99(m, 2H) 8.11-8.19(m, 1H) 8.30-8.37(m, 1H) 8.48(s, 1H) 8.87-8.92(m, 1H) 11.65(s, 1H). LC-MS 385. | 26 |

TABLE 4-continued

| Example | Structure | Name | NMR/LC-MS | Method |
|---|---|---|---|---|
| 116 | 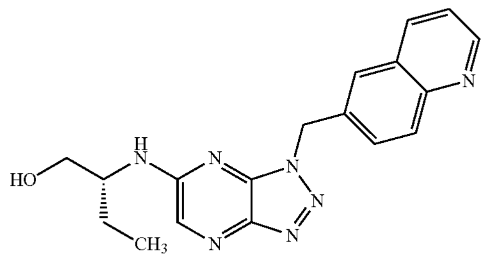 | (2R)-2-{[1-(quinolin-6-ylmethyl)-1H-[1,2,3]triazolo[4,5-b]pyrazin-6-yl]amino}butan-1-ol | 1H NMR(500 MHz, DMSO-D6) δ ppm 0.85(t, J=7.28Hz, 3H) 1.44-1.54(m, 1H) 1.61-1.73(m, 1H) 3.17-3.24(m, 1H) 3.63-3.64(m, 2H) 3.89-3.97(m, 1H) 5.79-5.91(m, 2H) 7.54(dd, J=8.52, 4.12Hz, 1H) 7.75-7.80(m, 1H) 7.88-7.94(m, 1H) 7.97(s, 1H) 8.00(d, J=8.52Hz, 1H) 8.08-8.12(m, 1H) 8.33-8.37(m, 1H) 8.87-8.92(m, 1H). LC-MS 350. | 26 |
| 117 | 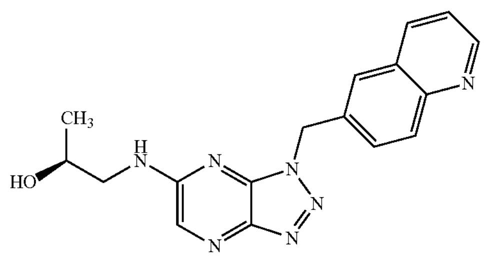 | (2S)-1-{[1-(quinolin-6-ylmethyl)-1H-[1,2,3]triazolo[4,5-b]pyrazin-6-yl]amino}propan-2-ol | 1H NMR(500 MHz, DMSO-D6) δ ppm 1.08(d, J=6.04Hz, 3H) 3.17-3.23(m, 2H) 3.79-3.91(m, 1H) 4.60-5.03(m, 1H) 5.80-5.92(m, 2H) 7.54(dd, J=8.24, 4.12Hz, 1H) 7.76(d, J=6.04Hz, 1H) 7.95(s, 1H) 8.01(d, J=8.52Hz, 1H) 8.10-8.17(m, 2H) 8.32-8.39(m, 1H) 8.90(d, J=4.12Hz, 1H). LC-MS 336. | 26 |
| 118 | 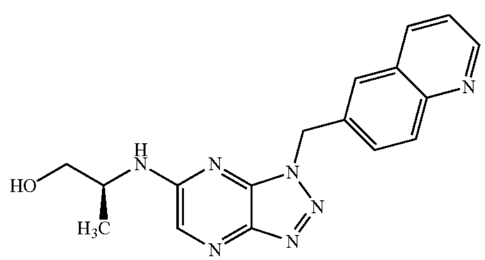 | (2S)-2-{[1-(quinolin-6-ylmethyl)-1H-[1,2,3]triazolo[4,5-b]pyrazin-6-yl]amino}propan-1-ol | 1H NMR(500 MHz, DMSO-D6) δ ppm 1.17(d, J=6.59Hz, 3H) 3.16-3.23(m, 1H) 3.61-3.67(m, 2H) 4.01-4.12(m, 1H) 5.79-5.91(m, 1H) 7.54(dd, J=8.24, 4.12Hz, 1H) 7.75-7.79(m, 1H) 7.93-8.03(m, 3H) 8.05-8.08(m, 1H) 8.33-8.38(m, 1H) 8.88-8.91(m, 1H, J=1.65Hz, 1H). LC-MS 336. | 26 |

TABLE 4-continued

| Example | Structure | Name | NMR/LC-MS | Method |
|---|---|---|---|---|
| 119 | 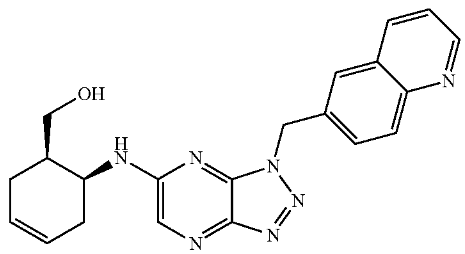 | [(1S,6R)-6-{[1-(quinolin-6-ylmethyl)-1H-[1,2,3]triazolo[4,5-b]pyrazin-6-yl]amino}cyclohex-3-en-1-yl]methanol | 1H NMR(500 MHz, DMSO-D6) δ ppm 2.03-2.18(m, 3H) 2.24-2.33(m, 1H) 2.41-2.44(m, 2H) 3.16-3.24(m, 2H) 4.39-4.47(m, 1H) 5.56-5.63(m, 1H) 5.68-5.76(m, 1H) 5.84-5.92(m, J=7.42Hz, 2H) 7.54(dd, J=8.10, 4.26Hz, 1H) 7.75-7.83(m, 2H) 7.96-8.03(m, 2H) 8.17-8.21(m, 1H) 8.32-8.38(m, 1H) 8.90(d, J=4.40Hz, 1H). LC-MS 388. | 26 |
| 120 | 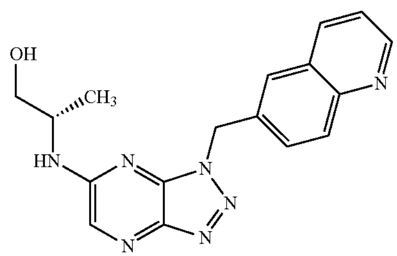 | (2R)-2-{[1-(quinolin-6-ylmethyl)-1H-[1,2,3]triazolo[4,5-b]pyrazin-6-yl]amino}propan-1-ol | 1H NMR(500 MHz, DMSO-D6) δ ppm 1.17(d, J=6.59Hz, 3H) 3.16-3.23(m, 1H) 3.61-3.67(m, 2H) 4.01-4.12(m, 1H) 5.79-5.91(m, 2H) 7.54(dd, J=8.24, 4.12Hz, 1H) 7.75-7.79(m, 1H) 7.93-8.03(m, 3H) 8.05-8.08(m, 1H) 8.38(m, 1H) 8.88-8.91(m, J=1.54Hz, 1H). LC-MS 336. | 26 |
| 121 | 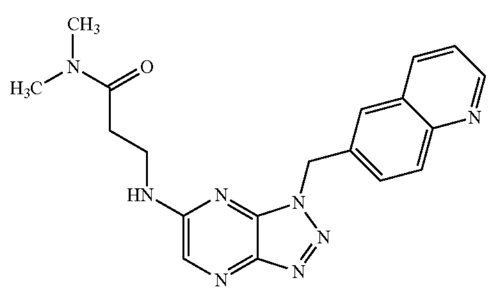 | N,N-dimethyl-N-3~-[1-(quinolin-6-ylmethyl)-1H-[1,2,3]triazolo[4,5-b]pyrazin-6-yl]-beta-alaninamide | 1H NMR(500 MHz, DMSO-d6) δ ppm 2.79-2.80(m, 8H) 3.55-3.60(m, J=6.04Hz, 2H) 5.90(s, 2H) 7.54(dd, J=8.10, 4.26Hz, 1H) 7.74-7.77(m, J=8.52Hz, 1H) 7.94(s, 1H) 7.97-8.03(m, J=8.52Hz, 1H) 8.05-8.10(m, 1H) 8.17(s, 1H) 8.36(d, J=8.79Hz, 1H) 8.89(s, 1H). LC-MS 377. | 26 |

TABLE 4-continued

| Example | Structure | Name | NMR/LC-MS | Method |
|---|---|---|---|---|
| 122 | 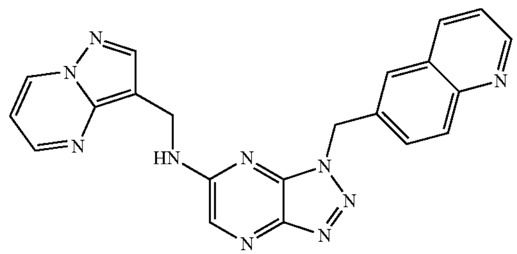 | N-(pyrazolo[1,5-a]pyrimidin-3-ylmethyl)-1-(quinolin-6-ylmethyl)-1H-[1,2,3]triazolo[4,5-b]pyrazin-6-amine | 1H NMR(500 MHz, DMSO-d6) δ ppm 4.74(s, 2H) 5.92(s, 2H) 6.99-7.05(m, 1H) 7.53(dd, J=8.38, 3.98Hz, 1H) 7.75(dd, J=8.65, 2.06Hz, 1H) 7.94(s, 1H) 7.96-8.02(m, 1H) 8.08-8.11(m, 1H) 8.25-8.26(m, 1H) 8.33(d, J=7.42Hz, 1H) 8.57-8.58(m, 2H) 8.89(s, 1H) 9.00-9.08(m, 1H). LC-MS 409. | 26 |
| 123 | 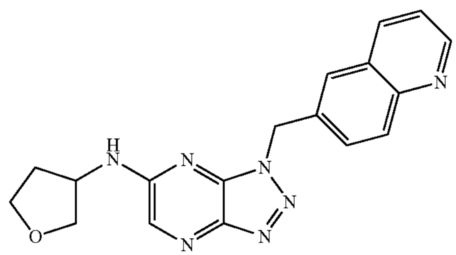 | 1-(quinolin-6-ylmethyl)-N-(tetrahydrofuran-3-yl)-1H-[1,2,3]triazolo[4,5-b]pyrazin-6-amine | 1H NMR(500 MHz, DMSO-d6) δ ppm 1.81-1.90(m, 1H) 2.20-2.27(m, 1H) 3.56-3.58(m, 1H) 3.71-3.77(m, 1H) 3.81-3.92(m, 3H) 5.90(s, 2H) 7.54(dd, J=8.52, 4.12Hz, 1H) 7.77(d, J=8.52Hz, 1H) 7.97(s, 1H) 7.99-8.03(m, J=8.52Hz, 1H) 8.04-8.09(m, 1H) 8.31-8.41(m, J=8.52Hz, 2H) 8.89(s, 1H). LC-MS 348. | 26 |
| 124 | 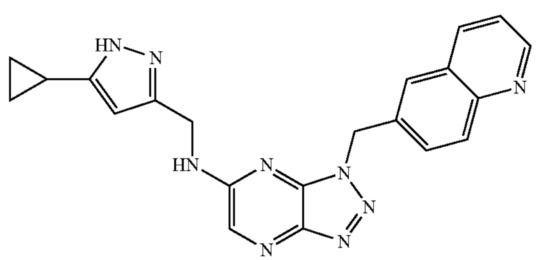 | N-((5-cyclopropyl-1H-pyrazol-3-yl)methyl)-1-(quinolin-6-ylmethyl)-1H-[1,2,3]triazolo[4,5-b]pyrazin-6-amine | 1H NMR(500 MHz, DMSO-d6) δ ppm 0.48-0.63(m, J=4.40Hz, 2H) 0.75-0.90(m, 2H) 1.70-1.81(m, 1H) 4.48(s, 2H) 5.82(s, 1H) 5.90(s, 2H) 7.53(d, J=8.38, 4.26Hz, 1H) 7.73-7.79(m, 1H) 7.93(s, 1H) 7.98-8.03(m, 1H) 8.09-8.13(m, 1H) 8.34(d, J=8.24Hz, 1H) 8.46(s, 1H) 8.85-8.92(m, 1H). LC-MS 398. | 26 |

TABLE 4-continued

| Example | Structure | Name | NMR/LC-MS | Method |
|---|---|---|---|---|
| 125 | 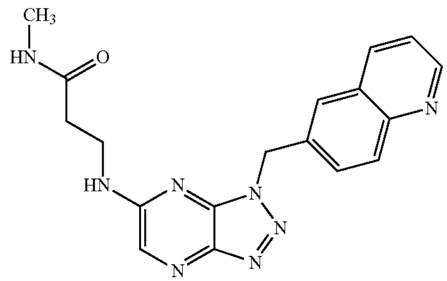 | N-methyl-N-3-[1-(quinolin-6-yl-methyl)-1H-[1,2,3]triazolo[4,5-b]pyrazin-6-yl]-beta-alaninamide | 1H NMR(500 MHz, DMSO-d6) δ ppm 2.43(t, J=6.32Hz, 2H) 2.66(s, 3H) 3.58(t, J=6.32Hz, 2H) 5.89(s, 2H) 7.54(dd, J=8.24, 4.12Hz, 1H) 7.72-7.82(m, 2H) 7.98(s, 1H) 7.99-8.04(m, J=8.52Hz, 1H) 8.05-8.08(m, 1H) 8.19(s, 1H) 8.37(d, J=8.24Hz, 1H) 8.89(s, 1H). LC-MS 363. | 26 |
| 126 | 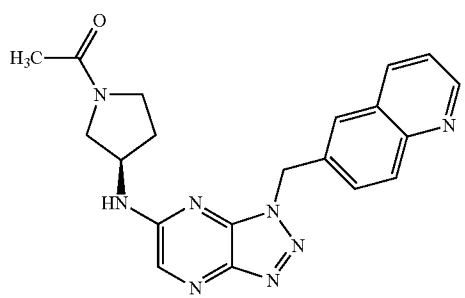 | N-[(3R)-1-acetyl-pyrrolidin-3-yl]-1-(quinolin-6-yl-methyl)-1H-[1,2,3]triazolo[4,5-b]pyrazin-6-amine | 1H NMR(500 MHz, DMSO-d6) δ ppm 1.81-1.82(m, 1H) 1.97-1.99(m, 1H) 3.68-3.79(m, 2H) 4.41-4.49(m, 1H) 5.90(s, 2H) 7.54(dd, J=8.10, 4.26Hz, 1H) 7.75-7.82(m, 1H) 8.00(s, 2H) 8.07(s, 1H) 8.32-8.44(m, 2H) 8.85-8.92(m, 1H) (five aliphatic protons not resolved, due to water and solvent peaks). LC-MS 389. | 26 |
| 127 | 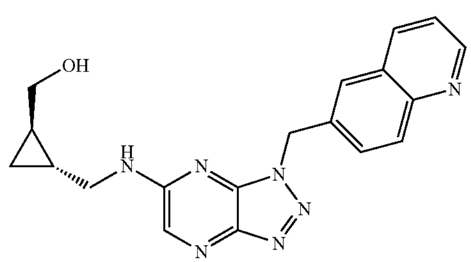 | [(1R,2R)-2-({[1-(quinolin-6-yl-methyl)-1H-[1,2,3]triazolo[4,5-b]pyrazin-6-yl]amino}methyl)cyclopropyl]methanol | 1H NMR(500 MHz, DMSO-d6) δ ppm 0.29-0.50(m, 2H) 0.86-1.03(m, 2H) 3.15-3.24(m, 2H) 5.88(s, 2H) 7.54(dd, J=8.10, 3.98Hz, 1H) 7.76(d, J=8.79Hz, 1H) 7.93(s, 1H) 8.01(d, J=8.52Hz, 1H) 8.08(s, 1H) 8.20(s, 1H) 8.35(d, J=8.24Hz, 1H) 8.89(s, 1H)(two aliphatic protons not resolved, due to water and solvent peaks). LC-MS 362. | 26 |

TABLE 4-continued

| Example | Structure | Name | NMR/LC-MS | Method |
|---|---|---|---|---|
| 128 | 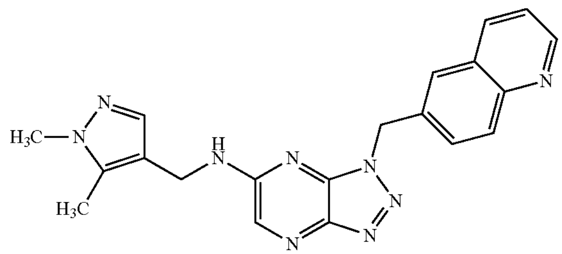 | N-{(1.5-dimethyl-1H-pyrazol-4-yl)methyl]-1-(quinolin-6-ylmethyl)-1H-[1,2,3]triazolo[4,5-b]pyrazin-6-amine | 1H NMR(500 MHz, DMSO-d6) δ ppm 2.19(s, 3H) 3.65(s, 3H) 4.31(s, 2H) 5.92(s, 2H) 7.34(s, 1H) (d, J=6.59Hz, 1H) 7.92(s, 1H) 7.99-8.03(m, J=8.24Hz, 1H) 8.04-8.07(m, 1H) 8.29-8.40(m, 2H) 8.89-8.90(m, 1H). LC-MS 386. | 26 |
| 129 | 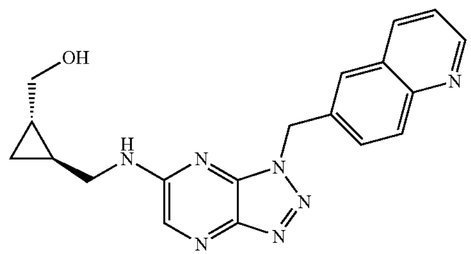 | [(1S,2S)-2-({[1-(quinolin-6-ylmethyl)-1H-[1,2,3]triazolo[4,5-b]pyrazin-6-yl]amino}methyl)cyclopropyl]methanol | 1H NMR(500 MHz, DMSO-d6) δ ppm 0.24-0.50(m, 2H) 0.86-1.02(m, 2H) 3.16-3.24(m, 2H) 5.88(s, 2H) 7.54(dd, J=8.10, 4.26Hz, 1H) 7.76(dd, J=8.20, 1.80Hz, 1H) 7.93(s, 1H) 7.97-8.04(m, J=8.79Hz, 1H) 8.08(s, 1H) 8.16-8.23(m, 1H) 8.36(d, J=7.69Hz, 1H) 8.86-8.89 (m, 1H)(two aliphatic protons not resolved, due to water peak). LC-MS 362. | 26 |
| 130 | 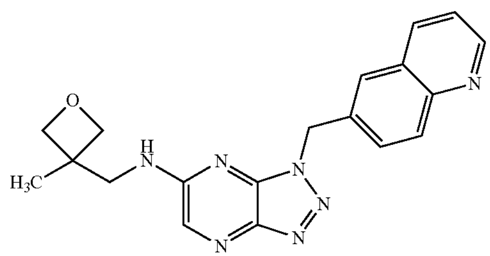 | N-[(3-methyloxetan-3-yl)methyl]-1-(quinolin-6-ylmethyl)-1H-[1,2,3]triazolo[4,5-b]pyrazin-6-amine | 1H NMR(500 MHz, DMSO-d6) δ ppm 1.22(s, 3H) 3.61(d, J=5.77Hz, 2H) 4.15(d, J=5.49Hz, 2H) 4.41(d, J=5.49Hz, 2H) 5.89(s, 2H) 7.54(dd, J=7.97, 4.12Hz, 1H) 7.74(d, J=8.79Hz, 1H) 7.97-8.04(m, J=8.52Hz, 1H) 8.08-8.15(m, 1H) 8.24(s, 1H) 8.34(d, J=7.69Hz, 1H) 8.87-8.90(m, 1H). LC-MS 362. | 26 |
| 131 | 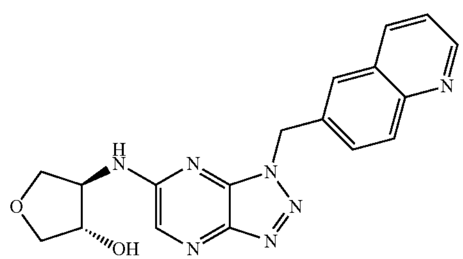 | (3S,4R)-4-{[1-(quinolin-6-ylmethyl)-1H-[123]triazolo[45-b]pyrazin-6-yl]amino}tetrahydrofuran-3-ol | 1H NMR(500 MHz, DMSO-d6) δ ppm 3.60(d, J=8.24Hz, 1H) 3.65(d, J=8.79Hz, 1H) 3.93(dd, J=9.34, 4.67Hz, 1H) 4.07(dd, J=9.34, 4.94Hz, 1H) 4.23-4.24(m, 2H) 5.92(s, 2H) 7.54(dd, J=8.38, 3.98Hz, 1H) 7.81(d, J=8.24Hz, 1H) 7.96-8.04(m, 2H) 8.09(s, 1H) 8.29-8.39(m, 2H) 8.86-8.93(m, 1H). LC-MS 364. | 26 |

TABLE 4-continued

| Example | Structure | Name | NMR/LC-MS | Method |
|---|---|---|---|---|
| 132 | 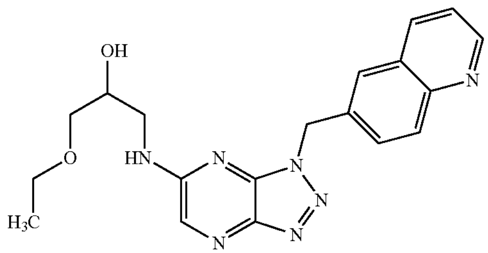 | 1-ethoxy-3-{[1-(quinolin-6-yl-methyl)-1H-[123]triazolo[45-b]pyrazin-6-yl]amino}propan-2-ol | 1H NMR(500 MHz, DMSO-d6) δ ppm 1.05(t, J=6.87Hz, 3H) 3.81-3.92(m, 2H) 5.87(s, 2H) 7.54(dd, J=8.52, 4.12Hz, 1H) 7.78(d, J=6.87Hz, 1H) 7.95(s, 1H) 8.00(d, J=8.79Hz, 1H) 8.11-8.18(m, 2H) 8.35(d, J=7.97Hz, 1H) 8.86-8.89(m, 1H) (five aliphatic protons not resolved, due to water and solvent peaks). LC-MS 380. | 26 |
| 133 | 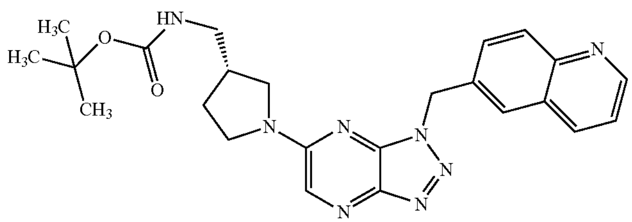 | tert-butyl ({(3R)-1-[1-(quinolin-6-yl-methyl)-1H-[1,2,3]triazolo[4,5-b]pyrazin-6-yl]pyrrolidin-3-yl}methyl)carbamate | (400 MHz, MeOD) d ppm 1.41(s, 9H) 1.79-1.91(m, 1H) 2.13-2.23(m, 1H) 2.50-2.61(m, 1H) 3.11-3.22(m, 2H) 3.39(dd, J=11.12, 6.82Hz, 1H) 3.58-3.67(m, 1H) 3.73-3.81(m, 2H) 5.93(s, 2H) 7.4(dd, J=8.46, 4.42Hz, 1H) 7.83(dd, J=8.84, 1.77Hz, 1H) 7.94(s, 1H) 8.01(d, J=8.84Hz, 1H) 8.13(s, 1H) 8.35(d, J=8.08Hz, 1H) 8.84(dd, J=4.29, 1.77Hz, 1H) | 27 |
| 134 | 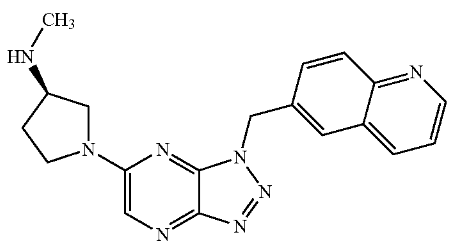 | (3R)-N-methyl-1-[1-(quinolin-6-yl-methyl)-1H-[1,2,3]triazolo[4,5-b]pyrazin-6-yl]pyrrolidin-3-amine | (400 MHz, MeOD) d ppm 2.33-2.43(m, 1H) 2.54-2.65(m, 1H) 2.83(s, 3H) 3.78-3.88(m, 1H) 3.90-4.01(m, 2H) 4.02-4.11(m, 2H) 6.10(s, 2H) 8.13(dd, J=7.96, 5.43Hz, 1H) 8.26(s, 1H) 8.28(s, 2H) 8.37(s, 1H) 9.22-9.27(m, 2H) | 27 |
| 135 | 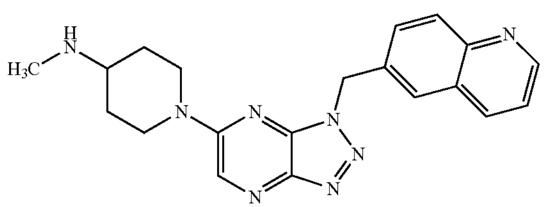 | N-methyl-1-[1-(quinolin-6-yl-methyl)-1H-[1,2,3]triazolo[4,5-b]pyrazin-6-yl]piperidin-4-amine | (400 MHz, MeOD) d ppm 1.60-1.71(m, 2H) 2.25(d, J=10.86Hz, 2H) 2.74(s, 3H) 3.12-3.22(m, 2H) 3.38-3.49(m, 1H) 4.79(d, J=13.89Hz, 2H) 6.09(s, 2H) 8.13(dd, 2H) 8.34, 5.56Hz, 1H) 8.23-8.31(m, 2H) 8.36(s, 1H) 8.56(s, 1H) 9.20-9.27(m, 2H) | 27 |

TABLE 4-continued

| Example | Structure | Name | NMR/LC-MS | Method |
|---|---|---|---|---|
| 136 | 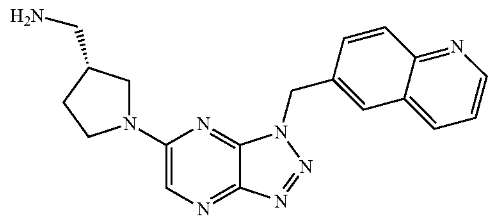 | 1-[(3R)-1-[1-(quinolin-6-ylmethyl)-1H-[1,2,3]triazolo[4,5-b]pyrazin-6-yl]pyrrolidin-3-yl]methanamine | (400 MHz, MeOD) d ppm 1.87-1.97(m, 1H) 2.31-2.41(m, 1H) 2.67-2.78(m, 1H) 3.08-3.19(m, 2H) 3.44(dd, J=11.24, 7.71Hz, 1H) 3.65-3.73(m, 1H) 3.89(ddd, J=11.31, 8.02, 3.66Hz, 1H) 3.98(dd, J=10.74, 7.71Hz, 1H) 6.06(s, 2H) 8.07(dd, J=8.34, 5.31Hz, 1H) 8.20(s, 1H) 8.23(d, J=1.77Hz, 1H) 8.24(s, 1H) 8.30(s, 1H) 9.15(d, J=8.59Hz, 1H) 9.20(dd, J=5.31, 1.52Hz, 1H) | 27 |
| 137 | 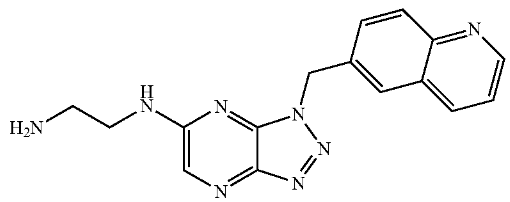 | N-[1-(quinolin-6-ylmethyl)-1H-[1,2,3]triazolo[4,5-b]pyrazin-6-yl]ethane-1,2-diamine | (400 MHz, MeOD) d ppm 3.27(t, J=5.94Hz, 3H) 3.81(t, J=5.81Hz, 2H) 6.11(s, 2H) 8.11-8.15(m, 2H) 8.24-8.27(m, 1H) 8.27-8.31(m, 1H) 8.37(d, J=0.76Hz, 1H) 9.24(d, J=6.57Hz, 2H) | 27 |
| 138 | 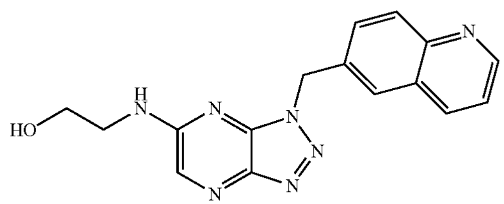 | 2-{[1-(quinolin-6-ylmethyl)-1H-[1,2,3]triazolo[4,5-b]pyrazin-6-yl]amino}ethanol | (400 MHz, DMSO-d6) d ppm 3.44(q, J=5.73Hz, 2H) 3.58(q, J=5.64Hz, 2H) 4.82(t, J=5.31Hz, 1H) 5.87(s, 2H) 7.53(dd, J=8.34, 4.29Hz, 1H) 7.76(dd, J=8.59, 2.02Hz, 1H) 7.93(d, J=1.01Hz, 1H) 8.00(d, J=8.59Hz, 1H) 8.10(s, 1H) 8.26(t, J=4.93Hz, 1H) 8.36(d, J=7.83Hz, 1H) 8.89(dd, J=4.04, 1.77Hz, 1H) | 27 |
| 139 | 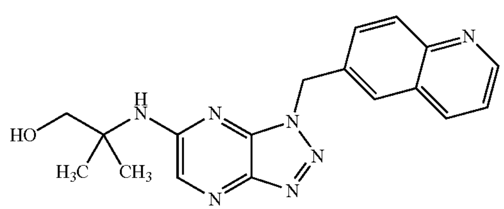 | 2-methyl-2-{[1-(quinolin-6-ylmethyl)-1H-[1,2,3]triazolo[4,5-b]pyrazin-6-yl]amino}propan-1-ol | (400 MHz, DMSO-d6) d ppm 1.30(s, 6H) 3.58(d, J=6.06Hz, 2H) 4.74(t, J=6.06Hz, 1H) 5.87(s, 2H) 7.53(dd, J=8.34, 4.29Hz, 1H) 7.62(s, 1H) 7.75(dd, J=8.97, 1.89Hz, 1H) 7.98-8.01(m, 2H) 8.08(s, 1H) 8.34(dd, J=8.21, 1.14Hz, 1H) 8.89(dd, J=4.17, 1.64Hz, 1H) | 27 |

TABLE 4-continued

| Example | Structure | Name | NMR/LC-MS | Method |
|---|---|---|---|---|
| 140 | (structure) | N-2~-[1-(quinolin-6-yl-methyl)-1H-[1,2,3]triazolo[4,5-b]pyrazin-6-yl]glycinamide | (400 MHz, DMSO-d6) d ppm 3.99(d, J=5.81Hz, 2H) 5.86(s, 2H) 7.17(s, 1H) 7.53(dd, J=8.34, 4.29Hz, 1H) 7.58(s, 1H) 7.80(dd, J=8.84, 2.02Hz, 1H) 7.95(d, J=1.52Hz, 1H) 8.02(d, J=8.59Hz, 1H) 8.21(s, 1H) 8.37(dd, J=8.59, 1.01Hz, 1H) 8.42(t, J=5.18Hz, 1H) 8.89(dd, J=4.04, 1.77Hz, 1H) | 27 |
| 141 | (structure) | 2-methyl-N~1~-[1-(quinolin-6-yl-methyl)-1H-[1,2,3]triazolo[4,5-b]pyrazin-6-yl]propane-1,2-diamine | (400 MHz, MeOD) d ppm 1.41(s, 6H) 3.72(s, 2H) 6.14(s, 2H) 8.07(dd, J=8.34, 5.31Hz, 1H) 8.14(s, 1H) 8.16-8.21(m, 1H) 8.22-8.27(m, 1H) 8.29(d, J=0.76Hz, 1H) 9.15(d, J=8.34Hz, 1H) 9.20(dd, J=5.31, 1.52Hz, 1H) | 27 |
| 142 | (structure) | 6-[[6-(tetra-hydro-2H-pyran-4-yloxy)-1H-[1,2,3]triazolo[4,5-b]pyrazin-1-yl]methyl]quinoline | (400 MHz, DMSO-d6) d ppm 1.58-1.68(m, 2H) 1.92-1.99(m, 2H) 3.44(ddd, J=11.75, 9.47, 2.78Hz, 2H) 3.79(ddd, J=11.75, 4.42, 4.29Hz, 2H) 5.19(ddd, J=13.14, 8.72, 3.92Hz, 1H) 6.06(s, 2H) 7.55(dd, J=8.34, 4.29Hz, 1H) 7.76(dd, J=8.72, 2.15Hz, 1H) 7.99-8.02(m, 2H) 8.36(dd, J=8.46, 1.14Hz, 1H) 8.39(s, 1H) 8.90(dd, J=4.17, 1.64Hz, 1H) | 28 |
| 143 | (structure) | 1-(quinolin-6-yl-methyl)-N-(tetrahydro-2H-pyran-4-yl)-1H-[1,2,3]triazolo[4,5-b]pyrazin-6-amine | (400 MHz, DMSO-d6) d ppm 1.36-1.46(m, 2H) 1.79-1.86(m, 2H) 3.35-3.41(m, 2H) 3.77-3.84(m, 2H) 3.86-3.96(m, 1H) 5.88(s, 2H) 7.54(dd, J=8.21, 4.17Hz, 1H) 7.72(dd, J=8.59, 2.02Hz, 1H) 7.95(d, J=1.52Hz, 1H) 7.99(d, J=8.59Hz, 1H) 8.02(s, 1H) 8.14(d, J=6.82Hz, 1H) 8.34(dd, J=8.34, 1.01Hz, 1H) 8.89(dd, J=4.17, 1.64Hz, 1H) | 27 |

TABLE 4-continued

| Example | Structure | Name | NMR/LC-MS | Method |
|---|---|---|---|---|
| 144 | 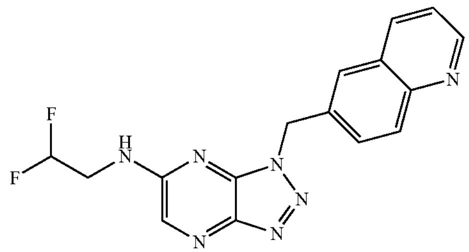 | N-(2,2-difluoroethyl)-1-(quinolin-6-ylmethyl)-1H-[1,2,3]triazolo[4,5-b]pyrazin-6-amine | (400 MHz, DMSO-d6) d ppm 3.78-3.89(m, 1H) 15.66, 15.66, 5.05, 4.29Hz, 2H) 5.92(s, 2H) 6.20(tt, J=55.93, 3.79, 3.60Hz, 1H) 7.54(dd, J=8.21, 4.17Hz, 1H) 7.77(dd, J=8.34, 1.26Hz, 1H) 7.96(s, 1H) 8.00(d, J=8.59Hz, 1H) 8.17(s, 1H) 8.34(d, J=8.34Hz, 1H) 8.55(t, J=5.18Hz, 1H) 8.89(d, J=4.04Hz, 1H) | 27 |
| 145 | 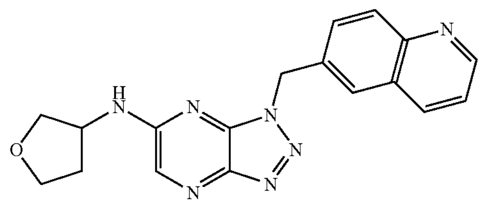 | 1-(quinolin-6-ylmethyl)-N-(tetrahydrofuran-3-yl)-1H-[1,2,3]triazolo[4,5-b]pyrazin-6-amine | (400 MHz, DMSO-d6) d ppm 1.80-1.9(m, 1H) 2.18-2.28(m, 1H) 3.57(dd, J=9.09, 3.28Hz, 1H) 3.73(td, J=8.15, 5.68Hz, 1H) 3.80-3.92(m, 2H) 4.37-4.47(m, 1H) 5.89(s, 2H) 7.54(dd, J=8.34, 4.04Hz, 1H) 7.76(dd, J=8.72, 1.64Hz, 1H) 7.96(s, 1H) 8.00(d, J=8.59Hz, 1H) 8.06(s, 1H) 8.36(d, J=8.34Hz, 1H) 8.44(d, J=6.06Hz, 1H) 8.89(dd, J=4.17, 1.39Hz, 1H) | 27 |
| 146 | 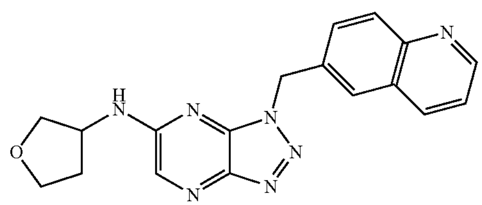 | 1-(quinolin-6-ylmethyl)-N-(tetrahydrofuran-3-yl)-1H-[1,2,3]triazolo[4,5-b]pyrazin-6-amine | (400 MHz, DMSO-d6) d ppm 1.80-1.91(m, 1H) 2.18-2.28(m, 1H) 3.57(dd, J=9.09, 3.28Hz, 1H) 3.73(td, J=8.15, 5.68Hz, 1H) 3.80-3.92(m, 2H) 4.37-4.47(m, 1H) 5.89(s, 2H) 7.54(dd, J=8.34, 4.04Hz, 1H) 7.76(dd, J=8.72, 1.64Hz, 1H) 7.96(s, 1H) 8.00(d, J=8.59Hz, 1H) 8.06(s, 1H) 8.36(d, J=8.34Hz, 1H) 8.44(d, J=6.06Hz, 1H) 8.89(dd, J=4.17, 1.39Hz, 1H) | 27 |
| 147 | 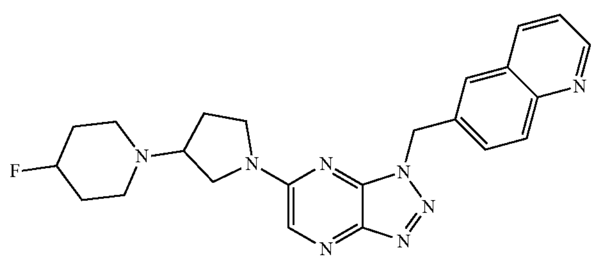 | 6-({6-[3-(4-fluoropiperidin-1-yl)pyrrolidin-1-yl]-1H-[1,2,3]triazolo[4,5-b]pyrazin-1-yl}methyl)quinoline | (400 MHz, DMSO-d6) d ppm 1.67-1.78(m, 2H) 1.80-1.92(m, 3H) 2.18-2.29(m, 1H) 2.33-2.45(m, 2H) 2.52-2.74(m, 3H) 2.92-3.04(m, 1H) 3.44-3.55(m, 1H) 3.75-3.85(m, 1H) 3.85-3.97(m, 1H) 4.56-4.83(m, 1H) 5.90(s, 2H) 7.53(dd, J=8.34, 4.29Hz, 1H) 7.75(dd, J=8.72, 1.64Hz, 1H) 7.94(s, 1H) 8.00(d, J=8.59Hz, 1H) 8.23(s, 1H) 8.36(d, J=8.34Hz, 1H) 8.89(dd, J=4.04, 1.52Hz, 1H) | 27 |

TABLE 4-continued

| Example | Structure | Name | NMR/LC-MS | Method |
|---|---|---|---|---|
| 148 | 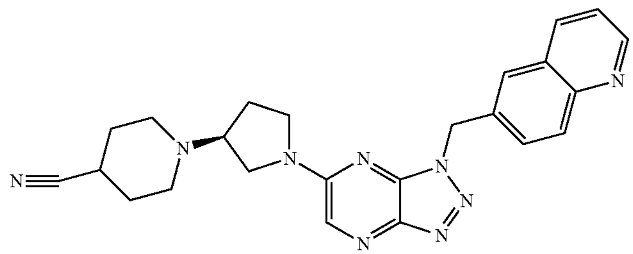 | 1-[(3R)-1-[1-(quinolin-6-ylmethyl)-1H-[1,2,3]triazolo[4,5-b]pyrazin-6-yl]pyrrolidin-3-yl]piperidine-4-carbonitrile | (400 MHz, DMSO-d6) d ppm 1.67-1.77(m, 2H) 1.80-1.92(m, 3H) 2.18-2.27(m, 1H) 2.31-2.43(m, 2H) 2.56-2.62(m, 1H) 2.63-2.73(m, 2H) 2.83-2.94(m, 1H) 2.94-3.06(m, 1H) 3.43-3.54(m, 1H) 3.74-3.84(m, 1H) 3.84-3.96(m, 1H) 5.91(s, 2H) 7.53(dd, J=8.34, 4.04Hz, 1H) 7.75(dd, J=8.72, 1.89Hz, 1H) 7.94(d, J=1.01Hz, 1H) 8.00(d, J=8.59Hz, 1H) 8.23(s, 1H) 8.36(d, J=8.59Hz, 1H) 8.89(dd, J=4.17, 1.64Hz, 1H) | 27 |
| 149 | 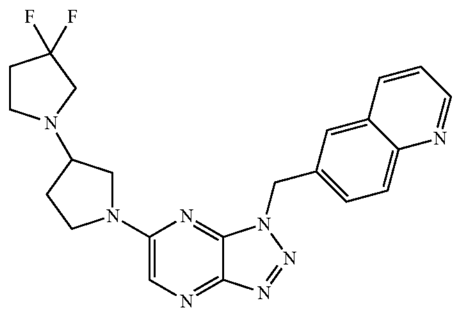 | 6-[[6-(3,3-difluoro-1,3'-bipyrrolidin-1'-yl)-1H-[1,2,3]triazolo[4,5-b]pyrazin-1-yl]methyl]quinoline | (400 MHz, DMSO-d6) d ppm 1.90-2.01(m, 1H) 2.14-2.18(m, 1H) 2.19-2.29(m, 2H) 2.78(t, J=7.83Hz, 2H) 2.96-3.07(m, 3H) 3.46(dd, J=10.11, 6.57Hz, 1H) 3.50-3.61(m, 1H) 3.70-3.81(m, 2H) 5.91(s, 2H) 7.53(dd, J=8.34, 4.04Hz, 1H) 7.73-7.79(m, 1H) 7.94(s, 1H) 8.00(d, J=8.59Hz, 1H) 8.22(s, 1H) 8.34-8.39(m, 1H) 8.86-8.92(m, 1H) | 31 |
| 150 | 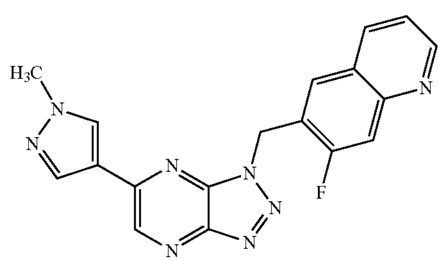 | 7-fluoro-6-[[6-(1-methyl-1H-pyrazol-4-yl)-1H-[1,2,3]triazolo[4,5-b]pyrazin-1-yl]methyl]quinoline | (400 MHz, DMSO-d6) d ppm 3.94(s, 3H) 6.17(s, 2H) 7.54(dd, J=8.34, 4.04Hz, 1H) 7.84(d, J=11.37Hz, 1H) 8.13(d, J=8.34Hz, 1H) 8.27(s, 1H) 8.44(d, J=8.34Hz, 1H) 8.62(s, 1H) 8.92(dd, J=4.17, 1.39Hz, 1H) 9.21(s, 1H) | 32 |

TABLE 4-continued

| Example | Structure | Name | NMR/LC-MS | Method |
|---|---|---|---|---|
| 151 | 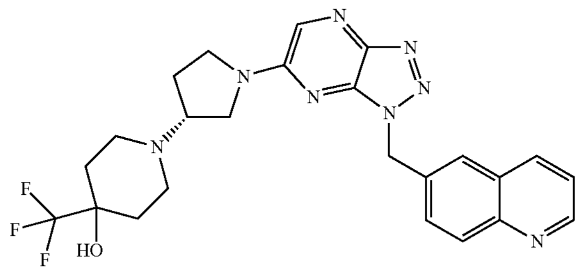 | 1-[(3R)-1-[1-(quinolin-6-yl-methyl)-1H-[1,2,3]triazolo[4,5-b]pyrazin-6-yl]pyrrolidin-3-yl]-4-(trifluoromethyl)piperidin-4-ol | (400 MHz, MeOD) d ppm 2.07-2.19(m, 3H) 2.30-2.42(m, 1H) 2.66-2.78(m, 1H) 3.40-3.51(m, 3H) 3.65-3.77(m, 3H) 3.78-3.88(m, 1H) 4.01-4.12(m, 1H) 4.12-4.23(m, 1H) 4.27(dd, J=11.24, 7.45Hz, 1H) 6.04(s, 2H) 7.81(dd, J=8.34, 4.80Hz, 1H) 8.00-8.07(m, 1H) 8.10-8.16(m, 2H) 8.25(s, 1H) 8.74(d, J=8.59Hz, 1H) 9.03(dd, J=4.80, 1.52Hz, 1H) | 27 |
| 152 | 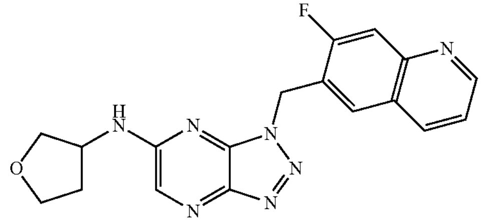 | 1-[(7-fluoroquinolin-6-yl)methyl]-N-(tetrahydrofuran-3-yl)-1H-[1,2,3]triazolo[4,5-b]pyrazin-6-amine | (400 MHz, DMSO-d6) d ppm 1.76-1.85(m, 1H) 2.11-2.21(m, 1H) 3.52(dd, J=9.09, 3.28Hz, 1H) 3.70(td, J=8.21, 5.56Hz, 1H) 3.77-3.86(m, 2H) 4.29-4.38(m, 1H) 5.93(s, 2H) 7.53(dd, J=8.34, 4.29Hz, 1H) 7.81(d, J=11.37Hz, 1H) 8.05(s, 1H) 8.09(d, J=8.34Hz, 1H) 8.41(d, J=6.82Hz, 2H) 8.90-8.99(m, 1H) | 27 |
| 153 | 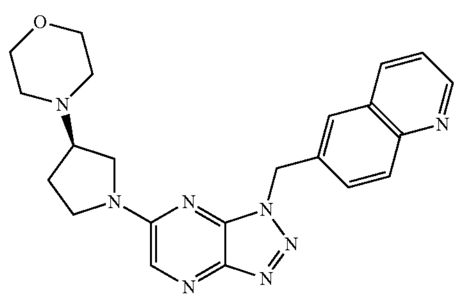 | 6-({6-[(3R)-3-morpholin-4-yl]pyrrolidin-1-yl}-1H-[1,2,3]triazolo[4,5-b]pyrazin-1-yl}methyl)quinoline | 1H NMR(400 MHz, MeOD) d ppm 2.45-2.56(m, 1H) 2.64-2.73(m, 1H) 3.33-3.42(m, 2H) 3.59-3.67(m, 2H) 3.68-3.75(m, 1H) 3.95-4.15(m, 7H) 4.26(dd, J=11.24, 7.45Hz, 1H) 6.10(s, 2H) 8.13(dd, J=8.34, 5.56Hz, 1H) 8.24-8.34(m, 3H) 8.39(s, 1H) 9.23-9.31(m, 2H) | 27 |

| Example | Structure | Name | NMR/LC-MS | Method |
|---|---|---|---|---|
| 154 | 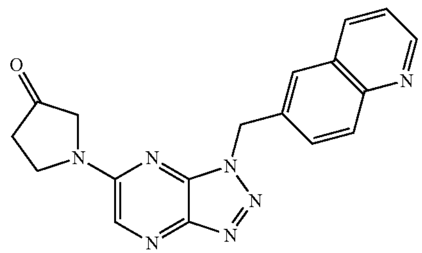 | 1-[1-(quinolin-6-yl-methyl)-1H-[1,2,3]tri-azolo[4,5-b]pyra-zin-6-yl]pyrro-lidin-3-one | 1H NMR(400 MHz, DMSO-d6) d ppm 2.75(t, J=7.71Hz, 2H) 4.00(t, J=7.71Hz, 2H) 4.10(ddd, J=10.86, 5.81, 5.56Hz, 2H) 5.95(s, 2H) 7.53(dd, J=8.34, 4.04Hz, 1H) 7.78(dd, J=8.59, 2.02Hz, 1H) 7.94-8.03(m, 2H) 8.32(s, 1H) 8.35-8.40(m, 1H) 8.89(dd, J=4.17, 1.64Hz, 1H) | 31 |
| 155 | 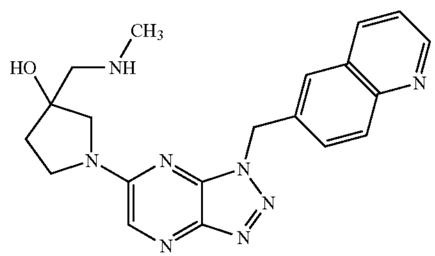 | 3-[(meth-ylamino)meth-yl]-1-[1-(quino-lin-6-yl-methyl)-1H-[1,2,3]tri-azolo[4,5-b]pyra-zin-6-yl]pyrro-lidin-3-ol | 1H NMR(400 MHz, MeOD) d ppm 2.23(s, 2H) 2.80(s, 3H) 3.32-3.41(m, 2H) 3.69-3.78(m, 1H) 3.83-3.94(m, 3H) 6.08(s, 2H) 8.13(dd, J=8.46, 5.43Hz, 1H) 8.20(s, 1H) 8.25-8.31(m, 2H) 8.37(s, 1H) 9.21-9.29(m, 2H) | 37 |
| 156 | 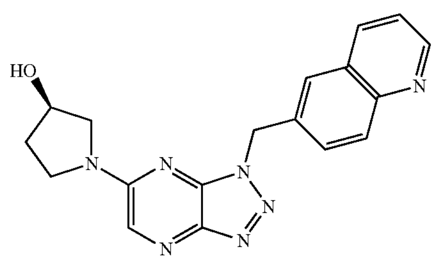 | (3R)-1-[1-(quino-lin-6-yl-methyl)-1H-[1,2,3]tri-azolo[4,5-b]pyra-zin-6-yl]pyrro-lidin-3-ol | 1H NMR(400 MHz, DMSO-d6) d ppm 1.96-2.04(m, 1H) 3.59-3.71(m, 3H) 4.44(bs, 1H) 5.14(m, 1H) .589(s, 2H) 7.52(dd, J=8.34, 4.29Hz, 1H) 7.76(dd, J=8.59, 2.02Hz, 1H) 7.92(d, J=1.52Hz, 1H) 8.00(d, J=8.59Hz, 1H) 8.20(s, 1H) 8.35(d, J=7.58Hz, 1H) 8.88(dd, J=4.17, 1.64Hz, 1H) | 27 |
| 157 | 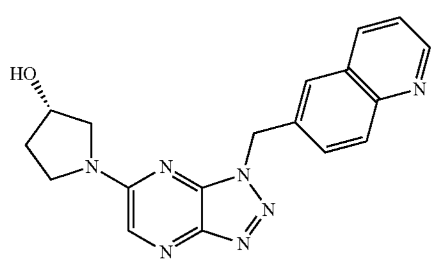 | (3S)-1-[1-(quino-lin-6-yl-methyl)-1H-[1,2,3]tri-azolo[4,5-b]pyra-zin-6-yl]pyrro-lidin-3-ol | 1H NMR(400 MHz, DMSO-d6) d ppm 1.96-2.07(m, 2H) 3.60-3.72(m, 3H) 4.44(bs, 1H) 5.10(bs, 1H) 5.90(s, 2H) 7.53(dd, J=8.34, 4.04Hz, 1H) 7.76(dd, J=8.72, 1.89Hz, 1H) 7.93(d, J=1.52Hz, 1H) 8.00(d, J=8.59Hz, 1H) 8.22(s, 1H) 8.33-8.40(m, 1H) 8.89(dd, J=4.04, 1.77Hz, 1H) | 27 |

| Example | Structure | Name | NMR/LC-MS | Method |
|---|---|---|---|---|
| 158 | 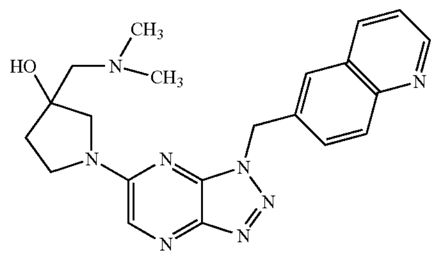 | 3-[(di-methylamino)meth-yl]-1-[1-(quino-lin-6-yl-methyl)-1H-[1,2,3]tri-azolo[4,5-b]pyra-zin-6-yl]pyrro-lidin-3-ol | 1H NMR(400 MHz, MeOD) d ppm 2.13(s, 2H) 2.56(s, 6H) 2.86(s, 2H) 3.61(d, J=11.37Hz, 1H) 3.74-3.86(m, 3H) 5.94(s, 2H) 7.54(dd, J=8.34, 4.55Hz, 1H) 7.83(dd, J=8.72, 1.64Hz, 1H) 7.94(s, 1H) 8.00(d, J=8.59Hz, 1H) 8.15(s, 1H) 8.34(d, J=8.34Hz, 1H) 8.81-8.87(m, 1H) | 37 |
| 159 | 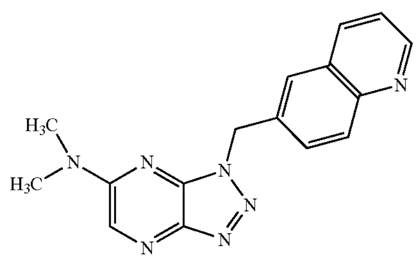 | N,N-dimethyl-1-(quino-lin-6-yl-methyl)-1H-[1,2,3]tri-azolo[4,5-b]pyra-zin-6-amine | 1H NMR(400 MHz, MeOD) d ppm 3.28(s, 6H) 6.02(s, 2H) 7.87(dd, J=8.34, 5.05Hz, 1H) 8.04-8.12(m, 1H) 8.12-8.23(m, 2H) 8.35(s, 1H) 8.84(d, J=8.34Hz, 1H) 9.06(dd, J=5.05, 1.52Hz, 1H) | 27 |
| 160 | 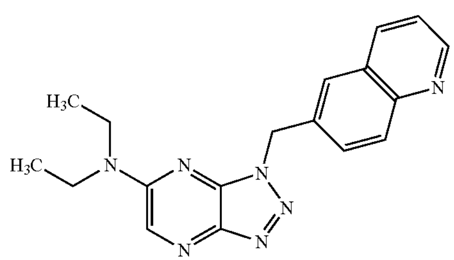 | N,N-diethyl-1-(quino-lin-6-yl-methyl)-1H-[1,2,3]tri-azolo[4,5-b]pyra-zin-6-amine | 1H NMR(400 MHz, MeOD) d ppm 1.22(t, J=6.95Hz, 6H) 3.69(q, J=7.07Hz, 4H) 6.00(s, 2H) 7.85(dd, J=8.34, 5.05Hz, 1H) 8.03-8.08(m, 1H) 8.11-8.16(m, 1H) 8.19(s, 1H) 8.28(s, 1H) 8.81(d, J=8.08Hz, 1H) 9.01-9.09(m, 1H) | 27 |

TABLE 4-continued

| Example | Structure | Name | NMR/LC-MS | Method |
|---|---|---|---|---|
| 161 | 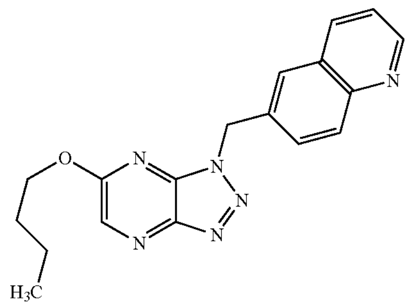 | 6-[(6-butoxy-1H-[1,2,3]tri-azolo[4,5-b]pyrazin-1-yl)methyl]quinoline | 1H NMR(400 MHz, MeOD) d ppm 0.95(t, J=7.33Hz, 3H) 1.48(dq, J=15.00, 7.46Hz, 2H) 1.75-1.83(m, 2H) 4.46(t, J=6.57Hz, 2H) 6.13(s, 2H) 7.92(dd, J=8.59, 5.05Hz, 1H) 8.08-8.13(m, 1H) 8.17-8.24(m, 2H) 8.29(s, 1H) 8.91(d, J=8.34Hz, 1H) 9.11(d, J=4.29Hz, 1H) | 28 |
| 162 | 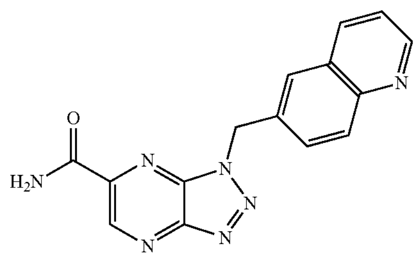 | 1-(quinolin-6-yl-methyl)-1H-[1,2,3]tri-azolo[4,5-b]pyrazine-6-carboxamide | 1H NMR(400 MHz, MeOD) d ppm 6.03(s, 2H) 7.83(dd, J=8.59, 4.80Hz, 1H) 8.05 (dd, J=8.97, 1.89Hz, 1H) 8.11-8.18(m, 2H) 8.35(s, 1H) 8.77(d, J=8.08Hz, 1H) 9.03(dd, J=4.80, 1.52Hz, 1H) | 36 |
| 163 | 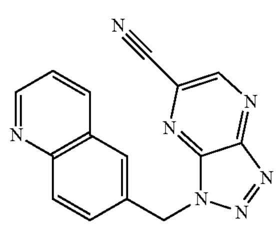 | 1-(quinolin-6-yl-methyl)-1H-[1,2,3]tri-azolo[4,5-b]pyrazine-6-carbonitrile | 1H NMR(400 MHz, DMSO-d6) d ppm 6.28(s, 2H) 7.55(dd, J=8.34, 4.29Hz, 1H) 7.81(dd, J=8.72, 2.15Hz, 1H) 7.99-8.04(m, 2H) 8.33-8.37(m, 1H) 8.91(dd, J=4.04, 1.77Hz, 1H) 9.41(s, 1H) | 33 |

TABLE 4-continued

| Example | Structure | Name | NMR/LC-MS | Method |
|---|---|---|---|---|
| 164 | 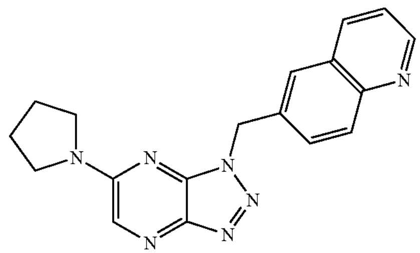 | 6-[(6-pyrrolidin-1-yl-1H-[1,2,3]tri-azolo[4,5-b]pyra-zin-1-yl)meth-yl]quinoline | 1H NMR(400 MHz, DMSO-d6) d ppm 1.90-2.00(m, 4H) 3.52-3.60(m, 4H) 5.90(s, 2H) 7.52(dd, J=8.34, 4.29Hz, 1H) 7.76(dd, J=8.59, 2.02Hz 1H) 7.93(d, J=1.77Hz, 1H) 8.00(d, J=8.59Hz, 1H) 8.21(s, 1H) 8.34-8.38(m, 1H) 8.89(dd, J=4.04, 1.77Hz, 1H) | 27 |
| 165 | 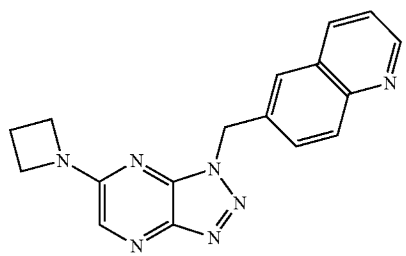 | 6-[(6-azetidin-1-yl-1H-[1,2,3]tri-azolo[4,5-b]pyra-zin-1-yl)meth-yl]quinoline | 1H NMR(400 MHz, DMSO-d6) d ppm 2.37-2.46(m, 2H) 4.22(t, J=7.45Hz, 4H) 5.90(s, 2H) 7.53(dd, J=8.21, 4.17Hz, 1H) 7.73(dd, J=8.59, 2.02Hz, 1H) 7.89(d, J=1.52Hz, 1H) 7.99-8.02(m, 2H) 8.34-8.38(m, 1H) 8.89(dd, J=4.29, 1.77Hz, 1H) | 27 |
| 166 | 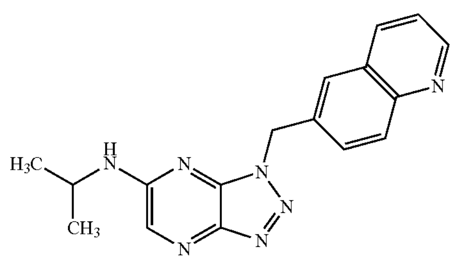 | N-isopropyl-1-(quino-lin-6-yl-methyl)-1H-[1,2,3]tri-azolo[4,5-b]pyra-zin-6-amine | 1H NMR(400 MHz, DMSO-d6) d ppm 1.17(d, J=6.32Hz, 6H) 4.00-4.10(m, J=6.57, 6.57, 6.57Hz, 1H) 5.87(s, 2H) 7.53(dd, J=8.34, 4.29Hz, 1H) 7.75(dd, J=8.84, 2.02Hz, 1H) 7.94(d, J=1.77Hz, 1H) 7.97-8.02(m, 2H) 8.08(d, J=7.07Hz, 1H) 8.32-8.36(m, 1H) 8.88(dd, J=4.29, 1.77Hz, 1H) | 27 |
| 167 | 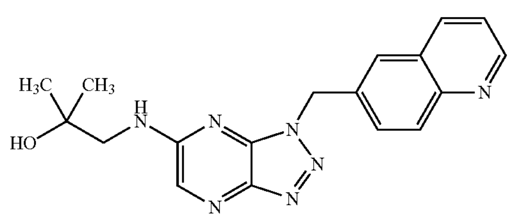 | 2-methyl-1-{[1-(quino-lin-6-ylmeth-yl)-1H-[1,2,3]tri-azolo[4,5-b]pyra-zin-6-yl]ami-no}propan-2-ol | 1H NMR(400 MHz, DMSO-d6) d ppm 1.08(s, 6H) 3.34-3.36(m, 2H) 4.62(s, 1H) 5.87(s, 2H) 7.74(dd, J=8.34, 4.29Hz, 1H) 7.92(s, 1H) 8.72, 1.89Hz, 1H) 7.99(d, J=8.59Hz, 1H) 8.08(t, J=5.18Hz, 1H) 8.23(s, 1H) 8.34(d, J=7.33Hz, 1H) 8.89(dd, J=4.04, 1.77Hz, 1H) | 27 |

| Example | Structure | Name | NMR/LC-MS | Method |
|---|---|---|---|---|
| 168 | 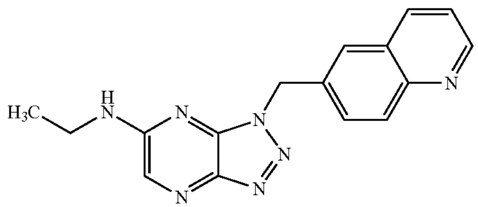 | N-ethyl-1-(quinolin-6-ylmethyl)-1H-[1,2,3]triazolo[4,5-b]pyrazin-6-amine | 1H NMR(400 MHz, DMSO-d6) d ppm 1.17(t, J=7.20Hz, 3H) 3.38(td, J=7.20, 5.31Hz, 2H) 5.88(s, 2H) 7.54(dd, J=8.34, 4.29Hz, 1H) 7.75(dd, J=8.84, 2.02Hz, 1H) 7.93(d, J=1.52Hz, 1H) 7.98-8.05(m, 2H) 8.20(t, J=4.80Hz, 1H) 8.32-8.38(m, 1H) 8.89(dd, J=4.17, 1.64Hz, 1H) | 27 |
| 169 | 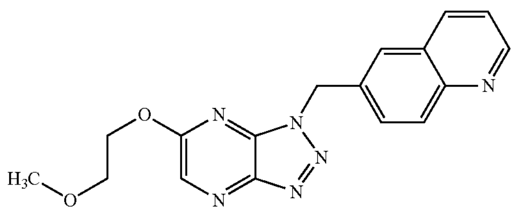 | 6-[[6-(2-methoxyethoxy)-1H-[1,2,3]triazolo[4,5-b]pyrazin-1-yl]methyl]quinoline | 1H NMR(400 MHz, MeOD) d ppm 3.35(s, 3H) 3.70-3.80(m, 2H) 4.62(dd, J=5.43, 3.92Hz, 2H) 6.09(s, 2H) 7.57(dd, J=8.34, 4.29Hz, 1H) 7.87(dd, J=8.72, 1.89Hz, 1H) 7.98-8.06(m, 2H) 8.31-8.40(m, 2H) 8.87(dd, J=4.29, 1.52Hz, 1H) | 28 |
| 170 | 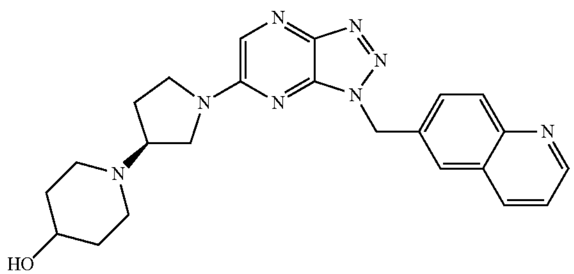 | 1-[(3R)-1-[1-(quinolin-6-ylmethyl)-1H-[1,2,3]triazolo[4,5-b]pyrazin-6-yl]pyrrolidin-3-yl]piperidin-4-ol | 1H NMR(400 MHz, DMSO-d6) d ppm 1.33-1.44(m, 2H) 1.69-1.77(m, 3H) 2.08-2.17(m, 3H) 2.66-2.76(m, 1H) 2.80(d, J=10.36Hz, 1H) 2.86-2.96(m, 1H) 3.40-3.48(m, 3H) 3.49-3.60(m, 1H) 3.80(d, J=8.59Hz, 1H) 4.58(s, 1H) 5.90(s, 2H) 7.52(dd, J=8.34, 4.04Hz, 1H) 7.75(dd, J=8.72, 1.89Hz, 1H) 7.92-7.97(m, 1H) 8.00(d, J=8.84Hz, 1H) 8.18-8.27(m, 1H) 8.35(d, J=8.34Hz, 1H) 8.89(dd, J=4.29, 1.52Hz, 1H) | 27 |
| 171 | 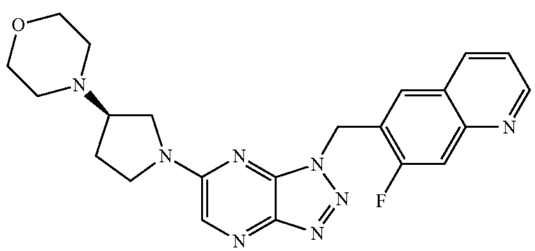 | 7-fluoro-6-({6-[(3R)-3-morpholin-4-yl-pyrrolidin-1-yl]-1H-[1,2,3]triazolo[4,5-b]pyrazin-1-yl}methyl)quinoline | 1H NMR(400 MHz, DMSO-d6) d ppm 1.77-1.88(m, 1H) 2.15-2.26(m, 1H) 2.35-2.47(m, 3H) 2.85-2.96(m, 1H) 3.40-3.52(m, 2H) 3.53-3.63(m, 5H) 3.70-3.91(m, 2H) 5.93(s, 2H) 7.53(dd, J=8.34, 4.29Hz, 1H) 7.77-7.87(m, 1H) 8.08(dd, J=3.16, 1.64Hz, 1H) 8.21(s, 1H) 8.41(d, J=8.34Hz, 1H) 8.90-8.98(m, 1H | 27 |

| Example | Structure | Name | NMR/LC-MS | Method |
|---|---|---|---|---|
| 172 | 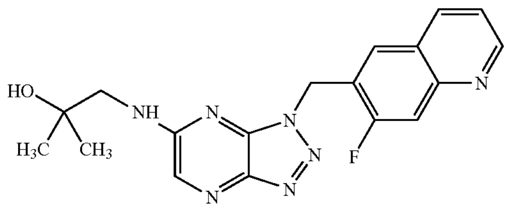 | 1-({1-[(7-fluoroquinolin-6-yl)methyl]-1H-[1,2,3]triazolo[4,5-b]pyrazin-6-yl}amino)-2-methylpropan-2-ol | ¹H NMR(400 MHz, DMSO-d6) d ppm 1.02(s, 6H) 3.27(d, J=4.04Hz, 2H) 5.96(s, 2H) 7.53(dd, J=8.46, 4.17Hz, 1H) 7.80(d, J=11.37Hz, 1H) 8.04(d, J=8.08Hz, 2H) 8.21(s, 1H) 8.39(d, J=8.08Hz, 1H) 8.92(d, J=4.04Hz, 1H) | 27 |
| 173 | 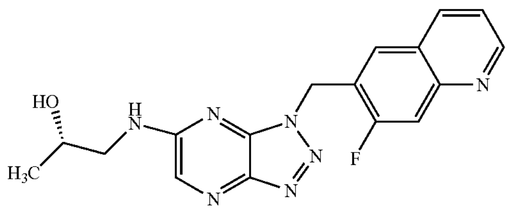 | (2)-1-({1-[(7-fluoroquinolin-6-yl)methyl]-1H-[1,2,3]triazolo[4,5-b]pyrazin-6-yl}amino)propan-2-ol | 1H NMR(400 MHz, DMSO-d6) d ppm 1.02(d, J=6.32Hz, 3H) 3.13-3.23(m, 2H) 3.26-3.31(m, 1H) 3.73-3.83(m, 1H) 4.79(d, J=4.80Hz, 1H) 5.95(s, 2H) 7.53(dd, J=8.34, 4.29Hz, 1H) 7.80(d, J=11.37Hz, 1H) 8.05(d, J=8.34Hz, 1H) 8.09-8.16(m, 1H) 8.20(s, 1H) 8.40(d, J=7.83Hz, 1H) 8.90-8.96(m, 1H) | 27 |
| 174 | 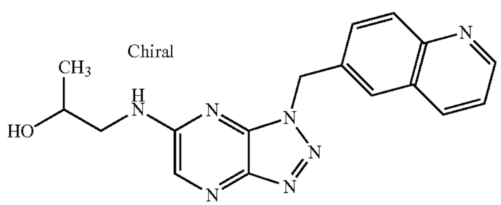 | 1-{[1-(quinolin-6-ylmethyl)-1H-[1,2,3]triazolo[4,5-b]pyrazin-6-yl]amino}propan-2-ol | (400 MHz, DMSO-d6) d ppm 1.07(d, J=6.32Hz, 3H) 3.23(ddd, J=13.14, 6.44, 6.19Hz, 1H) 3.36-3.41(m, 1H) 3.78-3.87(m, J=5.79, 5.79, 5.70, 5.70, 5.56, 5.56Hz, 1H) 4.82(d, J=4.80Hz, 1H) 5.87(s, 2H) 7.53(dd, J=8.34, 4.29Hz, 1H) 7.75(dd, J=8.72, 1.64Hz, 1H) 7.94(s, 1H) 8.00(d, J=8.59Hz, 1H) 8.13(s, 1H) 8.17-8.24(m, 1H) 8.35(d, J=8.08Hz, 1H) 8.89(dd, J=4.04, 1.52Hz, 1H) | 27 |
| 175 | 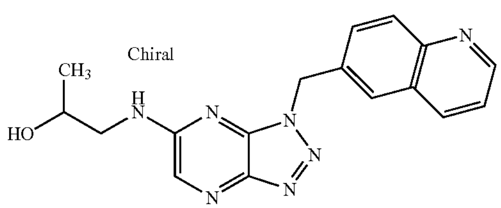 | 1-{[1-(quinolin-6-ylmethyl)-1H-[1,2,3]triazolo[4,5-b]pyrazin-6-yl]amino}propan-2-ol | (400 MHz, DMSO-d6) d ppm 1.07(d, J=6.32Hz, 3H) 3.23(ddd, J=13.14, 6.44, 6.19Hz, 1H) 3.36-3.41(m, 1H) 3.78-3.87(m, J=5.79, 5.79, 5.70, 5.70, 5.56, 5.56Hz, 1H) 4.82(d, J=4.80Hz, 1H) 5.87(s, 2H) 7.53(dd, J=8.34, 4.29Hz, 1H) 7.75(dd, J=8.72, 1.64Hz, 1H) 7.94(s, 1H) 8.00(d, J=8.59Hz, 1H) 8.13(s, 1H) 8.17-8.24(m, 1H) 8.35(d, J=8.08Hz, 1H) 8.89(dd, J=4.04, 1.52Hz, 1H) | 27 |

TABLE 4-continued

TABLE 4-continued

| Example | Structure | Name | NMR/LC-MS | Method |
|---|---|---|---|---|
| 176 | Chiral | 1-[1-(quinolin-6-yl-methyl)-1H-[1,2,3]tri-azolo[4,5-b]pyra-zin-6-yl]pyrro-lidine-3-carbox-amide | (400 MHz, DMSO-d6) d ppm 2.05-2.16(m, 1H) 2.17-2.28(m, 1H) 3.04-3.15(m, 1H) 3.53-3.62(m, 1H) 3.62-3.70(m, 1H) 3.70-3.75(m, 1H) 3.75-3.85(m, 1H) 5.90(s, 2H) 7.04(s, 1H) 7.50-7.59(m, 2H) 7.76(dd, J=8.46, 1.39Hz, 1H) 7.93(s, 1H) 8.00(d, J=8.59Hz, 1H) 8.22(s, 1H) 8.36(d, J=8.08Hz, 1H) 8.86-8.93(m, 1H) | 29 |
| 177 | Chiral | 1-[1-(quinolin-6-yl-methyl)-1H-[1,2,3]tri-azolo[4,5-b]pyra-zin-6-yl]pyrro-lidine-3-carboxamide | (400 MHz, DMSO-d6) d ppm 2.05-2.16(m, 1H) 2.17-2.28(m, 1H) 3.04-3.15(m, 1H) 3.53-3.62(m, 1H) 3.62-3.70(m, 1H) 3.70-3.75(m, 1H) 3.75-3.85(m, 1H) 5.90(s, 2H) 7.04(s, 1H) 7.50-7.59(m, 2H) 7.76(dd, J=8.46, 1.39Hz, 1H) 7.93(s, 1H) 8.00(d, J=8.59Hz, 1H) 8.22(s, 1H) 8.36(d, J=8.08Hz, 1H) 8.86-8.93(m, 1H) | 29 |
| 178 | 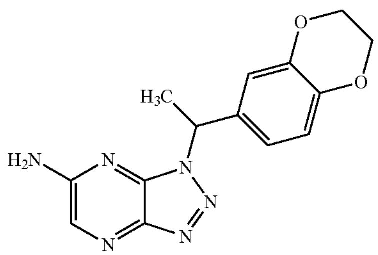 | 3-[1-(2,3-Dihydro-benzo[1,4]dioxin-6-yl)-eth-yl]-3H-[1,2,3]tri-azolo[4,5-b]pyra-zin-6-ylamine | 1H NMR(400 MHz, DMSO-D6) δ ppm 7.99(s, 1H) 7.41(s, 1H) 6.71-6.84(m, 4H) 5.88(d, J=7.33Hz, 1H) 4.09-4.25(m, 4H) 1.92(d, J=7.07Hz, 3H) | 15 |
| 179 | 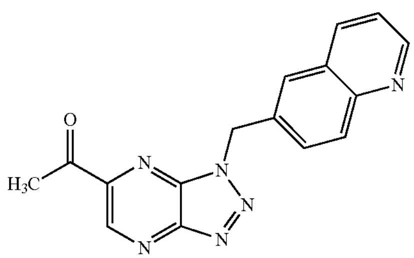 | 1-(3-Quinolin-6-yl-methyl-3H-[1,2,3]tri-azolo[4,5-b]pyra-zin-5-yl)-ethanone | 1H NMR(400 MHz, DMSO-D6) δ ppm 9.31(s, 1H) 8.91(dd, J=4.29, 1.77Hz, 1H) 8.37(d, J=8.34Hz, 1H) 8.01-8.11(m, 2H) 7.87(dd, J=8.84, 2.02Hz, 1H) 7.55(dd, J=8.34, 4.29Hz, 1H) 6.29(s, 2H) 2.74(s, 3H) | 21 |

| Example | Structure | Name | NMR/LC-MS | Method |
|---|---|---|---|---|
| 180 | 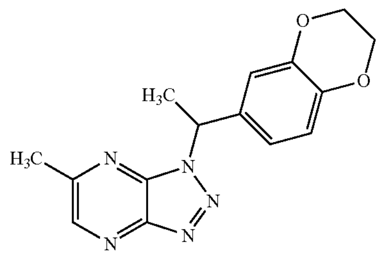 | 1-[1-(3,4-Dihydrobenzo[1,4]dioxin-6-yl)-ethyl]-6-methyl-1H-[1,2,3]triazolo[4,5-b]pyrazine | 1H NMR(400 MHz, DMSO-D6) δ ppm 8.74(s, 1H) 6.91(d, J=2.02Hz, 1H) 6.76-6.88(m, 2H) 6.25(q, J=6.82Hz, 1H) 4.18(s, 4H) 2.72(s, 3H) 2.03(d, J=7.07Hz, 3H) | 17 |
| 181 | 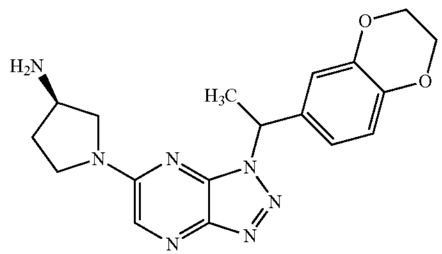 | (R)-1-{3-[1-(2,3-Dihydrobenzo[1,4]dioxin-6-yl)-ethyl]-3H-[1,2,3]triazolo[4,5-b]pyrazin-5-yl}-pyrrolidin-3-ylamine | 1H NMR(400 MHz, DMSO-D6) δ ppm 8.39(s, 2H) 8.15-8.28(m, 1H) 6.86-6.98(m, 2H) 6.73-6.86(m, 1H) 6.00(dd, J=7.07, 3.03Hz, 1H) 4.13-4.27(m, 4H) 3.93-4.08(m, 1H) 3.66-3.90(m, 4H) 2.35(s, 1H) 2.20(s, 1H) 1.99(d, J=7.07Hz, 3H) | 16 |
| 182 | 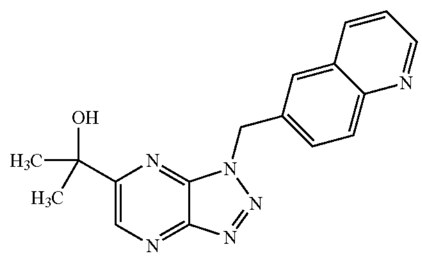 | 2-(3-Quinolin-6-ylmethyl-3H-[1,2,3]triazolo[4,5-b]pyrazin-5-yl)-propan-2-ol | 1H NMR(400 MHz, DMSO-d6) δ ppm 9.15(s, 1H) 8.89(dd, J=4.17, 1.64Hz, 1H) 8.35(d, J=8.34Hz, 1H) 7.92-8.09(m, 2H) 7.76-7.85(m, 1H) 7.54(dd, J=8.34, 4.29Hz, 1H) 6.17(s, 2H) 5.79(s, 1H) 1.55(s, 6H) | 22 |
| 183 | 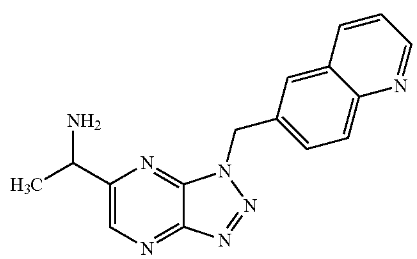 | 1-(3-Quinolin-6-ylmethyl-3H-[1,2,3]triazolo[4,5-b]pyrazin-5-yl)-ethylamine | 1H NMR(400 MHz, DMSO-d6) δ ppm 9.04(s, 1H) 8.89(dd, J=4.29, 1.77Hz, 1H) 8.36(dd, J=8.34, 1.01Hz, 1H) 7.94-8.10(m, 2H) 7.79(dd, J=8.72, 2.15Hz, 1H) 7.53(dd, J=8.21, 4.17Hz, 1H) 6.17(s, 2H) 4.30(q, J=6.57Hz, 1H) 1.90(s, 3H) 1.36-1.50(m, J=6.44, 6.44Hz, 3H) | 23 |

| Example | Structure | Name | NMR/LC-MS | Method |
|---|---|---|---|---|
| 184 | 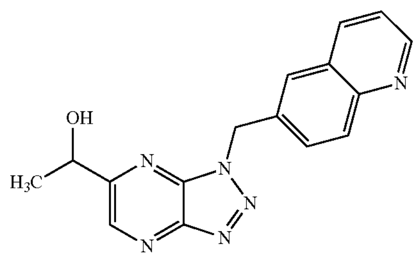 | 1-(3-Quinolin-6-yl-methyl-3H-[1,2,3]triazolo[4,5-b]pyrazin-5-yl)-ethanol | 1H NMR(400 MHz, DMSO-d6) δ ppm 9.01(s, 1H) 8.90(dd, J=4.04, 1.77Hz, 1H) 8.28-8.43(m, 1H) 8.02(d, J=8.59Hz, 1H) 7.97(d, J=1.77Hz, 1H) 7.79(dd, J=8.84, 2.02Hz, 1H) 7.54(dd, J=8.34, 4.04Hz, 1H) 6.19(s, 2H) 5.91(d, J=4.80Hz, 1H) 4.86-5.13(m, 1H) 1.43-1.55(m, 3H) | 23 |
| 185 | 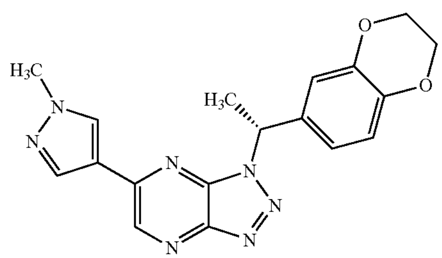 | 1-[(R)-1-(2,3-Dihydro-benzo[1,4]dioxin-6-yl)-ethyl]-6-(1-methyl-1H-pyrazol-4-yl)-1H-[1,2,3]triazolo[4,5-b]pyrazine | 1H NMR(400 MHz, DMSO-D6) δ ppm 9.16(s, 1H) 8.63(s, 1H) 8.29(s, 1H) 7.00(d, J=2.27Hz, 1H) 6.93(dd, J=8.46, 2.15Hz, 1H) 6.81(d, J=8.34Hz, 1H) 6.23(d, J=7.33Hz, 1H) 4.18(s, 4H) 3.94(s, 3H) 2.07(d, J=7.33Hz, 3H) | 40 |
| 186 | 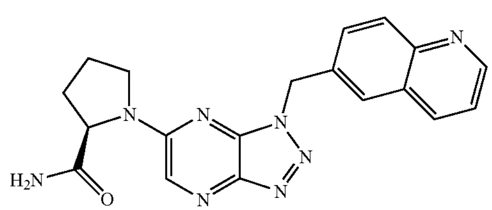 | 1-[1-(quinolin-6-yl-methyl)-1H-[1,2,3]triazolo[4,5-b]pyrazin-6-yl]-D-prolinamide | (400 MHz, MeOD) δ ppm 2.12-2.23(m, 3H) 2.35-2.46(m, 1H) 3.72(dt, J=9.66, 7.55Hz, 1H) 3.89-3.96(m, 1H) 4.64(dd, J=8.34, 2.27Hz, 1H) 5.86-5.97(m, 2H) 7.54(dd, J=8.34, 4.29Hz, 1H) 7.89(dd, J=8.72, 1.89Hz, 1H) 8.00-8.04(m, 2H) 8.21(s, 1H) 8.42(d, J=7.58Hz, 1H) 8.84(dd, J=4.29, 1.77Hz, 1H) | 27 |
| 187 | 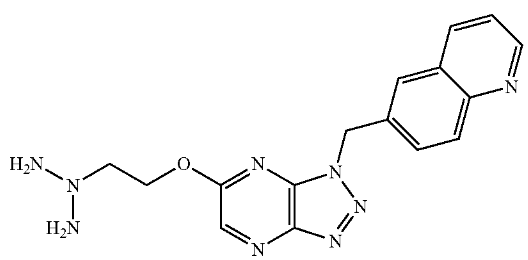 | N,N-dimethyl-2-{[1-(quinolin-6-yl-methyl)-1H-[1,2,3]triazolo[4,5-b]pyrazin-6-yl]oxy}-ethanamine | (400 MHz, DMSO-d6) δ ppm 2.13(s, 6H) 2.61(t, J=5.67Hz, 2H) 4.50(t, J=5.67Hz, 2H) 6.06(s, 2H) 7.54(dd, J=8.31, 4.03Hz, 1H) 7.78(dd, J=8.69, 2.14Hz, 1H) 7.97(d, J=1.76Hz, 1H) 8.01(d, J=8.81Hz, 1H) 8.36(dd, J=8.31, 1.01Hz, 1H) 8.42(s, 1H) 8.90(dd, J=4.15, 1.64Hz, 1H) | 28 |

TABLE 4-continued

| Example | Structure | Name | NMR/LC-MS | Method |
|---|---|---|---|---|
| 188 | 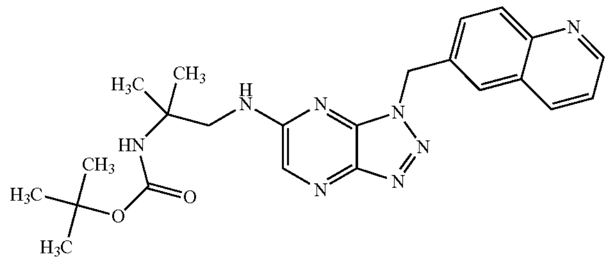 | tert-butyl(1,1-dimethyl-2-{[1-(quinolin-6-ylmethyl)-1H-[1,2,3]triazolo[4,5-b]pyrazin-6-yl]amino}ethyl)carbamate | (400 MHz, DMSO-d6) δ ppm 1.16(s, 6H) 1.34(s, 9H) 3.59(d, J=5.81Hz, 2H) 5.87(s, 2H) 6.57(s, 1H) 7.53(dd, J=8.34, 4.29Hz, 1H) 7.77(dt, J=8.59, 1.52Hz, 1H) 7.95-8.01(m, 2H) 8.04(t, J=5.43Hz, 1H) 8.16(s, 1H) 8.35(dd, J=8.34, 1.01Hz, 1H) 8.89(dd, J=4.29, 1.77Hz, 1H) | 27 |
| 189 | 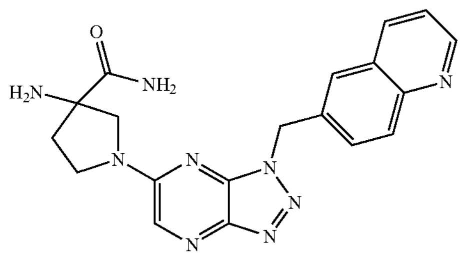 | 3-amino-1-[1-(quinolin-6-ylmethyl)-1H-[1,2,3]triazolo[4,5-b]pyrazin-6-yl]pyrrolidine-3-carboxamide | (400 MHz, MeOD) δ ppm 2.03-2.13(m, 1H) 2.49-2.61(m, 1H) 3.68(d, J=11.87Hz, 1H) 3.83-3.94(m, 2H) 3.99(d, J=11.62Hz, 1H) 5.95(s, 2H) 7.54(dd, J=8.34, 4.55Hz, 1H) 7.84(dd, J=8.72, 1.89Hz, 1H) 7.95(d, J=1.52Hz, 1H) 8.00(d, J=8.59Hz, 1H) 8.15(s, 1H) 8.35(d, J=8.34Hz, 1H) 8.84(dd, J=4.29, 1.77Hz, 1H) | 27 |
| 190 | 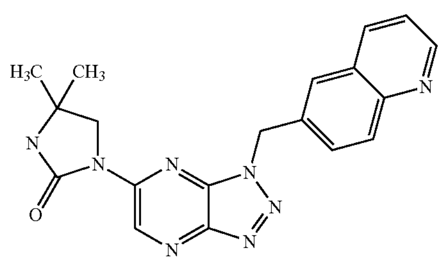 | 4,4-dimethyl-1-[1-(quinolin-6-ylmethyl)-1H-[1,2,3]triazolo[4,5-b]pyrazin-6-yl]imidazolidin-2-one | (400 MHz, DMSO-d6) δ ppm 1.32(s, 6H) 3.79(s, 2H) 6.04(s, 2H) 7.54(dd, J=8.34, 4.29Hz, 1H) 7.79(dd, J=8.59, 2.02Hz, 1H) 7.97(d, J=1.77Hz, 1H) 8.00-8.04(m, 2H) 8.37(dd, J=8.34, 1.01Hz, 1H) 8.90(dd, J=4.17, 1.64Hz, 1H) 9.72(s, 1H) | 30 |

| Example | Structure | Name | NMR/LC-MS | Method |
|---|---|---|---|---|
| 191 | 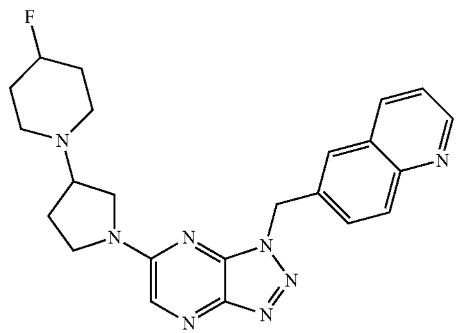 | 6-({6-[3-(4-fluoro-piperidin-1-yl)pyrro-lidin-1-yl]-1H-[1,2,3]tri-azolo[4,5-b]pyra-zin-1-yl}methyl)quinoline | (400 MHz, DMSO-d6) δ ppm 1.67-1.78(m, 2H) 1.80-1.92(m, 3H) 2.17-2.29(m, 1H) 2.35-2.46(m, 2H) 2.53-2.71(m, 3H) 2.93-3.03(m, 1H) 3.44-3.54(m, 1H) 3.76-3.85(m, 1H) 3.85-3.97(m, 1H) 4.54-4.83(m, 1H) 5.90(s, 2H) 7.53(dd, J=8.34, 4.29Hz, 1H) 7.75(dd, J=8.72, 1.89Hz, 1H) 7.94(s, 1H) 8.00(d, J=8.59Hz, 1H) 8.23(s, 1H) 8.36(d, J=8.34Hz, 1H) 8.89(dd, J=4.17, 1.64Hz, 1H) | 27 |
| 192 | 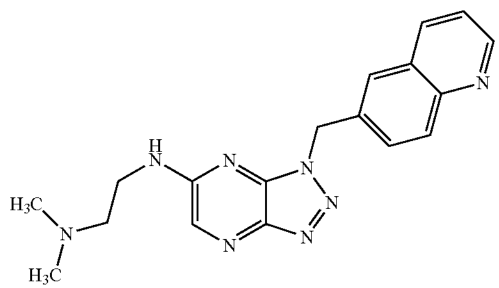 | N,N-dimethyl-N²-[1-(quino-lin-6-ylmeth-yl)-1H-[1,2,3]tri-azolo[4,5-b]pyra-zin-6-yl]eth-ane-1,2-diamine | 1H NMR(400 MHz, DMSO-d6) δ ppm 2.10(s, 6H) 2.39(t, J=6.44Hz, 2H) 3.42(q, J=6.23Hz, 2H) 5.88(s, 2H) 7.53(dd, J=8.34, 4.29Hz, 1H) 7.73(dd, J=8.72, 1.89Hz, 1H) 7.91(s, 2H) 7.99(d, J=8.84Hz, 1H) 8.07-8.16(m, 2H) 8.35(d, J=8.34Hz, 1H) 8.89(dd, J=4.17, 1.64Hz, 1H) | 27 |
| 193 | 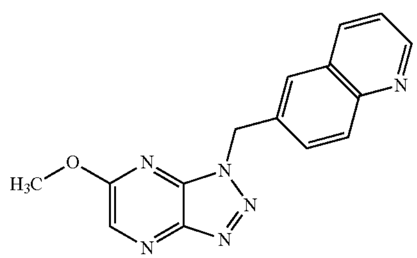 | 6-[(6-methoxy-1H-[1,2,3]tri-azolo[4,5-b]pyra-zin-1-yl)meth-yl]quinoline | 1H NMR(400 MHz, MeOD) δ ppm 4.08(s, 3H) 6.36(s, 2H) 7.95(dd, J=8.46, 5.18Hz, 1H) 8.14-8.22(m, 2H) 8.29(s, 1H) 8.94(d, J=7.83Hz, 1H) 9.13(d, J=4.04Hz, 1H) 9.40(s, 1H) | 28 |

TABLE 4-continued

| Example | Structure | Name | NMR/LC-MS | Method |
|---|---|---|---|---|
| 194 | 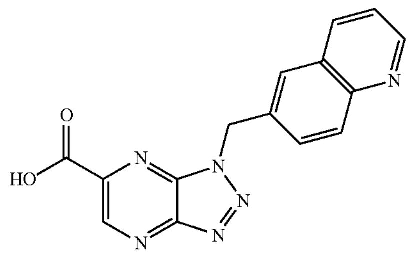 | 1-(quinolin-6-ylmethyl)-1H-[1,2,3]triazolo[4,5-b]pyrazine-6-carboxylic acid | 1H NMR(400 MHz, DMSO-d6) d ppm 6.24(s, 2H) 7.61(dd, J=8.34, 4.55Hz, 1H) 7.83(dd, J=8.72, 1.89Hz, 1H) 7.94(s, 1H) 8.02(d, J=8.84Hz, 1H) 8.47(d, J=8.08Hz, 1H) 8.95(dd, J=4.42, 1.64Hz, 1H) 9.34(s, 1H) | 35 |
| 195 | 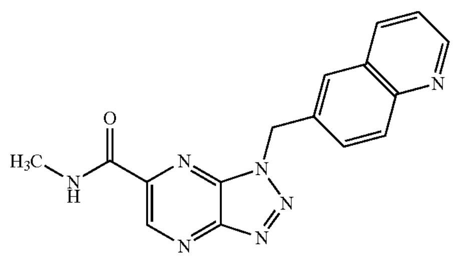 | N-methyl-1-(quinolin-6-ylmethyl)-1H-[1,2,3]triazolo[4,5-b]pyrazine-6-carboxamide | 1H NMR(400 MHz, DMSO-d6) δ ppm 2.92(d, J=4.80Hz, 3H) 6.28(s, 2H) 7.69(dd, J=8.34, 4.55Hz, 1H) 7.98(dd, J=8.72, 1.89Hz, 1H) 8.08-8.13(m, 2H) 8.55(d, J=7.83Hz, 1H) 9.02(dd, J=4.42, 1.64Hz, 1H) 9.13(q, J=4.46Hz, 1H) 9.41(s, 1H) | 36 |
| 196 | 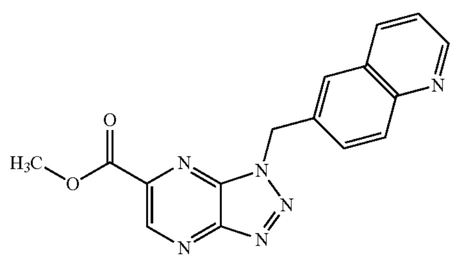 | methyl 1-(quinolin-6-ylmethyl)-1H-[1,2,3]triazolo[4,5-b]pyrazine-6-carboxylate | 1H NMR(400 MHz, DMSO-d6) δ ppm 3.95(s, 3H) 6.25(s, 2H) 7.49(dd, J=8.34, 4.29Hz, 4H) 7.75(dd, J=8.84, 2.02Hz, 1H) 7.88(s, 1H) 7.98(d, J=8.84Hz, 1H) 8.29(d, J=8.34Hz, 1H) 8.86(dd, J=4.17, 1.64Hz, 1H) 9.38(s, 1H) | 34 |
| 197 | 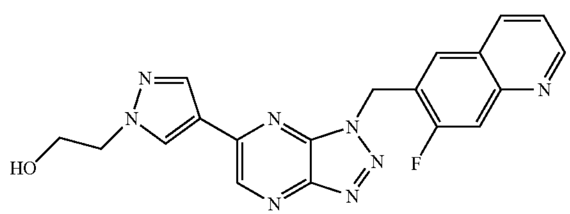 | 2-(4-{1-[(7-fluoroquinolin-6-yl)methyl]-1H-[1,2,3]triazolo[4,5-b]pyrazin-6-yl}-1H-pyrazol-1-yl)ethanol | 1H NMR(400 MHz, DMSO-d6) δ ppm 3.78(t, J=5.43Hz, 2H) 4.24(t, J=5.43Hz, 2H) 6.18(s, 2H) 7.54(dd, J=8.34, 4.29Hz, 1H) 7.84(d, J=11.37Hz, 1H) 8.15(d, J=8.34Hz, 1H) 8.29(s, 1H) 8.44(d, J=7.33Hz, 1H) 8.62(s, 1H) 8.93(dd, J=4.29, 1.52Hz, 1H) 9.23(s, 1H) | 39 |

TABLE 4-continued

| Example | Structure | Name | NMR/LC-MS | Method |
|---|---|---|---|---|
| 198 | 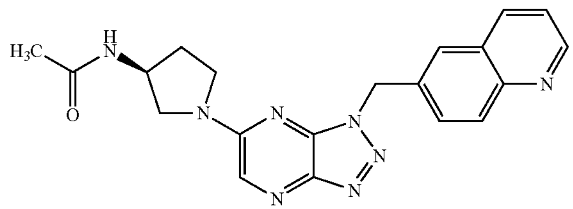 | N-{(3S)-1-[1-(quinolin-6-ylmethyl)-1H-[1,2,3]triazolo[4,5-b]pyrazin-6-yl]pyrrolidin-3-yl}acetamide | 1H NMR(400 MHz, DMSO-d6) δ ppm 1.81(s, 3H) 1.87-1.98(m, 1H) 2.13-2.24(m, 1H) 3.41-3.50(m, 2H) 3.60-3.78(m, 2H) 4.39(bs, 1H) 5.91(s, 2H) 7.52(dd, J=8.34, 4.29Hz, 1H) 7.76(dd, J=8.72, 1.89Hz, 1H) 7.94(d, J=1.77Hz, 1H) 8.00(d, J=8.84Hz, 1H) 8.19(d, J=6.57Hz, 1H) 8.22(s, 1H) 8.35(d, J=7.33Hz, 1H) 8.89(dd, J=4.04, 1.77Hz, 1H) | 27 |
| 199 | 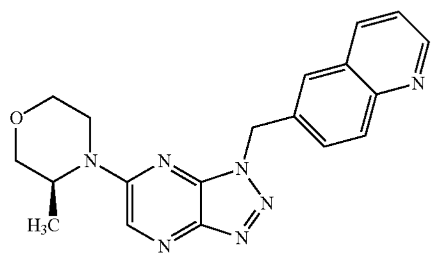 | 6-({6-[(3S)-3-methylmorpholin-4-yl]-1H-[123]triazolo[45-b]pyrazin-1-yl}methyl)quinoline | 1H NMR(500 MHz, DMSO-d6) d ppm 1.21(d, J=6.04Hz, 3H) 3.73-3.77(m, 5H) 5.92-5.93(m, 2H) 7.49-7.58(m, 1H) 7.73-7.82(m, 1H) 7.94-8.04(m, 2H) 8.30-8.39(m, 1H) 8.46-8.53(m, 1H) 8.84-8.93(m, 1H)(two aliphatic protons not resolved, due to water peak) | 27 |
| 200 | 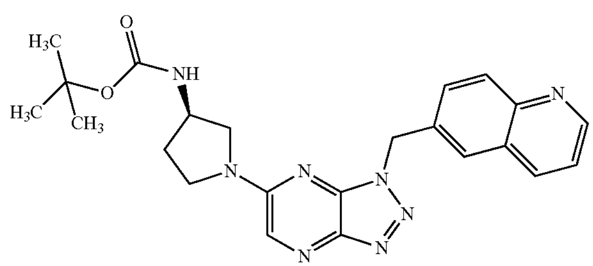 | (R)-tert-butyl 1-(3-(quinolin-6-ylmethyl)-3H-[1,2,3]triazolo[4,5-b]pyrazin-5-yl)pyrrolidin-3-ylcarbamate | (400 MHz, DMSO-d$_6$) δ ppm 1.38(s, 9H) 1.88-1.99(m, 1H) 2.10-2.22(m, 1H) 3.44(dd, J=11.49, 4.42Hz, 1H) 3.61-3.73(m, 3H) 4.12-4.23(m, 1H) 5.91(s, 2H) 7.27(d, J=5.56Hz, 1H) 7.53(dd, J=8.34, 4.29Hz, 1H) 7.76(dd, J=8.72, 1.89Hz, 1H) 7.93(dd, J=1.26Hz, 1H) 8.00(d, J=.84Hz, 1H) 8.21(s, 1H) 8.33-8.38(m, 1H) 8.89(dd, J=4.29, 1.77Hz, 1H) | 26 |

TABLE 4-continued

| Example | Structure | Name | NMR/LC-MS | Method |
|---|---|---|---|---|
| 201 | 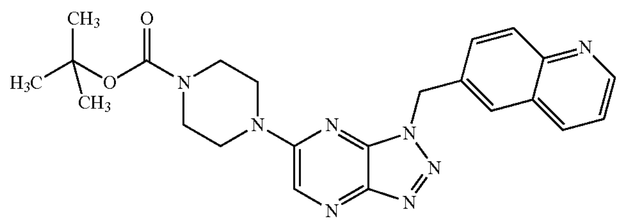 | tert-butyl 4-(3-(quinolin-6-ylmethyl)-3H-[1,2,3]triazolo[4,5-b]pyrazin-5-yl)piperazine-1-carboxylate | (400 MHz, DMSO-d₆) δ ppm 1.42(s, 9H) 3.41-3.49(m, 4H) 3.75-3.82(m, 4H) 5.93(s, 2H) 7.54(dd, J=8.34, 4.29Hz, 1H) 7.76(dd, J=8.84, 2.02Hz, 1H) 7.96(d, J=1.52Hz, 1H) 8.01(d, J=8.84Hz, 1H) 8.37(d, J=7.33Hz, 1H) 8.56(s, 1H) 8.89(dd, J=4.17, 1.64Hz, 1H) | 26 |
| 202 | 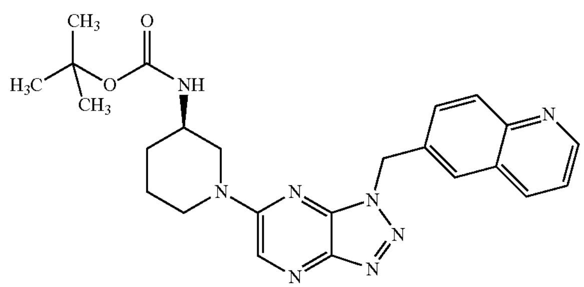 | (R)-tert-butyl 1-(3-(quinolin-6-ylmethyl)-3H-[1,2,3]triazolo[4,5-b]pyrazin-5-yl)piperidin-3-ylcarbamate | (400 MHz, MeOD) δ ppm 1.43(s, 9H) 1.54-1.65(m, 2H) 1.79-1.89(m, 1H) 1.94-2.03(m, 1H) 3.24-3.27(m, 1H) 3.35-3.45(m, 1H) 3.50-3.61(m, 1H) 4.10-4.18(m, 1H) 4.37(dd, J=13.52, 3.41Hz, 1H) 5.93(s, 2H) 7.53(dd, J=8.34, 4.29Hz, 1H) 7.87(d, J=7.83Hz, 1H) 7.98-8.03(m, 2H) 8.37(d, J=7.83Hz, 1H) 8.42(s, 1H) 8.83(dd, J=4.29, 1.77Hz, 1H) | 26 |
| 203 | 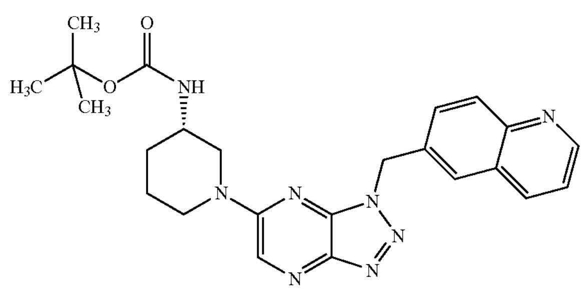 | (S)-tert-butyl 1-(3-(quinolin-6-ylmethyl)-3H-[1,2,3]triazolo[4,5-b]pyrazin-5-yl)piperidin-3-ylcarbamate | (400 MHz, DICHLOROMETHANE-d₂) δ ppm 1.43(s, 9H) 1.58-1.69(m, 2H) 1.76-1.86(m, 1H) 1.95-2.04(m, 1H) 3.30-3.40(m, 1H) 3.46-3.57(m, 1H) 3.63-3.73(m, 1H) 3.92-4.01(m, 1H) 4.23(dd, J=13.14, 3.28Hz, 1H) 5.86(s, 2H) 7.40(dd, J=8.34, 4.29Hz, 1H) 7.81(d, J=8.59Hz, 1H) 7.89(s, 1H) 8.04(d, J=8.59Hz, 1H) 8.17(d, J=8.59Hz, 1H) 8.31(s, 1H) 8.87(dd, J=4.17, 1.64Hz, 1H) | 26 |

TABLE 4-continued

| Example | Structure | Name | NMR/LC-MS | Method |
|---|---|---|---|---|
| 204 | 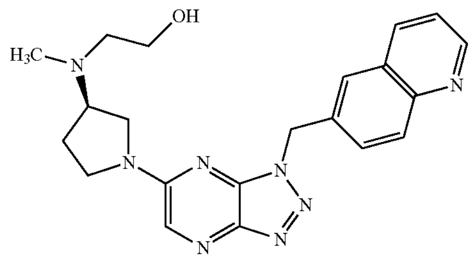 | 2-(methyl{(3R)-1-[1-(quinolin-6-yl-methyl)-1H-[1,2,3]triazolo[4,5-b]pyrazin-6-yl]pyrrolidin-3-yl]amino)ethanol. TFA salt | 1H NMR(400 MHz, MeOD) d ppm 2.43(td, J=8.21, 5.05Hz, 1H) 2.64-2.74(m, 1H) 3.04(s, 3H) 3.34-3.46(m, 3H) 3.70-3.79(m, 1H) 3.86-3.97(m, 3H) 4.00-4.08(m, 1H) 4.20-4.32(m, 2H) 6.07(s, 2H) 7.90(dd, J=8.34, 5.05Hz, 1H) 8.07-8.11(m, 1H) 8.18(d, J=8.84Hz, 2H) 8.27(s, 1H) 8.86(d, J=7.83Hz, 1H) 9.09(dd, J=4.80, 1.52Hz, 1H) | 41 |
| 205 | 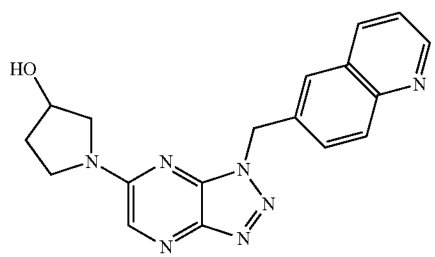 | 1-[1-(quinolin-6-yl-methyl)-1H-[1,2,3]triazolo[4,5-b]pyrazin-6-yl]pyrrolidin-3-ol. TFA salt | 1H NMR(400 MHz, DMSO-d6) d ppm 1.96-2.04(m, 2H) 3.61-3.72(m, 3H) 4.39-4.49(m, 1H) 5.05-5.17(m, 1H) 5.91(s, 2H) 7.53(dd, J=8.34, 4.29Hz, 1H) 7.76(dd, J=8.59, 2.02Hz, 1H) 7.93(s, 1H) 8.01(d, J=8.84Hz, 1H) 8.22(s, 1H) 8.36(d, J=7.58Hz, 1H) 8.89(dd, J=4.29, 1.77Hz, 1H) | 41 |
| 206 | 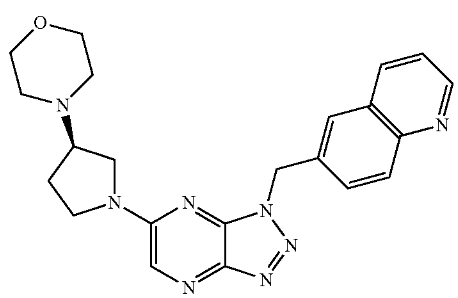 | 6-({6-[(3R)-3-morpholin-4-yl]pyrrolidin-1-yl]-1H-[1,2,3]triazolo[4,5-b]pyrazin-1-yl}methyl)quinoline. TFA salt | 1H NMR(400 MHz, DMSO-d6) d ppm 1.76-1.88(m, 1H) 2.16-2.27(m, 1H) 2.36-2.46(m, 3H) 2.86-2.97(m, 1H) 3.40-3.441(m, 3H) 3.55-3.66(m, 4H) 3.79-3.94(m, 2H) 4.29Hz, 1H) 7.75(dd, J=8.84, 2.02Hz, 5.91(s, 2H) 7.53(dd, J=8.34, 1H) 7.94(s, 1H) 8.00(d, J=8.59Hz, 1H) 8.23(s, 1H) 8.36(d, J=7.58Hz, 1H) 8.89(dd, J=4.17, 1.64Hz, 1H) | 41 |

TABLE 4-continued

| Example | Structure | Name | NMR/LC-MS | Method |
|---|---|---|---|---|
| 207 | 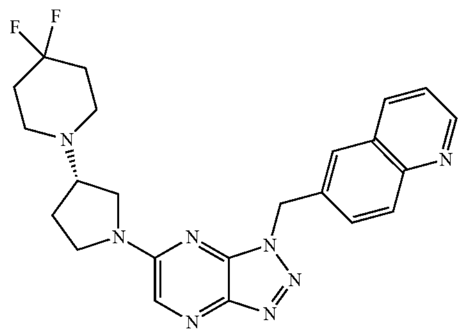 | 6-({6-[(3S)-3-(4,4-di-fluoropiperidin-1-yl)pyrro-lidin-1-yl]-1H-[1,2,3]tri-azolo[4,5-b]pyra-zin-1-yl}meth-yl)quinoline. TFA salt | 1H NMR(400 MHz, DMSO-d6) d ppm 1.86-2.02(m, 5H) 2.18-2.28(m, 1H) 2.54-2.65(m, 4H) 3.04-3.16(m, 1H) 3.33-3.38(m, 1H) 3.45-3.57(m, 1H) 3.75-3.85(m, 1H) 3.85-3.97(m, 1H) 5.90(s, 2H) 7.53(dd, J=8.34, 4.29Hz, 1H) 7.75(dd, J=8.72, 1.89Hz, 1H) 7.94(d, J=1.26Hz, 1H) 8.00(d, J=8.84Hz, 1H) 8.23(s, 1H) 8.33-8.38(m, 1H) 8.89(dd, J=4.17, 1.64Hz, 1H) | 41 |
| 208 | 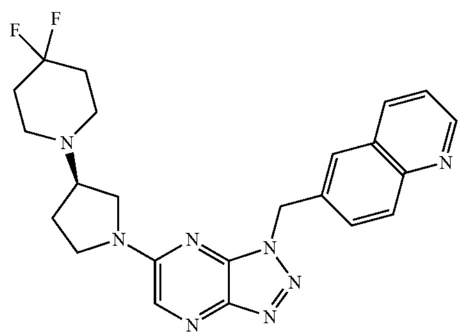 | 6-({6-[(3R)-3-(4,4-di-fluoropiperidin-1-yl)pyrro-lidin-1-yl]-1H-[1,2,3]tri-azolo[4,5-b]pyra-zin-1-yl}meth-yl)quinoline. TFA salt | 1H NMR(400 MHz, DMSO-d6) d ppm 1.89-1.97(m, 5H) 2.18-2.25(m, 1H) 2.52-2.664(m, 4H) 3.03-3.14(m, 1H) 3.45-3.55(m, 2H) 3.70-3.82(m, 1H) 3.86-3.94(m, 1H) 5.90(s, 2H) 7.52(dd, J=8.34, 4.04Hz, 1H) 7.75(dd, J=8.72, 1.89Hz, 1H) 7.93(s, 1H) 8.00(d, J=8.59Hz, 1H) 8.22(s, 1H) 8.35(d, J=7.58Hz, 1H) 8.88(dd, J=4.29, 1.52Hz, 1H) | 41 |

TABLE 5

| Example | Structure | Name | NMR | Method |
|---|---|---|---|---|
| 209 | (structure with MeSO3H) | 2-[4-(3-Quinolin-6-ylmethyl-3H-[1,2,3]triazolo[4,5-b]pyrazin-5-yl)-pyrazol-1-yl]-ethanol mesylate salt | 1H NMR(400MHz, DMSO-d6) d ppm 9.06-9.30(m, 1H) 8.89(dd, J=4.17, 1.64Hz, 1H) 8.64(s, 1H) 8.33-8.40 (m, 1H) 8.33(s, 1H) 7.94-8.09(m, 2H) 7.82(dd, J=8.59, 2.02Hz, 1H) 7.53(dd, J=8.34, 4.04Hz, 1H) 6.15 (s, 2H) 5.01(s, 1H) 4.24(t, J=5.31 Hz, 2H) 3.78(t, J=5.31 Hz, 2H) | 42 |
| 210 | (structure) | [4-(3-Quinolin-6-ylmethyl-3H-[1,2,3]triazolo[4,5-b]pyrazin-5-yl)-pyrazol-1-yl]-acetic acid | 1H NMR(300MHz, DMSO-d6) δ ppm 9.21(s, 1H) 8.89(dd, J=4.14, 1.70 Hz, 1H) 8.56(s, 1H) 8.38(dd, J=8.19, 1.60Hz, 1H) 8.22(s, 1H) 7.98-8.08(m, 2H) 7.83(dd, J=8.67, 1.88Hz, 1H) 7.53(dd, J=8.29, 4.33 Hz, 1H) 6.15(s, 2H) 4.59(s, 2H) | 43 |
| 211 | (structure) | N,N-dimethyl-3-(4-(3-(quinolin-6-ylmethyl)-3H-[1,2,3]triazolo[4,5-b]pyrazin-5-yl)-1H-pyrazol-1-yl)propan-1-amine | 1H NMR(400MHz, DMSO-d6) δ ppm 9.47(s, 1H), 9.24(s, 1H), 8.94(dd, J=4.29, 1.77Hz, 1H), 8.70(s, 1H), 8.44(d, J=7.83Hz, 1H), 8.38(s, 1H), 8.06(d, J=8.59Hz, 1H), 8.00(s, 1H), 7.85(dd, J=8.72, 1.89Hz, 1H), 7.59(dd, J=8.34, 4.29Hz, 1H), 6.17 (s, 2H), 4.30(t, J=6.69 Hz, 2H), 3.07 (dt, J=10.55, 5.21Hz, 2H), 2.77(d, J=4.55Hz, 6H), 2.16-2.25(m, 2H). LC-MS 413. | 44 |
| 212 | (structure) | 6-[(S)-1-(6-Bromo-[1,2,3]triazolo[4,5-b]pyrazin-1-yl)-ethyl]-quinoline | 1H NMR(300MHz, DMSO-d6) δ ppm 8.99(s, 1H) 8.90(dd, J=4.14, 1.70 Hz, 1H) 8.28-8.46(m, 1H) 7.94-8.08 (m, 2H) 7.82(dd, J=8.85, 2.07 Hz, 1H) 7.54(dd, J=8.29, 4.14Hz, 1H) 6.50-6.66(m, J=7.16Hz, 1H) 2.19(d, J=6.97Hz, 3H) | 44 |
| 213 | (structure) | 6-{1-[6-(1-Methyl-1H-pyrazol-4-yl)-[1,2,3]triazolo[4,5-b]pyrazin-1-yl]-ethyl}-quinoline | 1H NMR(300MHz, DMSO-d6) δ ppm 9.18(s, 1H) 8.89(dd, J=4.14, 1.51 Hz, 1H) 8.62(s, 1H) 8.35-8.43 (m, 1H) 8.28(s, 1H) 7.96-8.11(m, 2H) 7.81-7.94(m, J=1.88Hz, 1H) 7.53(dd, J=8.29, 4.14Hz, 1H) 6.46-6.65(m, J=7.35Hz, 1H) 3.94 (s, 3H) 2.25(d, J=7.16Hz, 3H) | 42 |
| 214 | (structure) | 6-{(S)-1-[6-(1-Methyl-1H-pyrazol-4-yl)-[1,2,3]triazolo[4,5-b]pyrazin-1-yl]-ethyl}-quinoline | 1H NMR(300 MHz, DMSO-d6) δ ppm 9.20(s, 1H) 8.87-8.96(m, 1H) 8.57-8.72(m, 1H) 8.36-8.47(m, 1H) 8.30(s, 1H) 7.98-8.14(m, J=19.97Hz, 2H) 7.81-7.97(m, 1H) 7.48-7.60(m, J=8.29Hz, 1H) 6.50-6.69(m, J=7.54Hz, 1H) 3.96(s, 3H) 2.27(d, J=6.97Hz, 3H) | 42 |

TABLE 5-continued

| Example | Structure | Name | NMR | Method |
|---|---|---|---|---|
| 215 | 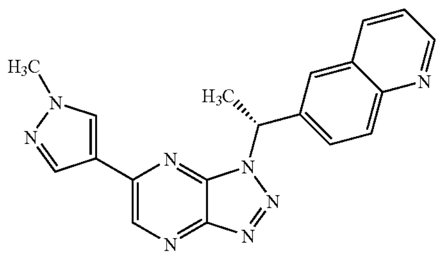 | 6-{(R)-1-[6-(1-Methyl-1H-pyrazol-4-yl)-[1,2,3]triazolo[4,5-b]pyrazin-1-yl]-ethyl}-quinoline | 1H NMR(300 MHz, DMSO-d6) δ ppm 9.20(s, 1H) 8.87-8.96(m, 1H) 8.57-8.72(m, 1H) 8.36-8.47(m, 1H) 8.30(s, 1H) 7.98-8.14(m, J=19.97Hz, 2H) 7.81-7.97(m, 1H) 7.48-7.60(m, J=8.29Hz, 1H) 6.50-6.69(m, J=7.54Hz, 1H) 3.96(s, 3H) 2.27(d, J=6.97Hz, 3H) | 42 |
| 216 | 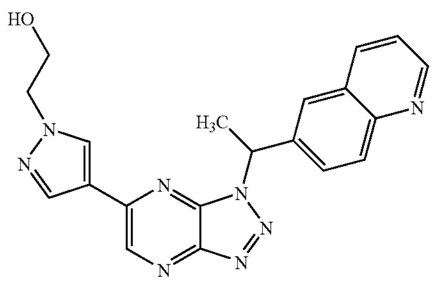 | 2-{4-[3-(1-Quinolin-6-yl-ethyl)-3H-[1,2,3]triazolo[4,5-b]pyrazin-5-yl]-pyrazol-1-yl}-ethanol | 1H NMR(300 MHz, DMSO-d6) δ ppm 9.20(s, 1H) 8.82-8.92(m, 1H) 8.62(s, 1H) 8.34-8.45(m, 1H) 8.22-8.33(m, 1H) 8.05-8.11(m, 1H) 7.96-8.04(m, 1H) 7.82-7.93(m, 1H) 7.44-7.59(m, 1H) 6.47-6.64(m, 1H) 4.88-5.05(m, 1H) 4.17-4.28(m, 2H) 3.71-3.86(m, 2H) 2.24(d, J=7.16Hz, 3H) | 42 |
| 217 | 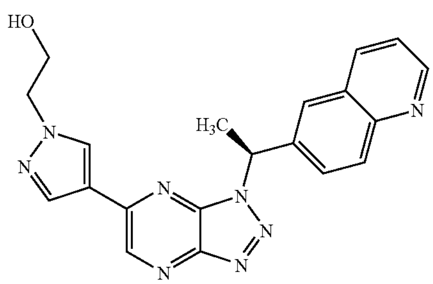 | 2-{4-[3-((S)-1-Quinolin-6-yl-ethyl)-3H-[1,2,3]triazolo[4,5-b]pyrazin-5-yl]-pyrazol-1-yl}-ethanol | 1H NMR(300 MHz, DMSO-d6) δ ppm 9.20(s, 1H) 8.89(dd, J=4.14, 1.70 Hz, 1H) 8.63(s, 1H) 8.35-8.46(m, 1H) 8.27-8.33(m, 1H) 7.97-8.11(m, 2H) 7.84-7.94(m, 1H) 7.53(dd, J=8.19, 4.24Hz, 1H) 6.49-6.66(m, 1H) 4.98(t, J=5.27 Hz, 1H) 4.24(t, J=5.27Hz, 2H) 3.72-3.84(m, 2H) 2.24 (d, J=7.16 Hz, 3H) | 42 |
| 218 | 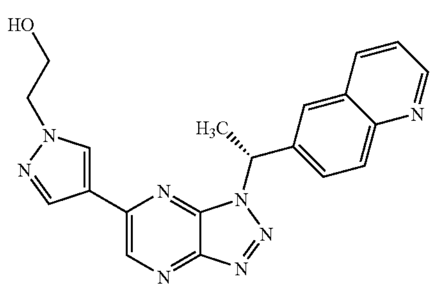 | 2-{4-[3-((R)-1-Quinolin-6-yl-ethyl)-3H-[1,2,3]triazolo[4,5-b]pyrazin-5-yl]-pyrazol-1-yl}-ethanol | 1H NMR(300 MHz, DMSO-d6) δ ppm 9.20(s, 1H) 8.89(dd, J=4.14, 1.70 Hz, 1H) 8.63(s, 1H) 8.35-8.46(m, 1H) 8.27-8.33(m, 1H) 7.97-8.11(m, 2H) 7.84-7.94(m, 1H) 7.53(dd, J=8.19, 4.24Hz, 1H) 6.49-6.66(m, 1H) 4.98(t, J=5.27Hz, 1H) 4.24(t, J=5.27Hz, 2H) 3.72-3.84(m, 2H) 2.24(d, J=7.16Hz, 3H) | 42 |
| 219 | 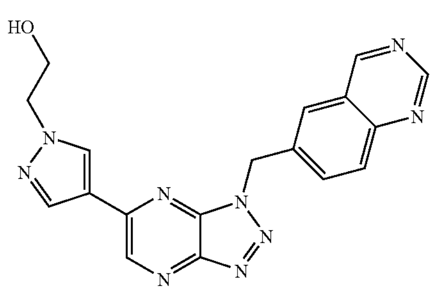 | 2-[4-(3-Quinazolin-6-ylmethyl-3H-[1,2,3]triazolo[4,5-b]pyrazin-5-yl)-pyrazol-1-yl]-ethanol | 1H NMR(400 MHz, MeOD) d ppm 3.95(t, J=5.31Hz, 2H) 4.33(t, J=5.31Hz, 2H) 6.23(s, 2H) 8.05(d, J=8.84Hz, 1H) 8.14-8.22(m, 2H) 8.30(s, 1H) 8.54(s, 1H) 9.11(s, 1H) 9.24(s, 1H) 9.53(s, 1H) | 42 |

TABLE 5-continued

| Example | Structure | Name | NMR | Method |
|---|---|---|---|---|
| 220 | 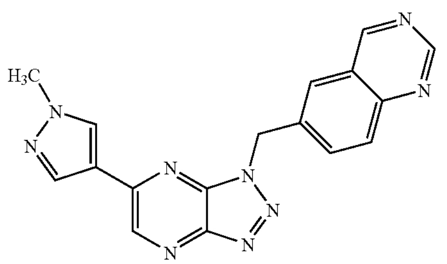 | 6-[6-(1-Methyl-1H-pyrazol-4-yl)-[1,2,3]triazolo[4,5-b]pyrazin-1-ylmethyl]-quinazoline | 1H NMR(400 MHz, DMSO-D6) d ppm 3.93(s, 3H) 4.09(q, J=5.14Hz, 1H) 6.19(s, 2H) 8.00-8.06(m, 1H) 8.08-8.15(m, 2H) 8.29(s, 1H) 8.62(s, 1H) 9.21(s, 1H) 9.28(s, 1H) 9.60(s, 1H) | 46 |

Biological Assays

General

In vitro assays may be used to determine the level of activity and effect of the different compounds of the present invention on one or more of the PKs. Similar assays can be designed along the same lines for any PK using techniques well known in the art. See for example, Technikova-Dobrova Z, Sardanelli A M, Papa S FEBS Lett. 1991 Nov. 4; 292: 69-72.

A general procedure is as follows: compounds and kinase assay reagents are introduced into test wells. The assay is initiated by addition of the kinase enzyme. Enzyme inhibitors reduce the measured activity of the enzyme.

Presently, the continuous-coupled spectrophotometric assay was used to determine the level of activity and effect of the different compounds of the present invention on the tyrosine kinase activity of HGFR on the Met-2 substrate peptide. In the continuous-coupled spectrophotometric assay the time-dependent production of ADP by the kinase is determined by analysis of the rate of consumption of NADH by measurement of the decrease in absorbance at 340 nm. As the PK produces ADP it is re-converted to ATP by reaction with phosphoenol pyruvate and pyruvate kinase. Pyruvate is also produced in this reaction. Pyruvate is subsequently converted to lactate by reaction with lactate dehydrogenase, which simultaneously converts NADH to NAD. NADH has a measurable absorbance at 340 nm whereas NAD does not.

The presently preferred protocol for conducting the continuous-coupled spectrophotometric experiments for specific PKs is provided below. However, adaptation of this protocol for determining the activity of compounds against other RTKs, as well as for CTKs and STKs, is well within the scope of knowledge of those skilled in the art.

HGFR Continuous-coupled Spectrophotometric Assay

This assay was used to analyze the tyrosine kinase activity of HGFR on the Met-2 substrate peptide, a peptide derived from the activation loop of the HGFR. Assay results in the form of Ki values (μM) are summarized in Table 6.

Materials and Reagents:
1. HGFR enzyme from Upstate (Met, active) Cat. # 14-526
2. Met-2 Peptide (HGFR Activation Loop) Ac-ARDMY-DKEYYSVHNK (MW=1960). Dissolve up in 200 mM HEPES, pH 7.5 at 10 mM stock.
3. 1 M PEP (phospho-enol-pyruvate) in 200 mM HEPES, pH 7.5
4. 100 mM NADH (B-Nicotinamide Adenine Dinucleotide, Reduced Form) in 200 mM HEPES, pH 7.5
5. 4 M $MgCl_2$ (Magnesium Chloride) in $ddH_2O$
6. 1 M DTT (Dithiothreitol) in 200 mM HEPES, pH 7.5
7. 15 Units/mL LDH (Lactic Dehydrogenase)
8. 15 Units/mL PK (Pyruvate Kinase)
9. 5M NaCl dissolved in $ddH_2O$
10. Tween-20 (Protein Grade) 10% Solution
11. 1 M HEPES buffer: (N-[2-Hydroxethyl]piperazine-N-[2-ethanesulfonic acid]) Sodium Salt. Dissolve in $ddH_2O$, adjust pH to 7.5, bring volume to 1 L. Filter at 0.1 μm.
12. HPLC Grade Water; Burdick and Jackson #365-4, 1×4 liters (or equivalent)
13. 100% DMSO (SIGMA)
14. Costar # 3880—black clear flat bottom half area plates for $K_i$ determination and % inhibition
15. Costar # 3359-96 well polypropylene plates, round bottom for serial dilutions
16. Costar # 3635—UV-plate clear flat bottom plates for % inhibition
17. Beckman DU-650 w/micro cell holders
18. Beckman 4-position micro cell cuvette Procedure:

Prep Dilution Buffer (DB) for Enzyme (For 30 mL prep)
1. DB final concentration is 2 mM DTT, 25 mM $NaCl_2$, 5 mM $MgCl_2$, 0.01% Tween-20, and 50 mM HEPES buffer, pH 7.5.
2. Make up 50 mM HEPES by adding 1.5 mL 1 M HEPES into 28.1 mL of $ddH_2O$. Add rest of the reagents. Into 50 mL conical vial, add 60 μL of 1 M DTT, 150 μL 5M $NaCl_2$, 150 μL 1 M $MgCl_2$, and 30 μL of 10% Tween-20 to give total volume of 30 mL.
3. Vortex for 5-10 seconds.
4. Aliquot out DB at 1 mL/tube and label tubes as "DB HGFR"
5. Note: This can be prepared and stored ahead of time.
6. Freeze un-used aliquots in microcentrifuge tubes at −20° C. freezer.

Prep Compounds
1. For compound dilution plate, add 4 μL of 10 mM stock into column 1 of plate, and bring volume to 100 μL with 100% DMSO.
2. Set up the Precision 2000 dilution method. A final concentration of 200 μM compound in 50% DMSO, 100 mM HEPES (1:2 serial dilution).

Prep Coupled Enzymatic Buffer:
1. Final concentration in assay:

| Reagent (Stock Conc.) | Final Conc. In Assay |
|---|---|
| a. PEP (1 M) | 1 mM |
| b. NADH (100 mM) | 300 μM |
| c. MgCl$_2$ (4 M) | 20 mM |
| d. DTT (1 M) | 2 mM |
| e. ATP (500 mM) | 300 μM |
| f. HEPES 200 mM (pH 7.5) | 100 mM |
| g. Pyruvate Kinase (PK) | 15 units/mL |
| h. Lactic Dehydrogenase (LDH) | 15 units/mL |
| i. Met-2 peptide (10 mM) | 0.500 mM |
| j. HGFR | 50 nM |

2. For a 10 mL reaction buffer add 10 μL of 1M PEP, 33 μL of 100 mM NADH, 50 μL of 4M MgCl$_2$, 20 μL of 1M DTT, 6 μL of 500 mM ATP, and 500 μL of 10 mM Met-2 peptide into 100 mM HEPES buffer pH 7.5 and vortex/mix.
3. Add coupling enzymes, LDH and PK, into reaction mix. Mix by gentle inversion.

Running Samples
1. Spectrophotometer settings:

| | |
|---|---|
| i. Absorbance wavelength (λ): | 340 nm |
| ii. Incubation time: | 10 min |
| iii. Run time: | 10 min |
| iv. Temperature: | 37° C. |

2. Add 85 μL of CE reaction mix into each well of assay plate.
3. Add 5 μL of diluted compound into a well of the assay plate.
4. Add 5 μL of 50% DMSO for negative control into last column of assay plate.
5. Mix with multi-channel pipettor or orbital shaker.
6. Pre-incubate for 10 minutes at 37° C.
7. Add 10 μL of 500 nM HGFR to each well of assay plate; the final HGFR concentration is 50 nM in a total final volume of 100 μL.
8. Measure activity for 10 minutes at A=340 nm and 37° C.

TABLE 6

| Example | Ki |
|---|---|
| 1 | 0.008 |
| 2 | 0.011 |
| 3 | 0.064 |
| 4 | 0.069 |
| 5 | 0.02 |
| 6 | 0.011 |
| 7 | 0.002 |
| 8 | 0.006 |
| 9 | 0.009 |
| 10 | 0.004 |
| 11 | 0.004 |
| 12 | 0.038 |
| 13 | 0.003 |
| 14 | 0.04 |
| 15 | 0.016 |
| 16 | 0.003 |
| 17 | 0.046 |
| 18 | 0.005 |
| 19 | 0.003 |
| 20 | 0.003 |

TABLE 6-continued

| Example | Ki |
|---|---|
| 21 | 0.004 |
| 22 | 0.012 |
| 23 | 0.006 |
| 24 | 0.001 |
| 25 | 0.005 |
| 26 | 0.019 |
| 27 | 0.045 |
| 28 | 0.015 |
| 29 | 0.024 |
| 30 | 0.008 |
| 31 | 0.059 |
| 32 | 0.069 |
| 33 | 0.01 |
| 34 | 0.033 |
| 35 | 0.004 |
| 36 | 0.002 |
| 37 | 0.004 |
| 38 | 0.003 |
| 39 | 0.021 |
| 40 | 0.012 |
| 41 | 0.036 |
| 42 | 0.08 |
| 43 | 0.045 |
| 44 | 0.046 |
| 45 | 0.019 |
| 46 | 0.043 |
| 47 | 0.046 |
| 48 | 0.062 |
| 49 | 0.033 |
| 50 | 0.024 |
| 51 | 0.015 |
| 52 | 0.088 |
| 53 | 0.068 |
| 54 | 0.042 |
| 55 | 0.005 |
| 56 | 0.037 |
| 57 | 0.011 |
| 58 | 0.005 |
| 59 | 0.011 |
| 60 | 0.03 |
| 61 | 0.01 |
| 62 | 0.013 |
| 63 | 0.022 |
| 64 | 0.004 |
| 65 | 0.047 |
| 66 | 0.018 |
| 67 | 0.041 |
| 68 | 0.027 |
| 69 | 0.003 |
| 70 | 0.021 |
| 71 | 0.023 |
| 72 | 0.031 |
| 73 | 0.037 |
| 74 | 0.033 |
| 75 | 0.023 |
| 76 | 0.065 |
| 77 | 0.019 |
| 78 | 0.037 |
| 79 | 0.011 |
| 80 | 0.021 |
| 81 | 0.043 |
| 82 | 0.015 |
| 83 | 0.034 |
| 84 | 0.026 |
| 85 | 0.012 |
| 86 | 0.021 |
| 87 | 0.054 |
| 88 | 0.05 |
| 89 | 0.041 |
| 90 | 0.039 |
| 91 | 0.025 |
| 92 | 0.016 |
| 93 | 0.029 |
| 94 | 0.036 |
| 95 | 0.02 |
| 96 | 0.017 |
| 97 | 0.02 |

TABLE 6-continued

| Example | Ki |
|---|---|
| 98 | 0.013 |
| 99 | 0.021 |
| 100 | 0.037 |
| 101 | 0.023 |
| 102 | 0.024 |
| 103 | 0.039 |
| 104 | 0.049 |
| 105 | 0.029 |
| 106 | 0.009 |
| 107 | 0.047 |
| 108 | 0.026 |
| 109 | 0.022 |
| 110 | 0.023 |
| 111 | 0.027 |
| 112 | 0.029 |
| 113 | 0.008 |
| 114 | 0.04 |
| 115 | 0.012 |
| 116 | 0.01 |
| 117 | 0.011 |
| 118 | 0.041 |
| 119 | 0.030 |
| 120 | 0.041 |
| 121 | 0.022 |
| 122 | 0.025 |
| 123 | 0.008 |
| 124 | 0.035 |
| 125 | 0.015 |
| 126 | 0.016 |
| 127 | 0.040 |
| 128 | 0.028 |
| 129 | 0.013 |
| 130 | 0.007 |
| 131 | 0.054 |
| 132 | 0.008 |
| 133 | 0.051 |
| 134 | 0.007 |
| 135 | 0.035 |
| 136 | 0.03 |
| 137 | 0.027 |
| 138 | 0.009 |
| 139 | 0.021 |
| 140 | 0.047 |
| 141 | 0.006 |
| 142 | 0.049 |
| 143 | 0.009 |
| 144 | 0.003 |
| 145 | 0.005 |
| 146 | 0.007 |
| 147 | 0.034 |
| 148 | 0.030 |
| 149 | 0.015 |
| 150 | 0.001 |
| 151 | 0.02 |
| 152 | 0.001 |
| 153 | 0.015 |
| 154 | 0.039 |
| 155 | 0.043 |
| 156 | 0.032 |
| 157 | 0.018 |
| 158 | 0.031 |
| 159 | 0.013 |
| 160 | 0.013 |
| 161 | 0.014 |
| 162 | 0.017 |
| 163 | 0.025 |
| 164 | 0.014 |
| 165 | 0.026 |
| 166 | 0.004 |
| 167 | 0.013 |
| 168 | 0.004 |
| 169 | 0.026 |
| 170 | 0.021 |
| 171 | 0.01 |
| 172 | 0.004 |
| 173 | 0.004 |
| 174 | 0.007 |

TABLE 6-continued

| Example | Ki |
|---|---|
| 175 | 0.008 |
| 176 | 0.023 |
| 177 | 0.029 |
| 178 | 0.333 |
| 179 | 0.148 |
| 180 | 0.412 |
| 181 | 0.177 |
| 182 | 0.857 |
| 183 | 0.837 |
| 184 | 0.231 |
| 185 | 0.098 |
| 186 | 0.564 |
| 187 | 0.106 |
| 188 | 0.103 |
| 189 | 0.187 |
| 190 | 0.647 |
| 191 | 0.142 |
| 192 | 0.140 |
| 193 | 0.108 |
| 194 | 0.811 |
| 195 | 0.117 |
| 196 | 0.174 |
| 197 | 0.004 |
| 198 | 0.031 |
| 199 | 0.138 |
| 200 | 0.162 |
| 201 | 0.182 |
| 202 | 0.620 |
| 203 | 0.570 |
| 204 | 0.037 |
| 205 | 0.022 |
| 206 | 0.022 |
| 207 | 0.023 |
| 208 | 0.156 |
| 209 | 0.005 |
| 210 | 0.006 |
| 211 | 0.006 |
| 212 | 0.042 |
| 213 | 0.003 |
| 214 | 0.001 |
| 215 | 0.027 |
| 216 | 0.004 |
| 217 | 0.003 |
| 218 | 0.035 |
| 219 | 0.061 |
| 220 | 0.044 |

What is claimed is:
1. A compound of the formula I:

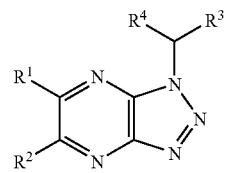

wherein:
$R^1$ is selected from hydrogen, Br, Cl, F, —O(CH$_2$)$_n$CH$_3$, —NR$^{10}$C(O)OR$^{12}$, —(CR$^{12}$R$^{13}$)$_n$NR$^{10}$R$^{11}$, —O(CH$_2$)$_n$OR$^{10}$, —(CH$_2$)$_n$OR10, —C(O)R$^{10}$, —C(O)OR$^{10}$, —C(O)NR$^{10}$R$^{11}$, —NR$^{10}$R$^{11}$, —S(O)$_2$R$^{10}$, —S(O)R$^{10}$, —S(O)$_2$NR$^{10}$R$^{11}$, —CF$_3$, —CF$_2$H, —NR$^{10}$C(O)NR$^{10}$R$^{11}$, —NR$^{10}$C(O)R$^{11}$, —NR$^{10}$S(O)$_2$R$^{11}$, —N(CH$_2$)$_n$(C$_3$-C$_8$ cycloalkyl), —ON, —NO$_2$, C$_1$-C$_6$ alkyl, C$_3$-C$_8$ cycloalkyl, 3-8 membered heteroalicyclic, 3-8 membered heteroalicyclic-(3-8 membered heteroalicyclic), 8-10 membered heterobicyclic, 5-7 membered heteroaryl, C$_6$-C$_{10}$ aryl, C$_2$-C$_6$ alkenyl, and C$_2$-C$_6$ alkynyl wherein $C_1$-$C_6$ alkyl, $C_3$-$C_8$ cycloalkyl, 3-8 membered heteroalicyclic, 8-10 membered heterobicyclic, 5-7 membered heteroaryl, $C_6$-$C_{10}$ aryl, $C_2$-$C_6$ alkenyl, and $C_2$-$C_6$ alkynyl are optionally substituted by one or more moieties selected from the group consisting of Br, Cl, F, —$(CH_2)_n$OH(OR$^{10}$)CH$_3$, —$(CH_2)_n$OR$^{10}$, —$(CH_2)_n$O(CH$_3$)$_2$OR$^{10}$, —O(O)R$^{10}$, —O(O)OR$^{10}$, —(CR$^{10}$R$^{11}$)$_n$O(O)OR$^{10}$, —C(O)NR$^{10}$R$^{11}$, —(CR$^{10}$R$^{11}$)O(O)NR$^{10}$R$^{11}$, —(CH$_2$)$_n$NR$^{10}$R$^{11}$, —S(O)$_2$R$^{10}$, —S(O)R$^{10}$, —S(O)$_2$NR$^{10}$R$^{11}$, —CF$_3$, —CF$_2$H, —(CH$_2$)$_n$NR$^{10}$C(O)NR$^{10}$R$^{11}$, —(CH$_2$)$_n$NR$^{10}$C(O)OR$^{11}$, —NR$^{10}$C(O)R$^{11}$, —NR$^{10}$C(O)OR$^{11}$, —NR$^{10}$S(O)$_2$R$^{11}$, —ON, —NO$_2$, oxo, $C_1$-$C_6$ alkyl, $C_3$-$C_8$ cycloalkyl, —(CH$_2$)$_n$(3-8 membered heteroalicyclic), —(CH$_2$)$_n$(5-7 membered heteroaryl), —(C$_2$)$_n$(C$_6$-C$_{10}$ aryl), $C_2$-$C_6$ alkenyl, and $C_2$-$C_6$ alkynyl;

$R^2$ is H;

$R^3$ is selected from

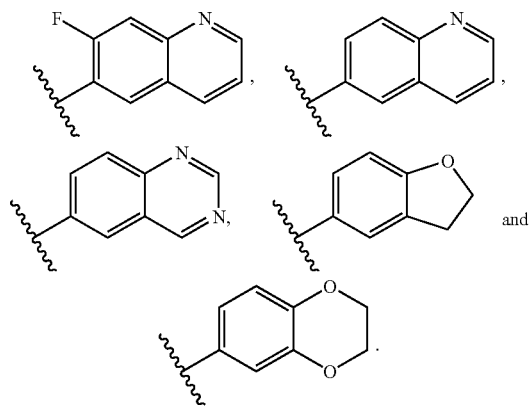

$R^{10}$ and $R^{11}$ are independently selected from H, —(CH$_2$)$_n$OR$^{12}$, —(CH$_2$)$_n$C(CH$_3$)$_2$OR$^{12}$, —CHR$^{12}$(CH$_2$)$_n$OR$^{13}$, —C(O)OR$^{12}$, —(CH$_2$)$_n$CHR$^{12}$OR$^{13}$, —C(CH$_3$)$_2$(CH$_2$)$_n$OR$^{12}$, —CH$_2$CF$_2$H, —(CH$_2$)$_n$C(CH$_3$)$_2$NR$^{12}$R$^{13}$, —(CH$_2$)$_n$NR$^{12}$R$^{13}$, —(CH$_2$)$_n$CHOR$^{12}$(CH$_2$)$_n$OR$^{13}$, —(CH$_2$)$_n$(NR$^{12}$R$^{13}$)C(O)NR$^{12}$R$^{13}$, —(CH$_2$)$_n$S(O)$_2$R$^{12}$, —(CH$_2$)$_n$C(O)NR$^{12}$R$^{13}$, —NR$^{12}$(CH$_2$)$_n$(5-7 membered heteroaryl), —NR$^{12}$(CH$_2$)$_n$(3-8 membered heterocycle), —(CH$_2$)$_n$(8-10 membered heterobicyclic), —(CH$_2$)$_n$(3-8 membered heteroalicyclic), $C_1$-$C_6$ alkyl, $C_3$-$C_8$ cycloalkyl, $C_6$-$C_{10}$ aryl, $C_2$-$C_6$ alkenyl, 3-8 membered heteroalicyclic and $C_2$-$C_6$ alkynyl, wherein said 5-7 membered heteroaryl, 3-8 membered heterocycle and 8-10 membered heterobicyclic are optionally substituted by one or more moieties selected from the group consisting of —(CH$_2$)$_n$OR$^{12}$, $C_1$-$C_6$ alkyl, $C_3$-$C_8$ cycloalkyl, $C_6$-$C_{10}$ aryl, $C_2$-$C_6$ alkenyl, 3-8 membered heteroalicyclic and $C_2$-$C_6$ alkynyl; or when $R^{10}$ and $R^{11}$ are attached to the same atom, $R^{10}$ and $R^{11}$ optionally combine to form a 3-8 membered heteroalicyclic ring;

$R^{12}$ and $R^{13}$ are independently selected from H, $C_1$-$C_6$ alkyl, —C(O)CH$_3$, $C_3$-$C_8$ cycloalkyl, $C_6$-$C_{10}$ aryl, $C_2$-$C_6$ alkenyl, 5-7 membered heteroaryl and $C_2$-$C_6$ alkynyl, wherein said 5-7 membered heteroaryl is optionally substituted by one or more moieties selected from the group consisting of $C_1$-$C_6$ alkyl, $C_3$-$C_8$ cycloalkyl, $C_6$-$C_{10}$ aryl, $C_2$-$C_6$ alkenyl, and $C_2$-$C_6$ alkynyl; or when $R^{12}$ and $R^{13}$ are attached to the same atom, $R^{12}$ and $R^{13}$ optionally combine to form a 3-8 membered heteroalicyclic ring;

$R^4$ is selected from the group consisting of hydrogen, and $C_1$-$C_6$ alkyl; and each n is independently 0, 1, 2, 3 or 4;

wherein 3-8 membered heteroalicyclic and 3-8 membered heterocycle are independently selected from the group consisting of aziridinyl, oxetanyl, thiapanyl, azepanyl, tetrahydrofuranyl, tetrahydrothiophenyl, pyrolidinyl, tetrahydropyranyl, tetrahydrothioipyranyl, piperidinyl, 1,4-dioxanyl, 1,4-oxathianyl, morpholinyl, 1,4-dithianyl, piperazinyl, 1,4-azathianyl, azepanyl, 1,4-oxaazepanyl, 1,4-dithiepanyl, 1,4-thieazapanyl, 1,4-diazepanyl, 3,4-dihydro-2H-pyranyl, 5,6-dihydro-2H-pyranyl, 2H-pyranyl, 1,2,3,4-tetrahydropyridinyl, 1,2,5,6-tetrahydropyridinyl, 1,2-dihydropyridyl, and imidazolidinyl;

wherein 8-10 membered heterobicyclic is selected from the group consisting of benzofuranyl, benzothiphenyl, indolyl, benzimidazolyl, indazolyl, benzotriazolyl, pyrrolo[2,3-b]pyridinyl, pyrrolo[2,3-c]pyridinyl, pyrrolo[3,2-b]pyridinyl, pyrrolo[3,2-c]pyridinyl, imidazo[4,5-b]pyridinyl, imidazo[4,5-c]pyridinyl, pyrazolo[4,3-d]pyridinyl, pyrazolo[4,3-c]pyridinyl, pyrazolo[3,4-c]pyridinyl, pyrazolo[3,4-b]pyridinyl, isoindolyl, Quinolinyl, isoquinoliinyl, quinazolinyl, quinaxolinyl, indazolyl, purinyl, indolininyl, imidazo[1,2-a]pyridinyl, pyrazolo[1,5-a]pyridinyl, pyrrolo[1,2-b]pyridazinyl, imidazo[1,2-c]pyrimidinyl, 3H-indolyl, indolyl, isoindolinyl, 2,3-dihydrobenzofuranyl, 1,3-dihydrobenzofuranyl, 1H-isoindolyl, 1,2,3,4-tetrahydroquinoxalinyl, 1,2-dihydroquinoxalinyl, 1,2-dihydroquinazolinyl, 3,4-dihydroquinazolinyl, 3,3a-dihydropyrazolo[1,5-a]pyrimidinyl, 5,6,7,8-tetrahydro-[1,2,4]triazolo[4,3-a]pyrazinyl, octahydropyrrolo[1,2-a]pyrazine, 4,5,6,7-tetrahydro-1H-pyrazolo[4,3-c]pyridinyl, and 4,5,6,7-tetrahydro-1H-pyrazolo[3,4-c]pyridine;

wherein 5-7 membered heteroaryl is selected from the group consisting of pyrrolyl, furanyl, thiophenyl, pyrazolyl, imidazolyl, isoxazolyl, oxazolyl, thiazolyl, 1,2,3-triazolyl, 1,3,4-triazolyl, 1-oxa-2,3-diazolyl, 1-oxa-2,4-diazolyl, 1-oxa-2,5-diazolyl, 1-oxa-3,4-diazolyl, tetrazolyl, pyridinyl, pyridazinyl, and pyrimidinyl;

or a pharmaceutically acceptable salt thereof.

2. The compound of claim 1, wherein $R^1$ is selected from —OR$^{10}$, —O(CH$_2$)$_n$CH$_3$, —NR$^{10}$C(O)OR$^{12}$, —(CR$^{12}$R$^{13}$)$_n$NR$^{10}$R$^{11}$, —OCH$_2$(CH$_2$)$_n$OR$^{10}$, —C(O)NR$^{10}$R$^{11}$, —NR$^{10}$R$^{11}$, $C_1$-$C_6$ alkyl, 3-8 membered heteroalicyclic, 3-8 membered heteroalicyclic-(3-8 membered heteroalicyclic), 8-10 membered heterobicyclic, 5-7 membered heteroaryl, $C_6$-$C_{10}$ aryl and $C_2$-$C_6$ alkenyl, wherein $C_1$-$C_6$ alkyl, 3-8 membered heteroalicyclic, 3-8 membered heteroalicyclic-(3-8 membered heteroalicyclic), 8-10 membered heterobicyclic, 5-7 membered heteroaryl, $C_6$-$C_{10}$ aryl and $C_2$-$C_6$ alkenyl are optionally substituted by one or more moieties selected from the group consisting of Br, Cl, F, —(CH$_2$)$_n$CH(OR$^{10}$)CH$_3$, —(CH$_2$)$_n$OR$^{10}$, —(CH$_2$)$_n$C(CH$_3$)$_2$OR$^{10}$, —(CH$_2$)$_n$(3-8 membered heteroalicyclic), —C(O)R$^{10}$, —C(O)OR$^{10}$, —(CR$^{10}$R$^{11}$)$_n$C(O)OR$^{10}$, —C(O)NR$^{10}$R$^{11}$, —(CR$^{10}$R$^{11}$)$_n$C(O)NR$^{10}$R$^{11}$, —(CH$_2$)$_n$NR$^{10}$R$^{11}$, —S(O)R$^{10}$, —S(O)$_2$NR$^{10}$R$^{11}$, —CF$_3$, —CF$_2$H, —(CH$_2$)$_n$NR$^{10}$C(O)NR$^{10}$R$^{11}$, —(CH$_2$)$_n$NR$^{10}$C(O)OR$^{11}$, —NR$^{10}$C(O)R$^{11}$, —NR$^{10}$C(O)OR$^{11}$, —NR$^{10}$S(O)$_2$R$^{11}$, —ON, —NO$_2$, oxo, $C_1$-$C_6$ alkyl, $C_3$-$C_8$ cycloalkyl, —(C$_2$)$_n$(3-8 membered heteroalicyclic), —(C$_2$)$_n$(5-7 membered heteroaryl), —(C$_2$)$_n$(C$_6$-$C_{10}$ aryl), $C_2$-$C_6$ alkenyl, and $C_2$-$C_6$ alkynyl.

3. The compound of claim 1, wherein $R^1$ is selected from Br, —$OR^{10}$, —$O(CH_2)_nCH_3$, —$NR^{10}C(O)OR^{12}$, —$(CR^{12}R^{13})_nNR^{10}R^{11}$, —$OCH_2(CH_2)_nOR^{10}$, —$C(O)NR^{10}R^{11}$, —$NR^{10}R^{11}$, $C_1$-$C_6$ alkyl, 3-8 membered heteroalicyclic, 3-8 membered heteroalicyclic-(3-8 membered heteroalicyclic), 8-10 membered heterobicyclic, 5-7 membered heteroaryl, $C_6$-$C_{10}$ aryl and $C_2$-$C_6$ alkenyl, wherein $C_1$-$C_6$ alkyl, 3-8 membered heteroalicyclic, 3-8 membered heteroalicyclic-(3-8 membered heteroalicyclic), 8-10 membered heterobicyclic, 5-7 membered heteroaryl, $C_6$-$C_{10}$ aryl and $C_2$-$C_6$ alkenyl are optionally substituted by one or more moieties selected from the group consisting of Br, Cl, F, —$(CH_2)_nCH(OR^{10})CH_3$, —$(CH_2)_nOR^{10}$, —$(CH_2)_nC(CH_3)_2OR^{10}$, —$(CH_2)_n$(3-8 membered heteroalicyclic), —$C(O)R^{10}$, —$C(O)OR^{10}$, —$(CR^{10}R^{11})_nC(O)OR^{10}$, —$C(O)NR^{10}R^{11}$, —$(CR^{10}R^{11})_nC(O)NR^{10}R^{11}$, —$(CH_2)_nNR^{10}R^{11}$, —$S(O)_2R^{10}$, —$S(O)R^{10}$, —$S(O)_2NR^{10}R^{11}$, —$CF_3$, —$CF_2H$, —$(CH_2)_nNR^{10}C(O)NR^{10}R^{11}$, —$(CH_2)_nNR^{10}C(O)OR^{11}$, —$NR^{10}C(O)R^{11}$, —$NR^{10}C(O)OR^{11}$, —$NR^{10}S(O)_2R^{11}$, —CN, —$NO_2$, oxo, $C_1$-$C_6$ alkyl, $C_3$-$C_8$ cycloalkyl, —$(CH_2)_n$(3-8 membered heteroalicyclic), —$(CH_2)_n$(5-7 membered heteroaryl), —$(CH_2)_n(C_6$-$C_{10}$ aryl), $C_2$-$C_6$ alkenyl, and $C_2$-$C_6$ alkynyl.

4. The compound according to claim 1, wherein $R^4$ is H.

5. The compound according to claim 1, wherein $R^4$ is $C_1$-$C_6$ alkyl.

6. The compound according to claim 1, wherein $R^4$ is methyl.

7. The compound of claim 1, wherein said compound is selected from 6-((6-(1-methyl-1H-pyrazol-4-yl)-1H-[1,2,3]triazolo[4,5-b]pyrazin-1-yl)methyl)quinoline, N-(piperidin-4-yl)-4-(3-(quinolin-6-ylmethyl)-3H-[1,2,3]triazolo[4,5-b]pyrazin-5-yl)benzamide, N-(2-aminoethyl)-4-(3-(quinolin-6-ylmethyl)-3H-[1,2,3]triazolo[4,5-b]pyrazin-5-yl)benzamide, N-(2-(dimethylamino)ethyl)-4-(3-(quinolin-6-ylmethyl)-3H-[1,2,3]triazolo[4,5-b]pyrazin-5-yl)benzamide, 6-((6-(4-methyl-1H-imidazol-1-yl)-1H-[1,2,3]triazolo[4,5-b]pyrazin-1-yl)methyl)quinoline, N-methyl-4-(3-(quinolin-6-ylmethyl)-3H-[1,2,3]triazolo[4,5-b]pyrazin-5-yl)benzamide, 6-((6-(3-methoxyphenyl)-1H-[1,2,3]triazolo[4,5-b]pyrazin-1-yl)methyl)quinoline, 6-((6-(4-methoxyphenyl)-1H-[1,2,3]triazolo[4,5-b]pyrazin-1-yl)methyl)quinoline, 6-((6-(1H-pyrazol-4-yl)-1H-[1,2,3]triazolo[4,5-b]pyrazin-1-yl)methyl)quinoline, (R)-1-(3-(quinolin-6-ylmethyl)-3H-[1,2,3]triazolo[4,5-b]pyrazin-5-yl)pyrrolidin-3-amine, (4-(3-(quinolin-6-ylmethyl)-3H-[1,2,3]triazolo[4,5-b]pyrazin-5-yl)phenyl)methanol, (4-(3-(quinolin-6-ylmethyl)-3H-[1,2,3]triazolo[4,5-b]pyrazin-5-yl)phenyl)methanamine, 6-[6-(1-ethoxy-vinyl)-[1,2,3]triazolo[4,5-b]pyrazin-1-ylmethyl]-quinoline, 2-[4-(3-quinolin-6-ylmethyl-3H-[1,2,3]triazolo[4,5-b]pyrazin-5-yl)-pyrazol-1-yl]-ethanol, 6-[6-(2-methyl-5-trifluoromethyl-2H-pyrazol-3-yl)-[1,2,3]triazolo[4,5-b]pyrazin-1-ylmethyl]-quinoline, and 6-[6-(2H-pyrazol-3-yl)-[1,2,3]triazolo[4,5-b]pyrazin-1-ylmethyl]-quinoline; or a pharmaceutically acceptable salt thereof.

8. The compound of claim 1, wherein said compound is 2-[4-(3-quinolin-6-ylmethyl-3H-[1,2,3]triazolo[4,5-b]pyrazin-5-yl)-pyrazol-1-yl]-ethanol.

9. A pharmaceutical composition comprising a compound according to the formula (I) as defined in claim 1 or a pharmaceutically acceptable salt thereof, and a pharmaceutically acceptable excipient.

10. The compound of claim 1, wherein said compound is 2-[4-(3-quinolin-6-ylmethyl-3H-[1,2,3]triazolo[4,5-b]pyrazin-5-yl)-pyrazol-1-yl]-ethanol mesylate salt.

11. A pharmaceutical composition comprising a compound according to claim 10, and a pharmaceutically acceptable excipient.

* * * * *